United States Patent
Holst et al.

(10) Patent No.: US 12,390,522 B2
(45) Date of Patent: *Aug. 19, 2025

(54) NUCLEIC ACIDS ENCODING HUMAN ENDOGENOUS RETROVIRUS K (HERV-K) ENVELOPE PROTEINS CONTAINING MODIFIED IMMUNOSUPPRESSIVE DOMAINS (ISD) AND USES THEREOF

(71) Applicant: INPROTHER APS, Copenhagen (DK)

(72) Inventors: Peter Holst, Soeborg (DK); Christian Thirion, Munich (DE); Lasse Neukirch, Flensburg (DE)

(73) Assignee: INPROTHER APS, Copenhagen (DK)

( * ) Notice: Subject to any disclaimer, the term of this patent is extended or adjusted under 35 U.S.C. 154(b) by 647 days.

This patent is subject to a terminal disclaimer.

(21) Appl. No.: 17/271,888

(22) PCT Filed: Aug. 30, 2019

(86) PCT No.: PCT/EP2019/073273
§ 371 (c)(1),
(2) Date: Feb. 26, 2021

(87) PCT Pub. No.: WO2020/043908
PCT Pub. Date: Mar. 5, 2020

(65) Prior Publication Data
US 2023/0181716 A1  Jun. 15, 2023

(51) Int. Cl.
| | | |
|---|---|---|
| *A61K 39/21* | (2006.01) | |
| *A61K 39/235* | (2006.01) | |
| *A61P 35/00* | (2006.01) | |
| *A61P 35/04* | (2006.01) | |
| *C07K 14/005* | (2006.01) | |
| *C12N 7/00* | (2006.01) | |
| *C12N 15/86* | (2006.01) | |
| *A61K 39/00* | (2006.01) | |

(52) U.S. Cl.
CPC ............ *A61K 39/21* (2013.01); *A61K 39/235* (2013.01); *A61P 35/00* (2018.01); *A61P 35/04* (2018.01); *C07K 14/005* (2013.01); *C12N 7/00* (2013.01); *C12N 15/86* (2013.01); *A61K 2039/525* (2013.01); *A61K 2039/5258* (2013.01); *A61K 2039/545* (2013.01); *A61K 2039/585* (2013.01); *C12N 2710/10043* (2013.01); *C12N 2740/10022* (2013.01); *C12N 2740/10023* (2013.01); *C12N 2740/10034* (2013.01); *C12N 2740/10071* (2013.01)

(58) Field of Classification Search
CPC .......... A61K 39/21; C12N 2740/10022; C12N 2740/10034
See application file for complete search history.

(56) References Cited

U.S. PATENT DOCUMENTS

| | | | |
|---|---|---|---|
| 11,351,247 B2 * | 6/2022 | Holst | ............... A61P 35/04 |
| 2007/0185025 A1 | 8/2007 | Palacios et al. | |
| 2014/0248305 A1 | 9/2014 | Ertl et al. | |

FOREIGN PATENT DOCUMENTS

| | | |
|---|---|---|
| CN | 1961001 A | 5/2007 |
| EP | 1 997 895 A1 | 12/2008 |
| JP | 2005-508154 A | 3/2005 |
| JP | 2008-506357 A | 3/2008 |
| JP | 2009-544614 A | 12/2009 |
| JP | 2013-510091 A | 3/2013 |
| WO | WO-2005/095442 A1 | 10/2005 |
| WO | WO-2013/059426 A1 | 4/2013 |

OTHER PUBLICATIONS

Morozov, V. A., et al., Aug. 2013, The Transmembrane Protein of the Human Endogenous Retrovirus-K (HERV-K) Modulates Cytokine Release and Gene Expression, PLoS One 8(8):e70399, pp. 1-9.*
Schlecht-Louf, G., et al., Feb. 2010, Retroviral Infection In Vivo Requires an Immune Escape Virulence Factor Encrypted in the Envelope Protein of Oncoretroviruses, Proc. Natl. Acad. Sci. 107(8):3782-3787.*
Vargiu, L., et al., 2016, Classification and characterization of human endogenous retroviruses; mosaic forms are common, Retrovirol. 13:7, pp. 1-29.*
Bénit, L., et al., Dec. 2001, Identification, phylogeny, and evolution of retroviral elements based on their envelope genes, J. Virol. 75(23):11709-11719.*
Mangeney, M., et al., Dec. 2007, Placental syncytins: Genetic disjunction between the fusogenic and immunosuppressive activity of retroviral envelope proteins, PNAS 104(51):20534-20539.*
Grandi, N., and E. Tramontano, Mar. 2018, HERV envelop proteins: Physiologic role and pathogenic potential in cancer and autoimmunity, Front. Microbiol. 9:462, pp. 1-26.*
Zhou, W., et al., 2023, Vaccines' New Era-RNA Vaccine, Viruses 15,1760, pp. 1-19.*
Zittersteijn, H. A., et al., May 2020, A primer to gene therapy: Progress, prospects, and problems, J. Inherit. Metab. Dis. 44:54-71.*

(Continued)

*Primary Examiner* — Jeffrey S Parkin
(74) *Attorney, Agent, or Firm* — Foley & Lardner LLP

(57) ABSTRACT

The present invention relates to an adenoviral vector capable of encoding a virus-like particle (VLP), said VLP displaying an inactive immune-suppressive domain (ISD). The vaccine of the invention shows an improved immune response from either of both of the response pathways initiated by CD4 T cells or CD8 T cells.

15 Claims, 29 Drawing Sheets
Specification includes a Sequence Listing.

(56) References Cited

OTHER PUBLICATIONS

Kohnken, R., et al., Feb. 2017, Overview of the Use of Muring Models in Leukemia and Lymphoma Research, Front. Oncol. 7: Article 22, pp. 1-11.*
International Search Report and Written Opinion issued in corresponding International Application No. PCT/EP2018/073404 on Oct. 19, 2018, twelve (12) pages.
International Search Report and Written Opinion issued in related International Patent Application No. PCT/EP2019/073273 on Oct. 8, 2019, sixteen (16) pages.
Morozov et al., "The Transmembrane Protein of the Human Endogenous Retrovirus-K (HERV-K) Modulates Cytokine Release and Gene Expression", PLOS One, vol. 8, No. 8, Aug. 7, 2013, pp. 1-9.
Waechter et al., "Novel Neutralizing Antibodies targeting the N-Terminal Helical Region of the Transmembrane Envelope Protein p15E of the Porcine Endogenous Retrovirus (PERV)" Immunologic Research, vol. 58, No. 1, Jun. 1, 2013, pp. 9-19.
Schlecht-Louf et al., "Retroviral infection in vivo requires an immune escape virulence factor encrypted in the envelope protein of oncoretroviruses", PNAS, Feb. 23, 2010, pp. 3782-3787, vol. 107, No. 8.
Non-Final Office Action in U.S. Appl. No. 17/732,076 dated Sep. 20, 2023.
1st Office Action issued a Chinese Application No. 201980071472. 7, dated Jun. 4, 2024.

\* cited by examiner

1) pIX-p15E:
TGTT[...]EVVLQNRRGLDLLFLKEGGLCAALKEECCFYADHTGLVRDSMAKLRERLSQRQKLFESQQGWFEGLFN
2) pIX-p15E-ISD:
TGTT[...]EVVLQNRRGLDLLFLKṚGGLCAF̣LKEECCFYADHTGLVRDSMAKLRERLSQRQKLFESQQGWFEGLFN
3) pIX-p15E-trunc-wC:
TGTT[...]EVVLQNRRGLDLLFLKEGGLC
4) pIX-p15E-trunc-w/oC:
TGTT[...]EVVLQNRRGLDLLFLKEGGL
Immunosuppressive domain (ISD) marked by underline
ISD mutation marked with "#"
Fig. 12
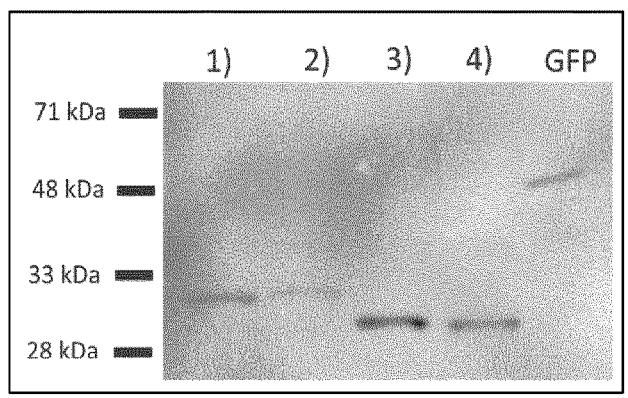
Fig. 13A
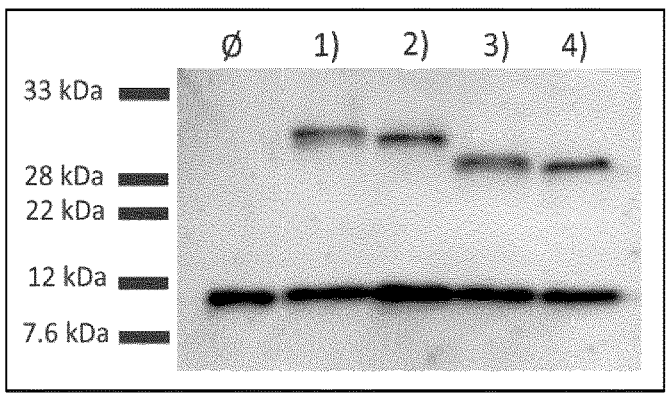
Fig. 13B

Figure 16

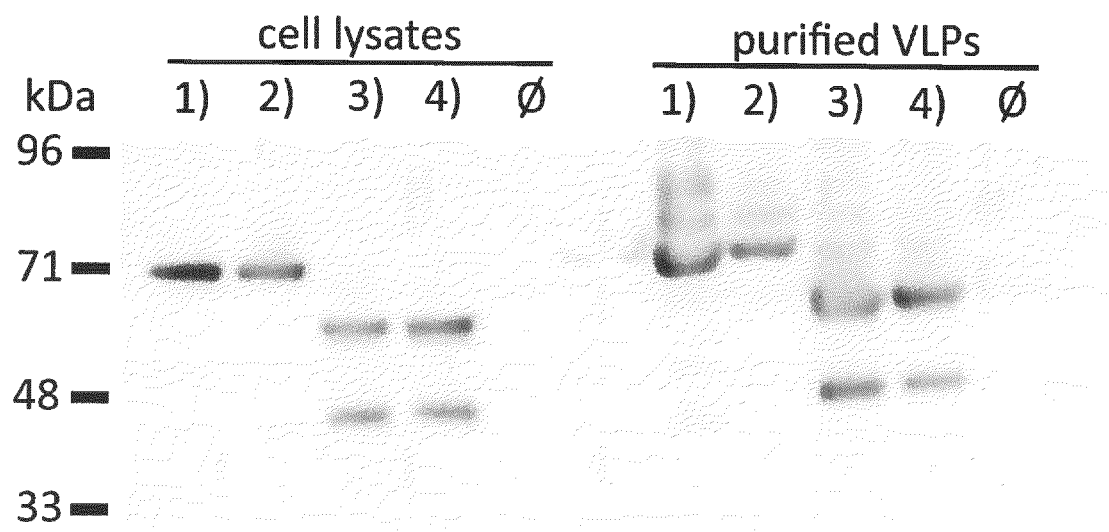
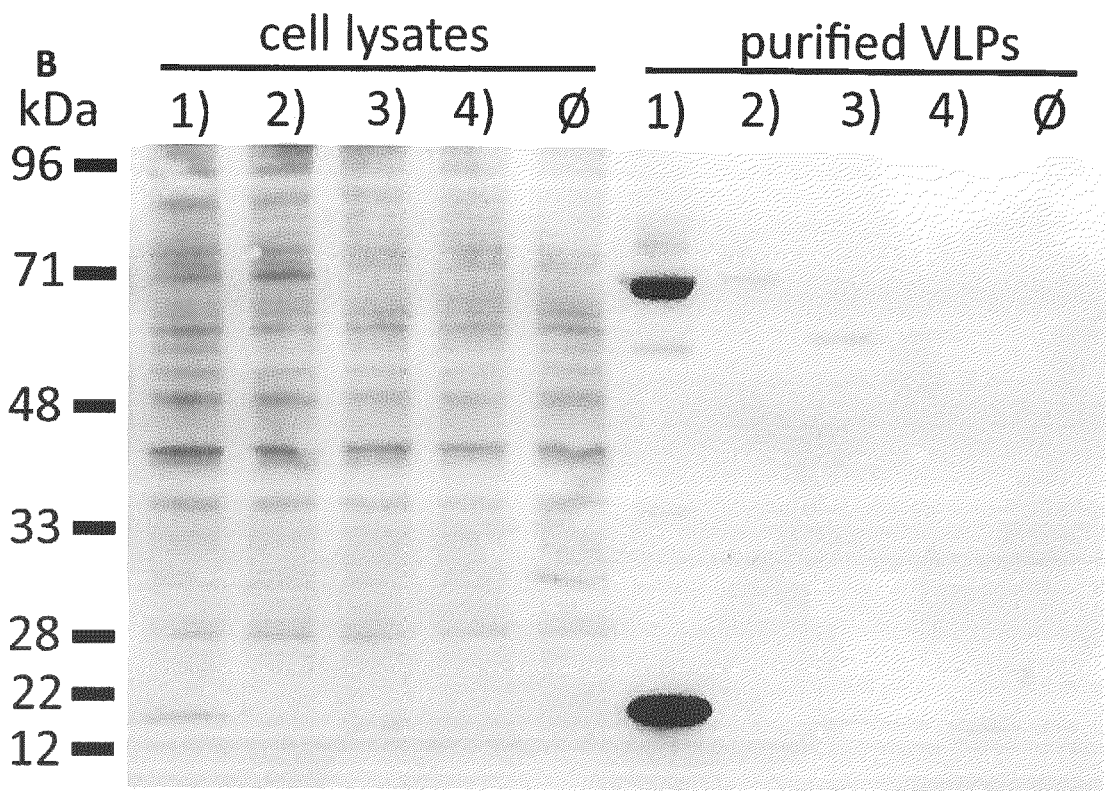
Fig. 18A and B

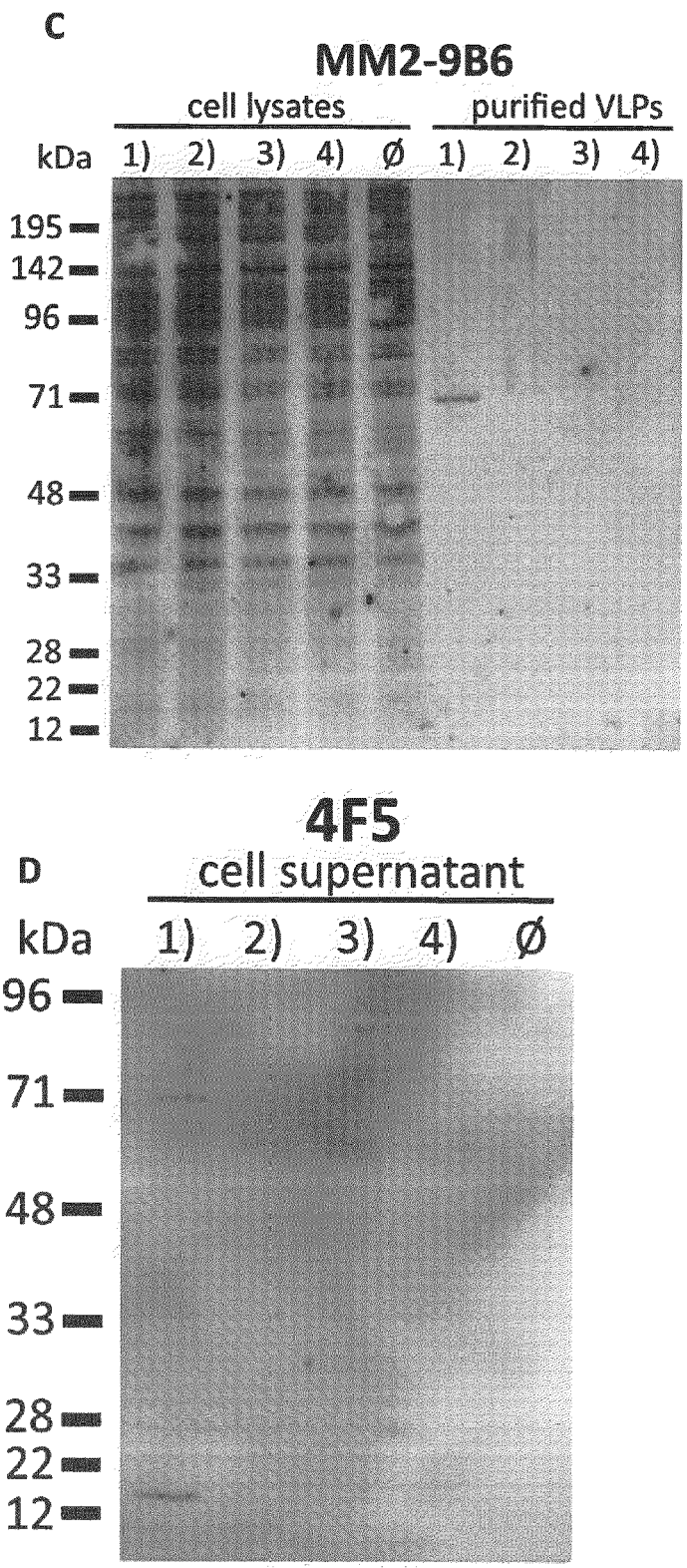
Fig. 18C and D

C

D

SEQUENCE LISTING

```
<160> NUMBER OF SEQ ID NOS: 57

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: ISD of HERV-K HML-2 broadly conserved sequence

<400> SEQUENCE: 1

Leu Ala Asn Gln Ile Asn Asp Leu Arg Gln Thr Val Ile Trp
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: ISD of Env protein from HERV-K18

<400> SEQUENCE: 2

Leu Ala Ser Gln Ile Asn Asp Leu Arg Gln Thr Val Ile Trp
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: ISD of Env protein from HERV-H

<400> SEQUENCE: 3

Leu Gln Asn Arg Arg Gly Leu Asp Leu Leu Thr Ala Glu Lys Gly Gly
1               5                   10                  15
```

Leu

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: ISD of Env protein from HERV-W

<400> SEQUENCE: 4

Leu Gln Asn Arg Arg Ala Leu Asp Leu Leu Thr Ala Glu Arg Gly Gly
1               5                   10                  15

Thr

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: ISD of Env protein from HERV-FRD

<400> SEQUENCE: 5

Leu Gln Asn Arg Arg Gly Leu Asp Met Leu Thr Ala Ala Gln Gly Gly
1               5                   10                  15

Ile

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: ISD of Env protein from human HERV-E

<400> SEQUENCE: 6

Tyr Gln Asn Arg Leu Ala Leu Asp Tyr Leu Leu Ala Ala Glu Gly Gly
1               5                   10                  15

Val

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: ISD of Env protein from MuLV/MelARV

<400> SEQUENCE: 7

Leu Gln Asn Arg Arg Gly Leu Asp Leu Leu Phe Leu Lys Glu Gly Gly
1               5                   10                  15

Leu

<210> SEQ ID NO 8
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: Mutated ISD of Envprotein from MuLV/MelARV

<400> SEQUENCE: 8

Leu Gln Asn Arg Arg Gly Leu Asp Leu Leu Phe Leu Lys Arg Gly Gly
1               5                   10                  15

Leu

<210> SEQ ID NO 9
<211> LENGTH: 699
<212> TYPE: PRT
<213> ORGANISM: Homo sapiens

<400> SEQUENCE: 9

Met Asn Pro Ser Glu Met Gln Arg Lys Ala Pro Pro Arg Arg Arg Arg
1               5                   10                  15

His Arg Asn Arg Ala Pro Leu Thr His Lys Met Asn Lys Met Val Thr
                20                  25                  30

Ser Glu Glu Gln Met Lys Leu Pro Ser Thr Lys Lys Ala Glu Pro Pro
            35                  40                  45

Thr Trp Ala Gln Leu Lys Lys Leu Thr Gln Leu Ala Thr Lys Tyr Leu
    50                  55                  60

Glu Asn Thr Lys Val Thr Gln Thr Pro Glu Ser Met Leu Leu Ala Ala
65                  70                  75                  80

Leu Met Ile Val Ser Met Val Val Ser Leu Pro Met Pro Ala Gly Ala
                85                  90                  95

Ala Ala Ala Asn Tyr Thr Tyr Trp Ala Tyr Val Pro Phe Pro Pro Leu
            100                 105                 110

Ile Arg Ala Val Thr Trp Met Asp Asn Pro Thr Glu Val Tyr Val Asn
        115                 120                 125

Asp Ser Val Trp Val Pro Gly Pro Ile Asp Asp Arg Cys Pro Ala Lys
    130                 135                 140

Pro Glu Glu Glu Gly Met Met Ile Asn Ile Ser Ile Gly Tyr His Tyr
145                 150                 155                 160

Pro Pro Ile Cys Leu Gly Arg Ala Pro Gly Cys Leu Met Pro Ala Val
                165                 170                 175

Gln Asn Trp Leu Val Glu Val Pro Thr Val Ser Pro Ile Cys Arg Phe
            180                 185                 190

Thr Tyr His Met Val Ser Gly Met Ser Leu Arg Pro Arg Val Asn Tyr
        195                 200                 205

Leu Gln Asp Phe Ser Tyr Gln Arg Ser Leu Lys Phe Arg Pro Lys Gly
    210                 215                 220

Lys Pro Cys Pro Lys Glu Ile Pro Lys Glu Ser Lys Asn Thr Glu Val
225                 230                 235                 240

Leu Val Trp Glu Glu Cys Val Ala Asn Ser Ala Val Ile Leu Gln Asn
                245                 250                 255

Asn Glu Phe Gly Thr Ile Ile Asp Trp Ala Pro Arg Gly Gln Phe Tyr
            260                 265                 270

His Asn Cys Ser Gly Gln Thr Gln Ser Cys Pro Ser Ala Gln Val Ser
        275                 280                 285

Pro Ala Val Asp Ser Asp Leu Thr Glu Ser Leu Asp Lys His Lys His
    290                 295                 300

Lys Lys Leu Gln Ser Phe Tyr Pro Trp Glu Trp Gly Glu Lys Gly Ile
```

```
              305                 310                 315                 320
      Ser Thr Pro Arg Pro Lys Ile Val Ser Pro Val Ser Gly Pro Glu His
                      325                 330                 335

Pro Glu Leu Trp Arg Leu Thr Val Ala Ser His His Ile Arg Ile Trp
                      340                 345                 350

Ser Gly Asn Gln Thr Leu Glu Thr Arg Asp Arg Lys Pro Phe Tyr Thr
                      355                 360                 365

Ile Asp Leu Asn Ser Ser Leu Thr Val Pro Leu Gln Ser Cys Val Lys
              370                 375                 380

Pro Pro Tyr Met Leu Val Val Gly Asn Ile Val Ile Lys Pro Asp Ser
      385                 390                 395                 400

Gln Thr Ile Thr Cys Glu Asn Cys Arg Leu Leu Thr Cys Ile Asp Ser
                      405                 410                 415

Thr Phe Asn Trp Gln His Arg Ile Leu Leu Val Arg Ala Arg Glu Gly
                      420                 425                 430

Val Trp Ile Pro Val Ser Met Asp Arg Pro Trp Glu Ala Ser Pro Ser
                      435                 440                 445

Val His Ile Leu Thr Glu Val Leu Lys Gly Val Leu Asn Arg Ser Lys
              450                 455                 460

Arg Phe Ile Phe Thr Leu Ile Ala Val Ile Met Gly Leu Ile Ala Val
      465                 470                 475                 480

Thr Ala Thr Ala Ala Val Ala Gly Val Ala Leu His Ser Ser Val Gln
                      485                 490                 495

Ser Val Asn Phe Val Asn Asp Trp Gln Lys Asn Ser Thr Arg Leu Trp
                      500                 505                 510

Asn Ser Gln Ser Ser Ile Asp Gln Lys Leu Ala Asn Gln Ile Asn Asp
              515                 520                 525

Leu Arg Gln Thr Val Ile Trp Met Gly Asp Arg Leu Met Ser Leu Glu
              530                 535                 540

His Arg Phe Gln Leu Gln Cys Asp Trp Asn Thr Ser Asp Phe Cys Ile
      545                 550                 555                 560

Thr Pro Gln Ile Tyr Asn Glu Ser Glu His His Trp Asp Met Val Arg
                      565                 570                 575

Arg His Leu Gln Gly Arg Glu Asp Asn Leu Thr Leu Asp Ile Ser Lys
                      580                 585                 590

Leu Lys Glu Gln Ile Phe Glu Ala Ser Lys Ala His Leu Asn Leu Val
              595                 600                 605

Pro Gly Thr Glu Ala Ile Ala Gly Val Ala Asp Gly Leu Ala Asn Leu
      610                 615                 620

Asn Pro Val Thr Trp Val Lys Thr Ile Gly Ser Thr Thr Ile Ile Asn
      625                 630                 635                 640

Leu Ile Leu Ile Leu Val Cys Leu Phe Cys Leu Leu Leu Val Cys Arg
                      645                 650                 655

Cys Thr Gln Gln Leu Arg Arg Asp Ser Asp His Arg Glu Arg Ala Met
                      660                 665                 670

Met Thr Met Ala Val Leu Ser Lys Arg Lys Gly Gly Asn Val Gly Lys
                      675                 680                 685

Ser Lys Arg Asp Gln Ile Val Thr Val Ser Val
              690                 695

<210> SEQ ID NO 10
<211> LENGTH: 666
<212> TYPE: PRT
<213> ORGANISM: Homo sapiens
```

```
<400> SEQUENCE: 10

Met Gly Gln Thr Lys Ser Lys Ile Lys Ser Lys Tyr Ala Ser Tyr Leu
1               5                   10                  15

Ser Phe Ile Lys Ile Leu Leu Lys Arg Gly Val Lys Val Ser Thr
            20                  25                  30

Lys Asn Leu Ile Lys Leu Phe Gln Ile Ile Glu Gln Phe Cys Pro Trp
            35                  40                  45

Phe Pro Glu Gln Gly Thr Leu Asp Leu Lys Asp Trp Lys Arg Ile Gly
    50                  55                  60

Lys Glu Leu Lys Gln Ala Gly Arg Lys Gly Asn Ile Ile Pro Leu Thr
65                  70                  75                  80

Val Trp Asn Asp Trp Ala Ile Ile Lys Ala Ala Leu Glu Pro Phe Gln
                85                  90                  95

Thr Glu Glu Asp Ser Val Ser Val Ser Asp Ala Pro Gly Ser Cys Ile
                100                 105                 110

Ile Asp Cys Asn Glu Asn Thr Arg Lys Lys Ser Gln Lys Glu Thr Glu
            115                 120                 125

Gly Leu His Cys Glu Tyr Val Ala Glu Pro Val Met Ala Gln Ser Thr
        130                 135                 140

Gln Asn Val Asp Tyr Asn Gln Leu Gln Glu Val Ile Tyr Pro Glu Thr
145                 150                 155                 160

Leu Lys Leu Glu Gly Lys Gly Pro Glu Leu Val Gly Pro Ser Glu Ser
                165                 170                 175

Lys Pro Arg Gly Thr Ser Pro Leu Pro Ala Gly Gln Val Pro Val Thr
            180                 185                 190

Leu Gln Pro Gln Lys Gln Val Lys Glu Asn Lys Thr Gln Pro Pro Val
    195                 200                 205

Ala Tyr Gln Tyr Trp Pro Pro Ala Glu Leu Gln Tyr Arg Pro Pro Pro
210                 215                 220

Glu Ser Gln Tyr Gly Tyr Pro Gly Met Pro Pro Ala Pro Gln Gly Arg
225                 230                 235                 240

Ala Pro Tyr Pro Gln Pro Pro Thr Arg Arg Leu Asn Pro Thr Ala Pro
            245                 250                 255

Pro Ser Arg Gln Gly Ser Lys Leu His Glu Ile Ile Asp Lys Ser Arg
            260                 265                 270

Lys Glu Gly Asp Thr Glu Ala Trp Gln Phe Pro Val Thr Leu Glu Pro
                275                 280                 285

Met Pro Pro Gly Glu Gly Ala Gln Glu Gly Glu Pro Pro Thr Val Glu
    290                 295                 300

Ala Arg Tyr Lys Ser Phe Ser Ile Lys Lys Leu Lys Asp Met Lys Glu
305                 310                 315                 320

Gly Val Lys Gln Tyr Gly Pro Asn Ser Pro Tyr Met Arg Thr Leu Leu
                325                 330                 335

Asp Ser Ile Ala His Gly His Arg Leu Ile Pro Tyr Asp Trp Glu Ile
            340                 345                 350

Leu Ala Lys Ser Ser Leu Ser Pro Ser Gln Phe Leu Gln Phe Lys Thr
            355                 360                 365

Trp Trp Ile Asp Gly Val Gln Glu Val Arg Arg Asn Arg Ala Ala
        370                 375                 380

Asn Pro Pro Val Asn Ile Asp Ala Asp Gln Leu Leu Gly Ile Gly Gln
385                 390                 395                 400

Asn Trp Ser Thr Ile Ser Gln Gln Ala Leu Met Gln Asn Glu Ala Ile
```

```
                    405                 410                 415
Glu Gln Val Arg Ala Ile Cys Leu Arg Ala Trp Glu Lys Ile Gln Asp
                420                 425                 430
Pro Gly Ser Thr Cys Pro Ser Phe Asn Thr Val Arg Gln Gly Ser Lys
            435                 440                 445
Glu Pro Tyr Pro Asp Phe Val Ala Arg Leu Gln Asp Val Ala Gln Lys
        450                 455                 460
Ser Ile Ala Asp Glu Lys Ala Arg Lys Val Ile Val Glu Leu Met Ala
465                 470                 475                 480
Tyr Glu Asn Ala Asn Pro Glu Cys Gln Ser Ala Ile Lys Pro Leu Lys
                485                 490                 495
Gly Lys Val Pro Ala Gly Ser Asp Val Ile Ser Glu Tyr Val Lys Ala
                500                 505                 510
Cys Asp Gly Ile Gly Gly Ala Met His Lys Ala Met Leu Met Ala Gln
            515                 520                 525
Ala Ile Thr Gly Val Val Leu Gly Gly Gln Val Arg Thr Phe Gly Arg
        530                 535                 540
Lys Cys Tyr Asn Cys Gly Gln Ile Gly His Leu Lys Lys Asn Cys Pro
545                 550                 555                 560
Val Leu Asn Lys Gln Asn Ile Thr Ile Gln Ala Thr Thr Thr Gly Arg
                565                 570                 575
Glu Pro Pro Asp Leu Cys Pro Arg Cys Lys Lys Gly Lys His Trp Ala
                580                 585                 590
Ser Gln Cys Arg Ser Lys Phe Asp Lys Asn Gly Gln Pro Leu Ser Gly
            595                 600                 605
Asn Glu Gln Arg Gly Gln Pro Gln Ala Pro Gln Gln Thr Gly Ala Phe
        610                 615                 620
Pro Ile Gln Pro Phe Val Pro Gln Gly Phe Gln Gly Gln Gln Pro Pro
625                 630                 635                 640
Leu Ser Gln Val Phe Gln Gly Ile Ser Gln Leu Pro Gln Tyr Asn Asn
                645                 650                 655
Cys Pro Pro Pro Gln Ala Ala Val Gln Gln
                660                 665

<210> SEQ ID NO 11
<211> LENGTH: 699
<212> TYPE: PRT
<213> ORGANISM: Homo sapiens

<400> SEQUENCE: 11

Met Asn Pro Ser Glu Met Gln Arg Lys Ala Pro Pro Arg Arg Arg Arg
1               5                   10                  15
His Arg Asn Arg Ala Pro Leu Thr His Lys Met Asn Lys Met Val Thr
                20                  25                  30
Ser Glu Glu Gln Met Lys Leu Pro Ser Thr Lys Lys Ala Glu Pro Pro
            35                  40                  45
Thr Trp Ala Gln Leu Lys Lys Leu Thr Gln Leu Ala Thr Lys Tyr Leu
        50                  55                  60
Glu Asn Thr Lys Val Thr Gln Thr Pro Glu Ser Met Leu Leu Ala Ala
65                  70                  75                  80
Leu Met Ile Val Ser Met Val Val Ser Leu Pro Met Pro Ala Gly Ala
                85                  90                  95
Ala Ala Ala Asn Tyr Thr Tyr Trp Ala Tyr Val Pro Phe Pro Pro Leu
                100                 105                 110
```

Ile Arg Ala Val Thr Trp Met Asp Asn Pro Ile Glu Val Tyr Val Asn
            115                 120                 125

Asp Ser Val Trp Val Pro Gly Pro Thr Asp Asp His Cys Pro Ala Lys
    130                 135                 140

Pro Glu Glu Gly Met Met Ile Asn Ile Ser Ile Gly Tyr Arg Tyr
145                 150                 155                 160

Pro Pro Ile Cys Leu Gly Arg Ala Pro Gly Cys Leu Met Pro Ala Val
            165                 170                 175

Gln Asn Trp Leu Val Glu Val Pro Thr Val Ser Pro Ile Ser Arg Phe
            180                 185                 190

Thr Tyr His Met Val Ser Gly Met Ser Leu Arg Pro Arg Val Asn Tyr
            195                 200                 205

Leu Gln Asp Phe Ser Tyr Gln Arg Ser Phe Lys Phe Arg Pro Lys Gly
            210                 215                 220

Lys Pro Cys Pro Lys Glu Ile Pro Lys Glu Ser Lys Asn Thr Glu Val
225                 230                 235                 240

Leu Val Trp Glu Glu Cys Val Ala Asn Ser Ala Val Ile Leu Gln Asn
            245                 250                 255

Asn Glu Phe Gly Thr Ile Ile Asp Trp Ala Pro Arg Gly Gln Phe Tyr
            260                 265                 270

His Asn Cys Ser Gly Gln Thr Gln Ser Cys Pro Ser Ala Gln Val Ser
            275                 280                 285

Pro Ala Val Asp Ser Asp Leu Thr Glu Ser Leu Asp Lys His Lys His
            290                 295                 300

Lys Lys Leu Gln Ser Phe Tyr Pro Trp Glu Trp Gly Glu Lys Gly Ile
305                 310                 315                 320

Ser Thr Pro Arg Pro Lys Ile Ile Ser Pro Val Ser Gly Pro Glu His
            325                 330                 335

Pro Glu Leu Trp Arg Leu Thr Val Ala Ser His His Ile Arg Ile Trp
            340                 345                 350

Ser Gly Asn Gln Thr Leu Glu Thr Arg Asp Arg Lys Pro Phe Tyr Thr
            355                 360                 365

Val Asp Leu Asn Ser Ser Val Thr Val Pro Leu Gln Ser Cys Ile Lys
            370                 375                 380

Pro Pro Tyr Met Leu Val Val Gly Asn Ile Val Ile Lys Pro Asp Ser
385                 390                 395                 400

Gln Thr Ile Thr Cys Glu Asn Cys Arg Leu Leu Thr Cys Ile Asp Ser
            405                 410                 415

Thr Phe Asn Trp Gln His Arg Ile Leu Leu Val Arg Ala Arg Glu Gly
            420                 425                 430

Val Trp Ile Pro Val Ser Met Asp Arg Pro Trp Glu Thr Ser Pro Ser
            435                 440                 445

Ile His Thr Leu Thr Glu Val Leu Lys Gly Val Leu Asn Arg Ser Lys
            450                 455                 460

Arg Phe Ile Phe Thr Leu Ile Ala Val Ile Met Gly Leu Ile Ala Val
465                 470                 475                 480

Thr Ala Thr Ala Ala Val Ala Gly Val Ala Leu His Ser Ser Val Gln
            485                 490                 495

Ser Val Asn Phe Val Asn Asp Trp Gln Lys Asn Ser Thr Arg Leu Trp
            500                 505                 510

Asn Ser Gln Ser Ser Ile Asp Gln Lys Leu Ala Asn Gln Ile Asn Asp
            515                 520                 525

Leu Arg Gln Thr Val Ile Trp Met Gly Asp Arg Leu Met Ser Leu Glu

```
                530             535                 540
            His Arg Phe Gln Leu Gln Cys Asp Trp Asn Thr Ser Asp Phe Ser Ile
            545                 550                 555                 560

Thr Pro Gln Ile Tyr Asn Glu Ser Glu His His Trp Asp Met Val Arg
                                565                 570                 575

Arg His Leu Gln Gly Arg Glu Asp Asn Leu Thr Leu Asp Ile Ser Lys
                                580                 585                 590

Leu Lys Glu Gln Ile Phe Glu Ala Ser Lys Ala His Leu Asn Leu Val
                                595                 600                 605

Pro Gly Thr Glu Ala Ile Ala Gly Val Ala Asp Gly Leu Ala Asn Leu
                                610                 615                 620

Asn Pro Val Thr Trp Val Lys Thr Ile Gly Ser Thr Thr Ile Ile Asn
            625                 630                 635                 640

Leu Ile Leu Ile Leu Val Cys Leu Phe Cys Leu Leu Leu Val Cys Arg
                                645                 650                 655

Cys Thr Gln Gln Leu Arg Arg Asp Ser Asp His Arg Glu Arg Ala Met
                                660                 665                 670

Met Thr Met Ala Val Leu Ser Lys Arg Lys Gly Gly Asn Val Gly Lys
                                675                 680                 685

Ser Lys Arg Asp Gln Ile Val Thr Val Ser Val
                                690                 695

<210> SEQ ID NO 12
<211> LENGTH: 666
<212> TYPE: PRT
<213> ORGANISM: Homo sapiens

<400> SEQUENCE: 12

Met Gly Gln Thr Lys Ser Lys Ile Lys Ser Lys Tyr Ala Ser Tyr Leu
            1               5                   10                  15

Ser Phe Ile Lys Ile Leu Leu Lys Arg Gly Gly Val Lys Val Ser Thr
                            20                  25                  30

Lys Asn Leu Ile Lys Leu Phe Gln Ile Ile Glu Gln Phe Cys Pro Trp
                        35                  40                  45

Phe Pro Glu Gln Gly Thr Leu Asp Leu Lys Asp Trp Lys Arg Ile Gly
                    50                  55                  60

Lys Glu Leu Lys Gln Ala Gly Arg Lys Gly Asn Ile Ile Pro Leu Thr
            65                  70                  75                  80

Val Trp Asn Asp Trp Ala Ile Ile Lys Ala Ala Leu Glu Pro Phe Gln
                            85                  90                  95

Thr Glu Glu Asp Ser Val Ser Val Ser Asp Ala Pro Gly Ser Cys Ile
                        100                 105                 110

Ile Asp Cys Asn Glu Asn Thr Arg Lys Lys Ser Gln Lys Glu Thr Glu
                    115                 120                 125

Ser Leu His Cys Glu Tyr Val Ala Glu Pro Val Met Ala Gln Ser Thr
            130                 135                 140

Gln Asn Val Asp Tyr Asn Gly Leu Gln Glu Val Ile Tyr Pro Glu Thr
                            145                 150                 155                 160

Leu Lys Leu Glu Gly Lys Val Pro Glu Leu Val Gly Pro Ser Glu Ser
                        165                 170                 175

Lys Pro Arg Gly Thr Ser Arg Leu Pro Ala Gly Gln Val Pro Val Thr
                    180                 185                 190

Leu Gln Pro Gln Thr Gln Val Lys Glu Asn Lys Thr Gln Pro Pro Val
                195                 200                 205
```

-continued

```
Ala Tyr Gln Tyr Trp Pro Pro Ala Glu Leu Gln Tyr Arg Pro Pro Leu
210                 215                 220

Glu Ser Gln Tyr Gly Tyr Pro Gly Met Pro Pro Ala Pro Gln Gly Arg
225                 230                 235                 240

Ala Pro Tyr Pro Gln Pro Pro Thr Arg Arg Leu Asn Pro Thr Ala Pro
                245                 250                 255

Pro Ser Arg Arg Gly Ser Glu Leu His Glu Ile Ile Asp Lys Ser Arg
                260                 265                 270

Lys Glu Gly Asp Thr Glu Ala Trp Gln Phe Pro Val Thr Leu Glu Pro
            275                 280                 285

Met Pro Pro Gly Glu Gly Ala Gln Glu Gly Pro Pro Thr Val Glu
290                 295                 300

Ala Arg Tyr Lys Ser Phe Ser Ile Lys Met Leu Lys Asp Met Lys Glu
305                 310                 315                 320

Gly Val Lys Gln Tyr Gly Pro Asn Ser Pro Tyr Met Arg Thr Leu Leu
                325                 330                 335

Asp Ser Ile Ala His Gly His Arg Leu Ile Pro Tyr Asp Trp Glu Ile
                340                 345                 350

Leu Ala Lys Ser Ser Leu Ser Pro Ser Gln Phe Leu Gln Phe Lys Thr
                355                 360                 365

Trp Trp Ile Asp Gly Val Gln Glu Gln Val Arg Arg Asn Arg Ala Ala
370                 375                 380

Asn Pro Pro Val Asn Ile Asp Ala Asp Gln Leu Leu Gly Ile Gly Gln
385                 390                 395                 400

Asn Trp Ser Thr Ile Ser Gln Gln Ala Leu Met Gln Asn Glu Ala Ile
                405                 410                 415

Glu Gln Val Arg Ala Ile Cys Leu Arg Ala Trp Glu Lys Ile Gln Asp
                420                 425                 430

Pro Gly Ser Thr Cys Pro Ser Phe Asn Thr Val Arg Gln Gly Ser Lys
                435                 440                 445

Glu Pro Tyr Pro Asp Phe Val Ala Arg Leu Gln Asp Val Ala Gln Lys
            450                 455                 460

Ser Ile Ala Ile Glu Lys Ala Arg Lys Val Ile Val Glu Leu Met Ala
465                 470                 475                 480

Tyr Glu Asn Pro Asn Pro Glu Cys Gln Ser Ala Ile Lys Pro Leu Lys
                485                 490                 495

Gly Lys Val Pro Ala Gly Ser Asp Val Ile Ser Glu Tyr Val Lys Ala
                500                 505                 510

Cys Asp Gly Met Gly Gly Ala Met His Lys Ala Met Leu Met Ala Gln
            515                 520                 525

Ala Ile Thr Gly Val Val Leu Gly Gly Gln Val Arg Thr Phe Gly Gly
530                 535                 540

Lys Cys Tyr Asn Cys Gly Gln Ile Gly His Leu Lys Lys Asn Cys Pro
545                 550                 555                 560

Val Leu Asn Lys Gln Asn Ile Thr Ile Gln Ala Thr Thr Thr Gly Arg
                565                 570                 575

Glu Pro Pro Asp Leu Cys Pro Arg Cys Lys Lys Gly Lys His Trp Ala
                580                 585                 590

Ser Gln Cys Arg Ser Lys Phe Asp Lys Asn Gly Gln Pro Leu Ser Gly
                595                 600                 605

Asn Glu Gln Arg Gly Gln Pro Gln Ala Pro Gln Thr Gly Ala Phe
610                 615                 620

Pro Ile Gln Pro Phe Val Pro His Gly Phe Gln Gly Gln Gln Pro Pro
```

```
            625                 630                 635                 640
Leu Ser Gln Val Phe Gln Gly Ile Ser Gln Leu Pro Gln Tyr Asn Asn
                    645                 650                 655
Cys Pro Pro Gln Ala Ala Val Gln Gln
                660                 665

<210> SEQ ID NO 13
<211> LENGTH: 699
<212> TYPE: PRT
<213> ORGANISM: Homo sapiens

<400> SEQUENCE: 13

Met Asn Pro Ser Glu Met Gln Arg Lys Ala Pro Arg Arg Arg Arg
1               5                   10                  15

His Arg Asn Arg Ala Pro Leu Thr His Lys Met Asn Lys Met Val Thr
                20                  25                  30

Ser Glu Glu Gln Met Lys Leu Pro Ser Thr Lys Lys Ala Glu Pro Pro
            35                  40                  45

Thr Trp Ala Gln Leu Lys Lys Leu Thr Gln Leu Ala Thr Lys Tyr Leu
        50                  55                  60

Glu Asn Thr Lys Val Thr Gln Thr Pro Glu Ser Met Leu Leu Ala Ala
65                  70                  75                  80

Leu Met Ile Val Ser Met Val Val Ser Leu Pro Met Pro Ala Gly Ala
                85                  90                  95

Ala Val Ala Asn Tyr Thr Asn Trp Ala Tyr Val Pro Phe Pro Pro Leu
                100                 105                 110

Ile Arg Ala Val Thr Trp Met Asp Asn Pro Ile Glu Val Tyr Val Asn
                115                 120                 125

Asp Ser Val Trp Val Pro Gly Pro Ile Asp Arg Cys Pro Ala Lys
            130                 135                 140

Pro Glu Glu Glu Gly Met Met Ile Asn Ile Ser Ile Gly Tyr Arg Tyr
145                 150                 155                 160

Pro Pro Ile Cys Leu Gly Arg Ala Pro Gly Cys Leu Met Pro Ala Val
                165                 170                 175

Gln Asn Trp Leu Val Glu Val Pro Thr Val Ser Pro Ile Ser Arg Phe
                180                 185                 190

Thr Tyr His Met Val Ser Gly Met Ser Leu Arg Pro Arg Val Asn Tyr
                195                 200                 205

Leu Gln Asp Phe Ser Tyr Gln Arg Ser Leu Lys Phe Arg Pro Lys Gly
            210                 215                 220

Lys Pro Cys Pro Lys Glu Ile Pro Lys Glu Ser Lys Asn Thr Glu Val
225                 230                 235                 240

Leu Val Trp Glu Glu Cys Val Ala Asn Ser Ala Val Ile Leu Gln Asn
                245                 250                 255

Asn Glu Phe Gly Thr Ile Ile Asp Trp Ala Pro Arg Gly Gln Phe Tyr
                260                 265                 270

His Asn Cys Ser Gly Gln Thr Gln Ser Cys Pro Ser Ala Gln Val Ser
            275                 280                 285

Pro Ala Val Asp Ser Asp Leu Thr Glu Ser Leu Asp Lys His Lys His
            290                 295                 300

Lys Lys Leu Gln Ser Phe Tyr Pro Trp Glu Trp Gly Lys Arg Ile
305                 310                 315                 320

Ser Thr Pro Arg Pro Lys Ile Val Ser Pro Val Ser Gly Pro Glu His
                325                 330                 335
```

```
Pro Glu Leu Trp Arg Leu Thr Val Ala Ser His His Ile Arg Ile Trp
            340                 345                 350

Ser Gly Asn Gln Thr Leu Glu Thr Arg Asp Arg Lys Pro Phe Tyr Thr
        355                 360                 365

Val Asp Leu Asn Ser Ser Leu Thr Leu Pro Leu Gln Ser Cys Val Lys
    370                 375                 380

Pro Pro Tyr Met Leu Val Val Gly Asn Ile Val Ile Lys Pro Asp Ser
385                 390                 395                 400

Gln Thr Ile Thr Cys Glu Asn Cys Arg Leu Leu Thr Cys Ile Asp Ser
            405                 410                 415

Thr Phe Asn Trp Gln His Arg Ile Leu Leu Val Arg Ala Arg Glu Gly
        420                 425                 430

Val Trp Ile Pro Val Ser Met Asp Arg Pro Trp Glu Ala Ser Pro Ser
    435                 440                 445

Val His Ile Leu Thr Glu Val Leu Lys Gly Val Leu Asn Arg Ser Lys
    450                 455                 460

Arg Phe Ile Phe Thr Leu Ile Ala Val Ile Met Gly Leu Ile Ala Val
465                 470                 475                 480

Thr Ala Thr Ala Ala Val Ala Gly Val Ala Leu His Ser Ser Val Gln
            485                 490                 495

Ser Val Asn Phe Val Asn Asp Gly Gln Lys Asn Ser Thr Arg Leu Trp
        500                 505                 510

Asn Ser Gln Ser Ser Ile Asp Gln Lys Leu Ala Asn Gln Ile Asn Asp
        515                 520                 525

Leu Arg Gln Thr Val Ile Trp Met Gly Asp Arg Leu Met Ser Leu Glu
    530                 535                 540

His Arg Phe Gln Leu Gln Cys Asp Trp Asn Thr Ser Asp Phe Cys Ile
545                 550                 555                 560

Thr Pro Gln Ile Tyr Asn Asp Ser Glu His His Trp Asp Met Val Arg
            565                 570                 575

Arg His Leu Gln Gly Arg Glu Asp Asn Leu Thr Leu Asp Ile Ser Lys
        580                 585                 590

Leu Lys Glu Gln Ile Phe Glu Ala Ser Lys Ala His Leu Asn Leu Val
    595                 600                 605

Pro Gly Thr Glu Ala Ile Ala Gly Val Ala Asp Gly Leu Ala Asn Leu
    610                 615                 620

Asn Pro Val Thr Trp Val Lys Thr Ile Gly Ser Thr Thr Ile Ile Asn
625                 630                 635                 640

Leu Ile Leu Ile Leu Val Cys Leu Phe Cys Leu Leu Leu Val Cys Arg
            645                 650                 655

Cys Thr Gln Gln Leu Arg Arg Asp Ser Asp His Arg Glu Arg Ala Met
        660                 665                 670

Met Thr Met Ala Val Leu Ser Lys Arg Lys Gly Gly Asn Val Gly Lys
    675                 680                 685

Ser Lys Arg Asp Gln Ile Val Thr Val Ser Val
    690                 695

<210> SEQ ID NO 14
<211> LENGTH: 647
<212> TYPE: PRT
<213> ORGANISM: Homo sapiens

<400> SEQUENCE: 14

Met Gly Gln Thr Lys Ser Lys Ile Lys Ser Lys Tyr Ala Ser Tyr Leu
1               5                   10                  15
```

Ser Phe Ile Lys Ile Leu Leu Lys Arg Gly Val Lys Val Ser Thr
            20                  25                  30

Lys Asn Leu Ile Lys Leu Phe Gln Ile Ile Glu Gln Phe Cys Pro Trp
            35                  40                  45

Phe Pro Glu Gln Gly Thr Leu Asp Leu Lys Asp Trp Lys Arg Ile Gly
 50                  55                  60

Lys Glu Leu Lys Gln Ala Gly Arg Lys Gly Asn Ile Ile Pro Leu Thr
 65                  70                  75                  80

Val Trp Asn Asp Trp Ala Ile Ile Lys Ala Ala Leu Glu Pro Phe Gln
                85                  90                  95

Thr Glu Glu Asp Ser Ile Ser Val Ser Asp Ala Pro Gly Ser Cys Leu
                100                 105                 110

Ile Asp Cys Asn Glu Asn Thr Arg Lys Lys Ser Gln Lys Glu Thr Glu
                115                 120                 125

Ser Leu His Cys Glu Tyr Val Ala Glu Pro Val Met Ala Gln Ser Thr
            130                 135                 140

Gln Asn Val Asp Tyr Asn Gln Leu Gln Glu Val Ile Tyr Pro Glu Thr
145                 150                 155                 160

Leu Lys Leu Glu Gly Lys Gly Pro Glu Leu Val Gly Pro Ser Glu Ser
                165                 170                 175

Lys Pro Arg Gly Thr Ser Pro Leu Pro Ala Gly Gln Val Pro Val Thr
            180                 185                 190

Leu Gln Pro Gln Lys Gln Val Lys Glu Asn Lys Thr Gln Pro Pro Val
            195                 200                 205

Ala Tyr Gln Tyr Trp Pro Pro Ala Glu Leu Gln Tyr Arg Pro Pro Pro
            210                 215                 220

Glu Ser Gln Tyr Gly Tyr Pro Gly Met Pro Pro Ala Pro Gln Gly Arg
225                 230                 235                 240

Glu Pro Tyr Pro Gln Pro Pro Thr Arg Arg Leu Asn Pro Thr Ala Pro
                245                 250                 255

Pro Ser Arg Gln Gly Ser Glu Leu His Glu Ile Ile Asp Lys Ser Arg
            260                 265                 270

Lys Glu Gly Asp Thr Glu Ala Trp Gln Phe Pro Val Thr Leu Glu Pro
            275                 280                 285

Met Pro Pro Gly Glu Gly Ala Gln Glu Gly Glu Pro Pro Thr Val Glu
290                 295                 300

Ala Arg Tyr Lys Ser Phe Ser Ile Lys Met Leu Lys Asp Met Lys Glu
305                 310                 315                 320

Gly Val Lys Gln Tyr Gly Pro Asn Ser Pro Tyr Met Arg Thr Leu Leu
                325                 330                 335

Asp Ser Ile Ala His Gly His Arg Leu Ile Pro Tyr Asp Trp Glu Ile
            340                 345                 350

Leu Ala Lys Ser Ser Leu Ser Pro Ser Gln Phe Leu Gln Phe Lys Thr
            355                 360                 365

Trp Trp Ile Asp Gly Val Gln Glu Gln Val Arg Arg Asn Arg Ala Ala
            370                 375                 380

Asn Pro Pro Val Asn Ile Asp Ala Asp Gln Leu Leu Gly Ile Gly Gln
385                 390                 395                 400

Asn Trp Ser Thr Ile Ser Gln Gln Ala Leu Met Gln Asn Glu Ala Ile
                405                 410                 415

Glu Gln Val Arg Ala Ile Cys Leu Arg Ala Trp Glu Lys Ile Gln Asp
            420                 425                 430

```
-continued

Pro Gly Ser Thr Cys Pro Ser Phe Asn Thr Val Arg Gln Gly Ser Lys
            435                 440                 445

Glu Pro Tyr Pro Asp Phe Val Ala Arg Leu Gln Asp Val Ala Gln Lys
450                 455                 460

Ser Ile Ala Asp Glu Lys Ala Arg Lys Val Ile Val Glu Leu Met Ala
465                 470                 475                 480

Tyr Glu Asn Ala Asn Pro Glu Cys Gln Ser Ala Ile Lys Pro Leu Lys
                485                 490                 495

Gly Lys Val Pro Ala Gly Ser Asp Val Ile Ser Glu Tyr Val Lys Ala
            500                 505                 510

Cys Asp Gly Ile Gly Gly Ala Met His Lys Ala Met Leu Met Ala Gln
            515                 520                 525

Ala Ile Thr Gly Val Val Leu Gly Gly Gln Val Arg Thr Phe Gly Gly
            530                 535                 540

Lys Cys Tyr Asn Cys Gly Gln Ile Gly His Leu Lys Lys Asn Cys Pro
545                 550                 555                 560

Val Leu Asn Lys Gln Asn Ile Thr Ile Gln Ala Thr Thr Thr Gly Arg
                565                 570                 575

Glu Pro Pro Asp Leu Cys Pro Arg Cys Lys Lys Gly Lys His Trp Ala
            580                 585                 590

Ser Gln Cys Arg Ser Lys Phe Asp Lys Asn Gly Gln Pro Leu Ser Gly
            595                 600                 605

Asn Glu Gln Arg Gly Gln Pro Gln Ala Pro Gln Gln Thr Gly Ala Phe
            610                 615                 620

Pro Ile Gln Pro Phe Val Pro Gln Gly Phe Gln Asp Asn Asn Pro His
625                 630                 635                 640

Cys Pro Lys Cys Phe Arg Glu
                645

<210> SEQ ID NO 15
<211> LENGTH: 698
<212> TYPE: PRT
<213> ORGANISM: Homo sapiens

<400> SEQUENCE: 15

Met Asn Pro Ser Glu Met Gln Arg Lys Ala Pro Arg Arg Arg Arg
1               5                   10                  15

His Arg Asn Arg Ala Pro Leu Thr His Lys Met Asn Lys Met Val Thr
            20                  25                  30

Ser Glu Glu Gln Met Lys Leu Pro Ser Thr Lys Lys Ala Glu Pro Pro
        35                  40                  45

Thr Trp Ala Gln Leu Lys Lys Leu Thr Gln Leu Ala Thr Lys Tyr Leu
    50                  55                  60

Glu Asn Thr Lys Val Thr Gln Thr Pro Glu Ser Met Leu Leu Ala Ala
65                  70                  75                  80

Leu Met Ile Val Ser Met Val Val Ser Leu Pro Met Pro Ala Gly Ala
                85                  90                  95

Ala Ala Ala Asn Tyr Thr Asn Trp Ala Tyr Val Pro Phe Pro Pro Leu
            100                 105                 110

Ile Arg Ala Val Thr Trp Met Asp Asn Pro Ile Glu Val Tyr Val Asn
            115                 120                 125

Asp Ser Val Trp Val Pro Gly Pro Ile Asp Asp Arg Cys Pro Ala Lys
        130                 135                 140

Pro Glu Glu Glu Gly Met Met Ile Asn Ile Ser Ile Gly Tyr Arg Tyr
145                 150                 155                 160
```

```
Pro Ile Cys Leu Gly Arg Ala Pro Gly Cys Leu Met Pro Ala Val Gln
            165                 170                 175

Asn Trp Leu Val Glu Val Pro Ile Val Ser Pro Ile Cys Arg Phe Thr
            180                 185                 190

Tyr His Met Val Ser Gly Met Ser Leu Arg Pro Arg Val Asn Tyr Leu
            195                 200                 205

Gln Asp Phe Ser Tyr Gln Arg Ser Leu Lys Phe Arg Pro Lys Gly Lys
            210                 215                 220

Pro Cys Pro Lys Glu Ile Pro Lys Glu Ser Lys Asn Thr Glu Val Leu
225                 230                 235                 240

Val Trp Glu Glu Cys Val Ala Asn Ser Ala Val Ile Leu Gln Asn Asn
            245                 250                 255

Glu Phe Gly Thr Ile Ile Asp Trp Thr Pro Gln Gly Gln Phe Tyr His
            260                 265                 270

Asn Cys Ser Gly Gln Thr Gln Ser Cys Pro Ser Ala Gln Val Ser Pro
            275                 280                 285

Ala Val Asp Ser Asp Leu Thr Glu Ser Leu Asp Lys His Lys His Lys
            290                 295                 300

Lys Leu Gln Ser Phe Tyr Pro Trp Glu Trp Gly Glu Lys Gly Ile Ser
305                 310                 315                 320

Thr Pro Arg Pro Lys Ile Ile Ser Pro Val Ser Gly Pro Glu His Pro
            325                 330                 335

Glu Leu Trp Arg Leu Thr Val Ala Ser His His Ile Arg Ile Trp Ser
            340                 345                 350

Gly Asn Gln Thr Leu Glu Thr Arg Asp Arg Lys Pro Phe Tyr Thr Val
            355                 360                 365

Asp Leu Asn Ser Ser Leu Thr Leu Pro Leu Gln Ser Cys Val Lys Pro
            370                 375                 380

Pro Tyr Met Leu Val Val Gly Asn Ile Val Ile Lys Pro Asp Ser Gln
385                 390                 395                 400

Thr Ile Thr Cys Glu Asn Cys Arg Leu Leu Thr Cys Ile Asp Ser Thr
            405                 410                 415

Phe Asn Trp Gln His Arg Ile Leu Leu Val Arg Ala Arg Glu Gly Val
            420                 425                 430

Trp Ile Pro Val Ser Met Asp Arg Pro Trp Glu Ala Ser Pro Ser Ile
            435                 440                 445

His Ile Leu Thr Glu Val Leu Lys Gly Val Leu Asn Arg Ser Lys Arg
            450                 455                 460

Phe Ile Phe Thr Leu Ile Ala Val Ile Met Gly Leu Ile Ala Val Thr
465                 470                 475                 480

Ala Thr Ala Ala Val Ala Gly Val Ala Leu His Ser Ser Val Gln Ser
            485                 490                 495

Val Asn Phe Val Asn Asp Gly Gln Lys Asn Ser Thr Arg Leu Trp Asn
            500                 505                 510

Ser Gln Ser Ser Ile Asp Gln Lys Leu Ala Asn Gln Ile Asn Asp Leu
            515                 520                 525

Arg Gln Thr Val Ile Trp Met Gly Asp Arg Leu Met Ser Leu Glu His
            530                 535                 540

Arg Phe Gln Leu Gln Cys Asp Trp Asn Thr Ser Asp Phe Cys Ile Thr
545                 550                 555                 560

Pro Gln Ile Tyr Asn Glu Ser Glu His His Trp Asp Met Val Arg Arg
            565                 570                 575
```

-continued

His Leu Gln Gly Arg Glu Asp Asn Leu Thr Leu Asp Ile Ser Lys Leu
              580                 585                 590

Lys Glu Gln Ile Phe Glu Ala Ser Lys Ala His Leu Asn Leu Val Pro
          595                 600                 605

Gly Thr Glu Ala Ile Ala Gly Val Ala Asp Gly Leu Ala Asn Leu Asn
          610                 615                 620

Pro Val Thr Trp Val Lys Thr Ile Gly Ser Thr Thr Ile Ile Asn Leu
625                 630                 635                 640

Ile Leu Ile Leu Val Cys Leu Phe Cys Leu Leu Val Cys Arg Cys
              645                 650                 655

Thr Gln Gln Leu Arg Arg Asp Ser Asp His Arg Glu Arg Ala Met Met
              660                 665                 670

Thr Met Ala Val Leu Ser Lys Arg Lys Gly Gly Asn Val Gly Lys Ser
          675                 680                 685

Lys Arg Asp Gln Ile Val Thr Val Ser Val
          690                 695

<210> SEQ ID NO 16
<211> LENGTH: 666
<212> TYPE: PRT
<213> ORGANISM: Homo sapiens

<400> SEQUENCE: 16

Met Gly Gln Thr Lys Ser Lys Ile Lys Ser Lys Tyr Ala Ser Tyr Leu
1               5                   10                  15

Ser Phe Ile Lys Ile Leu Leu Lys Arg Gly Gly Val Lys Val Ser Thr
            20                  25                  30

Lys Asn Leu Ile Lys Leu Phe Gln Ile Ile Glu Gln Phe Cys Pro Trp
        35                  40                  45

Phe Pro Glu Gln Gly Thr Leu Asp Leu Lys Asp Trp Lys Arg Ile Gly
    50                  55                  60

Lys Glu Leu Lys Gln Ala Gly Arg Lys Gly Asn Ile Ile Pro Leu Thr
65                  70                  75                  80

Val Trp Asn Asp Trp Ala Ile Ile Lys Ala Ala Leu Glu Pro Phe Gln
                85                  90                  95

Thr Glu Glu Asp Ser Ile Ser Val Ser Asp Ala Pro Gly Ser Gly Ile
            100                 105                 110

Ile Asp Cys Asn Glu Lys Thr Arg Lys Lys Ser Gln Lys Glu Thr Glu
        115                 120                 125

Ser Leu His Cys Glu Tyr Val Ala Glu Pro Val Met Ala Gln Ser Thr
    130                 135                 140

Gln Asn Val Asp Tyr Asn Gln Leu Gln Glu Val Ile Tyr Pro Glu Thr
145                 150                 155                 160

Leu Lys Leu Glu Gly Lys Gly Pro Glu Leu Val Gly Pro Ser Glu Ser
                165                 170                 175

Lys Pro Arg Gly Thr Ser Pro Leu Pro Ala Gly Gln Val Pro Val Thr
            180                 185                 190

Leu Gln Pro Gln Lys Gln Val Lys Glu Asn Lys Thr Gln Pro Pro Val
        195                 200                 205

Ala Tyr Gln Tyr Trp Pro Pro Ala Glu Leu Gln Tyr Arg Pro Pro Pro
    210                 215                 220

Glu Ser Gln Tyr Gly Tyr Pro Gly Met Pro Pro Ala Pro Gln Gly Arg
225                 230                 235                 240

Ala Pro Tyr Pro Gln Pro Pro Thr Arg Arg Leu Asn Pro Thr Ala Pro
                245                 250                 255

```
Pro Ser Arg Gln Gly Ser Glu Leu His Glu Ile Ile Asp Lys Ser Arg
            260                 265                 270

Lys Glu Gly Asp Thr Glu Ala Trp Gln Phe Pro Val Thr Leu Glu Pro
            275                 280                 285

Met Pro Pro Gly Glu Gly Ala Gln Glu Gly Pro Pro Thr Val Glu
290                 295                 300

Ala Arg Tyr Lys Ser Phe Ser Ile Lys Ile Leu Lys Asp Met Lys Glu
305                 310                 315                 320

Gly Val Lys Gln Tyr Gly Pro Asn Ser Pro Tyr Met Arg Thr Leu Leu
                325                 330                 335

Asp Ser Ile Ala His Gly His Arg Leu Ile Pro Tyr Asp Trp Glu Ile
            340                 345                 350

Leu Ala Lys Ser Ser Leu Ser Pro Ser Gln Phe Leu Gln Phe Lys Thr
            355                 360                 365

Trp Trp Ile Asp Gly Val Gln Glu Gln Val Arg Arg Asn Arg Ala Ala
            370                 375                 380

Asn Pro Pro Val Asn Ile Asp Ala Asp Gln Leu Leu Gly Ile Gly Gln
385                 390                 395                 400

Asn Trp Ser Thr Ile Ser Gln Gln Ala Leu Met Gln Asn Glu Ala Ile
                405                 410                 415

Glu Gln Val Arg Ala Ile Cys Leu Arg Ala Trp Glu Lys Ile Gln Asp
            420                 425                 430

Pro Gly Ser Thr Cys Pro Ser Phe Asn Thr Val Arg Gln Gly Ser Lys
            435                 440                 445

Glu Pro Tyr Pro Asp Phe Val Ala Arg Leu Gln Asp Val Ala Gln Lys
            450                 455                 460

Ser Ile Ala Asp Glu Lys Ala Arg Lys Val Ile Val Glu Leu Met Ala
465                 470                 475                 480

Tyr Glu Asn Ala Asn Pro Glu Cys Gln Ser Ala Ile Lys Pro Leu Lys
                485                 490                 495

Gly Lys Val Pro Ala Gly Ser Asp Val Ile Ser Glu Tyr Val Lys Ala
            500                 505                 510

Cys Asp Gly Ile Gly Gly Ala Met His Lys Ala Met Leu Met Ala Gln
            515                 520                 525

Ala Ile Thr Gly Val Val Leu Gly Gly Gln Val Arg Thr Phe Gly Gly
            530                 535                 540

Lys Cys Tyr Asn Cys Gly Gln Ile Gly His Leu Lys Lys Asn Cys Pro
545                 550                 555                 560

Val Leu Asn Lys Gln Asn Ile Thr Ile Gln Ala Thr Thr Thr Gly Arg
                565                 570                 575

Glu Pro Pro Asp Leu Cys Pro Arg Cys Lys Lys Gly Lys His Trp Ala
            580                 585                 590

Ser Gln Cys Arg Ser Lys Phe Asp Lys Asn Gly Gln Pro Leu Ser Gly
            595                 600                 605

Asn Glu Gln Arg Gly Gln Pro Gln Ala Pro Gln Gln Thr Gly Ala Phe
            610                 615                 620

Pro Ile Gln Pro Phe Val Pro Gln Gly Phe Gln Gly Gln Gln Pro Pro
625                 630                 635                 640

Leu Ser Gln Val Phe Gln Gly Ile Ser Gln Leu Pro Gln Tyr Asn Asn
                645                 650                 655

Cys Pro Pro Pro Gln Val Ala Val Gln Gln
            660                 665
```

-continued

```
<210> SEQ ID NO 17
<211> LENGTH: 699
<212> TYPE: PRT
<213> ORGANISM: Homo sapiens

<400> SEQUENCE: 17

Met Asn Pro Ser Glu Met Gln Arg Lys Ala Pro Arg Arg Arg Arg
1               5                   10                  15

His Arg Asn Arg Ala Pro Leu Thr His Lys Met Asn Lys Met Val Thr
                20                  25                  30

Ser Glu Glu Gln Met Lys Leu Pro Ser Thr Lys Lys Ala Glu Pro Pro
            35                  40                  45

Thr Trp Ala Gln Leu Lys Lys Leu Thr Gln Leu Ala Thr Lys Tyr Leu
    50                  55                  60

Glu Asn Thr Lys Val Thr Gln Thr Pro Glu Ser Met Leu Leu Ala Ala
65                  70                  75                  80

Leu Met Ile Val Ser Met Val Val Ser Leu Pro Met Pro Ala Gly Ala
                85                  90                  95

Ala Ala Ala Asn Tyr Thr Tyr Trp Ala Tyr Val Pro Phe Pro Pro Leu
            100                 105                 110

Ile Arg Ala Val Thr Trp Met Asp Asn Pro Ile Glu Ile Tyr Val Asn
            115                 120                 125

Asp Ser Val Trp Val Pro Gly Pro Thr Asp Asp Cys Cys Pro Ala Lys
130                 135                 140

Pro Glu Glu Glu Gly Met Met Ile Asn Ile Ser Ile Gly Tyr Arg Tyr
145                 150                 155                 160

Pro Pro Ile Cys Leu Gly Arg Ala Pro Gly Cys Leu Met Pro Ala Val
                165                 170                 175

Gln Asn Trp Leu Val Glu Val Pro Thr Val Ser Pro Ile Ser Arg Phe
            180                 185                 190

Thr Tyr His Met Val Ser Gly Met Ser Leu Arg Pro Arg Val Asn Tyr
        195                 200                 205

Leu Gln Asp Phe Ser Tyr Gln Arg Ser Leu Lys Phe Arg Pro Lys Gly
    210                 215                 220

Lys Pro Cys Pro Lys Glu Ile Pro Lys Glu Ser Lys Asn Thr Glu Val
225                 230                 235                 240

Leu Val Trp Glu Glu Cys Val Ala Asn Ser Ala Val Ile Leu Gln Asn
                245                 250                 255

Asn Glu Phe Gly Thr Leu Ile Asp Trp Ala Pro Arg Gly Gln Phe Tyr
            260                 265                 270

His Asn Cys Ser Gly Gln Thr Gln Ser Cys Pro Ser Ala Gln Val Ser
        275                 280                 285

Pro Ala Val Asp Ser Asp Leu Thr Glu Ser Leu Asp Lys His Lys His
    290                 295                 300

Lys Lys Leu Gln Ser Phe Tyr Pro Trp Glu Trp Gly Glu Lys Gly Ile
305                 310                 315                 320

Ser Thr Ala Arg Pro Lys Ile Ile Ser Pro Val Ser Gly Pro Glu His
                325                 330                 335

Pro Glu Leu Trp Arg Leu Thr Val Ala Ser His His Ile Arg Ile Trp
            340                 345                 350

Ser Gly Asn Gln Thr Leu Glu Thr Arg Asp Arg Lys Pro Phe Tyr Thr
        355                 360                 365

Ile Asp Leu Asn Ser Ser Leu Thr Val Pro Leu Gln Ser Cys Val Lys
    370                 375                 380
```

```
Pro Pro Tyr Met Leu Val Val Gly Asn Ile Val Ile Lys Pro Asp Ser
385                 390                 395                 400

Gln Thr Ile Thr Cys Glu Asn Cys Arg Leu Leu Thr Cys Ile Asp Ser
            405                 410                 415

Thr Phe Asn Trp Gln His Arg Ile Leu Leu Val Arg Ala Arg Glu Gly
        420                 425                 430

Val Trp Ile Pro Val Ser Met Asp Arg Pro Trp Glu Ala Ser Pro Ser
    435                 440                 445

Val His Ile Leu Thr Glu Val Leu Lys Gly Val Leu Asn Arg Ser Lys
450                 455                 460

Arg Phe Ile Phe Thr Leu Ile Ala Val Ile Met Gly Leu Ile Ala Val
465                 470                 475                 480

Thr Ala Thr Ala Ala Val Ala Gly Val Ala Leu His Ser Ser Val Gln
            485                 490                 495

Ser Val Asn Phe Val Asn Asp Trp Gln Asn Asn Ser Thr Arg Leu Trp
        500                 505                 510

Asn Ser Gln Ser Ser Ile Asp Gln Lys Leu Ala Asn Gln Ile Asn Asp
    515                 520                 525

Leu Arg Gln Thr Val Ile Trp Met Gly Asp Arg Leu Met Ser Leu Glu
530                 535                 540

His Arg Phe Gln Leu Gln Cys Asp Trp Asn Thr Ser Asp Phe Cys Ile
545                 550                 555                 560

Thr Pro Gln Ile Tyr Asn Glu Ser Glu His His Trp Asp Met Val Arg
            565                 570                 575

Cys His Leu Gln Gly Arg Glu Asp Asn Leu Thr Leu Asp Ile Ser Lys
        580                 585                 590

Leu Lys Glu Gln Ile Phe Glu Ala Ser Lys Ala His Leu Asn Leu Val
    595                 600                 605

Pro Gly Thr Glu Ala Ile Ala Gly Val Ala Asp Gly Leu Ala Asn Leu
610                 615                 620

Asn Thr Val Thr Trp Val Lys Thr Ile Gly Ser Thr Thr Ile Ile Asn
625                 630                 635                 640

Leu Ile Leu Ile Leu Val Cys Leu Phe Cys Leu Leu Leu Val Tyr Arg
            645                 650                 655

Cys Thr Gln Gln Leu Arg Arg Asp Ser Asp His Arg Glu Arg Ala Met
        660                 665                 670

Met Thr Met Val Val Leu Ser Lys Arg Lys Gly Gly Asn Val Gly Lys
    675                 680                 685

Ser Lys Arg Asp Gln Ile Val Thr Val Ser Val
690                 695

<210> SEQ ID NO 18
<211> LENGTH: 666
<212> TYPE: PRT
<213> ORGANISM: Homo sapiens

<400> SEQUENCE: 18

Met Gly Gln Thr Lys Ser Lys Ile Lys Ser Lys Tyr Ala Ser Tyr Leu
1               5                   10                  15

Ser Phe Ile Lys Ile Leu Leu Lys Arg Gly Gly Val Lys Val Ser Thr
            20                  25                  30

Lys Asn Leu Ile Lys Leu Phe Gln Ile Ile Glu Gln Phe Cys Pro Trp
        35                  40                  45

Phe Pro Glu Gln Gly Thr Leu Asp Leu Lys Asp Trp Lys Arg Ile Gly
```

```
                50                  55                  60
Lys Glu Leu Lys Gln Ala Gly Arg Lys Gly Asn Ile Ile Pro Leu Thr
 65                  70                  75                  80

Val Trp Asn Asp Trp Ala Ile Ile Lys Ala Ala Leu Glu Pro Phe Gln
                 85                  90                  95

Thr Glu Glu Asp Ser Val Ser Val Ser Asp Ala Pro Gly Ser Cys Ile
                100                 105                 110

Ile Asp Cys Asn Glu Lys Thr Arg Lys Ser Gln Lys Glu Thr Glu
                115                 120                 125

Ser Leu His Cys Glu Tyr Val Ala Glu Pro Val Met Ala Gln Ser Thr
        130                 135                 140

Gln Asn Ala Asp Tyr Asn Gln Leu Gln Glu Val Ile Tyr Pro Glu Thr
145                 150                 155                 160

Leu Lys Leu Glu Gly Lys Gly Pro Glu Leu Met Gly Pro Ser Glu Ser
                165                 170                 175

Lys Pro Arg Gly Thr Ser Pro Leu Pro Ala Gly Gln Val Pro Val Thr
                180                 185                 190

Leu Gln Pro Gln Lys Gln Val Lys Glu Asn Lys Thr Gln Pro Pro Val
        195                 200                 205

Ala Tyr Gln Tyr Trp Pro Pro Ala Glu Leu Gln Tyr Gln Pro Pro Pro
210                 215                 220

Glu Ser Gln Tyr Gly Tyr Pro Gly Met Pro Pro Ala Pro Gln Gly Arg
225                 230                 235                 240

Ala Pro Tyr Pro Gln Pro Pro Thr Arg Arg Leu Asn Pro Thr Ala Pro
                245                 250                 255

Pro Ser Arg Gln Gly Ser Glu Leu His Glu Ile Ile Asp Lys Ser Arg
                260                 265                 270

Lys Glu Gly Asp Thr Glu Ala Trp Gln Phe Pro Val Thr Leu Glu Leu
        275                 280                 285

Met Pro Pro Gly Glu Gly Ala Gln Glu Gly Pro Pro Thr Val Glu
290                 295                 300

Ala Arg Tyr Lys Ser Phe Ser Ile Lys Met Leu Lys Asp Met Lys Glu
305                 310                 315                 320

Gly Val Lys Gln Tyr Gly Pro Asn Ser Pro Tyr Met Arg Thr Leu Leu
                325                 330                 335

Asp Ser Ile Ala His Gly His Arg Leu Ile Pro Tyr Asp Trp Glu Ile
        340                 345                 350

Leu Ala Lys Ser Ser Leu Ser Pro Ser Gln Phe Leu Gln Phe Lys Thr
        355                 360                 365

Trp Trp Ile Asp Gly Val Gln Glu Gln Val Arg Arg Asn Arg Ala Ala
        370                 375                 380

Asn Pro Pro Val Asn Ile Asp Ala Asp Gln Leu Leu Gly Ile Gly Gln
385                 390                 395                 400

Asn Trp Ser Thr Ile Ser Gln Gln Ala Leu Met Gln Asn Glu Ala Ile
                405                 410                 415

Glu Gln Val Arg Ala Ile Cys Leu Arg Ala Trp Glu Lys Ile Gln Asp
                420                 425                 430

Pro Gly Ser Thr Cys Pro Ser Phe Asn Thr Val Arg Gln Gly Ser Lys
        435                 440                 445

Glu Pro Tyr Pro Asp Phe Val Ala Arg Leu Gln Asp Val Ala Gln Lys
        450                 455                 460

Ser Ile Ala Asp Glu Lys Ala Arg Lys Val Ile Val Glu Leu Met Ala
465                 470                 475                 480
```

```
Tyr Glu Asn Ala Asn Pro Glu Cys Gln Ser Ala Ile Lys Pro Leu Lys
                485                 490                 495

Gly Lys Val Pro Ala Gly Ser Asp Val Ile Ser Glu Tyr Val Lys Ala
            500                 505                 510

Cys Asp Gly Met Gly Ala Met His Lys Ala Met Leu Met Ala Gln
        515                 520                 525

Ala Ile Thr Gly Val Val Leu Gly Gly Gln Val Arg Thr Phe Gly Gly
    530                 535                 540

Lys Cys Tyr Asn Cys Gly Gln Ile Gly His Leu Lys Lys Asn Cys Pro
545                 550                 555                 560

Val Leu Asn Lys Gln Asn Ile Thr Ile Gln Ala Thr Thr Thr Gly Arg
                565                 570                 575

Glu Pro Pro Asp Leu Cys Pro Arg Cys Lys Lys Gly Lys His Trp Ala
            580                 585                 590

Ser Gln Cys Arg Ser Lys Phe Asp Lys Asn Gly Gln Pro Leu Ser Gly
        595                 600                 605

Asn Glu Gln Arg Gly Gln Pro Gln Ala Pro Gln Gln Thr Gly Ala Phe
    610                 615                 620

Pro Ile Gln Pro Phe Val Pro Gln Gly Phe Gln Gly Gln Gln Pro Pro
625                 630                 635                 640

Leu Ser Gln Val Phe Gln Gly Ile Ser Gln Leu Pro Gln Tyr Asn Asn
                645                 650                 655

Cys Pro Pro Pro Gln Ala Ala Val Gln Gln
            660                 665

<210> SEQ ID NO 19
<211> LENGTH: 698
<212> TYPE: PRT
<213> ORGANISM: Homo sapiens

<400> SEQUENCE: 19

Met His Pro Ser Glu Met Gln Arg Lys Ala Pro Pro Arg Arg Arg Arg
1               5                   10                  15

His Arg Asn Arg Ala Pro Leu Thr His Lys Met Asn Lys Met Val Thr
            20                  25                  30

Ser Glu Gln Met Lys Leu Pro Ser Thr Lys Lys Ala Glu Pro Pro Thr
        35                  40                  45

Trp Ala Gln Leu Lys Lys Leu Thr Gln Leu Ala Thr Lys Tyr Leu Glu
    50                  55                  60

Asn Thr Lys Val Thr Gln Thr Pro Glu Ser Met Leu Leu Ala Ala Leu
65                  70                  75                  80

Met Ile Val Ser Met Val Val Ser Leu Pro Met Pro Ala Gly Ala Ala
                85                  90                  95

Ala Ala Asn Tyr Thr Asn Trp Ala Tyr Val Pro Phe Pro Pro Leu Ile
            100                 105                 110

Arg Ala Val Thr Trp Met Asp Asn Pro Ile Glu Val Tyr Val Asn Asp
        115                 120                 125

Ser Val Trp Val His Gly Pro Ile Asp Asp Arg Cys Pro Ala Lys Pro
    130                 135                 140

Glu Glu Glu Gly Met Met Ile Asn Ile Ser Ile Gly Tyr His Tyr Pro
145                 150                 155                 160

Pro Ile Cys Leu Gly Arg Ala Pro Gly Cys Leu Met Pro Ala Val Gln
                165                 170                 175

Asn Trp Leu Val Glu Val Pro Thr Val Ser Pro Ile Ser Arg Phe Thr
```

```
                180              185              190
Tyr Asn Met Val Ser Gly Met Ser Leu Arg Pro Arg Val Asn Tyr Leu
            195              200              205
Gln Asp Phe Ser Tyr Gln Arg Ser Leu Lys Phe Arg Pro Lys Gly Lys
        210              215              220
Pro Cys Pro Lys Glu Ile Pro Lys Glu Ser Lys Asn Thr Glu Val Leu
225              230              235              240
Val Trp Glu Glu Cys Val Ala Asn Ser Val Val Ile Leu Gln Asn Asn
                245              250              255
Glu Phe Gly Thr Ile Ile Asp Trp Ala Pro Arg Gly Gln Phe Tyr His
            260              265              270
Asn Cys Ser Gly Gln Thr Gln Ser Cys Pro Ser Ala Gln Val Ser Pro
        275              280              285
Ala Val Asp Ser Asp Leu Thr Glu Ser Leu Asp Lys His Lys His Lys
290              295              300
Lys Leu Gln Ser Phe Tyr Pro Trp Glu Trp Gly Glu Lys Gly Ile Ser
305              310              315              320
Thr Pro Arg Pro Lys Ile Ile Ser Pro Val Ser Gly Pro Glu His Pro
            325              330              335
Glu Leu Trp Arg Leu Thr Val Ala Ser His His Ile Arg Ile Trp Ser
            340              345              350
Gly Asn Gln Thr Leu Glu Thr Arg Asp Arg Lys Pro Phe Tyr Thr Val
        355              360              365
Asp Leu Asn Ser Ser Leu Thr Val Pro Leu Gln Ser Cys Val Lys Pro
    370              375              380
Pro Tyr Met Leu Val Val Gly Asn Ile Val Ile Lys Pro Asp Ser Gln
385              390              395              400
Thr Ile Thr Cys Glu Asn Cys Arg Leu Leu Thr Cys Ile Asp Ser Thr
            405              410              415
Phe Asn Trp Gln His Arg Ile Leu Leu Val Arg Ala Arg Glu Gly Val
            420              425              430
Trp Ile Pro Val Ser Met Asp Arg Pro Trp Glu Ala Ser Pro Ser Ile
        435              440              445
His Ile Leu Thr Glu Val Leu Lys Gly Val Leu Asn Arg Ser Lys Arg
    450              455              460
Phe Ile Phe Thr Leu Ile Ala Val Ile Met Gly Leu Ile Ala Val Thr
465              470              475              480
Ala Met Ala Ala Val Ala Gly Val Ala Leu His Ser Phe Val Gln Ser
            485              490              495
Val Asn Phe Val Asn Asp Trp Gln Lys Asn Ser Thr Arg Leu Trp Asn
        500              505              510
Ser Gln Ser Ser Ile Asp Gln Lys Leu Ala Asn Gln Ile Asn Asp Leu
    515              520              525
Arg Gln Thr Val Ile Trp Met Gly Asp Arg Leu Met Ser Leu Glu His
    530              535              540
Arg Phe Gln Leu Gln Cys Asp Trp Asn Thr Ser Asp Phe Cys Ile Thr
545              550              555              560
Pro Gln Ile Tyr Asn Glu Ser Glu His His Trp Asp Met Val Arg Arg
            565              570              575
His Leu Gln Gly Arg Glu Asp Asn Leu Thr Leu Asp Ile Ser Lys Leu
            580              585              590
Lys Glu Gln Ile Phe Glu Ala Ser Lys Ala His Leu Asn Leu Val Pro
        595              600              605
```

```
Gly Thr Glu Ala Ile Ala Gly Val Ala Asp Gly Leu Ala Asn Leu Asn
            610                 615                 620

Pro Val Thr Trp Val Lys Thr Ile Gly Ser Thr Thr Ile Ile Asn Leu
625                 630                 635                 640

Ile Leu Ile Leu Val Cys Leu Phe Cys Leu Leu Leu Val Cys Arg Cys
            645                 650                 655

Thr Gln Gln Leu Arg Arg Asp Ser Asp His Arg Glu Arg Ala Met Met
            660                 665                 670

Thr Met Val Val Leu Ser Lys Arg Lys Gly Gly Asn Val Gly Lys Ser
            675                 680                 685

Lys Arg Asp Gln Ile Val Thr Val Ser Val
690                 695

<210> SEQ ID NO 20
<211> LENGTH: 666
<212> TYPE: PRT
<213> ORGANISM: Homo sapiens

<400> SEQUENCE: 20

Met Gly Gln Thr Lys Ser Lys Ile Lys Ser Lys Tyr Ala Ser Tyr Leu
1               5                   10                  15

Ser Phe Ile Lys Ile Leu Leu Lys Arg Gly Gly Val Lys Val Ser Thr
            20                  25                  30

Lys Asn Leu Ile Lys Leu Phe Gln Ile Ile Glu Gln Phe Cys Pro Trp
            35                  40                  45

Phe Pro Glu Gln Gly Thr Leu Asp Leu Lys Asp Trp Lys Arg Ile Gly
50                  55                  60

Lys Glu Leu Lys Gln Ala Gly Arg Lys Gly Asn Ile Ile Pro Leu Thr
65                  70                  75                  80

Val Trp Asn Asp Trp Ala Ile Ile Lys Ala Ala Leu Glu Pro Phe Gln
            85                  90                  95

Thr Glu Glu Asp Ser Ile Ser Val Ser Asp Ala Pro Gly Ser Cys Ile
            100                 105                 110

Ile Asp Cys Asn Glu Asn Thr Arg Lys Lys Ser Gln Lys Glu Thr Glu
            115                 120                 125

Gly Leu His Cys Glu Tyr Ala Ala Glu Pro Val Met Ala Gln Ser Thr
            130                 135                 140

Gln Asn Val Asp Tyr Asn Gln Leu Gln Glu Val Ile Tyr Pro Glu Thr
145                 150                 155                 160

Leu Lys Leu Glu Gly Lys Gly Pro Glu Leu Val Gly Pro Ser Glu Ser
            165                 170                 175

Lys Pro Arg Gly Thr Ser Pro Leu Pro Ala Gly Gln Val Pro Val Thr
            180                 185                 190

Leu Gln Pro Gln Thr Gln Val Lys Glu Asn Lys Thr Gln Pro Pro Val
            195                 200                 205

Ala Tyr Gln Tyr Trp Pro Pro Ala Glu Leu Gln Tyr Arg Pro Pro Pro
            210                 215                 220

Glu Ser Gln Tyr Gly Tyr Pro Gly Met Pro Pro Ala Pro Gln Gly Arg
225                 230                 235                 240

Ala Pro Tyr Pro Gln Pro Pro Thr Arg Arg Leu Asn Pro Thr Ala Pro
            245                 250                 255

Pro Ser Arg Gln Gly Ser Glu Leu His Glu Ile Ile Asp Lys Ser Arg
            260                 265                 270

Lys Glu Gly Asp Thr Glu Ala Trp Gln Phe Pro Val Met Leu Glu Pro
```

```
                    275                 280                 285
Met Pro Pro Gly Glu Gly Ala Gln Glu Gly Pro Pro Thr Val Glu
    290                 295                 300
Ala Arg Tyr Lys Ser Phe Ser Ile Lys Met Leu Lys Asp Met Lys Glu
305                 310                 315                 320
Gly Val Lys Gln Tyr Gly Pro Asn Ser Pro Tyr Met Arg Thr Leu Leu
                325                 330                 335
Asp Ser Ile Ala His Gly His Arg Leu Ile Pro Tyr Asp Trp Glu Ile
                340                 345                 350
Leu Ala Lys Ser Ser Leu Leu Pro Ser Gln Phe Leu Gln Phe Lys Thr
                355                 360                 365
Trp Trp Ile Asp Gly Val Gln Glu Gln Val Gln Arg Asn Arg Ala Ala
                370                 375                 380
Asn Pro Pro Val Asn Ile Asp Ala Asp Gln Leu Leu Gly Ile Gly Gln
385                 390                 395                 400
Asn Trp Ser Thr Ile Ser Gln Gln Ala Leu Met Gln Asn Glu Ala Ile
                    405                 410                 415
Glu Gln Val Arg Ala Ile Cys Leu Arg Ala Trp Glu Lys Ile Gln Asp
                420                 425                 430
Pro Gly Ser Thr Cys Pro Ser Phe Asn Thr Val Arg Gln Ser Ser Lys
                435                 440                 445
Glu Pro Tyr Pro Asp Phe Val Ala Arg Leu Gln Asp Val Ala Gln Lys
                450                 455                 460
Ser Ile Ala Asp Glu Lys Ala Arg Lys Val Ile Val Glu Leu Met Ala
465                 470                 475                 480
Tyr Glu Asn Ala Asn Pro Glu Cys Gln Ser Ala Ile Lys Pro Leu Lys
                    485                 490                 495
Gly Lys Val Pro Ala Gly Ser Asp Val Ile Ser Glu Tyr Val Lys Ala
                500                 505                 510
Cys Asp Gly Ile Gly Gly Ala Met His Lys Ala Met Leu Met Ala Gln
                515                 520                 525
Ala Ile Thr Gly Val Val Leu Gly Gly Gln Val Arg Thr Phe Gly Gly
                530                 535                 540
Lys Cys Tyr Asn Cys Gly Gln Ile Gly His Leu Lys Lys Asn Cys Pro
545                 550                 555                 560
Val Leu Asn Lys Gln Asn Ile Thr Ile Gln Ala Thr Thr Thr Gly Arg
                    565                 570                 575
Glu Pro Pro Asp Leu Cys Pro Arg Cys Lys Lys Gly Lys His Trp Ala
                580                 585                 590
Ser Gln Cys Arg Ser Lys Phe Asp Lys Asn Gly Gln Pro Leu Ser Gly
                595                 600                 605
Asn Glu Gln Arg Gly Gln Pro Gln Ala Pro Gln Gln Thr Gly Ala Phe
                610                 615                 620
Pro Ile Gln Pro Phe Val Pro Gln Gly Phe Gln Gly Gln Gln Pro Pro
625                 630                 635                 640
Leu Ser Gln Val Phe Gln Gly Ile Ser Gln Leu Pro Gln Tyr Asn Asn
                    645                 650                 655
Cys Pro Pro Pro Gln Ala Val Gln Gln
                660                 665

<210> SEQ ID NO 21
<211> LENGTH: 661
<212> TYPE: PRT
<213> ORGANISM: Homo sapiens
```

<400> SEQUENCE: 21

```
Met Asn Pro Ser Glu Met Gln Arg Lys Ala Pro Pro Arg Arg Arg
1               5                   10                  15

His Arg Asn Arg Ala Pro Leu Thr His Lys Met Asn Lys Met Val Thr
            20                  25                  30

Ser Glu Glu Gln Met Lys Leu Pro Ser Thr Lys Lys Ala Glu Pro Pro
        35                  40                  45

Thr Trp Ala Gln Leu Lys Lys Leu Thr Gln Leu Ala Thr Lys Tyr Leu
    50                  55                  60

Glu Asn Thr Lys Val Thr Gln Thr Pro Glu Ser Met Leu Leu Ala Ala
65                  70                  75                  80

Leu Met Ile Val Ser Met Val Val Ser Leu Pro Met Pro Ala Gly Ala
                85                  90                  95

Ala Ala Ala Asn Tyr Thr Tyr Trp Ala Tyr Val Pro Phe Pro Pro Leu
            100                 105                 110

Ile Arg Ala Val Thr Trp Met Asp Asn Pro Ile Glu Val Tyr Val Asn
        115                 120                 125

Asp Ser Val Trp Val Pro Gly Pro Ile Asp Asp Arg Cys Pro Ala Lys
    130                 135                 140

Pro Glu Glu Glu Gly Met Met Ile Asn Ile Ser Ile Gly Tyr Arg Tyr
145                 150                 155                 160

Pro Pro Ile Cys Leu Gly Thr Ala Pro Gly Cys Leu Met Pro Ala Val
                165                 170                 175

Gln Asn Trp Leu Val Glu Val Pro Ile Val Ser Pro Ile Ser Arg Phe
            180                 185                 190

Thr Tyr His Met Val Ser Gly Met Ser Leu Arg Pro Arg Val Asn Tyr
        195                 200                 205

Leu Gln Asp Phe Ser Tyr Gln Arg Ser Leu Lys Phe Arg Pro Lys Gly
    210                 215                 220

Lys Pro Cys Pro Lys Glu Ile Pro Lys Glu Ser Lys Asn Thr Glu Val
225                 230                 235                 240

Leu Val Trp Glu Glu Cys Val Ala Asn Ser Ala Val Ile Leu Gln Asn
                245                 250                 255

Asn Glu Phe Gly Thr Ile Ile Asp Trp Ala Pro Arg Gly Gln Phe Tyr
            260                 265                 270

His Asn Cys Ser Gly Gln Thr Gln Ser Cys Pro Ser Ala Gln Val Ser
        275                 280                 285

Pro Ala Val Asp Ser Asp Leu Thr Glu Ser Leu Asp Lys His Lys His
    290                 295                 300

Lys Lys Leu Gln Ser Phe Tyr Pro Trp Glu Trp Gly Glu Lys Gly Ile
305                 310                 315                 320

Ser Thr Pro Arg Pro Lys Ile Val Ser Pro Val Ser Gly Pro Glu His
                325                 330                 335

Pro Glu Leu Trp Arg Leu Thr Val Ala Ser His His Ile Arg Ile Trp
            340                 345                 350

Ser Gly Asn Gln Thr Leu Glu Thr Arg Asp Arg Lys Pro Phe Tyr Thr
        355                 360                 365

Val Asp Leu Asn Ser Ser Leu Thr Val Pro Leu Gln Ser Cys Val Lys
    370                 375                 380

Pro Pro Tyr Met Leu Val Val Gly Asn Ile Val Ile Lys Pro Asp Ser
385                 390                 395                 400

Gln Thr Ile Thr Cys Glu Asn Cys Arg Leu Leu Thr Cys Ile Asp Ser
```

```
                405                 410                 415
Thr Phe Asn Trp Gln His Arg Ile Leu Leu Val Arg Ala Arg Glu Gly
            420                 425                 430

Val Trp Ile Pro Val Ser Met Asp Arg Pro Trp Glu Ala Ser Pro Ser
        435                 440                 445

Ile His Ile Leu Thr Glu Val Leu Lys Gly Val Leu Asn Arg Ser Lys
    450                 455                 460

Arg Phe Ile Phe Thr Leu Ile Ala Val Ile Met Gly Leu Ile Ala Val
465                 470                 475                 480

Thr Ala Thr Gly Ala Val Ala Gly Val Ala Leu His Ser Ser Val Gln
            485                 490                 495

Ser Val Asn Phe Val Asn Asp Trp Gln Lys Asn Ser Thr Arg Leu Trp
        500                 505                 510

Asn Ser Gln Ser Ser Ile Asp Gln Lys Leu Ala Asn Gln Ile Asn Asp
    515                 520                 525

Leu Arg Gln Thr Val Ile Trp Met Gly Asp Arg Leu Met Ser Leu Glu
530                 535                 540

His Arg Phe Gln Leu Gln Cys Asp Trp Asn Thr Ser Asp Phe Cys Ile
545                 550                 555                 560

Thr Pro Gln Ile Tyr Asn Glu Ser Glu His Trp Asp Met Val Arg
            565                 570                 575

Arg His Leu Gln Gly Arg Glu Asp Asn Leu Thr Leu Asp Ile Ser Lys
        580                 585                 590

Leu Lys Glu Gln Ile Phe Lys Ala Ser Lys Ala His Leu Asn Leu Val
    595                 600                 605

Pro Gly Thr Glu Ala Ile Ala Gly Val Ala Asp Gly Leu Ala Asn Leu
610                 615                 620

Asn Pro Val Thr Trp Val Lys Thr Ile Gly Ser Thr Thr Ile Ile Asn
625                 630                 635                 640

Leu Ile Leu Ile Leu Val Cys Leu Phe Cys Leu Leu Leu Val Cys Arg
            645                 650                 655

Cys Thr Gln Gln Leu
            660

<210> SEQ ID NO 22
<211> LENGTH: 588
<212> TYPE: PRT
<213> ORGANISM: Homo sapiens

<400> SEQUENCE: 22

Met Val Thr Pro Val Thr Trp Met Asp Asn Pro Ile Glu Ile Tyr Val
1               5                   10                  15

Asn Asp Ser Val Trp Val Pro Gly Pro Ile Asp Asp Arg Cys Pro Ala
            20                  25                  30

Lys Pro Glu Glu Glu Gly Met Met Ile Asn Ile Ser Ile Gly Tyr Arg
        35                  40                  45

Tyr Pro Pro Ile Cys Leu Gly Arg Ala Pro Gly Cys Leu Met Pro Ala
    50                  55                  60

Val Gln Asn Trp Leu Val Glu Val Pro Thr Val Ser Pro Ile Ser Arg
65                  70                  75                  80

Phe Thr Tyr His Met Val Ser Gly Met Ser Leu Arg Pro Arg Val Asn
                85                  90                  95

Tyr Leu Gln Asp Phe Ser Tyr Gln Arg Ser Leu Lys Phe Arg Pro Lys
            100                 105                 110
```

```
Gly Lys Pro Cys Pro Lys Glu Ile Pro Lys Glu Ser Lys Asn Thr Glu
            115                 120                 125

Val Leu Val Trp Glu Glu Cys Val Ala Asn Ser Ala Val Ile Leu Gln
130                 135                 140

Asn Asn Glu Phe Gly Thr Ile Ile Asp Trp Ala Pro Arg Gly Gln Phe
145                 150                 155                 160

Tyr His Asn Cys Ser Gly Gln Thr Gln Ser Cys Pro Ser Ala Gln Val
                165                 170                 175

Ser Pro Ala Val Asp Ser Asp Leu Thr Glu Ser Leu Asp Lys His Lys
            180                 185                 190

His Lys Lys Leu Gln Ser Phe Tyr Pro Trp Glu Trp Gly Glu Lys Arg
        195                 200                 205

Ile Ser Thr Pro Arg Pro Lys Ile Val Ser Pro Val Ser Gly Pro Glu
    210                 215                 220

His Pro Glu Leu Trp Arg Leu Thr Val Ala Ser His His Ile Arg Ile
225                 230                 235                 240

Trp Ser Gly Asn Gln Thr Leu Glu Thr Arg Asp Cys Lys Pro Phe Tyr
                245                 250                 255

Thr Ile Asp Leu Asn Ser Ser Leu Thr Val Pro Leu Gln Ser Cys Val
            260                 265                 270

Lys Pro Pro Tyr Met Leu Val Val Gly Asn Ile Val Ile Lys Pro Asp
        275                 280                 285

Ser Gln Thr Ile Thr Cys Glu Asn Cys Arg Leu Leu Ser Cys Ile Asp
    290                 295                 300

Ser Thr Phe Asn Trp Gln His Arg Ile Leu Leu Val Arg Ala Arg Glu
305                 310                 315                 320

Gly Val Trp Ile Pro Val Ser Met Asp Arg Pro Trp Glu Ala Ser Pro
                325                 330                 335

Ser Val His Ile Leu Thr Glu Val Leu Lys Gly Val Leu Asn Arg Ser
            340                 345                 350

Lys Arg Phe Ile Phe Thr Leu Ile Ala Val Ile Met Gly Leu Ile Ala
        355                 360                 365

Val Thr Ala Thr Ala Ala Val Ala Gly Val Ala Leu His Ser Ser Val
370                 375                 380

Gln Ser Val Asn Phe Val Asn Asp Trp Gln Lys Asn Ser Thr Arg Leu
385                 390                 395                 400

Trp Asn Ser Gln Ser Ser Ile Asp Gln Lys Leu Ala Asn Gln Ile Asn
                405                 410                 415

Asp Leu Arg Gln Thr Val Ile Trp Met Gly Asp Arg Leu Met Ser Leu
            420                 425                 430

Glu His Arg Phe Gln Leu Gln Cys Asp Trp Asn Thr Ser Asp Phe Cys
        435                 440                 445

Ile Thr Pro Gln Ile Tyr Asn Glu Ser Glu His His Trp Asp Met Val
    450                 455                 460

Arg Arg His Leu Gln Gly Arg Glu Asp Asn Leu Thr Leu Asp Ile Ser
465                 470                 475                 480

Lys Leu Lys Glu Gln Ile Phe Glu Ala Ser Lys Ala His Leu Asn Leu
                485                 490                 495

Val Pro Gly Thr Glu Ala Ile Ala Gly Val Ala Asp Gly Leu Ala Asn
            500                 505                 510

Leu Asn Pro Val Thr Trp Val Lys Thr Ile Gly Ser Thr Thr Ile Ile
        515                 520                 525

Asn Leu Ile Leu Ile Leu Val Cys Leu Phe Cys Leu Leu Leu Val Cys
```

```
                530             535             540
Arg Cys Thr Gln Gln Leu Arg Arg Asp Ser Asp His Arg Glu Arg Ala
545                 550             555                 560

Met Met Thr Met Ala Val Leu Ser Lys Arg Lys Gly Gly Asn Val Gly
                565             570             575

Lys Ser Lys Arg Asp Gln Ile Val Thr Val Ser Val
                580             585

<210> SEQ ID NO 23
<211> LENGTH: 666
<212> TYPE: PRT
<213> ORGANISM: Homo sapiens

<400> SEQUENCE: 23

Met Gly Gln Thr Lys Ser Lys Ile Lys Ser Lys Tyr Ala Ser Tyr Leu
1               5                   10                  15

Ser Phe Ile Lys Ile Leu Leu Lys Arg Gly Gly Val Lys Val Ser Thr
                20                  25                  30

Lys Asn Leu Ile Lys Leu Phe Gln Ile Ile Glu Gln Phe Cys Pro Trp
                35                  40                  45

Phe Pro Glu Gln Gly Thr Leu Asp Leu Lys Asp Trp Lys Arg Ile Gly
50                  55                  60

Lys Glu Leu Lys Gln Ala Gly Arg Lys Gly Asn Ile Ile Pro Leu Thr
65                  70                  75                  80

Val Trp Asn Asp Trp Ala Ile Ile Lys Ala Ala Leu Glu Pro Phe Gln
                85                  90                  95

Thr Glu Lys Asp Ser Val Ser Val Ser Asp Ala Leu Gly Ser Cys Ile
                100                 105                 110

Ile Asp Cys Asn Glu Asn Thr Arg Lys Lys Ser Gln Lys Glu Thr Glu
                115                 120                 125

Gly Leu His Cys Glu Tyr Val Ala Glu Pro Val Met Ala Gln Ser Thr
                130                 135                 140

Gln Asn Val Asp Tyr Asn Gln Leu Gln Glu Val Ile Tyr Pro Glu Thr
145                 150                 155                 160

Leu Lys Leu Glu Gly Lys Gly Pro Glu Leu Val Gly Pro Ser Glu Ser
                165                 170                 175

Lys Pro Arg Gly Thr Ser His Leu Pro Ala Gly Gln Val Pro Val Thr
                180                 185                 190

Leu Gln Pro Gln Lys Gln Val Lys Glu Asn Lys Thr Gln Pro Pro Val
                195                 200                 205

Ala Tyr Gln Tyr Trp Pro Pro Ala Glu Leu Gln Tyr Arg Pro Pro Pro
                210                 215                 220

Glu Ser Gln Tyr Gly Tyr Pro Gly Met Pro Pro Ala Pro Gln Gly Arg
225                 230                 235                 240

Ala Pro Tyr Pro Gln Pro Pro Thr Arg Arg Leu Asn Pro Thr Ala Pro
                245                 250                 255

Pro Ser Arg Gln Gly Ser Glu Leu His Glu Ile Ile Asp Lys Ser Arg
                260                 265                 270

Lys Glu Gly Asp Thr Glu Ala Trp Gln Phe Pro Val Thr Leu Glu Pro
                275                 280                 285

Met Pro Pro Gly Glu Gly Ala Gln Glu Gly Glu Pro Pro Thr Val Glu
                290                 295                 300

Ala Arg Tyr Lys Ser Phe Ser Ile Lys Met Leu Lys Asp Met Lys Glu
305                 310                 315                 320
```

Gly Val Lys Gln Tyr Gly Pro Asn Ser Pro Tyr Met Arg Thr Leu Leu
            325                 330                 335

Asp Ser Ile Ala His Gly His Arg Leu Ile Pro Tyr Asp Trp Glu Ile
            340                 345                 350

Leu Ala Lys Ser Ser Leu Ser Pro Ser Gln Phe Leu Gln Phe Lys Thr
            355                 360                 365

Trp Trp Ile Asp Gly Val Gln Glu Gln Val Arg Arg Asn Arg Ala Ala
        370                 375                 380

Asn Pro Pro Val Asn Ile Asp Ala Asp Gln Leu Leu Gly Ile Gly Gln
385                 390                 395                 400

Asn Trp Ser Thr Ile Ser Gln Gln Ala Leu Met Gln Asn Glu Ala Ile
                405                 410                 415

Glu Gln Val Arg Ala Ile Cys Leu Arg Ala Trp Glu Lys Ile Gln Asp
            420                 425                 430

Pro Gly Ser Thr Cys Pro Ser Phe Asn Thr Val Arg Gln Gly Ser Lys
            435                 440                 445

Glu Pro Tyr Pro Asp Phe Val Ala Arg Leu Gln Asp Val Ala Gln Lys
        450                 455                 460

Ser Ile Ala Asp Glu Lys Ala Arg Lys Val Ile Val Glu Leu Met Ala
465                 470                 475                 480

Tyr Glu Asn Ala Asn Pro Glu Cys Gln Ser Ala Ile Lys Pro Leu Lys
                485                 490                 495

Gly Lys Val Pro Ala Gly Ser Asp Val Ile Ser Glu Tyr Val Lys Ala
            500                 505                 510

Cys Asp Gly Ile Gly Gly Ala Met His Lys Ala Met Leu Met Ala Gln
            515                 520                 525

Ala Ile Thr Gly Val Val Leu Gly Gly Gln Val Arg Thr Phe Gly Gly
        530                 535                 540

Lys Cys Tyr Asn Cys Gly Gln Ile Gly His Leu Lys Lys Asn Cys Pro
545                 550                 555                 560

Val Leu Asn Lys Gln Asn Ile Thr Ile Gln Ala Thr Thr Thr Gly Arg
                565                 570                 575

Glu Pro Pro Asp Leu Cys Pro Arg Cys Lys Lys Gly Lys His Trp Ala
            580                 585                 590

Ser Gln Cys Arg Ser Lys Phe Asp Lys Asn Gly Gln Pro Leu Ser Gly
            595                 600                 605

Asn Glu Gln Arg Gly Gln Pro Gln Ala Pro Gln Gln Thr Gly Ala Phe
        610                 615                 620

Pro Ile Gln Pro Phe Val Pro Gln Gly Phe Gln Glu Gln Pro Pro
625                 630                 635                 640

Leu Ser Gln Val Phe Gln Gly Ile Ser Gln Leu Pro Gln Tyr Asn Asn
                645                 650                 655

Cys Pro Pro Pro Gln Ala Ala Val Gln Gln
            660                 665

<210> SEQ ID NO 24
<211> LENGTH: 588
<212> TYPE: PRT
<213> ORGANISM: Homo sapiens

<400> SEQUENCE: 24

Met Val Thr Pro Val Thr Trp Met Asp Asn Pro Ile Glu Val Tyr Val
1               5                   10                  15

Asn Asp Ser Glu Trp Val Pro Gly Pro Thr Asp Asp Arg Cys Pro Ala
            20                  25                  30

```
Lys Pro Glu Glu Gly Met Met Ile Asn Ile Ser Ile Gly Tyr Arg
             35                  40                  45

Tyr Pro Pro Ile Cys Leu Gly Thr Ala Pro Gly Cys Leu Met Pro Ala
 50                  55                  60

Val Gln Asn Trp Leu Val Glu Val Pro Ile Val Ser Pro Ile Ser Arg
 65                  70                  75                  80

Phe Thr Tyr His Met Val Ser Gly Met Ser Leu Arg Pro Arg Val Asn
                 85                  90                  95

Tyr Leu Gln Asp Phe Pro Tyr Gln Arg Ser Leu Lys Phe Arg Pro Lys
                100                 105                 110

Gly Lys Pro Cys Pro Lys Glu Ile Pro Lys Glu Ser Lys Asn Thr Glu
                115                 120                 125

Val Leu Val Trp Glu Glu Cys Val Ala Asn Ser Ala Val Ile Leu Gln
130                 135                 140

Asn Asn Glu Phe Gly Thr Ile Ile Asp Trp Ala Pro Arg Gly Gln Phe
145                 150                 155                 160

Tyr His Asn Cys Ser Gly Gln Thr Gln Ser Cys Pro Ser Ala Gln Val
                165                 170                 175

Ser Pro Ala Val Asp Ser Asp Leu Thr Glu Ser Leu Asp Lys His Lys
                180                 185                 190

His Lys Lys Leu Gln Ser Phe Tyr Pro Trp Glu Trp Gly Glu Lys Gly
                195                 200                 205

Ile Ser Thr Pro Arg Pro Lys Ile Ile Ser Pro Val Ser Gly Pro Glu
210                 215                 220

His Pro Glu Leu Trp Arg Leu Thr Val Ala Ser His His Ile Arg Ile
225                 230                 235                 240

Trp Ser Gly Asn Gln Thr Leu Glu Thr Arg Asp Arg Lys Pro Phe Tyr
                245                 250                 255

Thr Val Asp Leu Asn Ser Ser Leu Thr Leu Pro Leu Gln Ser Cys Val
                260                 265                 270

Lys Pro Pro Tyr Met Leu Val Val Gly Asn Ile Val Ile Lys Pro Asp
                275                 280                 285

Ser Gln Thr Ile Thr Cys Glu Asn Cys Arg Leu Leu Thr Cys Ile Asp
                290                 295                 300

Ser Thr Phe Asn Trp Gln His Arg Ile Leu Leu Val Arg Ala Arg Glu
305                 310                 315                 320

Gly Val Trp Ile Leu Val Ser Met Asp Arg Pro Trp Glu Ala Ser Pro
                325                 330                 335

Ser Val His Ile Leu Thr Glu Val Leu Lys Gly Val Leu Asn Arg Ser
                340                 345                 350

Lys Arg Phe Ile Phe Thr Leu Ile Ala Val Ile Met Gly Leu Ile Ala
                355                 360                 365

Val Thr Ala Thr Gly Ala Val Ala Gly Val Ala Leu His Ser Ser Val
                370                 375                 380

Gln Ser Val Asn Phe Val Asn Asp Trp Gln Lys Asn Ser Thr Arg Leu
385                 390                 395                 400

Trp Asn Ser Gln Ser Ser Ile Asp Gln Lys Leu Ala Asn Gln Ile Asn
                405                 410                 415

Asp Leu Arg Gln Thr Val Ile Trp Met Gly Asp Arg Leu Met Ser Leu
                420                 425                 430

Glu His Arg Phe Gln Leu Gln Cys Asp Trp Asn Thr Ser Asp Phe Cys
                435                 440                 445
```

```
Ile Thr Pro Gln Ile Tyr Asn Glu Ser Glu His His Trp Asp Met Val
    450                 455                 460

Arg His His Leu Gln Gly Arg Glu Asp Asn Leu Thr Leu Asp Ile Ser
465                 470                 475                 480

Lys Leu Lys Glu Gln Ile Phe Glu Ala Ser Lys Ala His Leu Asn Leu
                485                 490                 495

Val Pro Gly Thr Glu Ala Ile Ala Gly Val Ala Asp Gly Leu Ala Asn
            500                 505                 510

Leu Asn Pro Val Thr Trp Val Lys Thr Ile Gly Ser Thr Thr Ile Ile
        515                 520                 525

Asn Leu Ile Leu Ile Leu Val Cys Leu Phe Cys Leu Leu Leu Val Cys
    530                 535                 540

Arg Cys Thr Gln Gln Leu Arg Arg Asp Ser Asp His Arg Glu Arg Ala
545                 550                 555                 560

Met Met Thr Met Ala Val Leu Ser Lys Arg Lys Gly Gly Asn Val Gly
                565                 570                 575

Lys Ser Lys Arg Asp Gln Ile Val Thr Val Ser Val
            580                 585

<210> SEQ ID NO 25
<211> LENGTH: 666
<212> TYPE: PRT
<213> ORGANISM: Homo sapiens

<400> SEQUENCE: 25

Met Gly Gln Thr Lys Ser Lys Ile Lys Ser Lys Tyr Ala Ser Tyr Leu
1               5                   10                  15

Ser Phe Ile Lys Ile Leu Leu Lys Arg Gly Gly Val Lys Val Ser Thr
            20                  25                  30

Lys Asn Leu Ile Lys Leu Phe Gln Ile Ile Glu Gln Phe Cys Pro Trp
        35                  40                  45

Phe Pro Glu Gln Gly Thr Leu Asp Leu Lys Asp Trp Lys Arg Ile Gly
    50                  55                  60

Lys Glu Leu Lys Gln Ala Gly Arg Lys Gly Asn Ile Ile Pro Leu Thr
65                  70                  75                  80

Val Trp Asn Asp Trp Ala Ile Ile Lys Ala Ala Leu Glu Pro Phe Gln
                85                  90                  95

Thr Glu Glu Asp Ser Val Ser Val Ser Asp Ala Pro Gly Ser Cys Leu
            100                 105                 110

Ile Asp Cys Asn Glu Lys Thr Arg Lys Lys Ser Gln Lys Glu Thr Glu
        115                 120                 125

Ser Leu His Cys Glu Tyr Val Ala Glu Pro Val Met Ala Gln Ser Thr
    130                 135                 140

Gln Asn Val Asp Tyr Asn Gln Leu Gln Glu Val Ile Tyr Pro Glu Thr
145                 150                 155                 160

Leu Lys Leu Glu Gly Lys Gly Pro Glu Leu Val Gly Pro Ser Glu Ser
                165                 170                 175

Lys Pro Arg Gly Thr Ser Pro Leu Pro Ala Gly Gln Val Pro Val Thr
            180                 185                 190

Leu Gln Pro Gln Lys Gln Val Lys Glu Asn Lys Thr Gln Pro Pro Val
        195                 200                 205

Ala Tyr Gln Tyr Trp Pro Pro Ala Glu Leu Gln Tyr Arg Pro Pro Pro
    210                 215                 220

Glu Ser Gln Tyr Gly Tyr Pro Gly Met Pro Pro Ala Pro Gln Gly Arg
225                 230                 235                 240
```

```
Ala Pro Tyr Pro Gln Pro Pro Thr Arg Arg Leu Asn Pro Thr Ala Pro
            245                 250                 255

Pro Ser Arg Gln Gly Ser Glu Leu His Glu Ile Ile Asp Lys Ser Arg
        260                 265                 270

Lys Glu Gly Asp Thr Glu Ala Trp Gln Phe Pro Val Thr Leu Glu Pro
            275                 280                 285

Met Pro Pro Gly Glu Gly Ala Gln Glu Gly Glu Pro Pro Thr Val Glu
290                 295                 300

Ala Arg Tyr Lys Ser Phe Ser Ile Lys Met Leu Lys Asp Met Lys Glu
305                 310                 315                 320

Gly Val Lys Gln Tyr Gly Pro Asn Ser Pro Tyr Met Arg Thr Leu Leu
                325                 330                 335

Asp Ser Ile Ala Tyr Gly His Arg Leu Ile Pro Tyr Asp Trp Glu Ile
            340                 345                 350

Leu Ala Lys Ser Ser Leu Ser Pro Ser Gln Phe Leu Gln Phe Lys Thr
            355                 360                 365

Trp Trp Ile Asp Gly Val Gln Glu Gln Val Arg Arg Asn Arg Ala Ala
        370                 375                 380

Asn Pro Pro Val Asn Ile Asp Ala Asp Gln Leu Leu Gly Ile Gly Gln
385                 390                 395                 400

Asn Trp Ser Thr Ile Ser Gln Gln Ala Leu Met Gln Asn Glu Ala Ile
                405                 410                 415

Glu Gln Val Arg Ala Ile Cys Leu Arg Ala Trp Glu Lys Ile Gln Asp
            420                 425                 430

Pro Gly Ser Ala Cys Pro Ser Phe Asn Thr Val Arg Gln Gly Ser Lys
        435                 440                 445

Glu Pro Tyr Pro Asp Phe Val Ala Arg Leu Gln Asp Val Ala Gln Lys
        450                 455                 460

Ser Ile Ala Asp Glu Lys Ala Arg Lys Val Ile Val Glu Leu Met Ala
465                 470                 475                 480

Tyr Glu Asn Ala Asn Pro Glu Cys Gln Ser Ala Ile Lys Pro Leu Lys
                485                 490                 495

Gly Lys Val Pro Ala Gly Ser Asp Val Ile Ser Glu Tyr Val Lys Ala
            500                 505                 510

Cys Asp Gly Ile Gly Gly Ala Met His Lys Ala Met Leu Met Ala Gln
        515                 520                 525

Ala Ile Thr Gly Val Val Leu Gly Gly Gln Val Arg Thr Phe Gly Gly
530                 535                 540

Lys Cys Tyr Asn Cys Gly Gln Ile Gly His Leu Lys Lys Asn Cys Pro
545                 550                 555                 560

Val Leu Asn Lys Gln Asn Ile Thr Ile Gln Ala Thr Thr Thr Gly Arg
                565                 570                 575

Glu Pro Pro Asp Leu Cys Pro Arg Cys Lys Lys Gly Lys His Trp Ala
            580                 585                 590

Ser Gln Cys Arg Ser Lys Phe Asp Lys Asn Gly Gln Pro Leu Ser Gly
        595                 600                 605

Asn Glu Gln Arg Gly Gln Pro Gln Ala Pro Gln Gln Thr Gly Ala Phe
610                 615                 620

Pro Ile Gln Pro Phe Val Pro Gln Gly Phe Gln Gly Gln Gln Pro Pro
625                 630                 635                 640

Leu Ser Gln Val Phe Gln Gly Ile Ser Gln Leu Pro Gln Tyr Asn Asn
                645                 650                 655
```

```
Cys Pro Leu Pro Gln Ala Ala Val Gln Gln
            660                 665
```

<210> SEQ ID NO 26
<211> LENGTH: 560
<212> TYPE: PRT
<213> ORGANISM: Homo sapiens

<400> SEQUENCE: 26

```
Met Val Thr Pro Val Thr Trp Met Asp Asn Pro Ile Glu Val Tyr Val
1               5                   10                  15

Asn Asp Ser Val Trp Val Pro Gly Pro Thr Asp Asp Arg Cys Pro Ala
            20                  25                  30

Lys Pro Glu Glu Gly Met Met Ile Asn Ile Ser Ile Gly Tyr His
            35                  40                  45

Tyr Pro Pro Ile Cys Leu Gly Arg Ala Pro Gly Cys Leu Met Pro Ala
        50                  55                  60

Val Gln Asn Trp Leu Val Glu Val Pro Thr Val Ser Pro Asn Ser Arg
65                  70                  75                  80

Phe Thr Tyr His Met Val Ser Gly Met Ser Leu Arg Pro Arg Val Asn
                85                  90                  95

Cys Leu Gln Asp Phe Ser Tyr Gln Arg Ser Leu Lys Phe Arg Pro Lys
            100                 105                 110

Gly Lys Thr Cys Pro Lys Glu Ile Pro Lys Gly Ser Lys Asn Thr Glu
        115                 120                 125

Val Leu Val Trp Glu Glu Cys Val Ala Asn Ser Val Val Ile Leu Gln
    130                 135                 140

Asn Asn Glu Phe Gly Thr Ile Ile Asp Trp Ala Pro Arg Gly Gln Phe
145                 150                 155                 160

Tyr His Asn Cys Ser Gly Gln Thr Gln Ser Cys Pro Ser Ala Gln Val
                165                 170                 175

Ser Pro Ala Val Asp Ser Asp Leu Thr Glu Ser Leu Asp Lys His Lys
            180                 185                 190

His Lys Lys Leu Gln Ser Phe Tyr Leu Trp Glu Trp Glu Glu Lys Gly
        195                 200                 205

Ile Ser Thr Pro Arg Pro Lys Ile Ile Ser Pro Val Ser Gly Pro Glu
    210                 215                 220

His Pro Glu Leu Trp Arg Leu Thr Val Ala Ser His His Ile Arg Ile
225                 230                 235                 240

Trp Ser Gly Asn Gln Thr Leu Glu Thr Arg Tyr Arg Lys Pro Phe Tyr
                245                 250                 255

Thr Ile Asp Leu Asn Ser Ile Leu Thr Val Pro Leu Gln Ser Cys Val
            260                 265                 270

Lys Pro Pro Tyr Met Leu Val Val Gly Asn Ile Val Ile Lys Pro Ala
        275                 280                 285

Ser Gln Thr Ile Thr Cys Glu Asn Cys Arg Leu Phe Thr Cys Ile Asp
    290                 295                 300

Ser Thr Phe Asn Trp Gln His Arg Ile Leu Leu Val Arg Ala Arg Glu
305                 310                 315                 320

Gly Met Trp Ile Pro Val Ser Thr Asp Arg Pro Trp Glu Ala Ser Pro
                325                 330                 335

Ser Ile His Ile Leu Thr Glu Ile Leu Lys Gly Val Leu Asn Arg Ser
            340                 345                 350

Lys Arg Phe Ile Phe Thr Leu Ile Ala Val Ile Met Gly Leu Ile Ala
        355                 360                 365
```

```
Val Thr Ala Thr Ala Ala Val Ala Gly Val Ala Leu His Ser Ser Val
        370                 375                 380

Gln Ser Val Asn Phe Val Asn Tyr Trp Gln Lys Asn Ser Thr Arg Leu
385                 390                 395                 400

Trp Asn Ser Gln Ser Ser Ile Asp Gln Lys Leu Ala Ser Gln Ile Asn
                405                 410                 415

Asp Leu Arg Gln Thr Val Ile Trp Met Gly Asp Arg Leu Met Thr Leu
            420                 425                 430

Glu His His Phe Gln Leu Gln Cys Asp Trp Asn Thr Ser Asp Phe Cys
        435                 440                 445

Ile Thr Pro Gln Ile Tyr Asn Glu Ser Glu His His Trp Asp Met Val
    450                 455                 460

Arg Arg His Leu Gln Gly Arg Glu Asp Asn Leu Thr Leu Asp Ile Ser
465                 470                 475                 480

Lys Leu Lys Glu Gln Ile Phe Glu Ala Ser Lys Ala His Leu Asn Leu
                485                 490                 495

Val Pro Gly Thr Glu Ala Ile Ala Gly Val Ala Asp Gly Leu Ala Asn
            500                 505                 510

Leu Asn Pro Val Thr Trp Ile Lys Thr Ile Arg Ser Thr Met Ile Ile
        515                 520                 525

Asn Leu Ile Leu Ile Val Val Cys Leu Phe Cys Leu Leu Leu Val Cys
    530                 535                 540

Arg Cys Thr Gln Gln Leu Arg Arg Asp Ser Asp Ile Glu Asn Gly Pro
545                 550                 555                 560

<210> SEQ ID NO 27
<211> LENGTH: 584
<212> TYPE: PRT
<213> ORGANISM: Homo sapiens

<400> SEQUENCE: 27

Met Ile Phe Ala Gly Lys Ala Pro Ser Asn Thr Ser Thr Leu Met Lys
1               5                   10                  15

Phe Tyr Ser Leu Leu Leu Tyr Ser Leu Leu Phe Ser Phe Pro Phe Leu
            20                  25                  30

Cys His Pro Leu Pro Leu Pro Ser Tyr Leu His His Thr Ile Asn Leu
        35                  40                  45

Thr His Ser Leu Leu Ala Ala Ser Asn Pro Ser Leu Val Asn Asn Cys
    50                  55                  60

Trp Leu Cys Ile Ser Leu Ser Ser Ser Ala Tyr Thr Ala Val Pro Ala
65                  70                  75                  80

Val Gln Thr Asp Trp Ala Thr Ser Pro Ile Ser Leu His Leu Arg Thr
                85                  90                  95

Ser Phe Asn Ser Pro His Leu Tyr Pro Pro Glu Glu Leu Ile Tyr Phe
            100                 105                 110

Leu Asp Arg Ser Ser Lys Thr Ser Pro Asp Ile Ser His Gln Gln Ala
        115                 120                 125

Ala Ala Leu Leu Arg Thr Tyr Leu Lys Asn Leu Ser Pro Tyr Ile Asn
    130                 135                 140

Ser Thr Pro Pro Ile Phe Gly Pro Leu Thr Thr Gln Thr Thr Ile Pro
145                 150                 155                 160

Val Ala Ala Pro Leu Cys Ile Ser Trp Gln Arg Pro Thr Gly Ile Pro
                165                 170                 175

Leu Gly Asn Leu Ser Pro Ser Arg Cys Ser Phe Thr Leu His Leu Arg
```

```
            180                 185                 190
Ser Pro Thr Thr Asn Ile Asn Glu Thr Ile Gly Ala Phe Gln Leu His
            195                 200                 205
Ile Thr Asp Lys Pro Ser Ile Asn Thr Asp Lys Leu Lys Asn Ile Ser
            210                 215                 220
Ser Asn Tyr Cys Leu Gly Arg His Leu Pro Cys Ile Ser Leu His Pro
225                 230                 235                 240
Trp Leu Ser Ser Pro Cys Ser Ser Asp Ser Pro Pro Arg Pro Ser Ser
                245                 250                 255
Cys Leu Leu Ile Pro Ser Pro Glu Asn Asn Ser Glu Arg Leu Leu Val
                260                 265                 270
Asp Thr Arg Arg Phe Leu Ile His His Glu Asn Arg Thr Phe Pro Ser
            275                 280                 285
Thr Gln Leu Pro His Gln Ser Pro Leu Gln Pro Leu Thr Ala Ala Ala
            290                 295                 300
Leu Ala Gly Ser Leu Gly Val Trp Val Gln Asp Thr Pro Phe Ser Thr
305                 310                 315                 320
Pro Ser His Leu Phe Thr Leu His Leu Gln Phe Cys Leu Ala Gln Gly
                325                 330                 335
Leu Phe Phe Leu Cys Gly Ser Ser Thr Tyr Met Cys Leu Pro Ala Asn
                340                 345                 350
Trp Thr Gly Thr Cys Thr Leu Val Phe Leu Thr Pro Lys Ile Gln Phe
                355                 360                 365
Ala Asn Gly Thr Glu Glu Leu Pro Val Pro Leu Met Thr Pro Thr Gln
            370                 375                 380
Gln Lys Arg Val Ile Pro Leu Ile Pro Leu Met Val Gly Leu Gly Leu
385                 390                 395                 400
Ser Ala Ser Thr Val Ala Leu Gly Thr Gly Ile Ala Gly Ile Ser Thr
                405                 410                 415
Ser Val Met Thr Phe Arg Ser Leu Ser Asn Asp Phe Ser Ala Ser Ile
                420                 425                 430
Thr Asp Ile Ser Gln Thr Leu Ser Val Leu Gln Ala Gln Val Asp Ser
            435                 440                 445
Leu Ala Ala Val Val Leu Gln Asn Arg Arg Gly Leu Asp Leu Leu Thr
            450                 455                 460
Ala Glu Lys Gly Gly Leu Cys Ile Phe Leu Asn Glu Glu Cys Cys Phe
465                 470                 475                 480
Tyr Leu Asn Gln Ser Gly Leu Val Tyr Asp Asn Ile Lys Lys Leu Lys
                485                 490                 495
Asp Arg Ala Gln Lys Leu Ala Asn Gln Ala Ser Asn Tyr Ala Glu Pro
            500                 505                 510
Pro Trp Ala Leu Ser Asn Trp Met Ser Trp Val Leu Pro Ile Val Ser
            515                 520                 525
Pro Leu Ile Pro Ile Phe Leu Leu Leu Phe Gly Pro Cys Ile Phe
            530                 535                 540
Arg Leu Val Ser Gln Phe Ile Gln Asn Arg Ile Gln Ala Ile Thr Asn
545                 550                 555                 560
His Ser Ile Arg Gln Met Phe Leu Leu Thr Ser Pro Gln Tyr His Pro
                565                 570                 575
Leu Pro Gln Asp Leu Pro Ser Ala
            580

<210> SEQ ID NO 28
```

<211> LENGTH: 555
<212> TYPE: PRT
<213> ORGANISM: Homo sapiens

<400> SEQUENCE: 28

```
Met Ile Leu Ala Gly Arg Ala Pro Ser Asn Thr Ser Thr Leu Met Lys
1               5                   10                  15

Phe Tyr Ser Leu Leu Tyr Ser Leu Leu Phe Ser Phe Pro Phe Leu
            20                  25                  30

Tyr His Pro Leu Pro Leu Pro Ser Tyr Leu His His Thr Ile Asn Leu
        35                  40                  45

Thr His Ser Leu Pro Ala Ala Ser Asn Pro Ser Leu Ala Asn Asn Cys
    50                  55                  60

Trp Leu Cys Ile Ser Leu Ser Ser Ser Ala Tyr Ile Ala Val Pro Thr
65                  70                  75                  80

Leu Gln Thr Asp Arg Ala Thr Ser Pro Val Ser Leu His Leu Arg Thr
                85                  90                  95

Ser Phe Asn Ser Pro His Leu Tyr Pro Pro Glu Glu Leu Ile Tyr Phe
            100                 105                 110

Leu Asp Arg Ser Ser Lys Thr Ser Pro Asp Ile Ser His Gln Pro Ala
        115                 120                 125

Ala Ala Leu Leu His Ile Tyr Leu Lys Asn Leu Ser Pro Tyr Ile Asn
    130                 135                 140

Ser Thr Pro Pro Ile Phe Gly Pro Leu Thr Thr Gln Thr Thr Ile Pro
145                 150                 155                 160

Val Ala Ala Pro Leu Cys Ile Ser Arg Gln Arg Pro Thr Gly Ile Pro
                165                 170                 175

Leu Gly Asn Ile Ser Pro Ser Arg Cys Ser Phe Thr Leu His Leu Gln
            180                 185                 190

Ser Pro Thr Thr His Val Thr Glu Thr Ile Gly Val Phe Gln Leu His
        195                 200                 205

Ile Ile Asp Lys Pro Ser Ile Asn Thr Asp Lys Leu Lys Asn Val Ser
    210                 215                 220

Ser Asn Tyr Cys Leu Gly Arg His Leu Pro Tyr Ile Ser Leu His Pro
225                 230                 235                 240

Trp Leu Pro Ser Pro Cys Ser Ser Asp Ser Pro Arg Pro Ser Ser
                245                 250                 255

Cys Leu Leu Thr Pro Ser Pro Gln Asn Asn Ser Glu Arg Leu Leu Val
            260                 265                 270

Asp Thr Gln Arg Phe Leu Ile His His Glu Asn Arg Thr Ser Ser Ser
        275                 280                 285

Met Gln Leu Ala His Gln Ser Pro Leu Gln Pro Leu Thr Ala Ala Ala
    290                 295                 300

Leu Ala Gly Ser Leu Gly Val Trp Val Gln Asp Thr Pro Phe Ser Thr
305                 310                 315                 320

Pro Ser His Pro Phe Ser Leu His Leu Gln Phe Cys Leu Thr Gln Gly
                325                 330                 335

Leu Phe Phe Leu Cys Gly Ser Ser Thr Tyr Met Cys Leu Pro Ala Asn
            340                 345                 350

Trp Thr Gly Thr Cys Thr Leu Val Phe Leu Thr Pro Lys Ile Gln Phe
        355                 360                 365

Ala Asn Gly Thr Lys Glu Leu Pro Val Pro Leu Met Thr Leu Thr Pro
    370                 375                 380

Gln Lys Arg Val Ile Pro Leu Ile Pro Leu Met Val Gly Leu Gly Leu
```

```
            385                 390                 395                 400
   Ser Ala Ser Thr Ile Ala Leu Ser Thr Gly Ile Ala Gly Ile Ser Thr
                   405                 410                 415
   Ser Val Thr Thr Phe Arg Ser Pro Ser Asn Asp Phe Ser Ala Ser Ile
                   420                 425                 430
   Thr Asp Ile Ser Gln Thr Leu Ser Val Leu Gln Ala Gln Val Asp Ser
                   435                 440                 445
   Leu Ala Ala Val Val Leu Gln Asn Arg Arg Gly Leu Gly Leu Ser Ile
                   450                 455                 460
   Leu Leu Asn Glu Glu Cys Cys Phe Tyr Leu Asn Gln Ser Gly Leu Val
   465                 470                 475                 480
   Tyr Glu Asn Ile Lys Lys Leu Lys Asp Arg Ala Gln Lys Leu Ala Asn
                   485                 490                 495
   Gln Ala Ser Asn Tyr Ala Glu Ser Pro Trp Ala Leu Ser Asn Trp Met
                   500                 505                 510
   Ser Trp Val Leu Pro Ile Leu Ser Pro Leu Ile Pro Ile Phe Leu Leu
                   515                 520                 525
   Leu Leu Phe Gly Pro Cys Ile Phe His Leu Val Ser Gln Phe Ile Gln
                   530                 535                 540
   Asn Arg Ile Gln Ala Ile Thr Asn His Ser Ile
   545                 550                 555

<210> SEQ ID NO 29
<211> LENGTH: 215
<212> TYPE: PRT
<213> ORGANISM: Homo sapiens

<400> SEQUENCE: 29

Met Gly Asn Leu Pro Pro Ser Ile Pro Pro Ser Ser Pro Leu Ala Cys
   1                   5                   10                  15
   Val Leu Lys Asn Leu Lys Pro Leu Gln Leu Thr Pro Asp Leu Lys Pro
                   20                  25                  30
   Lys Cys Leu Ile Phe Phe Cys Asn Thr Ala Trp Pro Gln Tyr Lys Leu
                   35                  40                  45
   Asp Asn Gly Ser Lys Trp Pro Glu Asn Gly Thr Phe Asp Phe Ser Ile
                   50                  55                  60
   Leu Gln Asp Leu Asn Asn Phe Cys Arg Lys Met Gly Lys Trp Ser Glu
   65                  70                  75                  80
   Val Pro Tyr Val Gln Ala Phe Phe Thr Leu Arg Ser Leu Pro Ser Leu
                   85                  90                  95
   Cys Ser Gln Cys Asp Ala Ser Gln Ile Leu Leu Leu Ser Leu Pro Pro
                   100                 105                 110
   Val Pro Ser Val Pro Thr Pro Ser Val Ala Glu Ser Phe Arg Ser Ser
                   115                 120                 125
   Phe Ser Thr Asp Pro Ser Asp Leu Ser Pro Pro Gln Ala Ala Arg
                   130                 135                 140
   Arg Gln Ala Glu Leu Gly Pro Asn Ser Ser Ala Ser Ala Pro Pro
   145                 150                 155                 160
   Pro Tyr Asn Leu Phe Ile Ala Ser Pro Pro His Thr Trp Ser Gly Leu
                   165                 170                 175
   Gln Phe His Ser Met Thr Ser Leu Pro Pro Ala Gln Gln Phe Thr
                   180                 185                 190
   Leu Lys Lys Val Ala Gly Ala Lys Gly Ile Val Lys Val Asn Ala Pro
                   195                 200                 205
```

-continued

Phe Ser Leu Ser Gln Ile Arg
    210             215

<210> SEQ ID NO 30
<211> LENGTH: 538
<212> TYPE: PRT
<213> ORGANISM: Homo sapiens

<400> SEQUENCE: 30

Met Ala Leu Pro Tyr His Ile Phe Leu Phe Thr Val Leu Leu Pro Ser
1               5                   10                  15

Phe Thr Leu Thr Ala Pro Pro Cys Arg Cys Met Thr Ser Ser Ser
            20                  25                  30

Pro Tyr Gln Glu Phe Leu Trp Arg Met Gln Arg Pro Gly Asn Ile Asp
        35                  40                  45

Ala Pro Ser Tyr Arg Ser Leu Ser Lys Gly Thr Pro Thr Phe Thr Ala
    50                  55                  60

His Thr His Met Pro Arg Asn Cys Tyr His Ser Ala Thr Leu Cys Met
65                  70                  75                  80

His Ala Asn Thr His Tyr Trp Thr Gly Lys Met Ile Asn Pro Ser Cys
                85                  90                  95

Pro Gly Gly Leu Gly Val Thr Val Cys Trp Thr Tyr Phe Thr Gln Thr
            100                 105                 110

Gly Met Ser Asp Gly Gly Val Gln Asp Gln Ala Arg Glu Lys His
            115                 120                 125

Val Lys Glu Val Ile Ser Gln Leu Thr Arg Val His Gly Thr Ser Ser
130                 135                 140

Pro Tyr Lys Gly Leu Asp Leu Ser Lys Leu His Glu Thr Leu Arg Thr
145                 150                 155                 160

His Thr Arg Leu Val Ser Leu Phe Asn Thr Thr Leu Thr Gly Leu His
                165                 170                 175

Glu Val Ser Ala Gln Asn Pro Thr Asn Cys Trp Ile Cys Leu Pro Leu
            180                 185                 190

Asn Phe Arg Pro Tyr Val Ser Ile Pro Val Pro Glu Gln Trp Asn Asn
        195                 200                 205

Phe Ser Thr Glu Ile Asn Thr Thr Ser Val Leu Val Gly Pro Leu Val
    210                 215                 220

Ser Asn Leu Glu Ile Thr His Thr Ser Asn Leu Thr Cys Val Lys Phe
225                 230                 235                 240

Ser Asn Thr Thr Tyr Thr Thr Asn Ser Gln Cys Ile Arg Trp Val Thr
                245                 250                 255

Pro Pro Thr Gln Ile Val Cys Leu Pro Ser Gly Ile Phe Phe Val Cys
            260                 265                 270

Gly Thr Ser Ala Tyr Arg Cys Leu Asn Gly Ser Ser Glu Ser Met Cys
        275                 280                 285

Phe Leu Ser Phe Leu Val Pro Pro Met Thr Ile Tyr Thr Glu Gln Asp
    290                 295                 300

Leu Tyr Ser Tyr Val Ile Ser Lys Pro Arg Asn Lys Arg Val Pro Ile
305                 310                 315                 320

Leu Pro Phe Val Ile Gly Ala Gly Val Leu Gly Ala Leu Gly Thr Gly
                325                 330                 335

Ile Gly Gly Ile Thr Thr Ser Thr Gln Phe Tyr Tyr Lys Leu Ser Gln
            340                 345                 350

Glu Leu Asn Gly Asp Met Glu Arg Val Ala Asp Ser Leu Val Thr Leu
        355                 360                 365

```
Gln Asp Gln Leu Asn Ser Leu Ala Ala Val Val Leu Gln Asn Arg Arg
    370                 375                 380

Ala Leu Asp Leu Leu Thr Ala Glu Arg Gly Gly Thr Cys Leu Phe Leu
385                 390                 395                 400

Gly Glu Glu Cys Cys Tyr Tyr Val Asn Gln Ser Gly Ile Val Thr Glu
                405                 410                 415

Lys Val Lys Glu Ile Arg Asp Arg Ile Gln Arg Arg Ala Glu Glu Leu
            420                 425                 430

Arg Asn Thr Gly Pro Trp Gly Leu Leu Ser Gln Trp Met Pro Trp Ile
            435                 440                 445

Leu Pro Phe Leu Gly Pro Leu Ala Ala Ile Ile Leu Leu Leu Leu Phe
    450                 455                 460

Gly Pro Cys Ile Phe Asn Leu Leu Val Asn Phe Val Ser Ser Arg Ile
465                 470                 475                 480

Glu Ala Val Lys Leu Gln Met Glu Pro Lys Met Gln Ser Lys Thr Lys
                485                 490                 495

Ile Tyr Arg Arg Pro Leu Asp Arg Pro Ala Ser Pro Arg Ser Asp Val
            500                 505                 510

Asn Asp Ile Lys Gly Thr Pro Pro Glu Glu Ile Ser Ala Ala Gln Pro
            515                 520                 525

Leu Leu Arg Pro Asn Ser Ala Gly Ser Ser
    530                 535
```

<210> SEQ ID NO 31
<211> LENGTH: 538
<212> TYPE: PRT
<213> ORGANISM: Homo sapiens

<400> SEQUENCE: 31

```
Met Gly Leu Leu Leu Leu Val Leu Ile Leu Thr Pro Ser Leu Ala Ala
1               5                   10                  15

Tyr Arg His Pro Asp Phe Pro Leu Leu Glu Lys Ala Gln Gln Leu Leu
                20                  25                  30

Gln Ser Thr Gly Ser Pro Tyr Ser Thr Asn Cys Trp Leu Cys Thr Ser
            35                  40                  45

Ser Ser Thr Glu Thr Pro Gly Thr Ala Tyr Pro Ala Ser Pro Arg Glu
    50                  55                  60

Trp Thr Ser Ile Glu Ala Glu Leu His Ile Ser Tyr Arg Trp Asp Pro
65                  70                  75                  80

Asn Leu Lys Gly Leu Met Arg Pro Ala Asn Ser Leu Leu Ser Thr Val
                85                  90                  95

Lys Gln Asp Phe Pro Asp Ile Arg Gln Lys Pro Pro Ile Phe Gly Pro
            100                 105                 110

Ile Phe Thr Asn Ile Asn Leu Met Gly Ile Ala Pro Ile Cys Val Met
        115                 120                 125

Ala Lys Arg Lys Asn Gly Thr Asn Val Gly Thr Leu Pro Ser Thr Val
    130                 135                 140

Cys Asn Val Thr Phe Thr Val Asp Ser Asn Gln Gln Thr Tyr Gln Thr
145                 150                 155                 160

Tyr Thr His Asn Gln Phe Arg His Gln Pro Arg Phe Pro Lys Pro Pro
                165                 170                 175

Asn Ile Thr Phe Pro Gln Gly Thr Leu Leu Asp Lys Ser Ser Arg Phe
            180                 185                 190

Cys Gln Gly Arg Pro Ser Ser Cys Ser Thr Arg Asn Phe Trp Phe Arg
```

```
            195                 200                 205
Pro Ala Asp Tyr Asn Gln Cys Leu Gln Ile Ser Asn Leu Ser Ser Thr
210                 215                 220

Ala Glu Trp Val Leu Leu Asp Gln Thr Arg Asn Ser Leu Phe Trp Glu
225                 230                 235                 240

Asn Lys Thr Lys Gly Ala Asn Gln Ser Gln Thr Pro Cys Val Gln Val
                245                 250                 255

Leu Ala Gly Met Thr Ile Ala Thr Ser Tyr Leu Gly Ile Ser Ala Val
                260                 265                 270

Ser Glu Phe Phe Gly Thr Ser Leu Thr Pro Leu Phe His Phe His Ile
            275                 280                 285

Ser Thr Cys Leu Lys Thr Gln Gly Ala Phe Tyr Ile Cys Gly Gln Ser
290                 295                 300

Ile His Gln Cys Leu Pro Ser Asn Trp Thr Gly Thr Cys Thr Ile Gly
305                 310                 315                 320

Tyr Val Thr Pro Asp Ile Phe Ile Ala Pro Gly Asn Leu Ser Leu Pro
                325                 330                 335

Ile Pro Ile Tyr Gly Asn Ser Pro Leu Pro Arg Val Arg Arg Ala Ile
                340                 345                 350

His Phe Ile Pro Leu Leu Ala Gly Leu Gly Ile Leu Ala Gly Thr Gly
            355                 360                 365

Thr Gly Ile Ala Gly Ile Thr Lys Ala Ser Leu Thr Tyr Ser Gln Leu
370                 375                 380

Ser Lys Glu Ile Ala Asn Asn Ile Asp Thr Met Ala Lys Ala Leu Thr
385                 390                 395                 400

Thr Met Gln Glu Gln Ile Asp Ser Leu Ala Ala Val Val Leu Gln Asn
                405                 410                 415

Arg Arg Gly Leu Asp Met Leu Thr Ala Ala Gln Gly Gly Ile Cys Leu
                420                 425                 430

Ala Leu Asp Glu Lys Cys Cys Phe Trp Val Asn Gln Ser Gly Lys Val
            435                 440                 445

Gln Asp Asn Ile Arg Gln Leu Leu Asn Gln Ala Ser Ser Leu Arg Glu
450                 455                 460

Arg Ala Thr Gln Gly Trp Leu Asn Trp Glu Gly Thr Trp Lys Trp Phe
465                 470                 475                 480

Ser Trp Val Leu Pro Leu Thr Gly Pro Leu Val Ser Leu Leu Leu Leu
                485                 490                 495

Leu Leu Phe Gly Pro Cys Leu Leu Asn Leu Ile Thr Gln Phe Val Ser
                500                 505                 510

Ser Arg Leu Gln Ala Ile Lys Leu Gln Thr Asn Leu Ser Ala Gly Arg
            515                 520                 525

His Pro Arg Asn Ile Gln Glu Ser Pro Phe
530                 535

<210> SEQ ID NO 32
<211> LENGTH: 428
<212> TYPE: PRT
<213> ORGANISM: Homo sapiens

<400> SEQUENCE: 32

Met Gln Lys Leu Ile Met Gly Phe Ile Phe Leu Lys Phe Trp Thr Tyr
1               5                   10                  15

Thr Val Arg Ala Ser Thr Asp Leu Thr Gln Thr Gly Asp Cys Ser Gln
                20                  25                  30
```

Cys Ile His Gln Val Thr Glu Val Gly Gln Gln Ile Lys Thr Met Phe
 35                  40                  45

Leu Phe Tyr Ser Tyr Tyr Lys Cys Ile Gly Thr Leu Lys Glu Thr Cys
 50                  55                  60

Leu Tyr Asn Ala Thr Gln Tyr Asn Val Cys Ser Pro Gly Asn Asp Arg
 65                  70                  75                  80

Pro Asp Val Cys Tyr Asn Pro Ser Glu Pro Pro Ala Thr Thr Ile Phe
                 85                  90                  95

Glu Ile Arg Ile Arg Thr Gly Leu Phe Leu Gly Asp Thr Ser Lys Ile
                100                 105                 110

Ile Thr Arg Thr Glu Glu Lys Glu Ile Pro Lys Gln Ile Thr Leu Arg
            115                 120                 125

Phe Asp Ala Cys Ala Ala Ile Asn Ser Lys Lys Leu Gly Ile Gly Cys
130                 135                 140

Asp Ser Leu Asn Trp Glu Arg Ser Tyr Arg Ile Lys Asn Lys Tyr Val
145                 150                 155                 160

Cys His Glu Ser Gly Val Cys Glu Asn Cys Ala Tyr Trp Pro Cys Val
                165                 170                 175

Ile Trp Ala Thr Trp Lys Lys Asn Lys Lys Asp Pro Val Tyr Leu Gln
                180                 185                 190

Lys Gly Glu Ala Asn Pro Ser Cys Ala Ala Gly His Cys Asn Pro Leu
            195                 200                 205

Glu Leu Ile Ile Thr Asn Pro Leu Asp Pro His Trp Lys Lys Gly Glu
210                 215                 220

Arg Val Thr Leu Gly Ile Asp Gly Thr Gly Leu Asn Pro Gln Val Ala
225                 230                 235                 240

Ile Leu Ile Arg Gly Glu Val His Lys Cys Ser Pro Lys Pro Val Phe
                245                 250                 255

Gln Thr Phe Tyr Lys Glu Leu Asn Leu Pro Ala Pro Glu Phe Pro Lys
                260                 265                 270

Lys Thr Lys Asn Leu Phe Leu Gln Leu Ala Glu Asn Val Ala His Ser
            275                 280                 285

Leu Asn Val Thr Ser Cys Tyr Val Cys Gly Gly Thr Thr Ile Gly Asp
290                 295                 300

Arg Trp Pro Trp Glu Ala Arg Glu Leu Val Pro Thr Asp Pro Ala Pro
305                 310                 315                 320

Asp Ile Ile Pro Val Gln Lys Thr Gln Ala Ser Asn Phe Trp Val Leu
                325                 330                 335

Lys Thr Ser Ile Ile Gly Gln Tyr Cys Ile Ala Arg Glu Gly Lys Asp
            340                 345                 350

Phe Ile Ile Pro Val Gly Lys Leu Asn Cys Ile Gly Gln Lys Leu Tyr
355                 360                 365

Asn Ser Thr Thr Lys Thr Ile Thr Trp Trp Gly Ile Asn His Thr Glu
370                 375                 380

Lys Asn Pro Phe Ser Lys Phe Ser Lys Leu Lys Thr Ala Trp Ala His
385                 390                 395                 400

Pro Glu Ser His Gln Asp Trp Met Ala Pro Ala Gly Leu Tyr Trp Ile
                405                 410                 415

Cys Gly His Arg Ala Tyr Ile Arg Leu Pro Asn Lys
                420                 425

<210> SEQ ID NO 33
<211> LENGTH: 168
<212> TYPE: PRT

<213> ORGANISM: Homo sapiens

<400> SEQUENCE: 33

Met Leu Asn Arg Ile Ile Arg Leu Gln Ala Ile Leu Glu Ile Ile Thr
1               5                   10                  15

Asn Glu Thr Gly Arg Ala Leu Thr Val Leu Ala Arg Gln Glu Thr Gln
            20                  25                  30

Thr Arg Asn Ala Ile Tyr Gln Asn Arg Leu Ala Leu Asp Tyr Leu Leu
        35                  40                  45

Ala Ala Glu Gly Gly Val Cys Gly Lys Phe Asn Leu Thr Asn Tyr Cys
50                  55                  60

Leu Gln Ile Asp Asp Gln Gly Gln Val Val Glu Asn Ile Val Arg Asp
65                  70                  75                  80

Met Ala Lys Val Ala His Val Pro Val Gln Val Trp His Lys Phe Asn
                85                  90                  95

Pro Glu Ser Leu Phe Gly Lys Trp Phe Pro Ala Ile Gly Gly Phe Lys
            100                 105                 110

Thr Leu Ile Val Gly Val Leu Val Ile Gly Thr Cys Leu Leu Leu
        115                 120                 125

Pro Cys Val Leu Pro Leu Leu Phe Gln Met Ile Lys Tyr Phe Val Val
130                 135                 140

Thr Leu Val His Gln Lys Thr Ser Ala His Val Tyr Tyr Thr Asn His
145                 150                 155                 160

Tyr Arg Ser Ile Ser Gln Arg Asp
                165

<210> SEQ ID NO 34
<211> LENGTH: 110
<212> TYPE: PRT
<213> ORGANISM: Homo sapiens

<400> SEQUENCE: 34

Thr Pro Leu Gly Thr Met Leu Lys Asn Phe Lys Lys Gly Phe Asn Gly
1               5                   10                  15

Asp Tyr Gly Val Thr Met Thr Pro Gly Lys Leu Arg Thr Leu Cys Glu
            20                  25                  30

Ile Asp Trp Pro Thr Leu Glu Val Gly Trp Pro Ser Glu Gly Ser Leu
        35                  40                  45

Asp Gly Ser Leu Val Ser Lys Val Trp His Lys Val Thr Ser Lys Ser
50                  55                  60

Gly His Ser Asp Gln Phe Pro Tyr Ile Asp Thr Trp Leu Gln Leu Val
65                  70                  75                  80

Leu Asp Pro Pro Gln Trp Leu Arg Gly Gln Ala Ala Ala Val Leu Val
                85                  90                  95

Ala Lys Gly Gln Ile Val Lys Glu Gly Phe Cys Ser Thr Arg
            100                 105                 110

<210> SEQ ID NO 35
<211> LENGTH: 164
<212> TYPE: PRT
<213> ORGANISM: Homo sapiens

<400> SEQUENCE: 35

Gly Lys Ser Thr Pro Glu Val Leu Phe Asp Gln Thr Ser Glu Asp Pro
1               5                   10                  15

Leu Gln Glu Met Ala Pro Val Ile Pro Val Leu Pro Ser Pro Tyr Gln
            20                  25                  30

```
Gly Glu Arg Leu Pro Thr Phe Glu Ser Thr Val Leu Ala Pro Leu Pro
         35                  40                  45

Asp Lys Cys Ile Pro Arg Pro Leu Arg Val Asp Lys Arg Gly Gly Glu
 50                  55                  60

Ala Ser Gly Glu Thr Pro Pro Leu Ala Ala His Leu Arg Pro Lys Thr
 65                  70                  75                  80

Gly Ile Gln Met Pro Leu Arg Glu Gln Gln Tyr Thr Gly Ile Asp Glu
                 85                  90                  95

Asp Gly His Met Val Glu Ser Arg Val Phe Val Tyr Gln Pro Phe Thr
                100                 105                 110

Ser Ala Asp Leu Leu Asn Trp Lys Asn Asn Thr Pro Ser Tyr Thr Glu
                115                 120                 125

Lys Pro Gln Ala Leu Ile Asp Leu Leu Gln Thr Ile Ile Gln Thr His
130                 135                 140

Asn Pro Thr Trp Ala Asp Cys His Gln Leu Leu Met Phe Leu Phe Lys
145                 150                 155                 160

Thr Asp Glu Arg

<210> SEQ ID NO 36
<211> LENGTH: 39
<212> TYPE: PRT
<213> ORGANISM: Homo sapiens

<400> SEQUENCE: 36

Arg Val Leu Gln Ala Ala Thr Lys Trp Leu Glu Glu His Ala Leu Ala
1               5                  10                  15

Asp Tyr Gln Asn Pro Gln Glu Tyr Val Arg Thr Gln Leu Pro Gly Thr
                20                  25                  30

Asp Pro Gln Trp Asp Pro Asn
                35

<210> SEQ ID NO 37
<211> LENGTH: 120
<212> TYPE: PRT
<213> ORGANISM: Homo sapiens

<400> SEQUENCE: 37

Arg Glu Asp Met Gln Arg Leu Asn Arg Tyr Arg Lys Ala Leu Leu Glu
1               5                  10                  15

Gly Leu Lys Arg Arg Ala Gln Lys Ala Thr Asn Ile Asn Lys Val Ser
                20                  25                  30

Glu Val Ile Gln Gly Lys Glu Ser Pro Ala Lys Phe His Glu Arg
         35                  40                  45

Leu Cys Glu Ala Tyr Cys Met Tyr Thr Pro Phe Asp Pro Asp Ser Pro
 50                  55                  60

Glu Asn Gln Arg Met Ile Asn Met Ala Leu Val Ser Gln Ser Thr Glu
 65                  70                  75                  80

Asp Ile Arg Arg Lys Leu Gln Lys Lys Ala Gly Phe Ala Gly Met Asn
                85                  90                  95

Thr Ser Gln Leu Leu Glu Ile Ala Asn Gln Val Phe Val Asn Arg Asp
                100                 105                 110

Ala Ala Ser Arg Lys Glu Thr Thr
                115                 120

<210> SEQ ID NO 38
<211> LENGTH: 90
```

```
<212> TYPE: PRT
<213> ORGANISM: Homo sapiens

<400> SEQUENCE: 38

Arg Met Asn Val Arg Pro Gly Glu Thr Arg Leu Leu Ala Ala Ala Ile
1               5                   10                  15

Arg Gly Val Pro Pro Lys Glu Ala Arg Gln Lys Gly Gly Pro Gly Lys
                20                  25                  30

Glu Thr Gln Pro Gly Cys Gln Ser Leu Gln Cys Asn Gln Cys Ala Tyr
            35                  40                  45

Arg Lys Glu Ile Gly Tyr Trp Lys Asn Lys Cys Pro Gln Leu Lys Gly
        50                  55                  60

Lys Gln Gly Asp Ser Glu Gln Glu Ala Pro Asp Lys Glu Gly Ala
65                  70                  75                  80

Leu Leu Asn Leu Ala Glu Gly Leu Leu Asp
                85                  90

<210> SEQ ID NO 39
<211> LENGTH: 682
<212> TYPE: PRT
<213> ORGANISM: Homo sapiens

<400> SEQUENCE: 39

Met Arg Lys Leu Ile Val Gly Phe Ile Phe Leu Thr Phe Trp Thr Tyr
1               5                   10                  15

Thr Val Arg Ala Ser Thr Asp Leu Thr Gln Thr Gly Asp Cys Ser Gln
                20                  25                  30

Ser Ile His Gln Val Thr Glu Val Gly Gln Gln Ile Lys Thr Asn Phe
            35                  40                  45

Leu Phe Tyr Ser Tyr Tyr Glu Cys Met Gly Thr Leu Lys Glu Thr Cys
        50                  55                  60

Leu Tyr Asn Ala Thr Gln Tyr Lys Val Cys Ser Pro Gly Asn Asp Arg
65                  70                  75                  80

Pro Asp Val Cys Tyr Asn Pro Ser Glu Pro Pro Ala Thr Thr Val Phe
                85                  90                  95

Glu Ile Arg Leu Arg Thr Gly Leu Phe Leu Gly Asp Thr Ser Lys Ile
            100                 105                 110

Ile Thr Arg Thr Val Glu Lys Gly Ile Pro Lys Gln Ile Thr Leu Arg
        115                 120                 125

Phe Asp Ala Arg Ala Ala Ile Asn Ser Asn Lys Leu Gly Thr Arg Cys
130                 135                 140

Gly Ser Leu Asn Trp Glu Arg Ser Tyr Thr Val Gln Asn Lys Tyr Val
145                 150                 155                 160

Cys His Glu Ser Gly Val Cys Glu Asn Cys Ala Phe Trp Pro Cys Val
                165                 170                 175

Ile Trp Ala Thr Trp Lys Lys Asn Lys Lys Asp Pro Val His Leu Gln
            180                 185                 190

Lys Gly Glu Ala Asn Pro Ser Cys Ala Ala Gly His Cys Asn Pro Leu
        195                 200                 205

Glu Leu Ile Ile Thr Asn Pro Leu Asp Pro Trp Lys Lys Gly Glu
210                 215                 220

Arg Val Thr Leu Gly Ile Asp Gly Thr Gly Leu Asn Pro Gln Val Ala
225                 230                 235                 240

Ile Leu Val Arg Gly Glu Val His Lys Arg Ser Pro Lys Pro Val Phe
                245                 250                 255
```

```
Gln Thr Phe Tyr Glu Glu Leu Asn Leu Pro Ala Pro Glu Leu Pro Lys
            260                 265                 270

Lys Thr Lys Ser Leu Phe Leu Gln Leu Ala Gly Asn Val Ala His Ser
        275                 280                 285

Leu Asn Val Thr Ser Cys Tyr Val Cys Arg Gly Thr Thr Ile Gly Asp
    290                 295                 300

Arg Trp Pro Trp Glu Ala Arg Glu Leu Val Pro Thr Asp Pro Ala Pro
305                 310                 315                 320

Asp Ile Ile Pro Val Gln Lys Ala Gln Ala Ser Asn Phe Trp Val Leu
                325                 330                 335

Lys Thr Ser Ile Ile Gly Gln Tyr Cys Ile Ala Arg Glu Gly Lys Glu
        340                 345                 350

Phe Ile Val Pro Val Gly Lys Leu Asn Cys Ile Gly Gln Lys Leu Tyr
            355                 360                 365

Asn Ser Thr Thr Lys Thr Ile Thr Trp Trp Gly Leu Asn His Thr Glu
    370                 375                 380

Lys Asn Pro Phe Ser Lys Phe Ser Lys Leu Lys Thr Ala Trp Ala His
385                 390                 395                 400

Pro Glu Ser His Gln Asp Trp Thr Ala Pro Thr Gly Leu Tyr Arg Ile
                405                 410                 415

Cys Gly His Thr Ala Tyr Ile Gln Leu Pro Asn Lys Trp Ala Gly Ser
            420                 425                 430

Cys Val Ile Gly Thr Ile Lys Leu Ser Phe Phe Leu Leu Pro Ile Lys
        435                 440                 445

Thr Gly Glu Leu Leu Gly Phe Arg Val Tyr Thr Ser Arg Glu Lys Arg
    450                 455                 460

Gly Ile Val Ile Gly Asn Trp Lys Asp Asn Glu Trp Pro Pro Glu Arg
465                 470                 475                 480

Ile Ile Gln Tyr Tyr Gly Pro Ala Thr Trp Val Gln Asp Gly Ser Trp
                485                 490                 495

Gly Tyr Gln Thr Pro Ile Tyr Met Leu Asn Gln Ile Ile Arg Leu Gln
            500                 505                 510

Thr Val Leu Glu Ile Ile Thr Asn Glu Thr Gly Arg Ala Leu Thr Val
        515                 520                 525

Leu Ala Arg Gln Glu Thr Gln Met Arg Asn Ala Ile Tyr Gln Asn Arg
    530                 535                 540

Leu Ala Leu Asp Tyr Leu Leu Ala Ala Glu Gly Gly Val Cys Gly Lys
545                 550                 555                 560

Phe Asn Leu Thr Asn Cys Cys Leu Gln Ile Asp Asp Gln Gly Gln Val
                565                 570                 575

Ile Glu Asn Ile Val Arg Asp Met Thr Lys Leu Ala His Thr Pro Ile
            580                 585                 590

Gln Val Trp His Lys Phe Asp Pro Glu Ser Leu Phe Gly Lys Trp Phe
        595                 600                 605

Pro Ala Ile Gly Gly Phe Lys Thr Leu Ile Val Gly Val Leu Leu Val
    610                 615                 620

Ile Arg Thr Cys Leu Leu Leu Pro Cys Val Leu Pro Leu Leu Phe Gln
625                 630                 635                 640

Met Ile Lys Gly Ile Val Ala Thr Leu Val His Gln Lys Thr Ser Ala
                645                 650                 655

His Val Asn Tyr Met Asn His Tyr Arg Ser Ile Ser Gln Arg Asp Ser
            660                 665                 670

Lys Ser Glu Asp Glu Ser Glu Asn Ser His
```

<210> SEQ ID NO 40
<211> LENGTH: 523
<212> TYPE: PRT
<213> ORGANISM: Homo sapiens

<400> SEQUENCE: 40

```
Met Leu Lys Asn Phe Lys Lys Gly Phe Asn Gly Asp Tyr Gly Val Thr
1               5                   10                  15

Met Thr Pro Gly Lys Leu Arg Ile Leu Cys Glu Ile Asp Trp Pro Thr
            20                  25                  30

Leu Glu Val Gly Trp Pro Ser Glu Gly Ser Leu Asp Arg Ser Leu Val
        35                  40                  45

Ser Lys Val Trp His Lys Val Thr Gly Lys Ser Gly His Ser Asp Gln
    50                  55                  60

Phe Pro Tyr Ile Asp Thr Trp Leu Leu Gln Leu Val Gln Asp Pro Pro
65                  70                  75                  80

Gln Trp Leu Arg Gly Gln Ala Ala Val Leu Val Ala Lys Gly Gln
                85                  90                  95

Ile Ala Lys Glu Gly Ser Arg Ser Thr His Trp Gly Lys Ser Thr Pro
            100                 105                 110

Glu Val Leu Phe Asp Pro Thr Ser Glu Asp Pro Leu Gln Glu Met Ala
        115                 120                 125

Pro Val Ile Pro Val Leu Pro Ser Pro Tyr Gln Ala Glu Arg Leu Pro
130                 135                 140

Thr Phe Glu Pro Thr Val Leu Val Pro Pro Gln Asp Lys His Ile Pro
145                 150                 155                 160

Arg Pro Pro Arg Val Asp Lys Arg Gly Gly Glu Ala Ser Gly Glu Thr
            165                 170                 175

Pro Pro Leu Ala Ala Cys Leu Arg Pro Lys Thr Gly Ile Gln Met Pro
        180                 185                 190

Leu Arg Glu Gln Arg Tyr Thr Gly Ile Glu Glu Asp Gly His Met Val
    195                 200                 205

Glu Lys Arg Val Phe Val Tyr Gln Pro Phe Thr Ser Ala Asn Leu Leu
    210                 215                 220

Asn Trp Lys Asn Asn Thr Leu Ser Tyr Thr Glu Lys Pro Gln Ala Leu
225                 230                 235                 240

Ile Asp Leu Leu Gln Thr Ile Ile Gln Thr His Asn Ser Thr Arg Ala
            245                 250                 255

Asp Cys His Gln Leu Leu Met Phe Leu Phe Asn Thr Asp Glu Arg Gln
        260                 265                 270

Arg Val Leu Gln Ala Ala Thr Lys Trp Val Gln Glu His Ala Pro Ala
    275                 280                 285

Asp Tyr Gln Asn Pro Gln Glu Cys Val Arg Thr Gln Leu Pro Gly Thr
290                 295                 300

Asp Pro Gln Trp Asp Pro Asn Glu Arg Glu Asp Met Gln Arg Leu Asn
305                 310                 315                 320

Arg Asp Arg Glu Ala Val Leu Glu Gly Leu Lys Arg Gly Ala Gln Lys
            325                 330                 335

Ala Thr Asn Val Asn Lys Val Ser Glu Val Ile Arg Gly Lys Glu Glu
        340                 345                 350

Ser Pro Ala Gln Phe Tyr Gln Arg Leu Cys Glu Gly Tyr Arg Met Tyr
    355                 360                 365
```

```
Thr Pro Phe Asp Pro Val Ser Pro Glu Asn Gln Arg Met Val Asn Met
        370                 375                 380

Ala Leu Val Ser Gln Ser Ala Glu Asp Ile Arg Arg Lys Leu Gln Lys
385                 390                 395                 400

Gln Asp Gly Phe Ala Gly Thr Asn Thr Ser Gln Leu Leu Glu Val Ala
                405                 410                 415

Asn Gln Val Phe Val Asn Arg Asp Ala Val Ser Pro Lys Glu Asn Arg
            420                 425                 430

Arg Glu Asn Glu Arg Gln Ala Arg Arg Asn Ala Glu Leu Leu Ala Ala
        435                 440                 445

Ala Val Gly Gly Val Ser Ser Lys Arg Gln Lys Gly Gly Pro Gly
450                 455                 460

Lys Glu Thr Gln Pro Gly Cys Gln Ser Leu Gln Cys Asn Gln Cys Ala
465                 470                 475                 480

Tyr Cys Lys Glu Ile Gly Tyr Trp Lys Asn Lys Cys Pro Gln Leu Lys
                485                 490                 495

Gly Lys Gln Gly Asp Leu Glu Gln Glu Val Pro Asp Lys Glu Glu Gly
            500                 505                 510

Ala Leu Leu Asn Leu Ala Glu Glu Leu Leu Asp
        515                 520

<210> SEQ ID NO 41
<211> LENGTH: 669
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Env protein from MuLV/MelARV with mutated ISD

<400> SEQUENCE: 41

Met Glu Ser Thr Thr Leu Ser Lys Pro Phe Lys Asn Gln Val Asn Pro
1               5                   10                  15

Trp Gly Pro Leu Ile Val Leu Ile Leu Gly Gly Val Asn Pro Val
            20                  25                  30

Ala Leu Gly Asn Ser Pro His Gln Val Phe Asn Leu Ser Trp Glu Val
        35                  40                  45

Thr Asn Gly Asp Arg Glu Thr Val Trp Ala Ile Thr Gly Asn His Pro
50                  55                  60

Leu Trp Thr Trp Trp Pro Asp Leu Thr Pro Asp Leu Cys Met Leu Ala
65                  70                  75                  80

Leu His Gly Pro Ser Tyr Trp Gly Leu Glu Tyr Arg Ala Pro Phe Ser
                85                  90                  95

Pro Pro Pro Gly Pro Pro Cys Cys Ser Gly Ser Ser Asp Ser Thr Ser
            100                 105                 110

Gly Cys Ser Arg Asp Cys Glu Glu Pro Leu Thr Ser Tyr Thr Pro Arg
        115                 120                 125

Cys Asn Thr Ala Trp Asn Arg Leu Lys Leu Ser Lys Val Thr His Ala
130                 135                 140

His Asn Glu Gly Phe Tyr Val Cys Pro Gly Pro His Arg Pro Arg Trp
145                 150                 155                 160

Ala Arg Ser Cys Gly Gly Pro Glu Ser Phe Tyr Cys Ala Ser Trp Gly
                165                 170                 175

Cys Glu Thr Thr Gly Arg Ala Ser Trp Lys Pro Ser Ser Ser Trp Asp
            180                 185                 190
```

-continued

```
Tyr Ile Thr Val Ser Asn Asn Leu Thr Ser Asp Gln Ala Thr Pro Val
            195                 200                 205
Cys Lys Gly Asn Lys Trp Cys Asn Ser Leu Thr Ile Arg Phe Thr Ser
    210                 215                 220
Phe Gly Lys Gln Ala Thr Ser Trp Val Thr Gly His Trp Trp Gly Leu
225                 230                 235                 240
Arg Leu Tyr Val Ser Gly His Asp Pro Gly Leu Ile Phe Gly Ile Arg
                245                 250                 255
Leu Lys Ile Thr Asp Ser Gly Pro Arg Val Pro Ile Gly Pro Asn Pro
            260                 265                 270
Val Leu Ser Asp Arg Arg Pro Pro Ser Arg Pro Arg Pro Thr Arg Ser
        275                 280                 285
Pro Pro Pro Ser Asn Ser Thr Pro Thr Glu Thr Pro Leu Thr Leu Pro
    290                 295                 300
Glu Pro Pro Pro Ala Gly Val Glu Asn Arg Leu Leu Asn Leu Val Lys
305                 310                 315                 320
Gly Ala Tyr Gln Ala Leu Asn Leu Thr Ser Pro Asp Lys Thr Gln Glu
                325                 330                 335
Cys Trp Leu Cys Leu Val Ser Gly Pro Pro Tyr Tyr Glu Gly Val Ala
            340                 345                 350
Val Leu Gly Thr Tyr Ser Asn His Thr Ser Ala Pro Ala Asn Cys Ser
        355                 360                 365
Val Ala Ser Gln His Lys Leu Thr Leu Ser Glu Val Thr Gly Gln Gly
    370                 375                 380
Leu Cys Ile Gly Ala Val Pro Lys Thr His Gln Val Leu Cys Asn Thr
385                 390                 395                 400
Thr Gln Lys Thr Ser Asp Gly Ser Tyr Tyr Leu Val Ala Pro Thr Gly
                405                 410                 415
Thr Thr Trp Ala Cys Ser Thr Gly Leu Thr Pro Cys Ile Ser Thr Thr
            420                 425                 430
Ile Leu Asn Leu Thr Thr Asp Tyr Cys Val Leu Val Glu Leu Trp Pro
        435                 440                 445
Arg Val Thr Tyr His Ser Pro Ser Tyr Val Tyr His Gln Phe Glu Arg
    450                 455                 460
Arg Ala Lys Tyr Lys Arg Glu Pro Val Ser Leu Thr Leu Ala Leu Leu
465                 470                 475                 480
Leu Gly Gly Leu Thr Met Gly Gly Ile Ala Ala Gly Val Gly Thr Gly
                485                 490                 495
Thr Thr Ala Leu Val Ala Thr Gln Gln Phe Gln Gln Leu Gln Ala Ala
            500                 505                 510
Met His Asp Asp Leu Lys Glu Val Glu Lys Ser Ile Thr Asn Leu Glu
        515                 520                 525
Lys Ser Leu Thr Ser Leu Ser Glu Val Val Leu Gln Asn Arg Arg Gly
    530                 535                 540
Leu Asp Leu Leu Phe Leu Lys Arg Gly Gly Leu Cys Ala Phe Leu Lys
545                 550                 555                 560
Glu Glu Cys Cys Phe Tyr Ala Asp His Thr Gly Leu Val Arg Asp Ser
                565                 570                 575
Met Ala Lys Leu Arg Glu Arg Leu Ser Gln Arg Gln Lys Leu Phe Glu
            580                 585                 590
Ser Gln Gln Gly Trp Phe Glu Gly Leu Phe Asn Lys Ser Pro Trp Phe
        595                 600                 605
Thr Thr Leu Ile Ser Thr Ile Met Gly Pro Leu Ile Ile Leu Leu Leu
```

```
                610              615              620
Ile Leu Leu Phe Gly Pro Cys Ile Leu Asn Arg Leu Val Gln Phe Ile
625                 630                 635                 640

Lys Asp Arg Ile Ser Val Val Gln Ala Leu Val Leu Thr Gln Gln Tyr
                645                 650                 655

His Gln Leu Lys Thr Ile Gly Asp Cys Lys Ser Arg Glu
            660                 665
```

<210> SEQ ID NO 42
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: MuLV/MelARV env polyprotein P15E (amino acid
      94-136)

<400> SEQUENCE: 42

```
Cys Phe Tyr Ala Asp His Thr Gly Leu Val Arg Asp Ser Met Ala Lys
1               5                   10                  15

Leu Arg Glu Arg Leu Ser Gln Arg Gln Lys Leu Phe Glu Ser Gln Gln
            20                  25                  30

Gly Trp Phe Glu Gly Leu Phe Asn Lys Ser Pro
        35                  40
```

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Ad19_HERV-K ISD partial coding sequence

<400> SEQUENCE: 43
gccaaccaga tcaacgacct                                               20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Ad19_HERV-K mutated ISD partial coding sequence

<400> SEQUENCE: 44
gccaacgcca tcaacgacct                                               20

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: forward PCR primer for HERV-K Env including
      BspEI site

<400> SEQUENCE: 45
cccgtgtccg gacctgag                                                 18

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic
    primer
<220> FEATURE:
<223> OTHER INFORMATION: reverse PCR primer for HERV-K Env including
    XbaI site

<400> SEQUENCE: 46
gttctagact tgtcctgaat tttctggtta                                    30

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: HERV-K Env P-HKE peptide sequence used for
    analysis of T cell immune responses

<400> SEQUENCE: 47

Thr Tyr His Met Val Ser Gly Met Ser Leu
1               5                   10

<210> SEQ ID NO 48
<211> LENGTH: 1387
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: HERV-K (codon-optimized consensus protein
    sequence) of Gag-P2A-linked to Env protein that comprises a
    mutated ISD sequence

<400> SEQUENCE: 48

Met Gly Gln Thr Lys Ser Lys Ile Lys Ser Lys Tyr Ala Ser Tyr Leu
1               5                   10                  15

Ser Phe Ile Lys Ile Leu Leu Lys Arg Gly Gly Val Lys Val Ser Thr
            20                  25                  30

Lys Asn Leu Ile Lys Leu Phe Gln Ile Ile Glu Gln Phe Cys Pro Trp
        35                  40                  45

Phe Pro Glu Gln Gly Thr Leu Asp Leu Lys Asp Trp Lys Arg Ile Gly
    50                  55                  60

Lys Glu Leu Lys Gln Ala Gly Arg Lys Gly Asn Ile Ile Pro Leu Thr
65                  70                  75                  80

Val Trp Asn Asp Trp Ala Ile Ile Lys Ala Ala Leu Glu Pro Phe Gln
                85                  90                  95

Thr Glu Glu Asp Ser Val Ser Val Ser Asp Ala Pro Gly Ser Cys Ile
            100                 105                 110

Ile Asp Cys Asn Glu Asn Thr Arg Lys Lys Ser Gln Lys Glu Thr Glu
        115                 120                 125

Gly Leu His Cys Glu Tyr Val Ala Glu Pro Val Met Ala Gln Ser Thr
    130                 135                 140

Gln Asn Val Asp Tyr Asn Gln Leu Gln Glu Val Ile Tyr Pro Glu Thr
145                 150                 155                 160

-continued

Leu Lys Leu Glu Gly Lys Gly Pro Glu Leu Val Gly Pro Ser Glu Ser
            165                 170                 175

Lys Pro Arg Gly Thr Ser Pro Leu Pro Ala Gly Gln Val Pro Val Thr
            180                 185                 190

Leu Gln Pro Gln Lys Gln Val Lys Glu Asn Lys Thr Gln Pro Pro Val
            195                 200                 205

Ala Tyr Gln Tyr Trp Pro Pro Ala Glu Leu Gln Tyr Arg Pro Pro Pro
            210                 215                 220

Glu Ser Gln Tyr Gly Tyr Pro Gly Met Pro Ala Pro Gln Gly Arg
225                 230                 235                 240

Ala Pro Tyr Pro Gln Pro Pro Thr Arg Arg Leu Asn Pro Thr Ala Pro
            245                 250                 255

Pro Ser Arg Gln Gly Ser Glu Leu His Glu Ile Ile Asp Lys Ser Arg
            260                 265                 270

Lys Glu Gly Asp Thr Glu Ala Trp Gln Phe Pro Val Thr Leu Glu Pro
            275                 280                 285

Met Pro Pro Gly Glu Gly Ala Gln Glu Gly Pro Pro Thr Val Glu
            290                 295                 300

Ala Arg Tyr Lys Ser Phe Ser Ile Lys Met Leu Lys Asp Met Lys Glu
305                 310                 315                 320

Gly Val Lys Gln Tyr Gly Pro Asn Ser Pro Tyr Met Arg Thr Leu Leu
            325                 330                 335

Asp Ser Ile Ala His Gly His Arg Leu Ile Pro Tyr Asp Trp Glu Ile
            340                 345                 350

Leu Ala Lys Ser Ser Leu Ser Pro Ser Gln Phe Leu Gln Phe Lys Thr
            355                 360                 365

Trp Trp Ile Asp Gly Val Gln Glu Gln Val Arg Arg Asn Arg Ala Ala
            370                 375                 380

Asn Pro Pro Val Asn Ile Asp Ala Asp Gln Leu Leu Gly Ile Gly Gln
385                 390                 395                 400

Asn Trp Ser Thr Ile Ser Gln Gln Ala Leu Met Gln Asn Glu Ala Ile
            405                 410                 415

Glu Gln Val Arg Ala Ile Cys Leu Arg Ala Trp Glu Lys Ile Gln Asp
            420                 425                 430

Pro Gly Ser Thr Cys Pro Ser Phe Asn Thr Val Arg Gln Gly Ser Lys
            435                 440                 445

Glu Pro Tyr Pro Asp Phe Val Ala Arg Leu Gln Asp Val Ala Gln Lys
            450                 455                 460

Ser Ile Ala Asp Glu Lys Ala Arg Lys Val Ile Val Glu Leu Met Ala
465                 470                 475                 480

Tyr Glu Asn Ala Asn Pro Glu Cys Gln Ser Ala Ile Lys Pro Leu Lys
            485                 490                 495

Gly Lys Val Pro Ala Gly Ser Asp Val Ile Ser Glu Tyr Val Lys Ala
            500                 505                 510

Cys Asp Gly Ile Gly Gly Ala Met His Lys Ala Met Leu Met Ala Gln
            515                 520                 525

Ala Ile Thr Gly Val Val Leu Gly Gly Gln Val Arg Thr Phe Gly Gly
            530                 535                 540

Lys Cys Tyr Asn Cys Gly Gln Ile Gly His Leu Lys Lys Asn Cys Pro
545                 550                 555                 560

Val Leu Asn Lys Gln Asn Ile Thr Ile Gln Ala Thr Thr Thr Gly Arg
            565                 570                 575

Glu Pro Pro Asp Leu Cys Pro Arg Cys Lys Lys Gly Lys His Trp Ala

```
                580                585                590
Ser Gln Cys Arg Ser Lys Phe Asp Lys Asn Gly Gln Pro Leu Ser Gly
            595                600                605
Asn Glu Gln Arg Gly Gln Pro Gln Ala Pro Gln Gln Thr Gly Ala Phe
            610                615                620
Pro Ile Gln Pro Phe Val Pro Gln Gly Phe Gln Gly Gln Gln Pro Pro
625                630                635                640
Leu Ser Gln Val Phe Gln Gly Ile Ser Gln Leu Pro Gln Tyr Asn Asn
            645                650                655
Cys Pro Pro Pro Gln Ala Ala Val Gln Gln Gly Ser Gly Ala Thr Asn
            660                665                670
Phe Ser Leu Leu Lys Gln Ala Gly Asp Val Glu Glu Asn Pro Gly Pro
            675                680                685
Met Asn Pro Ser Glu Met Gln Arg Lys Ala Pro Pro Arg Arg Arg Arg
            690                695                700
His Arg Asn Arg Ala Pro Leu Thr His Lys Met Asn Lys Met Val Thr
705                710                715                720
Ser Glu Glu Gln Met Lys Leu Pro Ser Thr Lys Lys Ala Glu Pro Pro
            725                730                735
Thr Trp Ala Gln Leu Lys Lys Leu Thr Gln Leu Ala Thr Lys Tyr Leu
            740                745                750
Glu Asn Thr Lys Val Thr Gln Thr Pro Glu Ser Met Leu Leu Ala Ala
            755                760                765
Leu Met Ile Val Ser Met Val Val Ser Leu Pro Met Pro Ala Gly Ala
            770                775                780
Ala Ala Ala Asn Tyr Thr Tyr Trp Ala Tyr Val Pro Phe Pro Pro Leu
785                790                795                800
Ile Arg Ala Val Thr Trp Met Asp Asn Pro Ile Glu Val Tyr Val Asn
            805                810                815
Asp Ser Val Trp Val Pro Gly Pro Ile Asp Asp Arg Cys Pro Ala Lys
            820                825                830
Pro Glu Glu Glu Gly Met Met Ile Asn Ile Ser Ile Gly Tyr Arg Tyr
            835                840                845
Pro Pro Ile Cys Leu Gly Arg Ala Pro Gly Cys Leu Met Pro Ala Val
            850                855                860
Gln Asn Trp Leu Val Glu Val Pro Thr Val Ser Pro Ile Ser Arg Phe
865                870                875                880
Thr Tyr His Met Val Ser Gly Met Ser Leu Arg Pro Arg Val Asn Tyr
            885                890                895
Leu Gln Asp Phe Ser Tyr Gln Arg Ser Leu Lys Phe Arg Pro Lys Gly
            900                905                910
Lys Pro Cys Pro Lys Glu Ile Pro Lys Glu Ser Lys Asn Thr Glu Val
            915                920                925
Leu Val Trp Glu Glu Cys Val Ala Asn Ser Ala Val Ile Leu Gln Asn
            930                935                940
Asn Glu Phe Gly Thr Ile Ile Asp Trp Ala Pro Arg Gly Gln Phe Tyr
945                950                955                960
His Asn Cys Ser Gly Gln Thr Gln Ser Cys Pro Ser Ala Gln Val Ser
            965                970                975
Pro Ala Val Asp Ser Asp Leu Thr Glu Ser Leu Asp Lys His Lys His
            980                985                990
Lys Lys Leu Gln Ser Phe Tyr Pro  Trp Glu Trp Gly Glu  Lys Gly Ile
            995               1000               1005
```

```
Ser Thr Pro Arg Pro Lys Ile Val Ser Pro Val Ser Gly Pro Glu
    1010            1015            1020

His Pro Glu Leu Trp Arg Leu Thr Val Ala Ser His His Ile Arg
    1025            1030            1035

Ile Trp Ser Gly Asn Gln Thr Leu Glu Thr Arg Asp Arg Lys Pro
    1040            1045            1050

Phe Tyr Thr Val Asp Leu Asn Ser Ser Leu Thr Val Pro Leu Gln
    1055            1060            1065

Ser Cys Val Lys Pro Pro Tyr Met Leu Val Val Gly Asn Ile Val
    1070            1075            1080

Ile Lys Pro Asp Ser Gln Thr Ile Thr Cys Glu Asn Cys Arg Leu
    1085            1090            1095

Leu Thr Cys Ile Asp Ser Thr Phe Asn Trp Gln His Arg Ile Leu
    1100            1105            1110

Leu Val Arg Ala Arg Glu Gly Val Trp Ile Pro Val Ser Met Asp
    1115            1120            1125

Arg Pro Trp Glu Ala Ser Pro Ser Val His Ile Leu Thr Glu Val
    1130            1135            1140

Leu Lys Gly Val Leu Asn Arg Ser Lys Arg Phe Ile Phe Thr Leu
    1145            1150            1155

Ile Ala Val Ile Met Gly Leu Ile Ala Val Thr Ala Thr Ala Ala
    1160            1165            1170

Val Ala Gly Val Ala Leu His Ser Ser Val Gln Ser Val Asn Phe
    1175            1180            1185

Val Asn Asp Trp Gln Lys Asn Ser Thr Arg Leu Trp Asn Ser Gln
    1190            1195            1200

Ser Ser Ile Asp Gln Lys Leu Ala Asn Ala Ile Asn Asp Leu Arg
    1205            1210            1215

Gln Thr Val Ile Trp Met Gly Asp Arg Leu Met Ser Leu Glu His
    1220            1225            1230

Arg Phe Gln Leu Gln Cys Asp Trp Asn Thr Ser Asp Phe Cys Ile
    1235            1240            1245

Thr Pro Gln Ile Tyr Asn Glu Ser Glu His His Trp Asp Met Val
    1250            1255            1260

Arg Arg His Leu Gln Gly Arg Glu Asp Asn Leu Thr Leu Asp Ile
    1265            1270            1275

Ser Lys Leu Lys Glu Gln Ile Phe Glu Ala Ser Lys Ala His Leu
    1280            1285            1290

Asn Leu Val Pro Gly Thr Glu Ala Ile Ala Gly Val Ala Asp Gly
    1295            1300            1305

Leu Ala Asn Leu Asn Pro Val Thr Trp Val Lys Thr Ile Gly Ser
    1310            1315            1320

Thr Thr Ile Ile Asn Leu Ile Leu Ile Leu Val Cys Leu Phe Cys
    1325            1330            1335

Leu Leu Leu Val Cys Arg Cys Thr Gln Gln Leu Arg Arg Asp Ser
    1340            1345            1350

Asp His Arg Glu Arg Ala Met Met Thr Met Ala Val Leu Ser Lys
    1355            1360            1365

Arg Lys Gly Gly Asn Val Gly Lys Ser Lys Arg Asp Gln Ile Val
    1370            1375            1380

Thr Val Ser Val
    1385
```

<210> SEQ ID NO 49
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: HERV-K Env protein native ISD partial

<400> SEQUENCE: 49

Asn Ser Gln Ser Ser Ile Asp Gln Lys Leu Ala Asn Gln Ile Asn Asp
1               5                   10                  15

Leu Arg Gln Thr
            20

<210> SEQ ID NO 50
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: HERV-K Env protein mutated ISD partial

<400> SEQUENCE: 50

Asn Ser Gln Ser Ser Ile Asp Gln Lys Leu Ala Asn Ala Ile Asn Asp
1               5                   10                  15

Leu Arg Gln Thr
            20

<210> SEQ ID NO 51
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: MuLV/MelARV Env p15E protein (partial sequence)

<400> SEQUENCE: 51

Thr Gly Thr Thr Ala Leu Val Ala Thr Gln Gln Phe Gln Gln Leu Gln
1               5                   10                  15

Ala Ala Met His Asp Asp Leu Lys Glu Val Glu Lys Ser Ile Thr Asn
                20                  25                  30

Leu Glu Lys Ser Leu Thr Ser Leu Ser Glu Val Val Leu Gln Asn Arg
            35                  40                  45

Arg Gly Leu Asp Leu Leu Phe Leu Lys Glu Gly Gly Leu Cys Ala Ala
        50                  55                  60

Leu Lys Glu Glu Cys Cys Phe Tyr Ala Asp His Thr Gly Leu Val Arg
65                  70                  75                  80

Asp Ser Met Ala Lys Leu Arg Glu Arg Leu Ser Gln Arg Gln Lys Leu
                85                  90                  95

Phe Glu Ser Gln Gln Gly Trp Phe Glu Gly Leu Phe Asn
            100                 105

<210> SEQ ID NO 52
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: MuLV/MelARV p15E protein (partial sequence with mutated ISD)

<400> SEQUENCE: 52

```
Thr Gly Thr Thr Ala Leu Val Ala Thr Gln Gln Phe Gln Gln Leu Gln
1               5                   10                  15

Ala Ala Met His Asp Asp Leu Lys Glu Val Glu Lys Ser Ile Thr Asn
            20                  25                  30

Leu Glu Lys Ser Leu Thr Ser Leu Ser Glu Val Val Leu Gln Asn Arg
        35                  40                  45

Arg Gly Leu Asp Leu Leu Phe Leu Lys Arg Gly Gly Leu Cys Ala Phe
    50                  55                  60

Leu Lys Glu Glu Cys Cys Phe Tyr Ala Asp His Thr Gly Leu Val Arg
65                  70                  75                  80

Asp Ser Met Ala Lys Leu Arg Glu Arg Leu Ser Gln Arg Gln Lys Leu
                85                  90                  95

Phe Glu Ser Gln Gln Gly Trp Phe Glu Gly Leu Phe Asn
            100                 105
```

<210> SEQ ID NO 53
<211> LENGTH: 62
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: MuLV/MelARV p15E protein (partial sequence)

<400> SEQUENCE: 53

```
Thr Gly Thr Thr Ala Leu Val Ala Thr Gln Gln Phe Gln Gln Leu Gln
1               5                   10                  15

Ala Ala Met His Asp Asp Leu Lys Glu Val Glu Lys Ser Ile Thr Asn
            20                  25                  30

Leu Glu Lys Ser Leu Thr Ser Leu Ser Glu Val Val Leu Gln Asn Arg
        35                  40                  45

Arg Gly Leu Asp Leu Leu Phe Leu Lys Glu Gly Gly Leu Cys
    50                  55                  60
```

<210> SEQ ID NO 54
<211> LENGTH: 61
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: MuLV/MelARV p15E protein (partial sequence)

<400> SEQUENCE: 54

```
Thr Gly Thr Thr Ala Leu Val Ala Thr Gln Gln Phe Gln Gln Leu Gln
1               5                   10                  15

Ala Ala Met His Asp Asp Leu Lys Glu Val Glu Lys Ser Ile Thr Asn
            20                  25                  30

Leu Glu Lys Ser Leu Thr Ser Leu Ser Glu Val Val Leu Gln Asn Arg
        35                  40                  45

Arg Gly Leu Asp Leu Leu Phe Leu Lys Glu Gly Gly Leu
    50                  55                  60
```

```
<210> SEQ ID NO 55
<211> LENGTH: 1387
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HERV-K (codon-optimized consensus protein
      sequence) of Gag-P2A-Env

<400> SEQUENCE: 55
```

| Met | Gly | Gln | Thr | Lys | Ser | Lys | Ile | Lys | Ser | Lys | Tyr | Ala | Ser | Tyr | Leu |
|---|---|---|---|---|---|---|---|---|---|---|---|---|---|---|---|
| 1 | | | | 5 | | | | | 10 | | | | | 15 | |

| Ser | Phe | Ile | Lys | Ile | Leu | Leu | Lys | Arg | Gly | Gly | Val | Lys | Val | Ser | Thr |
|---|---|---|---|---|---|---|---|---|---|---|---|---|---|---|---|
| | | | 20 | | | | | 25 | | | | | 30 | | |

| Lys | Asn | Leu | Ile | Lys | Leu | Phe | Gln | Ile | Ile | Glu | Gln | Phe | Cys | Pro | Trp |
|---|---|---|---|---|---|---|---|---|---|---|---|---|---|---|---|
| | 35 | | | | | 40 | | | | | 45 | | | | |

| Phe | Pro | Glu | Gln | Gly | Thr | Leu | Asp | Leu | Lys | Asp | Trp | Lys | Arg | Ile | Gly |
|---|---|---|---|---|---|---|---|---|---|---|---|---|---|---|---|
| 50 | | | | | 55 | | | | | 60 | | | | | |

| Lys | Glu | Leu | Lys | Gln | Ala | Gly | Arg | Lys | Gly | Asn | Ile | Ile | Pro | Leu | Thr |
|---|---|---|---|---|---|---|---|---|---|---|---|---|---|---|---|
| 65 | | | | | 70 | | | | | 75 | | | | | 80 |

| Val | Trp | Asn | Asp | Trp | Ala | Ile | Ile | Lys | Ala | Ala | Leu | Glu | Pro | Phe | Gln |
|---|---|---|---|---|---|---|---|---|---|---|---|---|---|---|---|
| | | | | 85 | | | | | 90 | | | | | 95 | |

| Thr | Glu | Glu | Asp | Ser | Val | Ser | Val | Ser | Asp | Ala | Pro | Gly | Ser | Cys | Ile |
|---|---|---|---|---|---|---|---|---|---|---|---|---|---|---|---|
| | | | 100 | | | | | 105 | | | | | 110 | | |

| Ile | Asp | Cys | Asn | Glu | Asn | Thr | Arg | Lys | Lys | Ser | Gln | Lys | Glu | Thr | Glu |
|---|---|---|---|---|---|---|---|---|---|---|---|---|---|---|---|
| | | 115 | | | | | 120 | | | | | 125 | | | |

| Gly | Leu | His | Cys | Glu | Tyr | Val | Ala | Glu | Pro | Val | Met | Ala | Gln | Ser | Thr |
|---|---|---|---|---|---|---|---|---|---|---|---|---|---|---|---|
| 130 | | | | | 135 | | | | | 140 | | | | | |

| Gln | Asn | Val | Asp | Tyr | Asn | Gln | Leu | Gln | Glu | Val | Ile | Tyr | Pro | Glu | Thr |
|---|---|---|---|---|---|---|---|---|---|---|---|---|---|---|---|
| 145 | | | | | 150 | | | | | 155 | | | | | 160 |

| Leu | Lys | Leu | Glu | Gly | Lys | Gly | Pro | Glu | Leu | Val | Gly | Pro | Ser | Glu | Ser |
|---|---|---|---|---|---|---|---|---|---|---|---|---|---|---|---|
| | | | | 165 | | | | | 170 | | | | | 175 | |

| Lys | Pro | Arg | Gly | Thr | Ser | Pro | Leu | Pro | Ala | Gly | Gln | Val | Pro | Val | Thr |
|---|---|---|---|---|---|---|---|---|---|---|---|---|---|---|---|
| | | | 180 | | | | | 185 | | | | | 190 | | |

| Leu | Gln | Pro | Gln | Lys | Gln | Val | Lys | Glu | Asn | Lys | Thr | Gln | Pro | Pro | Val |
|---|---|---|---|---|---|---|---|---|---|---|---|---|---|---|---|
| | | 195 | | | | | 200 | | | | | 205 | | | |

| Ala | Tyr | Gln | Tyr | Trp | Pro | Pro | Ala | Glu | Leu | Gln | Tyr | Arg | Pro | Pro | Pro |
|---|---|---|---|---|---|---|---|---|---|---|---|---|---|---|---|
| 210 | | | | | 215 | | | | | 220 | | | | | |

| Glu | Ser | Gln | Tyr | Gly | Tyr | Pro | Gly | Met | Pro | Pro | Ala | Pro | Gln | Gly | Arg |
|---|---|---|---|---|---|---|---|---|---|---|---|---|---|---|---|
| 225 | | | | | 230 | | | | | 235 | | | | | 240 |

| Ala | Pro | Tyr | Pro | Gln | Pro | Pro | Thr | Arg | Arg | Leu | Asn | Pro | Thr | Ala | Pro |
|---|---|---|---|---|---|---|---|---|---|---|---|---|---|---|---|
| | | | | 245 | | | | | 250 | | | | | 255 | |

| Pro | Ser | Arg | Gln | Gly | Ser | Glu | Leu | His | Glu | Ile | Ile | Asp | Lys | Ser | Arg |
|---|---|---|---|---|---|---|---|---|---|---|---|---|---|---|---|
| | | | 260 | | | | | 265 | | | | | 270 | | |

| Lys | Glu | Gly | Asp | Thr | Glu | Ala | Trp | Gln | Phe | Pro | Val | Thr | Leu | Glu | Pro |
|---|---|---|---|---|---|---|---|---|---|---|---|---|---|---|---|
| | | 275 | | | | | 280 | | | | | 285 | | | |

| Met | Pro | Pro | Gly | Glu | Gly | Ala | Gln | Glu | Gly | Glu | Pro | Pro | Thr | Val | Glu |
|---|---|---|---|---|---|---|---|---|---|---|---|---|---|---|---|
| 290 | | | | | 295 | | | | | 300 | | | | | |

| Ala | Arg | Tyr | Lys | Ser | Phe | Ser | Ile | Lys | Met | Leu | Lys | Asp | Met | Lys | Glu |
|---|---|---|---|---|---|---|---|---|---|---|---|---|---|---|---|
| 305 | | | | | 310 | | | | | 315 | | | | | 320 |

| Gly | Val | Lys | Gln | Tyr | Gly | Pro | Asn | Ser | Pro | Tyr | Met | Arg | Thr | Leu | Leu |
|---|---|---|---|---|---|---|---|---|---|---|---|---|---|---|---|
| | | | | 325 | | | | | 330 | | | | | 335 | |

| Asp | Ser | Ile | Ala | His | Gly | His | Arg | Leu | Ile | Pro | Tyr | Asp | Trp | Glu | Ile |
|---|---|---|---|---|---|---|---|---|---|---|---|---|---|---|---|
| | | | 340 | | | | | 345 | | | | | 350 | | |

```
Leu Ala Lys Ser Ser Leu Ser Pro Ser Gln Phe Leu Gln Phe Lys Thr
        355                 360                 365

Trp Trp Ile Asp Gly Val Gln Glu Gln Val Arg Arg Asn Arg Ala Ala
370                 375                 380

Asn Pro Pro Val Asn Ile Asp Ala Asp Gln Leu Leu Gly Ile Gly Gln
385                 390                 395                 400

Asn Trp Ser Thr Ile Ser Gln Ala Leu Met Gln Asn Glu Ala Ile
                405                 410                 415

Glu Gln Val Arg Ala Ile Cys Leu Arg Ala Trp Glu Lys Ile Gln Asp
            420                 425                 430

Pro Gly Ser Thr Cys Pro Ser Phe Asn Thr Val Arg Gln Gly Ser Lys
        435                 440                 445

Glu Pro Tyr Pro Asp Phe Val Ala Arg Leu Gln Asp Val Ala Gln Lys
    450                 455                 460

Ser Ile Ala Asp Glu Lys Ala Arg Lys Val Ile Val Glu Leu Met Ala
465                 470                 475                 480

Tyr Glu Asn Ala Asn Pro Glu Cys Gln Ser Ala Ile Lys Pro Leu Lys
                485                 490                 495

Gly Lys Val Pro Ala Gly Ser Asp Val Ile Ser Glu Tyr Val Lys Ala
            500                 505                 510

Cys Asp Gly Ile Gly Gly Ala Met His Lys Ala Met Leu Met Ala Gln
        515                 520                 525

Ala Ile Thr Gly Val Val Leu Gly Gly Gln Val Arg Thr Phe Gly Gly
    530                 535                 540

Lys Cys Tyr Asn Cys Gly Gln Ile Gly His Leu Lys Lys Asn Cys Pro
545                 550                 555                 560

Val Leu Asn Lys Gln Asn Ile Thr Ile Gln Ala Thr Thr Thr Gly Arg
                565                 570                 575

Glu Pro Pro Asp Leu Cys Pro Arg Cys Lys Lys Gly Lys His Trp Ala
            580                 585                 590

Ser Gln Cys Arg Ser Lys Phe Asp Lys Asn Gly Gln Pro Leu Ser Gly
        595                 600                 605

Asn Glu Gln Arg Gly Gln Pro Gln Ala Pro Gln Gln Thr Gly Ala Phe
    610                 615                 620

Pro Ile Gln Pro Phe Val Pro Gln Gly Phe Gln Gly Gln Gln Pro Pro
625                 630                 635                 640

Leu Ser Gln Val Phe Gln Gly Ile Ser Gln Leu Pro Gln Tyr Asn Asn
                645                 650                 655

Cys Pro Pro Pro Gln Ala Ala Val Gln Gln Gly Ser Gly Ala Thr Asn
            660                 665                 670

Phe Ser Leu Leu Lys Gln Ala Gly Asp Val Glu Glu Asn Pro Gly Pro
        675                 680                 685

Met Asn Pro Ser Glu Met Gln Arg Lys Ala Pro Pro Arg Arg Arg
    690                 695                 700

His Arg Asn Arg Ala Pro Leu Thr His Lys Met Asn Lys Met Val Thr
705                 710                 715                 720

Ser Glu Glu Gln Met Lys Leu Pro Ser Thr Lys Lys Ala Glu Pro Pro
                725                 730                 735

Thr Trp Ala Gln Leu Lys Lys Leu Thr Gln Leu Ala Thr Lys Tyr Leu
            740                 745                 750

Glu Asn Thr Lys Val Thr Gln Thr Pro Glu Ser Met Leu Leu Ala Ala
        755                 760                 765

Leu Met Ile Val Ser Met Val Val Ser Leu Pro Met Pro Ala Gly Ala
```

```
              770             775             780
Ala Ala Ala Asn Tyr Thr Tyr Trp Ala Tyr Val Pro Phe Pro Pro Leu
785             790             795             800

Ile Arg Ala Val Thr Trp Met Asp Asn Pro Ile Glu Val Tyr Val Asn
            805             810             815

Asp Ser Val Trp Val Pro Gly Pro Ile Asp Asp Arg Cys Pro Ala Lys
                820             825             830

Pro Glu Glu Gly Met Met Ile Asn Ile Ser Ile Gly Tyr Arg Tyr
            835             840             845

Pro Pro Ile Cys Leu Gly Arg Ala Pro Gly Cys Leu Met Pro Ala Val
850             855             860

Gln Asn Trp Leu Val Glu Val Pro Thr Val Ser Pro Ile Ser Arg Phe
865             870             875             880

Thr Tyr His Met Val Ser Gly Met Ser Leu Arg Pro Arg Val Asn Tyr
                885             890             895

Leu Gln Asp Phe Ser Tyr Gln Arg Ser Leu Lys Phe Arg Pro Lys Gly
                900             905             910

Lys Pro Cys Pro Lys Glu Ile Pro Lys Glu Ser Lys Asn Thr Glu Val
                915             920             925

Leu Val Trp Glu Glu Cys Val Ala Asn Ser Ala Val Ile Leu Gln Asn
930             935             940

Asn Glu Phe Gly Thr Ile Ile Asp Trp Ala Pro Arg Gly Gln Phe Tyr
945             950             955             960

His Asn Cys Ser Gly Gln Thr Gln Ser Cys Pro Ser Ala Gln Val Ser
                965             970             975

Pro Ala Val Asp Ser Asp Leu Thr Glu Ser Leu Asp Lys His Lys His
                980             985             990

Lys Lys Leu Gln Ser Phe Tyr Pro  Trp Glu Trp Gly Glu  Lys Gly Ile
                995             1000            1005

Ser Thr  Pro Arg Pro Lys Ile  Val Ser Pro Val Ser  Gly Pro Glu
    1010            1015            1020

His Pro  Glu Leu Trp Arg Leu  Thr Val Ala Ser His  His Ile Arg
    1025            1030            1035

Ile Trp  Ser Gly Asn Gln Thr  Leu Glu Thr Arg Asp  Arg Lys Pro
    1040            1045            1050

Phe Tyr  Thr Val Asp Leu Asn  Ser Ser Leu Thr Val  Pro Leu Gln
    1055            1060            1065

Ser Cys  Val Lys Pro Pro Tyr  Met Leu Val Val Gly  Asn Ile Val
    1070            1075            1080

Ile Lys  Pro Asp Ser Gln Thr  Ile Thr Cys Glu Asn  Cys Arg Leu
    1085            1090            1095

Leu Thr  Cys Ile Asp Ser Thr  Phe Asn Trp Gln His  Arg Ile Leu
    1100            1105            1110

Leu Val  Arg Ala Arg Glu Gly  Val Trp Ile Pro Val  Ser Met Asp
    1115            1120            1125

Arg Pro  Trp Glu Ala Ser Pro  Ser Val His Ile Leu  Thr Glu Val
    1130            1135            1140

Leu Lys  Gly Val Leu Asn Arg  Ser Lys Arg Phe Ile  Phe Thr Leu
    1145            1150            1155

Ile Ala  Val Ile Met Gly Leu  Ile Ala Val Thr Ala  Thr Ala Ala
    1160            1165            1170

Val Ala  Gly Val Ala Leu His  Ser Ser Val Gln Ser  Val Asn Phe
    1175            1180            1185
```

```
Val Asn Asp Trp Gln Lys Asn Ser Thr Arg Leu Trp Asn Ser Gln
    1190                1195                1200

Ser Ser Ile Asp Gln Lys Leu Ala Asn Gln Ile Asn Asp Leu Arg
    1205                1210                1215

Gln Thr Val Ile Trp Met Gly Asp Arg Leu Met Ser Leu Glu His
    1220                1225                1230

Arg Phe Gln Leu Gln Cys Asp Trp Asn Thr Ser Asp Phe Cys Ile
    1235                1240                1245

Thr Pro Gln Ile Tyr Asn Glu Ser Glu His His Trp Asp Met Val
    1250                1255                1260

Arg Arg His Leu Gln Gly Arg Glu Asp Asn Leu Thr Leu Asp Ile
    1265                1270                1275

Ser Lys Leu Lys Glu Gln Ile Phe Glu Ala Ser Lys Ala His Leu
    1280                1285                1290

Asn Leu Val Pro Gly Thr Glu Ala Ile Ala Gly Val Ala Asp Gly
    1295                1300                1305

Leu Ala Asn Leu Asn Pro Val Thr Trp Val Lys Thr Ile Gly Ser
    1310                1315                1320

Thr Thr Ile Ile Asn Leu Ile Leu Ile Leu Val Cys Leu Phe Cys
    1325                1330                1335

Leu Leu Leu Val Cys Arg Cys Thr Gln Gln Leu Arg Arg Asp Ser
    1340                1345                1350

Asp His Arg Glu Arg Ala Met Met Thr Met Ala Val Leu Ser Lys
    1355                1360                1365

Arg Lys Gly Gly Asn Val Gly Lys Ser Lys Arg Asp Gln Ile Val
    1370                1375                1380

Thr Val Ser Val
    1385

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Pro Ser Tyr Val Tyr His Gln Phe
1               5

<210> SEQ ID NO 57
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: E or R
<220> FEATURE:
<221> NAME/KEY: MOD_RES
<222> LOCATION: (20)..(20)
<223> OTHER INFORMATION: A or F
```

-continued

```
<400> SEQUENCE: 57

Leu Gln Asn Arg Arg Gly Leu Asp Leu Leu Phe Leu Lys Xaa Gly Gly
1               5                   10                  15

Leu Cys Ala Xaa
            20
```

NUCLEIC ACIDS ENCODING HUMAN ENDOGENOUS RETROVIRUS K (HERV-K) ENVELOPE PROTEINS CONTAINING MODIFIED IMMUNOSUPPRESSIVE DOMAINS (ISD) AND USES THEREOF

RELATED APPLICATIONS

The present application claims priority under 35 U.S.C. § 371 to International Patent Application No. PCT/EP2019/073273, filed Aug. 30, 2019, which claims priority to International Patent Application No. PCT/EP2018/073404, filed Aug. 30, 2018. The contents of these applications are hereby incorporated by reference in their entireties.

SEQUENCE LISTING

The instant application contains a Sequence Listing which has been submitted electronically in ASCII format and is hereby incorporated by reference in its entirety. Said ASCII copy, created on Jul. 19, 2021, is named 103926-0700_SL.txt and is 184,451 bytes in size.

TECHNICAL FIELD

The disclosure relates to a vaccine for use in the prophylaxis and/or treatment of a disease. Notably, the disease may be derived from an endogenous retrovirus, i.e. such as cancer. The vaccine of the invention relates in particular to viruses capable of forming virus-like particles in eukaryotic cells. In a certain embodiment of the invention virus encoded virus-like particles (VE-VLP) are produced in the patient's body in order to develop an immunogenic response to an endogenous retrovirus.

BACKGROUND

More than a century ago the observation has been made that the development of cancer is closely connected to the immune system and today it is well-established that the immune system protects against emerging cancers on a regular basis. On the other hand, malignant cells develop strategies to escape the immune surveillance and unfold their deadly potential.

Although immune cells are able to detect and kill tumor cells, this system is not always functional, as evident from the almost 9 million annual deaths worldwide due to cancer. Vaccination approaches to induce specific immune responses against tumor cells is a relatively old topic in cancer immunotherapies but is still under development and just recently started to yield relevant results. One vaccination strategy involve the vaccination with attenuated tumor cells, e.g, irradiated autologous tumors or allogeneic tumor cell lines, often secreting the granulocyte-macrophage colony-stimulating factor (GM-CSF). In both cases the injected material encompasses cancer-antigens that are likely present in the actual tumor. Other vaccination strategies include the administration of peptides or proteins to induce specific immune responses. These antigens are either injected directly in combination with an adjuvant, or are encoded by DNA plasmids or viral vectors.

Although immunotherapy approaches are constantly improving, broadly acting and highly efficient vaccines are still missing. A particular reason for this is the previously described immunosuppression by tumor cells.

Endogenous retroviruses (ERVs) are the evidence of ancient infections with retroviruses in distant ancestors. Upon infection, viral RNA was reverse transcribed into proviral DNA, which was integrated into the host genome. Eventually, the provirus was integrated into cells of the germ line and became inheritable, giving rise to endogenous retroviruses. Over millions of years the viral DNA was passed down generations and became fixed in the populations. Today, every human genome consists of about 8% endogenous retroviral DNA, but these are just relics of the former retrovirus. Due to mutations, deletions and insertions most of the retroviral genes became inactivated or got completely lost from the genome. Today, no functional, full-length endogenous retrovirus is present in humans anymore. However, ERVs underwent duplication processes leading to the integration of several copies into the host genome with distinct functional proteins. Thus, in some cases the multitude of homologous ERVs has still the potential to produce viral particles. The human ERV type K (HERV-K, HML2) is one of the most recently acquired ERVs in the human genome and members of this family remained full-length open reading-frames for almost all viral proteins.

Different studies have highlighted a connection between ERV expression and the development and progression of cancer. The detection of ERVs in human tumors opened a new field in anti-cancer therapies with the prospect of new vaccination strategies. A prominent example for a human ERV (HERV) is HERV type K (HERV-K) that is associated with prostate cancer, breast cancer, ovarian cancer, lymphomas, melanomas, leukemia and sarcomas. Further examples are HERV-H expressed in colorectal cancer and Syncytin-1 in testicular cancer, ovarian cancer, breast cancer, lymphomas and leukemia.

It is not always easy to determine whether the expression of ERV proteins is a cause or a consequence of the developing tumor. Nevertheless, it is known that conditions within the cancer cell enable expression of ERVs. The general state of hypomethylation in tumor cells promotes activation of ERV genes that are usually silenced in healthy cells by DNA methylation (Downey, R. F., et al., Human endogenous retrovirus K and cancer: Innocent bystander or tumorigenic accomplice? Int J Cancer, 2015. 137(6): p. 1249-57. and Gimenez, J., et al., *Custom human endogenous retroviruses dedicated microarray identifies self-induced HERV-W family elements reactivated in testicular cancer upon methylation control*. Nucleic Acids Res, 2010. 38(7): p. 2229-46. Also exogenous factors can promote ERV expression. Activation of human ERVs was for example observed due to viral infections. HERV-W expression was detected after influenza and herpes simplex virus infection (Nellaker, C., et al., *Transactivation of elements in the human endogenous retrovirus W family by viral infection*. Retrovirology, 2006. 3: p. 44) while HERV-K was present after Epstein-Barr virus infection (Sutkowski, N., et al., Epstein-Barr virus transactivates the human endogenous retrovirus HERV-K18 that encodes a superantigen. Immunity, 2001. 15(4): p. 579-89). Regardless of the mechanism that leads to ERV expression, cancer cells maintain activation of these proteins by a selection pressure, indicating a beneficial effect of ERVs in tumors (Leong, S. P., et al., *Expression and modulation of a retrovirus-associated antigen by murine melanoma cells*. Cancer Res, 1988. 48(17): p. 4954-8.)

Not only human tumors are associated with ERV proteins, but also murine cancer cells express ERVs. This provides a perfect model organism to study effects of ERVs on tumor progression and to test ERV-targeting therapy approaches. One ERV model is the melanoma associated retrovirus (MelARV), which originates from a provirus of the murine leukemia virus (MuLV) present in the mouse genome. Most inbred mouse strains contain one or two inactive MuLV copies (Li, M., et al., *Sequence and insertion sites of murine melanoma-associated retrovirus*. J Virol, 1999. 73(11): p. 9178-86.) However, the AKR mouse strain has three insertions in the genome and is characterized by a high production of MuLV early in life causing frequent incidences of spontaneous lymphomas. Other mouse strains, like the C57BL/6, spontaneously produce MuLV particles only later in life. Several other murine cancer models likewise express MuLV/MelARV, similar to human ERVs.

As the immune system of a viral host is a natural defense mechanism against infections, many viruses and especially retroviruses have developed strategies to escape this surveillance. One mechanism that can be seen throughout different virus families [Duch et al., WO2013/050048] is the development of an immunosuppressive domain in the envelope proteins (Env) causing a suppression of the immune system on different levels. Immune cells including natural killer (NK), CD8 T or regulatory T (Treg) cells can be affected by viruses containing an ISD [Schlecht-Louf et al. (2010)].

Many ERVs contain proteins with immunosuppressive domains (ISD) and such a domain can also be found in the MelARV Env protein (Schlecht-Louf, G., et al., *Retroviral infection in vivo requires an immune escape virulence factor encrypted in the envelope protein of oncoretroviruses*. Proc Natl Acad Sci USA, 2010. 107(8): p. 3782-7 and Mangeney, M. and T. Heidmann, Tumor cells expressing a retroviral envelope escape immune rejection in vivo. Proc Natl Acad Sci USA, 1998. 95(25): p. 14920-5.). The importance of the ISD in MuLV or MelARV has been shown by introducing murine leukemia virus Env proteins into tumor cells that are normally rejected by immune cells (Mangeney, M. and T. Heidmann, Tumor cells expressing a retroviral envelope escape immune rejection in vivo. Proc Natl Acad Sci USA, 1998. 95(25): p. 14920-5). Env transduced tumor cells grew more rapidly despite the additional exogenous antigen. This observation was explained by a local immunosuppressive effect mediated by the Env protein. The ISD is affecting both the innate and adaptive immune system, as shown by inhibition of macrophages, NK cells and T cells alike (Lang, M. S., et al., *Immunotherapy with monoclonal antibodies directed against the immunosuppressive domain of p15E inhibits tumour growth*. Clin Exp Immunol, 1995. 102(3): p. 468-75). Furthermore, an effect on the regulatory T cell subset has been suggested that in turn suppresses other immune cells (Mangeney, M., et al., *Endogenous retrovirus expression is required for murine melanoma tumor growth in vivo*. Cancer Res, 2005. 65(7): p. 2588-91). The detailed mechanism of immunosuppression by the ISD is not completely understood yet, but the effect seems mostly mediated by the CKS-17 peptide within the ISD. CKS-17 has diverse effects on the immune system, mostly by altering cytokine expression (Haraguchi, S., R. A. Good, and N. K. Day-Good, *A potent immunosuppressive retroviral peptide: cytokine patterns and signaling pathways*. Immunol Res, 2008. 41(1): p. 46-55.).

One of the first therapeutic approaches to target ERV-expressing tumor cells included the administration of monoclonal antibodies. Thus, antibodies targeting HERV-K Env were able to reduce tumor growth of breast cancer cell lines. Wang-Johanning et al. showed that the observed effect of anti-HERV-K Env monoclonal antibodies was mediated by alteration of the cancer cell cycle and increased apoptosis. Another possible effect of such antibodies, not tested by Wang-Johanning et al. (Wang-Johanning, F., et al., *Immunotherapeutic potential of anti-human endogenous retrovirus-K envelope protein antibodies in targeting breast tumors*. J Natl Cancer Inst, 2012. 104(3): p. 189-210), could be the prevention of immunosuppression. Like MelARV Env, the HERV-K Env protein contains an ISD and has immune modulating functions (Morozov, V. A., V. L. Dao Thi, and J. Denner, *The transmembrane protein of the human endogenous retrovirus-K (HERV-K) modulates cytokine release and gene expression*. PLoS One, 2013. 8(8): p. e70399). The approach tested by Wang-Johanning et al. included xenograft tumors in immunodeficient athymic mice. Thus, the effect of HERV-K could only affect innate immune cells, such as NK cells.

Another part of the adaptive immune response that can help to eradicate tumors by targeting ERVs includes T cells. For instance, adoptively transferred T cells against a MuLV Env epitope in combination with IL-2 were able to eradicate lung metastases of melanoma cells (Yang, J. C. and D. Perry-Lalley, *The envelope protein of an endogenous murine retrovirus is a tumor-associated T-cell antigen for multiple murine tumors*. J Immunother, 2000. 23(2): p. 177-83). Similar experiments were performed in humanized mouse models for HERV-K. T cells were genetically modified to express on their surface a chimeric antigen receptor (CAR) that recognizes HERV-K Env on cancer cells. The cytotoxic CAR$^+$ T-cells were able to lyse tumor cells and prevented metastases as well as tumor growth.

In addition to the direct injection of antibodies or T cells, a more practical, cheaper and efficient strategy is the induction of immune responses by vaccination. A simple approach is the vaccination with virus-encoded antigens. However, this method is rather cumbersome as DCs have to be isolated and cultured first before they are pulsed with a defined HLA-restricted peptide and are re-injected into mice or patients.

A more elegant vaccination strategy is the presentation of antigens (e.g. viral envelope proteins) to the immune system on virus-like particles (VLPs), which are encoded by a recombinant adenovirus (FIG. 1). These particles do not contain viral nucleic acids and are therefore non-infectious. Nevertheless, VLPs are highly immunogenic and displayed proteins are presented in a natural context. For example, the viral Env protein integrated in VLPs is presented on a virus-like surface, which promotes correct folding and conformation. In addition to the advantage of a strong immunogenicity, the vaccination strategy with VLPs includes also practical benefits. Thus, VLPs are relatively easy to produce as they are built from just a single or few proteins and production can be performed in cell cultures.

In order to vaccinate against viruses or virus-related disease (e.g. ERV expressing cancer), the whole Env protein should ideally be displayed to the immune system to ensure an immune response against a full protein target. However, as the Env protein contains the ISD, the vaccine itself has an immunosuppressive ability, undesired for an immunization approach. To circumvent this drawback, mutations were introduced into the ISD to maintain natural conformation of the target protein while at the same time preventing the immunosuppression.

One of the firsts to test inactivating mutations in the ISD of viral proteins was Schlecht-Louf et al. [Schlecht-Louf et al. (2010)]. Based on comparison studies between the immunosuppressive syncytin-2 and the non-immunosuppressive syncytin-1 [Mangeney et al. (2007)], Schlecht-Louf et al. identified mutations that disable the activity of the ISD without ablating the general structure and functionality of the Env protein. This mutation strategy was applied to proteins of other viral origins (e.g. HTLV and XMRV) and more extensively tested for the Friend murine leukemia virus (F-MLV). The study did not only reveal the suppression of both NK and T cells by the ISD but showed also that a live-attenuated F-MLV virus comprising the mutated ISD in the Env protein served as a vaccine against the same virus with a WT ISD sequence. The protection was due to increased antibody levels as well as T cell responses against F-MLV epitopes. Their discovery was finally manifested in the patent application WO 2011/092199 with focus on the Xenotropic murine leukemia virus-related virus (XMRV) that has been related to human protstate cancer and chronic fatigue syndrome. Hence, WO 2011/092199 relates to ISD mutations specifically in the XMRV and to the utilization of such ISD mutated viruses for vaccination strategies.

Another application of ISD mutation was described in the patent application WO 2014/195510. In this case a mutation of the ISD was introduced in the Feline Immunodeficiency Virus (FIV) in order to decrease immunosuppression by the virus while still maintaining its natural conformation. WO 2014/195510 describes that specific mutations increased antibody responses against the FIV Env protein when administered in a vaccination approach, bound to MBP or transduced in engrafted tumor cells. Thus, WO 2014/195510 relates to mutations in the ISD of FIV Env and the use of such mutated proteins in vaccination approaches against infection with FIV or other lentiviruses.

Another approach, addressing a broader spectrum of ISD mutations in viral Env protein, is described in the patent application WO 2013/050048. In particular WO 2013/050048 relates to the generation of antigens by first identifying ISDs in enveloped RNA viruses and subsequently mutating these domains to decrease immunosuppression during vaccination. The ISD identification strategy is based on 4 parameters which are: 1) the peptide is located in the fusion protein of enveloped RNA viruses, 2) the peptide is capable of interacting with membranes, 3) a high degree of homology in the primary structure (sequence) of the peptide exists either within the Order, Family, Subfamily, Genus, or Species of viruses, 4) the position at the surface of the fusion protein at a given conformation is a feature of immunosuppressive domains, revealed by the 3D structure or antibody staining. After identification of a potential ISD in a viral Env of interest, the immunosuppressive function was validated and subsequently, mutations were introduced in the ISDs and reduction of immunosuppression of at least 25% was confirmed. Overall, WO 2013/050048 describes the identification of ISDs in enveloped RNA viruses, the generation of ISD mutated peptides, as well as the utilization of said peptides as vaccines and the generation of antibodies.

The importance of a simultaneous antigen presentation encoded in an adenoviral vector and on the surface of the viral capsid was shown by Bayer et al. [Bayer et al. (2010)]. The benefit of presenting antigens in an ordered structure that helps to cross-link B cell receptors was known previously. However, by encoding different F-MLV proteins, such as Gag and the Env subunits gp70 and p15E, while simultaneously displaying such antigens on the adenoviral capsid protein pIX, Bayer et al. showed that only the combination of encoded and capsid presented antigens was able to increase the level of functional antibodies. This observation was assigned to the fact that while the presentation on the adenoviral capsid helped to cross-link B cell receptors, encoded antigens were required for an essential CD4$^+$ T cell responses promoting affinity maturation of B cells. With this vaccination strategy Bayer et al. were able to reduce viral load of F-MLV after challenge. However, no indication of increased CD8$^+$ T cell responses against the target antigen could be observed.

Shoji et al. primarily focused on the optimization of an adenovirus-based HIV vaccine. Despite codon-optimization strategies and usage of diverse promoters, they co-encoded the Gag and Env protein in an adenovirus, coupled via a cleavable furin site (F2A). This allowed the simultaneous expression of both proteins and thus in situ formation of Gag based VLPs. In their study this setting showed the highest immune responses compared to other display strategies that did not promote in situ formation of VLPs [Shoji et al., 2012].

Duch et al. 2011 (US20110305749A1) produced VLP based retroviral HIV vaccines and demonstrated increased immunogenicity of ISD mutated HIV envelope proteins. The VLP immunogens were produced and purified ex vivo.

US2012189647 relates to a mutated envelope protein resulting from mutation of a immunosuppressive domain of a transmembrane subunit of a wild type envelope protein. US2009324553 relates to chimeric polytropic viral envelope polypeptides applicable for directed targeting and controlled fusion of virus particles with other cellular membranes.

In addition, a publication by Hohn et al. [Hohn et al., 2014] describes that when a codon-optimised version of HERV-K113 was expressed under a CMV promotor, virus assembly type and morphology were changed. In particular, VLP were retained at the cell surface and lacked Env.

Despite previous strategies of mutating ISDs in viral Env proteins and using adenovirus to encode and display viral antigens, the past vaccination strategies employing ISD mutations aimed exclusively at preventing viral infections [Schlecht-louf et al. 2010; WO 2011/092199; WO 2014/195510; US20110305749; WO 2014/195510]. Therefore, there is still a need to break tolerance to self-antigens. Moreover, the system of in situ synthesis of virus-like particles has been used before [Luo et al. (2003); Sohji et al. (2011); Andersson et al. (2016); Andersson & Holst (2016); Andersson et al. (2017)] for HIV Env and Malaria antigens but not for the display of the ISD mutated ERV Env on in situ synthesized VLPs. Moreover, in view of the findings by Hohn et al. there is also a need for an efficient system allowing the production of VLP, in particular HERV-K VLP.

The present invention aims at producing an effective vaccine for the prophylaxis and/or treatment of a disease caused by an endogenous retrovirus. The vaccine of the invention shows an improved immune response from either of both of the response pathways initiated by CD4 T cells or CD8 T cells.

SUMMARY

The present invention relates to a vaccine for use in the prophylaxis and/or treatment of a disease, comprising an adenoviral vector capable of encoding a virus-like particle (VLP), said VLP displaying an inactive immune-suppressive domain (ISD).

A number of virus vectors for producing VLPs is used in the development of vaccines, including HIV, baculovirus, lentivirus, and adenovirus. The present inventors show that the adenovirus vector encoding ERV with inactivated ISD surprisingly performs better than e.g. a HIV vector when combined with inactivated ISD. Thus, the present invention provides for an unexpected high immune response resulting in promotion of immunosuppression in tumors.

While any of the adenoviral vectors are expected to perform satisfactory in the present invention it is currently the opinion that the best result will be obtained when the adenoviral vector is derived from mammalian adenovirus types, human adenovirus types, chimpanzee adenovirus types, or gorilla adenovirus types. Human adenovirus vectors exist in at least 52 different serotypes e.g. type 1, 2, 5, 19, 28, 35, and 40. When a human adenovirus is selected the human adenovirus vector is derived from D group vectors, human adenovirus serotype Ad5, human adenovirus serotype Ad19a, human adenovirus serotype Ad26, or Chimpanzee adenovirus serotypes. The present inventors have used adenovirus type 5 (Ad5) as the starting point for the present vaccine vector due to good pre-clinical immunization results. The reason why Ad5 induces sufficient strong immune responses against a target protein is not only due to the efficient transport into antigen presenting cells (APCs) but also the adjuvant property of the vector itself that stimulates innate immunity. In addition, the transcription and release of immune-stimulatory cytokines like IFNs, IL-6, IL-12, IL-15 and TNF-α are induced. These cytokines have an important role in the immune system and serve as activators for cells of the adaptive immune response. A particular advantage of Ad5 is that immune responses against the vector are not too strong, as this would prevent transgene expression. Ad5 balances the innate immunity to a level that allows transgene expression while still activating adaptive immune responses. Having regarded to the publication by Matthew J. Johnson et al (J Immunol 2012; 188:6109-6118), which showed that recombinant adenovirus serotype 28 and recombinant adenovirus serotype 35 infected and led to the in vitro maturation and activation of both human and mouse dendritic cells more efficiently compared with recombinant adenovirus serotype 5, it was unexpected that the Ad5 showed the desired response in the experiments reported herein. In addition, it is shown in another paper by Matthew J. Johnson et al (Vaccine 32 (2014) 717-724) that recombinant adenovirus serotype 28 and recombinant adenovirus serotype 35 increase apoptosis of antigen presenting cells (APCs), such as monocytes, relative to rAd5 and mock infected controls.

The immune-suppressive domain (ISD) can be seen as mechanism for tumors to balance anti-tumor immune responses while simultaneously retaining a tumor-promoting inflammatory milieu induced by ERV activation, similar to natural infections. The ISD is affecting both the innate and adaptive immune system, due to inhibition of macrophages, NK cells and T cells alike. However, the detailed mechanism of immunosuppression by the ISD is not completely understood yet. As demonstrated by the present invention, inactivation of the ISD increases the response considerably.

The ISD segment may be inactivated by mutation or deletion of one or more amino acids. In case the inactivation is performed by a mutation one or more of the amino acids are exchanged with a different amino acid, usually selected among the other 19 naturally occurring amino acids. In case of a deletion any one or more of the amino acids in the ISD region may be deleted. The person skilled in the art will have adequate knowledge and experience of which amino acids to exchange to lead him or her to a satisfactory immune response, optionally through evaluation of initial trials.

In a certain embodiment of the present invention the ISD has the peptide sequence LANQINDLRQTVIW (SEQ ID NO. 1), LASQINDLRQTVIW (SEQ ID NO. 2), LQNRRGLDLLFLKEGGL (SEQ ID NO. 3), LQNRRALDLLTAERGGT (SEQ ID NO. 4), LQNRRGLDMLTAAQGGI (SEQ ID NO. 5), or YQNRLALDYLLAAEGGV (SEQ ID NO. 6) having at least one of the amino acids deleted or exchanged with a different amino acid. It is preferred that the amino acid different from the original is selected among naturally occurring amino acids. The ISD segment of the ERV encoded in Ad5 used in the examples of the present application has the following amino acid sequence: LQNRRGLDLLFLKEGGL (SEQ ID No. 7). The ISD can be inactivated by performing one or more mutations in the amino acid sequence. Whereas the person skilled in the art will be able to modify the amino acid sequence by performing any number or form of mutations or deletions, it is currently suitable to exchange a single amino acids i.e. the ISD preferably used in the present invention has the following sequence: LQNRRGLDLLFLKRGGL (SEQ ID No. 8).

It may be preferable to exchange one or more amino acids in a region upstream or downstream of the ISD segment. The mutation is a compensatory mutation intended to preserve the structure of the domain so that it can still work for an infectious virus. Thus, in a certain embodiment, at least one of the amino acids in a region of 10 amino acids upstream or downstream of the ISD is exchanged with a different amino acid. In the specific embodiment shown in FIG. 3 the $3^{rd}$ amino acid flanking the ISD region is exchanged with an A→F mutation.

For an ISD to be inactivated according to the present invention the immune suppressing ability needs to be reduced by 70% or more compared to the immune suppression performed by the original ISD. In a preferred embodiment of the present invention the ISD is inactivated 80% or more, such as 90% or more, such as 95% or more, such as 99% more compared to the immune suppression performed by the original ISD.

The present invention provides a general platform for displaying antigens to the body's immune system. Thus, in principle the coding for any type of protein it is desired to raise an immune response against can be incorporated in the adenovirus vector. In a preferred aspect of the invention the antigen is endogenous retrovirus envelope proteins (ERV Env) or immunogenic proteins derived from such proteins. It is generally believed that the vaccine of virus-encoded virus-like particles directs ERV Env to dendritic cells (DCs), which present antigens to cells of the adaptive immune system. Presentation on MHC class I induces activation and proliferation of CD8+ T cells. These cytotoxic T lymphocytes (CTLs), specific for antigens of ERV Env, infiltrate tumors and kill cells displaying the respective antigen. Presentation of antigens on MHC class II by professional antigen presenting cells (APCs) activates CD4+ T cells, which subsequently co-activate B cells. Activated B cells that encounter the ERV Env target protein in the circulation or antigens displayed on VLPs release antibodies specific for ERV Env. These antibodies are able to bind their target on cancer cells, inducing destruction and phagocytosis of the malignant cells. In this way, ERV-specific antibodies are bale to prevent tumor growth and metastasis. The regained immunogenicity of tumor cells enables priming of a set of diverse tumor-specific T cells recognizing different tumor-associated and tumor-specific antigens. The newly primed and expanded CTLs infiltrate the tumor and kill malignant cells.

While the present vaccine in principle may be used for immunizing a number of mammal species and in fact has been developed using a mouse model, the ERV protein in a preferred aspect of the invention is a human endogenous retrovirus (HERV) protein or an immunogenic part thereof. It has been estimated that every human genome consists of about 8% endogenous retroviral DNA. However, most of the endogenous retroviral DNA is just relics of the former retrovirus. ERVs are the evidence of ancient infections with retroviruses in distant ancestors. Upon infection, viral RNA was reverse transcribed into proviral DNA, which was integrated into the host genome. Eventually, the provirus was integrated into cells of the germ line and became inheritable, giving rise to endogenous retroviruses. Over millions of years the viral DNA was passed down generations and became fixed in the populations. It follows that a large part of the human genome potentially may be used as antigen-coding part of the adenoviral vector. Presently, HERV is preferably selected among the group consisting of HERV-K, HERV-H, HERV-W, HERV-FRD, and HERV-E. More specifically, the HERV-K may be selected among the group consisting of HERV-K108 (=ERVK-6), ERVK-19, HERV-K115 (=ERVK-8), ERVK-9, HERV-K113, ERVK-21, ERVK-25, HERV-K102 (=ERVK-7), HERV-K101 (=ERVK-24), HERV-K110 (=ERVK-18); HERV-H may be selected among the group consisting of HERV-H19 (=HERV-H_2q24.3), HERV-H_2q24.1; HERV-W may be selected as ERVW-1 (=Syncytin-1); and HERV-FRD may be selected as ERVFRD-1 (=Syncytin-2).

The adenoviral vector is constructed so as to allow the encoded ERV protein to be presented to the immune system to erect a suitable immunological response. In a suitable aspect of the invention the ERV protein epitope or an immunogenic part thereof is positioned between a transmembrane domain and the ISD.

Experiments reported herein show the application of adenovirus encoded ISD mutated HERV-K VLPs not only in Ad5 but also in another adenoviral serotype, i.e. Ad19 (see Examples 15 to 17). Previously, HERV-K have been associated with cancer expression and shown to contain a functional envelope ISD domain with in vitro activities similar to HIV (Morozov et al. 2013). In mice, HERV-K is a foreign antigen and with similar ISD domain activities the ISD mutations could not a priory be expect to enhance immune responses. However, it was surprisingly found that the ISD mutation increases antibody responses towards HERV-K Env p15E and SU domain proteins, T cell responses and anti-cancer protection. The mutations in HERV-K are different than the ones disclosed herein for MelARV as the virus families differ in the ISD sequences. However, based on the information provided herein and on common general knowledge the skilled person can identify suitable mutations inactivating the ISD also in other virus families. The HERV-K mutation used herein was inspired by ISD mutations in HIV shown to preserve infectivity of the virus and site specific conservation between HERV-K and HIV-1 (Morozov et al 2012). Upon analysis of vector transfected cells increased intracellular and cell surface expression of the HERV-K mutations were found (see Example 15 and FIG. 24), which may contribute to explain the increased immunogenicity and provide an additional mechanistic rationale for making ISD mutations in HERV-K family Env proteins using any genetic expression platform and constructs that may or may not form VLPs.

Thus, the present invention also relates to a nucleic acid molecule encoding ERV envelope protein or an immunogenic part thereof, wherein the ISD of said protein contains mutations that render the ISD inactive. Preferably, the ERV is a human endogenous retrovirus (HERV), more preferably the HERV is HERV-K. It is further preferred that the mutation in the ISD replaces Q525 with an alanine so that the sequence of the mutated ISD becomes NSQSSIDQKLANAINDLRQT (SEQ ID No.50) (instead of NSQSSIDQKLANQINDLRQT; SEQ ID No. 49). It is understood that corresponding mutations in an ISD with a different sequence are also envisaged. In a further preferred embodiment the nucleic acid molecule is comprised in an adenoviral vector. More preferably the adenoviral vector is adenoviral vector type 19 (Ad19). It is further preferred that the adenoviral vector comprising the nucleic acid encodes a VLP. The invention further relates to a protein encoded by said nucleic acid molecule or said vector. The nucleic acid molecule, the vector or the encoded protein are to be used in the treatment or prophylaxis of a disease, the disease preferably being cancer. The cancer to be treated is a cancer expressing the corresponding ERV. Preferably, the treatment comprises a "prime-boost-regimen", wherein first a prime with the adenovirus or the nucleic acid molecule is administered followed by the later administration of an MVA-, adenovirus or DNA boost. Preferably, the boost is an MVA boost. Different timings for the prime and boost are envisaged. In particular in cancer patients with minimal residual disease a long spacing between prime and boost is possible. In a preferred regimen, the boost is administered 4 to 8 weeks after the priming.

In a preferred aspect of the vaccine according to the invention the protein product of the adenoviral vector includes a gag protein, a 2A peptide, and an envelope protein (Env). Furthermore, the Env protein may comprise a Surface Unit (gp70), a cleavage site, and a transmembrane unit (p15E). In addition, the transmembrane unit (p15E) my comprise a fusion peptide, an immunosuppressive domain (ISD), a transmembrane anchor, and a cytoplasmatic tail.

To improve the immunosuppression of the vaccine is may be suitable that the p15E or an immunogenic part thereof is coupled to the adenoviral capsid protein pIX. To achieve this, p15E was N-terminally fused to the C-terminus of pIX. The highly ordered structure of pIX and its bound antigen on the adenoviral surface helps to cross-link B cell receptors. As another advantage, pIX is usually displayed as a trimer and could help to present the bound p15E antigen in a natural trimeric form as well. This modification was shown to increase the induction of specific antibodies in CD1 mice.

In a certain aspect of the present invention the signal peptide coded for by the adenoviral vector is exchanged with a signal peptide from Gaussia luciferase (LucSP). This signal peptide increases the transport of proteins to the outer cell membrane without altering the glycosylation status. Thus, including this signal peptide instead of the native sequence has the directs synthesized proteins to the membrane where they are integrated into VLPs.

In another aspect of the invention, the transmembrane anchor and the cytoplasmatic tail coded for by the adenoviral vector are exchanged with the transmembrane domain and cytoplasmic tail from Influenza A virus Hemagglutinin. The insertion increases expression of recombinant proteins on the cell surface and on VLPs, which results in strong and broad antibody responses. In a preferred embodiment the transmembrane anchor and the cytoplasmatic tail coded for by the adenoviral vector are exchanged with the transmembrane domain and cytoplasmic tail from Influenza A virus Hemagglutinin H3N2 (HA-TMCT).

In another aspect of the invention, a trimerization sequence is provided adjacent to the signal peptide. The trimerization sequence may be added to the protein to facilitate natural presentation. In a preferred aspect, the trimerization sequence is GCN4.

The protein product of adenovirus vector usually comprises a gag protein, wherein the gag protein is exogenous retroviral gag protein or endogenous retroviral gag protein.

The adenoviral vector usually requires a cell for production of the virus-like particle. Thus, the adenoviral vector infects a cell and produces the components for VLPs. In a certain aspect of the invention, the VLP is produced in an isolated cell line. Suitable examples include, Sf9 cells, vero cells, HeLa cells, etc. However, it is presently desired that the VLP is produced in a cell of the body of a patient having been infected by the adenoviral vector. This production is also referred to as Virus encoded virus-like particles (VE-VLPs) and has the advantage that an intermediary host for the production of VLPs is circumvented.

The invention also relates to a nucleic acid construct encoding a target protein capable of forming of a virus-like particle (VLP), wherein the target protein comprises an immune-suppressive domain (ISD), said ISD being inactive.

The present invention is particularly suitable for the prophylaxis and/or treatment of cancer. The type of cancer treated by the present invention is not particularly limited and includes prostate cancer, breast cancer, ovarian cancer, lymphomas, melanomas, leukemia, sarcomas, colorectal cancer, testicular cancer, ovarian cancer, breast cancer, lymphomas, lung cancer, and liver cancer.

Under certain conditions, it may be advantageous to treat a patient using a prime-boost regime. Thus in 1 of the embodiments of the present invention the use of the vaccine in the prophylaxis and/or treatment of cancer, comprises the step of priming the patient with the nucleic acid construct above at least 5 days before boosting with the vaccine disclosed above.

The present invention also relates to a vaccine for use in the prophylaxis and/or treatment of cancer, which comprises the step of post treating the patient 5 days or more after the exposure of the patient for the vaccine disclosed above with a virus encoded VLP different from the VLP derived from an adenoviral vector. In a certain embodiment, the virus encoded VLP different from the VLP derived from an adenoviral vector is a VLP derived from Modified Vaccina Ankara (MVA).

Further, it was surprisingly found that—contrary to what was reported by Hohn et al. 2014 with regard to codon optimized HERV-K113 under a CMV-promotor—the expression cassette used, i.e. Gag-p2A-Env with Env expressed in a 1:1 ratio with Gag again under a strong promotor did not result in retention at the cell membrane. Instead VLP were expressed which (again contrary to the results reported by Hohn et al. also contained Env. This shows that a genetic platform with Gag-p2a-Env performs better as compared to the construct without p2a (or a corresponding operative linker).

Thus, the present invention further relates to a nucleic acid molecule encoding a Gag protein and an ERV envelope protein (Env) or an immunogenic part thereof wherein the native genomic structure connecting Gag and the Env has been replaced by an operative linker. Preferably said operative linker is p2A. In other words, the present invention also relates to a nucleic acid molecule comprising a Gag-operative linker-Env expression cassette, preferably a Gag-p2A-Env cassette. Preferably, the ERV is HERV-K. More preferably the ERV is HERV-K113. It is further preferred that the HERV-K sequence is a HERV-K consensus sequence, more preferably a codon-optimized consensus sequence. Yet more preferably, the HERV-K codon-optimized consensus sequence is the following amino acid sequence (SEQ ID No. 55):

```
MGQTKSKIKSKYASYLSFIKILLKRGGVKVSTKNLIKLFQIIEQFCPWF
PEQGTLDLKDWKRIGKELKQAGRKGNIIPLTVWNDWAIIKAALEPFQTE
```

-continued
```
EDSVSVSDAPGSCIIDCNENTRKKSQKETEGLHCEYVAEPVMAQSTQNV
DYNQLQEVIYPETLKLEGKGPELVGPSESKPRGTSPLPAGQVPVTLQPQ
KQVKENKTQPPVAYQYWPPAELQYRPPPESQYGYPGMPPAPQGRAPYPQ
PPTRRLNPTAPPSRQGSELHEIIDKSRKEGDTEAWQFPVTLEPMPPGEG
AQEGEPPTVEARYKSFSIKMLKDMKEGVKQYGPNSPYMRTLLDSIAHGH
RLIPYDWEILAKSSLSPSQFLQFKTWWIDGVQEQVRRNRAANPPVNIDA
DQLLGIGQNWSTISQQALMQNEAIEQVRAICLRAWEKIQDPGSTCPSFN
TVRQGSKEPYPDFVARLQDVAQKSIADEKARKVIVELMAYENANPECQS
AIKPLKGKVPAGSDVISEYVKACDGIGGAMHKAMLMAQAITGVVLGGQV
RTFGGKCYNCGQIGHLKKNCPVLNKQNITIQATTTGREPPDLCPRCKKG
KHWASQCRSKFDKNGQPLSGNEQRGQPQAPQQTGAFPIQPFVPQGFQGQ
QPPLSQVFQGISQLPQYNNCPPPQAAVQQGSGATNFSLLKQAGDVEENP
GPMNPSEMQRKAPPRRRRHRNRAPLTHKMNKMVTSEEQMKLPSTKKAEP
PTWAQLKKLTQLATKYLENTKVTQTPESMLLAALMIVSMVVSLPMPAGA
AAANYTYWAYVPFPPLIRAVTWMDNPIEVYVNDSVWVPGPIDDRCPAKP
EEEGMMINISIGYRYPPICLGRAPGCLMPAVQNWLVEVPTVSPISRFTY
HMVSGMSLRPRVNYLQDFSYQRSLKFRPKGKPCPKEIPKESKNTEVLVW
EECVANSAVILQNNEFGTIIDWAPRGQFYHNCSGQTQSCPSAQVSPAVD
SDLTESLDKHKHKKLQSFYPWEWGEKGISTPRPKIVSPVSGPEHPELWR
LTVASHHIRIWSGNQTLETRDRKPFYTVDLNSSLTVPLQSCVKPPYMLV
VGNIVIKPDSQTITCENCRLLTCIDSTFNWQHRILLVRAREGVWIPVSM
DRPWEASPSVHILTEVLKGVLNRSKRFIFTLIAVIMGLIAVTATAAVAG
VALHSSVQSVNFVNDWQKNSTRLWNSQSSIDQKLANQINDLRQTVIWMG
DRLMSLEHRFQLQCDWNTSDFCITPQIYNESEHHWDMVRRHLQGREDNL
TLDISKLKEQIFEASKAHLNLVPGTEAIAGVADGLANLNPVTWVKTIGS
TTIINLILILVCLFCLLLVCRCTQQLRRDSDHRERAMMTMAVLSKRKGG
NVGKSKRDQIVTVSV.
```

It is further preferred that the HERV-K contains a mutation in its ISD (which is underlined and in bold print in the sequence above). A particularly preferred sequence containing such a mutation is shown in SEQ ID No. 48.

It is further preferred that the nucleic acid molecule is an adenoviral vector. It is envisaged that the nucleic acid can be used as a genetic vaccine, in particular in the prophylaxis and/or treatment of a disease, preferably cancer. Alternatively, the nucleic acid molecule can also be used to produce VLPs, in particular HERV-K VLPs in vitro. The resulting VLPs can then be used in immunotherapy, in particular in the prophylaxis and/or treatment of a disease, preferably cancer. It is understood that also in this context the cancer to be treated is a cancer expressing ERV.

In addition the present invention also relates to a VLP encoded by the nucleic acid molecule encoding a Gag protein and an ERV envelope protein (Env) or an immunogenic part thereof wherein the native genomic structure connecting Gag and the Env has been replaced by an operative linker. Preferably, said operative linker is p2A. It is further preferred that the ERV is HERV-K. More preferably the ERV is HERV-K113. Preferably, said VLP contains higher amounts of Env as compared to the HERV-K113 VLP produced according to the method described by Hohn et al. As mentioned above, the use of such VLPs in immunotherapy is envisaged. Moreover, the invention relates to the nucleic acid molecule or the VLP for use in the prophylaxis and/or treatment of a disease. It is preferred that the disease is cancer. It is understood that the cancer is a cancer expressing the corresponding ERV.

BRIEF DESCRIPTION OF THE DRAWINGS

In the following detailed portion of the present disclosure, the aspects, embodiments and implementations will be explained in more detail with reference to the example embodiments shown in the drawings, in which:

FIG. 12: Excerpts from amino acid sequences of p15E displayed on the adenoviral pIX protein. The full sequences are represented in the sequence listing: pIX-p15E (SEQ ID NO:51 (Residues 1-4 and 42-109 of SEQ ID NO: 51 disclosed in figure); pIX-p15E-ISD (SEQ ID NO:52 (Residues 1-4 and 42-109 of SEQ ID NO: 52 disclosed in figure)), pIX-p15E-truc-wC (SEQ ID NO: 53 (Residues 1-4 and 42-62 of SEQ ID NO: 53 disclosed in figure)); pIX-p15E-trunc-w/oC (SEQ ID NO:54 (Residues 1-4 and 42-61 of SEQ ID NO: 54 disclosed in figure)

FIG. 13: Characterization of adenoviral vectors displaying recombinant pIX. (A) pcDNA3-pIX-Taglinker-xxx plasmids encoding recombinant pIX were transfected into HEK293 cells to validate correct expression. Cell lysates of transfected cells were analyzed by western blotting using an anti-pIX antibody. Line 1) pIX-p15E, Line 2) pIX-p15E-ISD, Line 3) pIX-p15E_trunc-wC, Line 4) pIX-p15E_trunc-w/oC, Line GFP pIX-GFP. (B) Produced and purified viruses were analyzed for integration of recombinant pIX by western blotting using an anti-pIX antibody. The line numbers represent the same pIX modification as in (A) displayed on the Ad5 vector, while Line 0 represents a native Ad5 without pIX modification.

Figure 16:
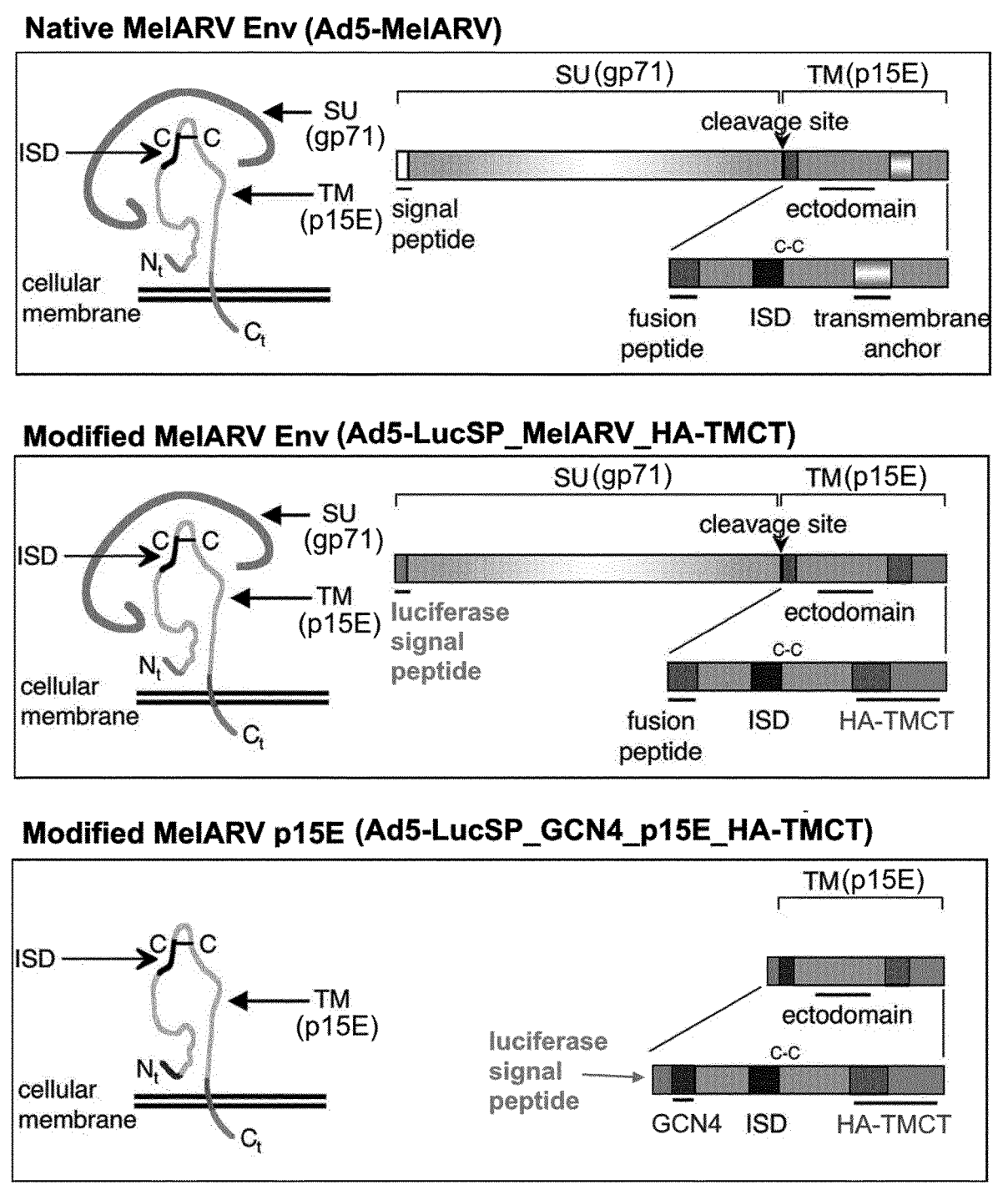

FIG. 16: Vaccine improvement strategy: Chimeric MelARV Env proteins with functional domains to improve display on VLPs. Two modified vaccines were produced with either full length MelARV Env (Ad5-LucSP_MelARV_Ha-TMCT) or p15E alone (Ad5-LucSP_GCN4_p15E_Ha-TMCT). In Ad5-LucSP_MelARV_HA-TMCT the native signal peptide of MelARV Env was exchanged for the luciferase signal peptide (LucSP). Furthermore, the native transmembrane domain and cytoplasmic tail (TMCT) were changed for the corresponding sequence of Influenza A virus Hemagglutinin H3N2 (HA-TMCT). In Ad5-LucSP_GCN4_p15E_HA-TMCT only p15E was encoded instead of the full length Env protein. p15E likewise contained the HA-TMCT and the LucSP was added at the N-terminus. Additionally, a trimerization sequence (GCN4) was included.

| Protein | Molecular weight [kDa] | Reference |
|---|---|---|
| MelARV Gag | 65 | (Andrawiss et al., J Virol. 2003 November; 77(21):11651-60. |
| MelARV Env precursor (uncleaved) | 85 | (Opstelten DJ et. al., J Virol. 1998 August; 72(8):6537-45) [45] |
| MelARV Env | 100 | (Opstelten DJ et. al., J Virol. 1998 August; 72(8):6537-45) [45] |
| MelARV gp70 (SU, Env) | 70 | (Opstelten DJ et. al., J Virol. 1998 August; 72(8):6537-45) [45] |
| MelARV p15E (TM, Env) | 15 | (Opstelten DJ et. al., J Virol. 1998 August; 72(8):6537-45) [45] |
| HERV-K Gag | 80 | (Tönjes RR, et al., J Virol. 1999 November; 73(11):9187-95) |
| HERV-K Env precursor (uncleaved) full-length unprocessed precursor | 90 (with signal peptide) 80 (without) | (Boller, K., et al., J Virol. 1997; 71(6):4581-8) |
| HERV-K gp70 (SU, Env) non-glycosylated proteins | 68 | (Dewannieux, M., et al., J Virol. 2005 December; 79 (24):15573-7) |
| HERV-K p15E(TM, Env) non-glycosylated proteins | 42 | (Dewannieux, M., et al., J Virol. 2005 December; 79 (24):15573-7) |

Moreover, Ad5_MelARV_Gag protein (65 kDa) was also detected in the cell lysate and SN of both cell lines (A1 and A2), meaning that both HERV-K and MelARV Gag proteins can be recognized by the same rabbit polyclonal anti-p2A antibody.

Figure 24:
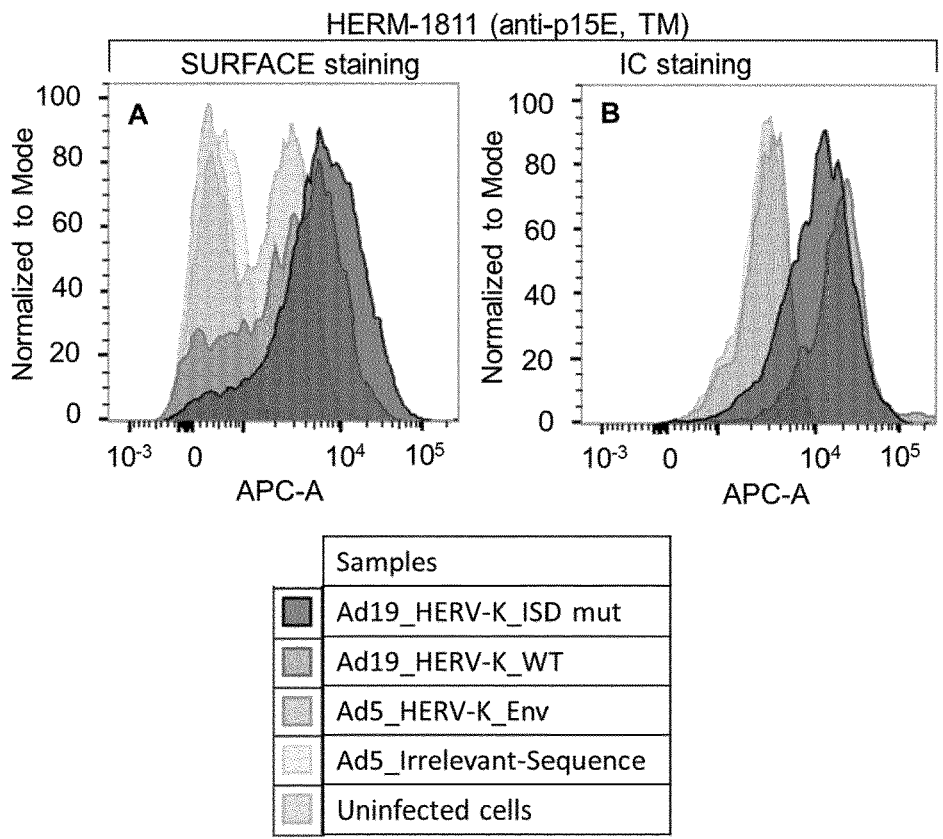

FIG. 24: Expression of HERV-K Env inside and on the cell surface upon Ad19_HERV-K_WT/ISDmut transfection. HERM-1811 antibody was used to show the production and presence of HERV-K Env protein both intracellularly and on the cell surface of A549 infected cells. Ad19_HERV-K Env WT (medium grey transparent)/ISDmut (dark grey transparent) infected cells expressed large amounts of HERV-K Env, whereas cells infected with an Ad5 vector encoding for HERV-K Env (very light grey transparent), showed a lower expression of the target protein suggesting that Ad19 transfection rate may be more efficient than that of Ad5. Cells infected with an irrelevant antigen encoded by an Ad19 vector (light grey) coincide with the uninfected cells (dark grey), and thus did not show any signal.

Figure 25:
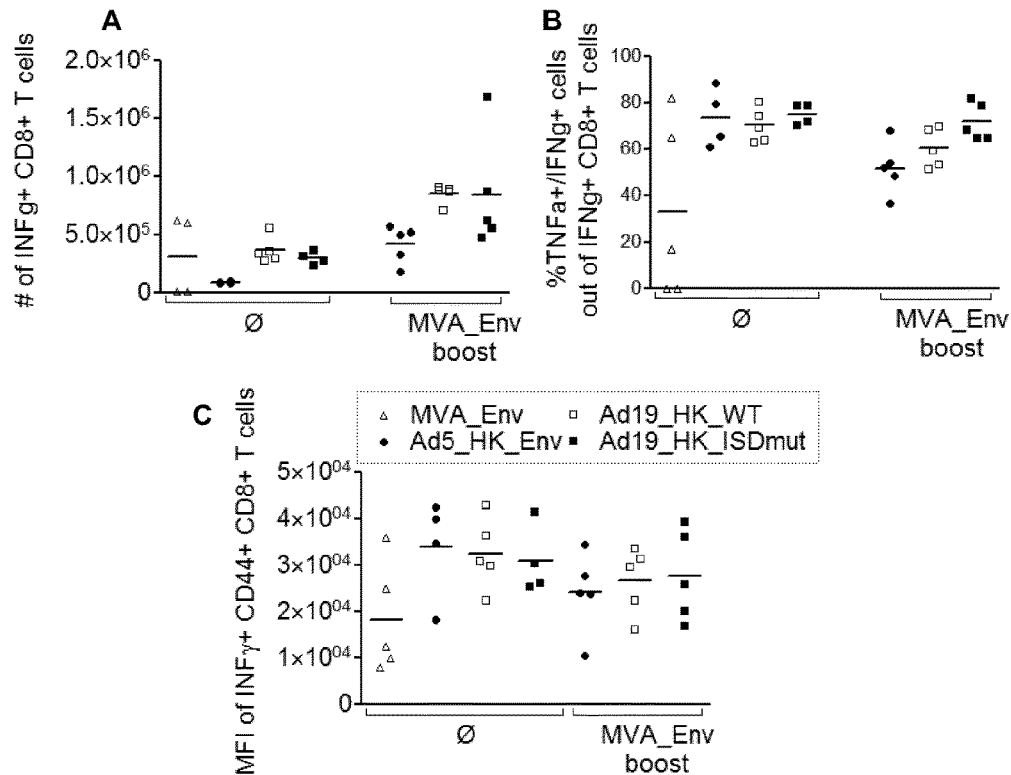

FIG. 25: ICS analysis of CD8+ T cell responses elicited by Ad19-HERV-K in BALB/c mice. The figures show the overall total number of activated (CD44+) CD8+ T cells secreting TNFα contained in each mouse spleen. (A) Number of IFNγ-positive CD8+ T cells from immunized mice with different adv-vaccines (prime-boost) followed by non-boost (Ø) and MVA Env boost regimen. (B) Percentage of IFNγ and TNFα-double positive CD8+ T cells. (C) Mean fluorescence intensity (MFI) of IFNγ-positive CD8+ T cells. The mean of each group of mice is indicated by horizontal lines. The asterisks (*) indicate the significant differences, with ($P \leq 0.05$);  ($P \leq 0.01$); * ($P \leq 0.001$).

Figure 26:
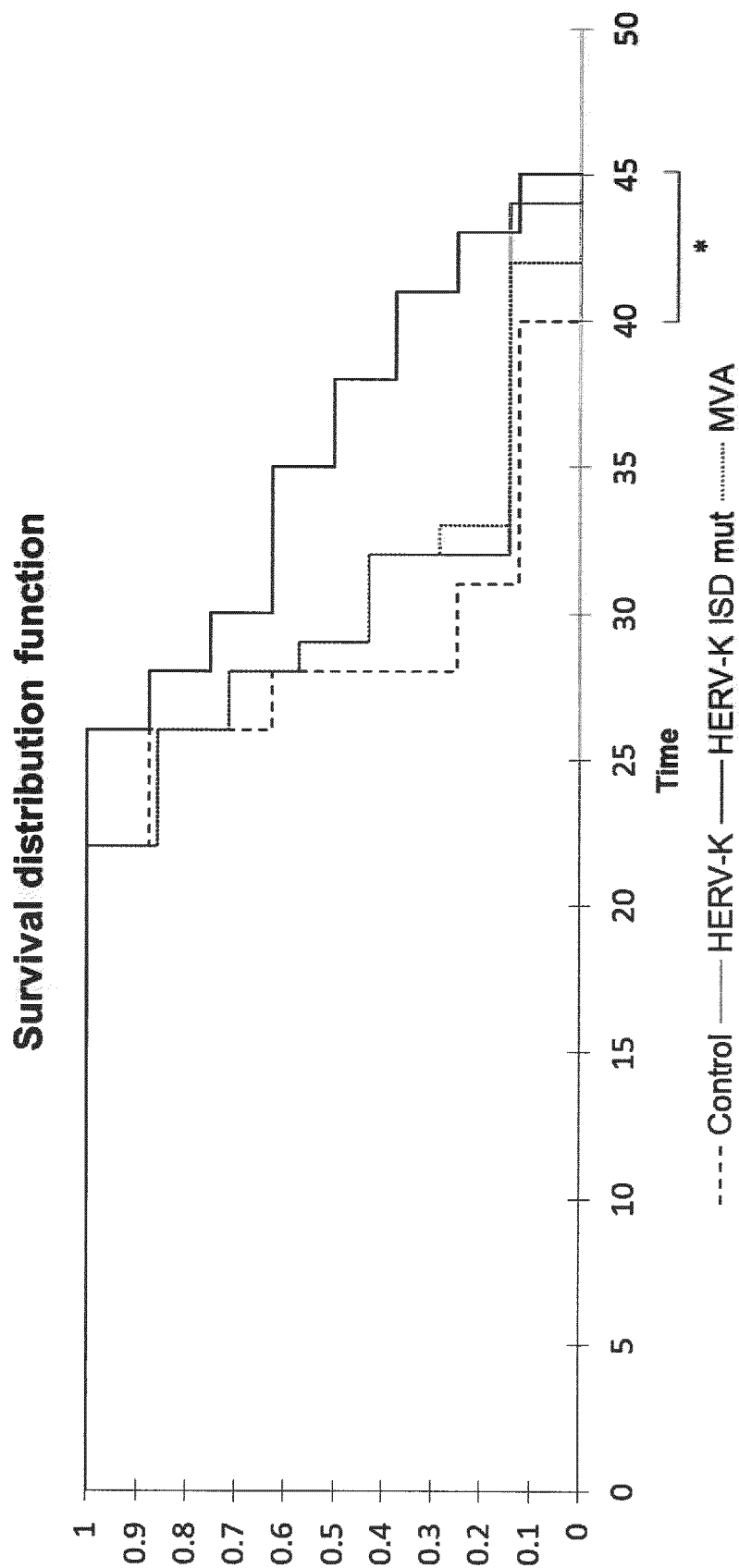

FIG. 26: Survival curve of tumor-challenged mice receiving a therapeutic vaccination. The efficacy of our Ad19_HERV-K WT/ISDmut vaccines (medium grey and dark grey) to reduce or prevent tumor growth and metastasis was tested in BALB/c mice challenged with RENCA cells, expressing HERV-K Env target protein. Our vaccines were compared with an irrelevant vaccine which did not express HERV-K (black), and with an MVA vaccine which did express the target protein (light grey). The lungs of the mice euthanized at day 40 (final endpoint) were blind-ranked regarding the progression of the lung metastasis. Kaplan-Meier estimator was used to analyze the survival of the different groups of vaccinated mice. The survival curves were compared using different statistical tests (Log-rank, Wilcoxon and Tarone-Ware) and were considered significant (*) when p-value<0.05.

Figure 27:
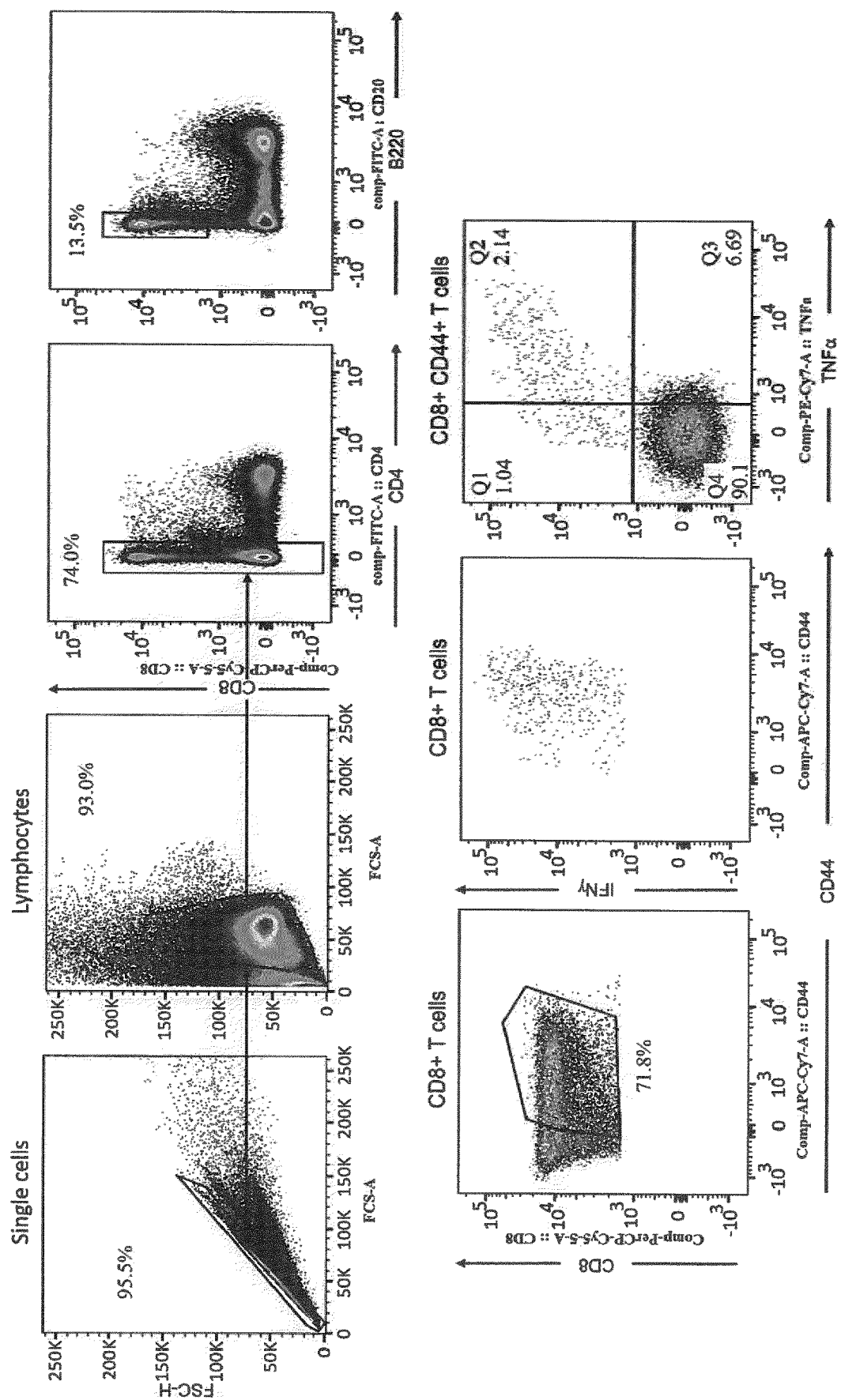

FIG. 27. Gating strategy. The black gates with arrows illustrate, which populations were used for gating the following plots. This picture was made from a positive result from BALB/c mice, immunized with an Adv-based vaccine (prime)+MVA Env (boost).

Figure 28:
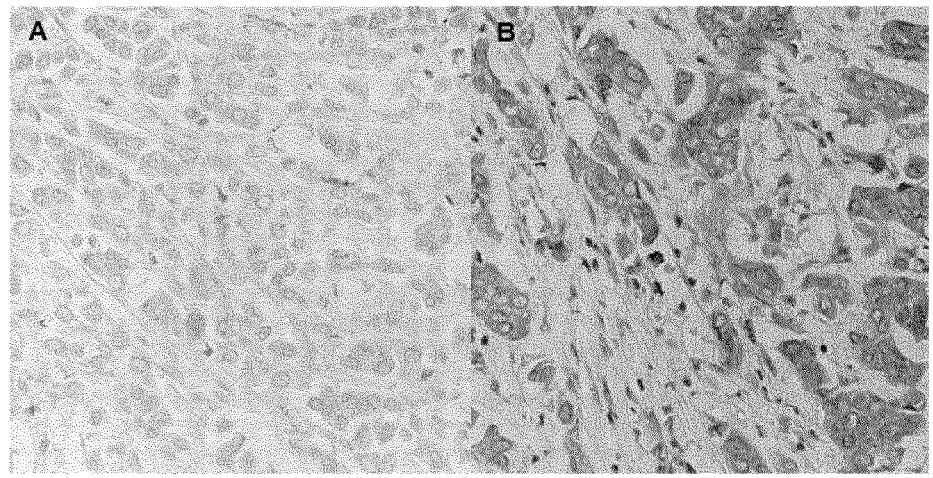

FIG. 28. HERV-K staining of human breast cancer tissue (H841). Tissue samples were obtained from a human mammary tumor. They were sliced at 4 µm and stained with 1:1000 diluted primary antibodies obtained from (A) non-immunized mice (pre-bleed serum) and (B) Ad5_HERV-K Env primed mice boosted with Ad19_HERV-K_ISD (8 w later) and MVA_Env (2 m later) vaccination regimens. 1:500 diluted biotin-labeled anti-mouse secondary antibody was used subsequently and cancer cells were ultimately stained with hematoxylin/eosin. HERV-K specific staining (dark grey) was clearly visualized in the right histological slide corroborating that high titer HERV-K antibodies from vaccinated mice are able to stain cancer tissue expressing the HERV-K target protein.

Figure 29:
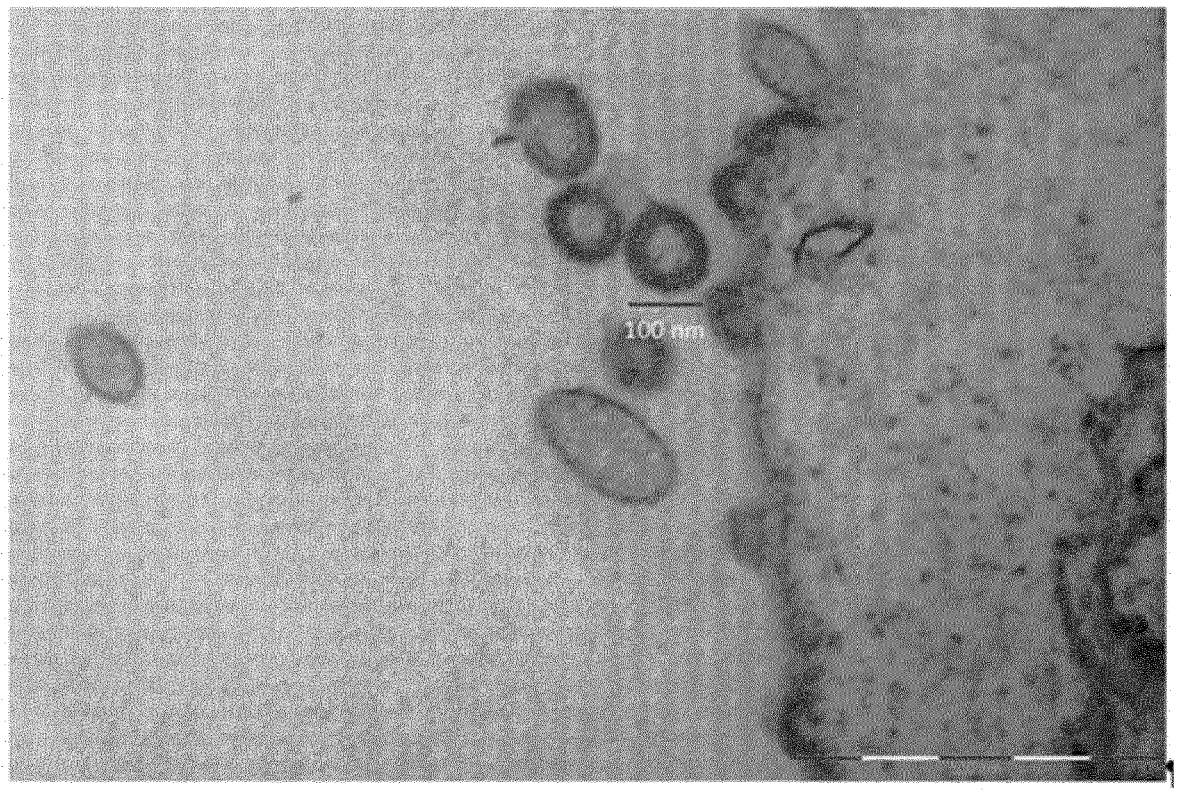

FIG. 29: Morphology of VLPs secreted from transfected cells. A549 cells were transfected with Ad19a-HERV-K ISDmut encoding for Gag_p2A_Env proteins. Cells were fixed after 24 h and the released VLPs (circles of approximately 100 nm) were observed using transmission electron microscopy.

DETAILED DESCRIPTION

Below native sequences are shown in which the individual elements of the sequences are indicated as follows:

Signal peptide
Surface subunit
Transmembrane subunit
Immunosuppressive domain (ISU/ISD)*
Transmembrane domain
Cytoplasmic tail The present invention covers the below mentioned sequences in which one, two or more of the amino acids in the immunosuppressive domain is exchanged with another naturally occurring amino acid.

1. HERV-K108 (=ERVK-6) having the amino acid sequence for the Env protein (SEQ ID No. 9):

MNPSEMQRKAPPRRRRHRNRAPLTHKMNKMVTSEEQMKLPSTKKAEPPTW
AQLKKLTQLATKYLENTKVTQTPESMLLAALMIVSMVVSLPMPAGAAAAN
YTYWAYVPFPPLIRAVTWMDNPTEVYVNDSVWVPGPIDDRCPAKPEEEGM
MINISIGYHYPPICLGRAPGCLMPAVQNWLVEVPTVSPICRFTYHMVSGM
SLRPRVNYLQDFSYQRSLKFRPKGKPCPKEIPKESKNTEVLVWEECVANS
AVILQNNEFGTIIDWAPRGQFYHNCSGQTQSCPSAQVSPAVDSDLTESLD
KHKHKKLQSFYPWEWGEKGISTPRPKIVSPVSGPEHPELWRLTVASHHIR
IWSGNQTLETRDRKPFYTIDLNSSLTVPLQSCVKPPYMLVVGNIVIKPDS
QTITCENCRLLTCIDSTFNWQHRILLVRAREGVWIPVSMDRPWEASPSVH
ILTEVLKGVLNRSKRFIFTLIAVIMGLIAVTATAAVAGVALHSSVQSVNF
VNDWQKNSTRLWNSQSSIDQKLANQINDLRQTVIWMGDRLMSLEHRFQLQ
CDWNTSDFCITPQIYNESEHHWDMVRRHLQGREDNLTLDISKLKEQIFEA
SKAHLNLVPGTEAIAGVADGLANLNPVTWVKT*IGSTTIINLILILVCLFC*
*LLLV*CRCTQQLRRDSDHRERAMMTMAVLSKRKGGNVGKSKRDQIVTVSV

And the Gag protein having the amino acid sequence (SEQ ID No. 10):

MGQTKSKIKSKYASYLSFIKILLKRGGVKVSTKNLIKLFQIIEQFCPWFP
EQGTLDLKDWKRIGKELKQAGRKGNIIPLTVWNDWAIIKAALEPFQTEED
SVSVSDAPGSCIIDCNENTRKKSQKETEGLHCEYVAEPVMAQSTQNVDYN
QLQEVIYPETLKLEGKPELVGPSESKPRGTSPLPAGQVPVTLQPQKQVK
ENKTQPPVAYQYWPPAELQYRPPPESQYGYPGMPPAPQGRAPYPQPPTRR
LNPTAPPSRQGSKLHEIIDKSRKEGDTEAWQFPVTLEPMPPGEGAQEGEP
PTVEARYKSFSIKKLKDMKEGVKQYGPNSPYMRTLLDSIAHGHRLIPYDW
EILAKSSLSPSQFLQFKTWWIDGVQEQVRRNRAANPPVNIDADQLLGIGQ
NWSTISQQALMQNEAIEQVRAICLRAWEKIQDPGSTCPSFNTVRQGSKEP
YPDFVARLQDVAQKSIADEKARKVIVELMAYENANPECQSAIKPLKGKVP
AGSDVISEYVKACDGIGGAMHKAMLMAQAITGVVLGGQVRTFGRKCYNCG
QIGHLKKNCPVLNKQNITIQATTTGREPPDLCPRCKKGKHWASQCRSKFD
KNGQPLSGNEQRGQPQAPQQTGAFPIQPFVPQGFQGQQPPLSQVFQGISQ
LPQYNNCPPPQAAVQQ

2. ERVK-19 having the amino acid sequence for the Env protein (SEQ ID No. 11):

MNPSEMQRKAPPRRRRHRNRAPLTHKMNKMVTSEEQMKLPSTKKAEPPTW
AQLKKLTQLATKYLENTKVTQTPESMLLAALMIVSMVVSLPMPAGAAAAN
YTYWAYVPFPPLIRAVTWMDNPIEVYVNDSVWVPGPTDDHCPAKPEEEGM
MINISIGYRYPPICLGRAPGCLMPAVQNWLVEVPTVSPISRFTYHMVSGM
SLRPRVNYLQDFSYQRSFKFRPKGKPCPKEIPKESKNTEVLVWEECVANS
AVILQNNEFGTIIDWAPRGQFYHNCSGQTQSCPSAQVSPAVDSDLTESLD
KHKHKKLQSFYPWEWGEKGISTPRPKIISPVSGPEHPELWRLTVASHHIR
IWSGNQTLETRDRKPFYTVDLNSSVTVPLQSCIKPPYMLVVGNIVIKPDS
QTITCENCRLLTCIDSTFNWQHRILLVRAREGVWIPVSMDRPWETSPSIH
TLTEVLKGVLNRSKRFIFTLIAVIMGLIAVTATAAVAGVALHSSVQSVNF
VNDWQKNSTRLWNSQSSIDQKLANQINDLRQTVIWMGDRLMSLEHRFQLQ
CDWNTSDFSITPQIYNESEHHWDMVRRHLQGREDNLTLDISKLKEQIFEA
SKAHLNLVPGTEAIAGVADGLANLNPVTWVKT*IGSTTIINLILILVCLFC*
*LLLV*CRCTQQLRRDSDHRERAMMTMAVLSKRKGGNVGKSKRDQIVTVSV and the Gag protein having the amino acid sequence (SEQ ID No. 12):

MGQTKSKIKSKYASYLSFIKILLKRGGVKVSTKNLIKLFQIIEQFCPWFP
EQGTLDLKDWKRIGKELKQAGRKGNIIPLTVWNDWAIIKAALEPFQTEED
SVSVSDAPGSCIIDCNENTRKKSQKETESLHCEYVAEPVMAQSTQNVDYN
QLQEVIYPETLKLEGKVPELVGPSESKPRGTSRLPAGQVPVTLQPQTQVK
ENKTQPPVAYQYWPPAELQYRPPLESQYGYPGMPPAPQGRAPYPQPPTRR
LNPTAPPSRRGSELHEIIDKSRKEGDTEAWQFPVTLEPMPPGEGAQEGEP
PTVEARYKSFSIKMLKDMKEGVKQYGPNSPYMRTLLDSIAHGHRLIPYDW
EILAKSSLSPSQFLQFKTWWIDGVQEQVRRNRAANPPVNIDADQLLGIGQ
NWSTISQQALMQNEAIEQVRAICLRAWEKIQDPGSTCPSFNTVRQGSKEP
YPDFVARLQDVAQKSIAIEKARKVIVELMAYENPNPECQSAIKPLKGKVP
AGSDVISEYVKACDGMGGAMHKAMLMAQAITGVVLGGQVRTFGGKCYNCG
QIGHLKKNCPVLNKQNITIQATTTGREPPDLCPRCKKGKHWASQCRSKFD
KNGQPLSGNEQRGQPQAPQQTGAFPIQPFVPHGFQGQQPPLSQVFQGISQ
LPQYNNCPPPQAAVQQ

3. HERV-K115 (=ERVK-8) having the amino acid sequence for the Env protein (SEQ ID No. 13):

MNPSEMQRKAPPRRRRHRNRAPLTHKMNKMVTSEEQMKLPSTKKAEPPTW
AQLKKLTQLATKYLENTKVTQTPESMLLAALMIVSLPMPAGAAVANYTNW
AYVPFPPLIRAVTWMDNPIEVYVNDSVWVPGPIDDRCPAKPEEEGMMINI
SIGYRYPPICLGRAPGCLMPAVQNWLVEVPTVSPISRFTYHMVSGMSLRP
RVNYLQDFSYQRSLKFRPKGKPCPKEIPKESKNTEVLVWEECVANSAVIL

QNNEFGTIIDWAPRGQFYHNCSGQTQSCPSAQVSPAVDSDLTESLDKHKH
KKLQSFYPWEWGEKRISTPRPKIVSPVSGPEHPELWRLTVASHHIRIWSG
NQTLETRDRKPFYTVDLNSSLTLPLQSCVKPPYMLVVGNIVIKPDSQTIT
CENCRLLTCIDSTFNWQHRILLVRAREGVWIPVSMDRPWEASPSVHILTE
VLKGVLNRSKRFIFTLIAVIMGLIAVTATAAVAGVALHSSVQSVNFVNDG
QKNSTRLWNSQSSIDQKLANQINDLRQTVIWMGDRLMSLEHRFQLQCDWN
TSDFCITPQIYNDSEHHWDMVRRHLQGREDNLTLDISKLKEQIFEASKAH
LNLVPGTEAIAGVADGLANLNPVTWVKT*IGSTTIINLILILVCLFCLLLV*
*CRCTQQLRRDSDHRERAMMTMAVLSKRKGGNVGKSKRDQIVTVSV*

And the Gag protein has the amino acid sequence (SEQ ID No. 14):

MGQTKSKIKSKYASYLSFIKILLKRGGVKVSTKNLIKLFQIIEQFCPWFP
EQGTLDLKDWKRIGKELKQAGRKGNIIPLTVWNDWAIIKAALEPFQTEED
SISVSDAPGSCLIDCNENTRKKSQKETESLHCEYVAEPVMAQSTQNVDYN
QLQEVIYPETLKLEGKGPELVGPSESKPRGTSPLPAGQVPVTLQPQKQVK
ENKTQPPVAYQYWPPAELQYRPPPESQYGYPGMPPAPQGREPYPQPPTRR
LNPTAPPSRQGSELHEIIDKSRKEGDTEAWQFPVTLEPMPPGEGAQEGEP
PTVEARYKSFSIKMLKDMKEGVKQYGPNSPYMRTLLDSIAHGHRLIPYDW
EILAKSSLSPSQFLQFKTWWIDGVQEQVRRNRAANPPVNIDADQLLGIGQ
NWSTISQQALMQNEAIEQVRAICLRAWEKIQDPGSTCPSFNTVRQGSKEP
YPDFVARLQDVAQKSIADEKARKVIVELMAYENANPECQSAIKPLKGKVP
AGSDVISEYVKACDGIGGAMHKAMLMAQAITGVVLGGQVRTFGGKCYNCG
QIGHLKKNCPVLNKQNITIQATTTGREPPDLCPRCKKGKHWASQCRSKFD
KNGQPLSGNEQRGQPQAPQQTGAFPIQPFVPQGFQDNNPHCPKCFRE

4. ERVK-9 having an amino acid sequence of the Env protein (SEQ ID No. 15):

MNPSEMQRKAPPRRRRHRNRAPLTHKMNKMVTSEEQMKLPSTKKAEPPTW
AQLKKLTQLATKYLENTKVTQTPESMLLAALMVVSLPMPAGAAAANYTNW
AYVPFPPLIRAVTWMDNPIEVYVNDSVWVPGPIDDRCPAKPEEEGMMIN
ISIGYRYPICLGRAPGCLMPAVQNWLVEVPISPICRFTYHMVSGMSLR
PRVNYLQDFSYQRSLKFRPKGKPCPKEIPKESKNTEVLVWEECVANSAV
ILQNNEFGTIIDWTPQGQFYHNCSGQTQSCPSAQVSPAVDSDLTESLDK
HKHKKLQSFYPWEWGEKGISTPRPKIISPVSGPEHPELWRLTVASHHIR
IWSGNQTLETRDRKPFYTVDLNSSLTLPLQSCVKPPYMLVVGNIVIKPD
SQTITCENCRLLTCIDSTFNWQHRILLVRAREGVWIPVSMDRPWEASPS
IHILTEVLKGVLNRSKRFIFTLIAVIMGLIAVTATAAVAGVALHSSVQS
VNFVNDGQKNSTRLWNSQSSIDQKLANQINDLRQTVMGDRLMSLEHR
FQLQCDWNTSDFCITPQIYNESEHHWDMVRRHLQGREDNLTLDISKLKE

QIFEASKAHLNLVPGTEAIAGVADGLANLNPVTWVKT*IGSTTIINLILI*
*LVCLFCLLLVCRCTQQLRRDSDHRERAMMTMAVLSKRKGGNVGKSKRD*
*QIVTVSV* and an amino acid sequence of the Gag protein (SEQ ID No. 16):

MGQTKSKIKSKYASYLSFIKILLKRGGVKVSTKNLIKLFQIIEQFCPWFP
EQGTLDLKDWKRIGKELKQAGRKGNIIPLTVWNDWAIIKAALEPFQTEED
SISVSDAPGSGIIDCNEKTRKKSQKETESLHCEYVAEPVMAQSTQNVDYN
QLQEVIYPETLKLEGKGPELVGPSESKPRGTSPLPAGQVPVTLQPQKQVK
ENKTQPPVAYQYWPPAELQYRPPPESQYGYPGMPPAPQGRAPYPQPPTRR
LNPTAPPSRQGSELHEIIDKSRKEGDTEAWQFPVTLEPMPPGEGAQEGEP
PTVEARYKSFSIKILKDMKEGVKQYGPNSPYMRTLLDSIAHGHRLIPYDW
EILAKSSLSPSQFLQFKTWWIDGVQEQVRRNRAANPPVNIDADQLLGIGQ
NWSTISQQALMQNEAIEQVRAICLRAWEKIQDPGSTCPSFNTVRQGSKEP
YPDFVARLQDVAQKSIADEKARKVIVELMAYENANPECQSAIKPLKGKVP
AGSDVISEYVKACDGIGGAMHKAMLMAQAITGVVLGGQVRTFGGKCYNCG
QIGHLKKNCPVLNKQNITIQATTTGREPPDLCPRCKKGKHWASQCRSKFD
KNGQPLSGNEQRGQPQAPQQTGAFPIQPFVPQGFQGQQPPLSQVFQGISQ
LPQYNNCPPPQVAVQQ

5. HERV-K113 having an amino acid sequence of the Env protein (SEQ ID No. 17):

MNPSEMQRKAPPRRRRHRNRAPLTHKMNKMVTSEEQMKLPSTKKAEPPTW
AQLKKLTQLATKYLENTKVTQTPESMLLAALMVVSLPMPAGAAAANYTYW
AYVPFPPLIRAVTWMDNPIEIYVNDSVWVPGPTDDCCPAKPEEEGMMINI
SIGYRYPPICLGRAPGCLMPAVQNWLVEVPTVSPISRFTYHMVSGMSLRP
RVNYLQDFSYQRSLKFRPKGKPCPKEIPKESKNTEVLVWEECVANSAVIL
QNNEFGTLIDWAPRGQFYHNCSGQTQSCPSAQVSPAVDSDLTESLDKHKH
KKLQSFYPWEWGEKGISTARPKIISPVSGPEHPELWRLTVASHHIRIWSG
NQTLETRDRKPFYTIDLNSSLTVPLQSCVKPPYMLVVGNIVIKPDSQTIT
CENCRLLTCIDSTFNWQHRILLVRAREGVWIPVSMDRPWEASPSVHILTE
VLKGVLNRSKRFIFTLIAVIMGLIAVTATAAVAGVALHSSVQSVNFVNDW
QNNSTRLWNSQSSIDQKLANQINDLRQTVIWMGDRLMSLEHRFQLQCDWN
TSDFCITPQIYNESEHHWDMVRCHLQGREDNLTLDISKLKEQIFEASKAH
LNLVPGTEAIAGVADGLANLNTVTWVKT*IGSTTIINLILILVCLFCLLLV*
*VYRCTQQLRRDSDHRERAMMTMVVLSKRKGGNVGKSKRDQIVTVSV* and an amino acid sequence of the Gag protein (SEQ ID No. 18):

MGQTKSKIKSKYASYLSFIKILLKRGGVKVSTKNLIKLFQIIEQFCPWFP
EQGTLDLKDWKRIGKELKQAGRKGNIIPLTVWNDWAIIKAALEPFQTEED

-continued

SVSVSDAPGSCIIDCNEKTRKKSQKETESLHCEYVAEPVMAQSTQNADYN

QLQEVIYPETLKLEGKGPELMGPSESKPRGTSPLPAGQVPVTLQPQKQVK

ENKTQPPVAYQYWPPAELQYQPPPESQYGYPGMPPAPQGRAPYPQPPTRR

LNPTAPPSRQGSELHEIIDKSRKEGDTEAWQFPVTLELMPPGEGAQEGEP

PTVEARYKSFSIKMLKDMKEGVKQYGPNSPYMRTLLDSIAHGHRLIPYDW

EILAKSSLSPSQFLQFKTWWIDGVQEQVRRNRAANPPVNIDADQLLGIGQ

NWSTISQQALMQNEAIEQVRAICLRAWEKIQDPGSTCPSFNTVRQGSKEP

YPDFVARLQDVAQKSIADEKARKVIVELMAYENANPECQSAIKPLKGKVP

AGSDVISEYVKACDGMGGAMHKAMLMAQAITGVVLGGQVRTFGGKCYNCG

QIGHLKKNCPVLNKQNITIQATTTGREPPDLCPRCKKGKHWASQCRSKFD

KNGQPLSGNEQRGQPQAPQQTGAFPIQPFVPQGFQGQQPPLSQVFQGISQ

LPQYNNCPPPQAAVQQ

6. ERVK-21 having an amino acid sequence of the Env protein (SEQ ID No. 19):

MHPSEMQRKAPPRRRRHRNRAPLTHKMNKMVTSEQMKLPSTKKAEPPTWA

QLKKLTQLATKYLENTKVTQTPESMLLAALMIVSMVVSLPMPAGAAAANY

TYWAYVPFPPLIRAVTWMDPIEVYVNDSVWVHGPIDDRCPAKPEEEGMM

INISIGYHYPPICLGRAPGCLMPAVQNWLVEVPTVSPISRFTYNMVSGM

SLRPRVNYLQDFSYQRSLKFRPKGKPCPKEIPKESKNTEVLVWEECVAN

SVVILQNNEFGTIIDWAPRGQFYHNCSGQTQSCPSAQVSPAVDSDLTES

LDKHKHKKLQSFYPWEWGEKGISTPRPKIISPVSGPEHPELWRLTVASH

HIRIWSGNQTLETRDRKPFYTVDLNSSLTVPLQSCVKPPYMLVVGNIVI

KPDSQTITCENCRLLTCIDSTFNWQHRILLVRAREGVWIPVSMDRPWEA

SPSIHILTEVLKGVLNRSKRFIFTLIAVIMGLIAVTAMAAVAGVALHSF

VQSVNFVNDWQKNSTRLWNSQSSIDQKLANQINDLRQTVIWMGDRLMSL

EHRFQLQCDWNTSDFCITPQIYNESEHHWDMVRRHLQGREDNLTLDISK

LKEQIFEASKAHLNLVPGTEAIAGVADGLANLNPVTWVKTIGSTTIINL

ILILVCLFCLLLVCRCTQQLRRDSDHRERAMMTMVVLSKRKGGNVGKSKR

DQIVTVSVKRDQIVTVSV having an amino acid sequence of the Env protein (SEQ ID No. 20):

MGQTKSKIKSKYASYLSFIKILLKRGGVKVSTKNLIKLFQIIEQFCPWFP

EQGTLDLKDWKRIGKELKQAGRKGNIIPLTVWNDWAIIKAALEPFQTEED

SISVSDAPGSCIIDCNENTRKKSQKETEGLHCEYAAEPVMAQSTQNVDYN

QLQEVIYPETLKLEGKGPELVGPSESKPRGTSPLPAGQVPVTLQPQTQVK

ENKTQPPVAYQYWPPAELQYRPPPESQYGYPGMPPAPQGRAPYPQPPTRR

LNPTAPPSRQGSELHEIIDKSRKEGDTEAWQFPVMLEPMPPGEGAQEGEP

PTVEARYKSFSIKMLKDMKEGVKQYGPNSPYMRTLLDSIAHGHRLIPYDW

EILAKSSLLPSQFLQFKTWWIDGVQEQVQRNRAANPPVNIDADQLLGIGQ

NWSTISQQALMQNEAIEQVRAICLRAWEKIQDPGSTCPSFNTVRQSSKEP

YPDFVARLQDVAQKSIADEKARKVIVELMAYENANPECQSAIKPLKGKVP

AGSDVISEYVKACDGIGGAMHKAMLMAQAITGVVLGGQVRTFGGKCYNCG

QIGHLKKNCPVLNKQNITIQATTTGREPPDLCPRCKKGKHWASQCRSKFD

KNGQPLSGNEQRGQPQAPQQTGAFPIQPFVPQGFQGQQPPLSQVFQGISQ

LPQYNNCPPPQAAVQQ

7. ERVK-25 having an amino acid sequence of the Env protein (SEQ ID No. 21):

MNPSEMQRKAPPRRRRHRNRAPLTHKMNKMVTSEEQMKLPSTKKAEPPTW

AQLKKLTQLATKYLENTKVTQTPESMLLAALMIVSMVVSLPMPAGAAAAN

YTYWAYVPFPPLIRAVTWMDNPIEVYVNDSVWVPGPIDDRCPAKPEEEGM

MINISIGYRYPPICLGTAPGCLMPAVQNWLVEVPIVSPISRFTYHMVSGM

SLRPRVNYLQDFSYQRSLKFRPKGKPCPKEIPKESKNTEVLVWEECVANS

AVILQNNEFGTIIDWAPRGQFYHNCSGQTQSCPSAQVSPAVDSDLTESLD

KHKHKKLQSFYPWEWGEKGISTPRPKIVSPVSGPEHPELWRLTVASHHIR

IWSGNQTLETRDRKPFYTVDLNSSLTVPLQSCVKPPYMLVVGNIVIKPDS

QTITCENCRLLTCIDSTFNWQHRILLVRAREGVWIPVSMDRPWEASPSIH

ILTEVLKGVLNRSKRFIFTLIAVIMGLIAVTATGAVAGVALHSSVQSVNF

VNDWQKNSTRLWNSQSSIDQKLANQINDLRQTVIWMGDRLMSLEHRFQLQ

CDWNTSDFCITPQIYNESEHHWDMVRRHLQGREDNLTLDISKLKEQIFKA

SKAHLNLVPGTEAIAGVADGLANLNPVTWVKTIGSTTIINLILILVCLFC

LLLVCRCTQQL

8. HERV-K102=ERVK-7 having an amino acid sequence of the Env protein (SEQ ID No. 22):

MVTPVTWMDNPIEIYVNDSVWVPGPIDDRCPAKPEEEGMMINISIGYRYP

PICLGRAPGCLMPAVQNWLVEVPTVSPISRFTYHMVSGMSLRPRVNYLQD

FSYQRSLKFRPKGKPCPKEIPKESKNTEVLVWEECVANSAVILQNNEFGT

IIDWAPRGQFYHNCSGQTQSCPSAQVSPAVDSDLTESLDKHKHKKLQSFY

PWEWGEKRISTPRPKIVSPVSGPEHPELWRLTVASHHIRIWSGNQTLETR

DCKPFYTIDLNSSLTVPLQSCVKPPYMLVVGNIVIKPDSQTITCENCRLL

SCIDSTFNWQHRILLVRAREGVWIPVSMDRPWEASPSVHILTEVLKGVLN

RSKRFIFTLIAVIMGLIAVTATAAVAGVALHSSVQSVNFVNDWQKNSTRL

WNSQSSIDQKLANQINDLRQTVIWMGDRLMSLEHRFQLQCDWNTSDFCIT

PQIYNESEHHWDMVRRHLQGREDNLTLDISKLKEQIFEASKAHLNLVPGT

EAIAGVADGLANLNPVTWVKTIGSTTIINLILILVCLFCLLLVCRCTQQL

RRDSDHRERAMMTMAVLSKRKGGNVGKSKRDQIVTVSV

And having an amino acid sequence of the Gag protein (SEQ ID No. 23):

MGQTKSKIKSKYASYLSFIKILLKRGGVKVSTKNLIKLFQIIEQFCPWFP
EQGTLDLKDWKRIGKELKQAGRKGNIIPLTVWNDWAIIKAALEPFQTEKD
SVSVSDALGSCIIDCNENTRKKSQKETEGLHCEYVAEPVMAQSTQNVDYN
QLQEVIYPETLKLEGKGPELVGPSESKPRGTSHLPAGQVPVTLQPQKQVK
ENKTQPPVAYQYWPPAELQYRPPPESQYGYPGMPPAPQGRAPYPQPPTRR
LNPTAPPSRQGSELHEIIDKSRKEGDTEAWQFPVTLEPMPPGEGAQEGEP
PTVEARYKSFSIKMLKDMKEGVKQYGPNSPYMRTLLDSIAHGHRLIPYDW
EILAKSSLSPSQFLQFKTWWIDGVQEQVRRNRAANPPVNIDADQLLGIGQ
NWSTISQQALMQNEAIEQVRAICLRAWEKIQDPGSTCPSFNTVRQGSKEP
YPDFVARLQDVAQKSIADEKARKVIVELMAYENANPECQSAIKPLKGKVP
AGSDVISEYVKACDGIGGAMHKAMLMAQAITGVVLGGQVRTFGGKCYNCG
QIGHLKKNCPVLNKQNITIQATTTGREPPDLCPRCKKGKHWASQCRSKFD
KNGQPLSGNEQRGQPQAPQQTGAFPIQPFVPQGFQEQQPPLSQVFQGISQ
LPQYNNCPPPQAAVQQ

9. HERV-K101=ERVK-24 having an amino acid sequence of the Env protein (SEQ ID No. 24):

MVTPVTWMDNPIEVYVNDSEWVPGPTDDRCPAKPEEEGMMINISIGYRYP
PICLGTAPGCLMPAVQNWLVEVPIVSPISRFTYHMVSGMSLRPRVNYLQD
FPYQRSLKFRPKGKPCPKEIPKESKNTEVLVWEECVANSAVILQNNEFGT
IIDWAPRGQFYHNCSGQTQSCPSAQVSPAVDSDLTESLDKHKHKKLQSFY
PWEWGEKGISTPRPKIISPVSGPEHPELWRLTVASHHIRIWSGNQTLETR
DRKPFYTVDLNSSLTLPLQSCVKPPYMLVVGNIVIKPDSQTITCENCRLL
TCIDSTFNWQHRILLVRAREGVWILVSMDRPWEASPSVHILTEVLKGVLN
RSKRFIFTLIAVIMGLIAVTATGAVAGVALHSSVQSVNFVNDWQKNSTRL
WNSQSSIDQKLANQINDLRQTVIWMGDRLMSLEHRFQLQCDWNTSDFCIT
PQIYNESEHHWDMVRRHHLQGREDNLTLDISKLKEQIFEASKAHLNLVPGT
EAIAGVADGLANLNPVTWVKT*IGSTTIINLILILVCLFCLLL*VCRCTQQL
RRDSDHRERAMMTMAVLSKRKGGNVGKSKRDQIVTVSV

And having an amino acid sequence of the Gag protein (SEQ ID No. 25):

MGQTKSKIKSKYASYLSFIKILLKRGGVKVSTKNLIKLFQIIEQFCPWFP
EQGTLDLKDWKRIGKELKQAGRKGNIIPLTVWNDWAIIKAALEPFQTEED
SVSVSDAPGSCLIDCNEKTRKKSQKETESLHCEYVAEPVMAQSTONVDYN
QLQEVIYPETLKLEGKGPELVGPSESKPRGTSPLPAGQVPVTLQPQKQVK
ENKTOPPVAYQYWPPAELQYRPPPESQYGYPGMPPAPQGRAPYPQPPTRR
LNPTAPPSRQGSELHEIIDKSRKEGDTEAWQFPVTLEPMPPGEGAQEGEP
PTVEARYKSFSIKMLKDMKEGVKQYGPNSPYMRTLLDSIAYGHRLIPYDW
EILAKSSLSPSQFLQFKTWWIDGVQEQVRRNRAANPPVNIDADQLLGIGQ
NWSTISQQALMQNEAIEQVRAICLRAWEKIQDPGSACPSFNTVRQGSKEP
YPDFVARLQDVAQKSIADEKARKVIVELMAYENANPECQSAIKPLKGKVP
AGSDVISEYVKACDGIGGAMHKAMLMAQAITGVVLGGQVRTFGGKCYNCG
QIGHLKKNCPVLNKQNITIQATTTGREPPDLCPRCKKGKHWASQCRSKED
KNGQPLSGNEQRGQPQAPQQTGAFPIQPFVPQGFQGQOPPLSQVFQGISQ
LPQYNNCPLPQAAVQQ

10. HERV-K110=ERVK-18 having an amino acid sequence of the Env protein (SEQ ID No. 26):

MVTPVTWMDNPIEVYVNDSVWVPGPTDDRCPAKPEEEGMMINISIGYHYP
PICLGRAPGCLMPAVQNWLVEVPTVSPNSRFTYHMVSGMSLRPRVNCLQD
FSYQRSLKFRPKGKTCPKEIPKGSKNTEVLVWEECVANSVVILQNNEFGT
IIDWAPRGQFYHNCSGQTQSCPSAQVSPAVDSDLTESLDKHKHKKLQSFY
LWEWEEKGISTPRPKIISPVSGPEHPELWRLTVASHHIRIWSGNQTLETR
YRKPFYTIDLNSILTVPLQSCVKPPYMLVVGNIVIKPASQTITCENCRLF
TCIDSTFNWQHRILLVRAREGMWIPVSTDRPWEASPSIHILTEILKGVLN
RSKRFIFTLIAVIMGLIAVTATAAVAGVALHSSVQSVNFVNYWQKNSTRL
WNSQSSIDQKLASQINDLRQTVIWMGDRLMTLEHHFQLQCDWNTSDFCIT
PQIYNESEHHWDMVRRHLQGREDNLTLDISKLKEQIFEASKAHLNLVPGT
EAIAGVADGLANLNPVTWIKT*IRSTMIINLILIVVCLFCLLL*VCRCTQQL
RRDSDIENGP

11. HERV-H19=HERV-H_2q24.3 having an amino acid sequence of the Env protein (SEQ ID No. 27):

MIFAGKAPSNTSTLMKFYSLLLYSLLFSFPPFLCHPLPLESYLHHTINLTH
------------------------------------------
SLLAASNPSLVNNCWLCISLSSSAYTAVPAVQTDWATSPISLHLRTSFNS
PHLYPPEELIYFLDRSSKTSPDISHQQAAALLRTYLKNLSPYINSTPPIF
GPLTTQTTIPVAAPLCISWQRPTGIPLGNLSPSRCSFTLHLRSPTTNINE
TIGAFQLHITDKPSINTDKLKNISSNYCLGRHLPCISLHPWLSSPCSSDS
PPRPSSCLLIPSPENNSERLLVDTRRFLIHHENRTFPSTQLPHQSPLQPL
TAAALAGSLGVWVQDTPFSTPSHLFTLHLQFCLAQGLFFLCGSSTYMCLP
ANWTGTCTLVFLTPKIQFANGTEELPVPLMTPTQQKRVIPLIPLMVGLGL
SASTVALGTGIAGISTSVMTFRSLSNDFSASITDISQTLSVLQAQVDSLA
AVVLQNRRGLDLLTAEKGGLCIFLNEECCFYLNQSGLVYDNIKKLKDRAQ
KLANQASNYAEPPWALSNWMSWV*LPIVSPLIPIFLLLLF GPCIF*RLVSQF
IQNRIQAITNHSIRQMFLLTSPQYHPLPQDLPSA

12. HERV-H_2q24.1 having an amino acid sequence of the Env protein (SEQ ID No. 28):

MILAGRAPSNTSTLMKFYSLLLYSLLFSFPLYHPLPLPSYLHHTINLTH
------------------------------------------
SLPAASNPSLANNCWLCISLSSSAYIAVPTLQTDRATSPVSLHLRTSFNS
PHLYPPEELIYFLDRSSKTSPDISHQPAAALLHIYLKNLSPYINSTPPIF

-continued
```
GPLTTQTTIPVAAPLCISRQRPTGIPLGNISPSRCSFTLHLQSPTTHVTE

TIGVFQLHIIDKPSINTDKLKNVSSNYCLGRHLPYISLHPWLPSPCSSDS

PPRPSSCLLTPSPQNNSERLLVDTQRFLIHHENRTSSSMQLAHQSPLQPL

TAAALAGSLGVWVQDTPFSTPSHPFSLHLQFCLTQGLFFLCGSSTYMCLP

ANWTGTCTLVFLTPKIQFANGTKELPVPLMTLTPQKRVIPLIPLMVGLGL

SASTIALSTGIAGISTSVTTFRSPSNDFSASITDISQTLSVLQAQVDSLA

AVVLQNRRGLGLSILLNEECCFYLNQSGLVYENIKKLKDRAQKLANQASN

YAESPWALSNWMSWVLPILSPLIPIFLLLLFGPCIFHLVSQFIQNRIQAI

TNHSI
```

13. HERV-W=ERVW-1=Syncytin-1 having an amino acid sequence of the Env protein (SEQ ID No. 30):

```
MGNLPPSIPPSSPLACVLKNLKPLQLTPDLKPKCLIFFCNTAWPQYKLDN

GSKWPENGTFDFSILQDLNNFCRKMGKWSEVPYVQAFFTLRSLPSLCSQC

DASQILLLSLPPVPSVPTPSVAESFRSSFSTDPSDLSPPPQAARRQAELG

PNSSSASAPPPYNLFIASPPHTWSGLQFHSMTSLPPPAQQFTLKKVAGAK

GIVKVNAPFSLSQIR
```

And having an amino acid sequence of the Gag protein (SEQ ID No. 29):

```
MALPYHIFLFTVLLPSFTLTAPPPCRCMTSSSPYQEFLWRMQRPGNIDAP

SYRSLSKGTPTFTAHTHMPRNCYHSATLCMHANTHYWTGKMINPSCPGGL

GVTVCWTYFTQTGMSDGGGVQDQAREKHVKEVISQLTRVHGTSSPYKGLD

LSKLHETLRTHTRLVSLFNTTLTGLHEVSAQNPTNCWICLPLNFRPYVSI

PVPEQWNNFSTEINTTSVLVGPLVSNLEITHTSNLTCVKFSNTTYTTNSQ

CIRWVTPPTQIVCLPSGIFFVCGTSAYRCLNGSSESMCFLSFLVPPMTIY

TEQDLYSYVISKPRNKRVPILPFVIGAGVLGALGTGIGGITTSTQFYYKL

SQELNGDMERVADSLVTLQDQLNSLAAVVLQNRRALDLLTAERGGTCLFL

GEECCYYVNQSGIVTEKVKEIRDRIQRRAEELRNTGPWGLLSQWMPWILP

FLGPLAAIILLLLFGPCIFNLLVNFVSSRIEAVKLQMEPKMQSKTKIYRR

PLDRPASPRSDVNDIKGTPPEEISAAQPLLRPNSAGSS
```

14. HERV-FRD=ERVFRD-1=Syncytin-2 having an amino acid sequence of the Env protein (SEQ ID No. 31):

```
MGLLLLVLILTPSLAAYRHPDFPLLEKAQQLLQSTGSPYSTNCWLCTSSS

TETPGTAYPASPREWTSIEAELHISYRWDPNLKGLMRPANSLLSTVKQDF

PDIRQKPPIFGPIFTNINLMGIAPICVMAKRKNGTNVGTLPSTVCNVTFT

VDSNQQTYQTYTHNQFRHQPRFPKPPNITFPQGTLLDKSSRFCQGRPSSC

STRNFWFRPADYNQCLQISNLSSTAEWVLLDQTRNSLFWENKTKGANQSQ

TPCVQVLAGMTIATSYLGISAVSEFFGTSLTPLFHFHISTCLKTQGAFYI

CGQSIHQCLPSNWTGTCTIGYVTPDIFIAPGNLSLPIPIYGNSPLPRVRR

AIHFIPLLAGLGILAGTGTGIAGITKASLTYSQLSKEIANNIDTMAKALT
```

```
TMQEQIDSLAAVVLQNRRGLDMLTAAQGGICLALDEKCCFWVNQSGKVQD

NIRQLLNQASSLRERATQGWLNWEGTWKWFSWVLPLTGPLVSLLLLLLFG

PCLLNLITQFVSSRLQAIKLQTNLSAGRHPRNIQESPF
```

15. HERV-E having an amino acid sequence of the Env protein (SEQ ID No. 32 and 33):

```
MQKLIMGFIFLKFWTYTVRASTDLTQTGDCSQCIHQVTEVGQQIKTMFLF

YSYYKCIGTLKETCLYNATQYNVCSPGNDRPDVCYNPSEPPATTIFEIRI

RTGLFLGDTSKIITRTEEKEIPKQITLRFDACAAINSKKLGIGCDSLNWE

RSYRIKNKYVCHESGVCENCAYWPCVIWATWKKNKKDPVYLQKGEANPSC

AAGHCNPLELIITNPLDPHWKKGERVTLGIDTGLNPQVAILIRGEVHKC

SPKPVFQTFYKELNLPAPEFPKKTKNLFLQLAENVAHSLNVTSCYVCGGT

TIGDRWPWEARELVPTDPAPDIIPVQKTQASNFWVLKTSIIGQYCIAREG

KDFIIPVGKLNCIGQKLYNSTTKTITWWGINHTEKNPFSKFSKLKTAWAH

PESHQDWMAPAGLYWICGHRAYIRLPNK*

MLNRIIRLQAILEIITNETGRALTVLARQETQTRNAIYQNRLALDYLLAA

EGGVCGKFNLTNYCLQIDDQGQVVENIVRDMAKVAHVPVQVWHKFNPESL

FGKWFPAIGGFKTLIVGVLLVIGTCLLLPCVLPLLFQMIKYFVVTLVHQK

TSAHVYYTNHYRSISQRD
```

And having an amino acid sequence of the Gag protein (SEQ ID No. 34 to 38):

```
TPLGTMLKNFKKGFNGDYGVTMTPGKLRTLCEIDWPTLEVGWPSEGSLDG

SLVSKVWHKVTSKSGHSDQFPYIDTWLQLVLDPPQWLRGQAAAVLVAKGQ

IVKEGFCSTR*GKSTPEVLFDQTSEDPLQEMAPVIPVLPSPYQGERLPTF

ESTVLAPLPDKCIPRPLRVDKRGGEASGETPPLAAHLRPKTGIQMPLREQ

QYTGIDEDGHMVESRVFVYQPFTSADLLNWKNNTPSYTEKPQALIDLLQT

IIQTHNPTWADCHQLLMFLFKTDER*RVLQAATKWLEEHALADYQNPQEY

VRTQLPGTDPQWDPN*REDMQRLNRYRKALLEGLKRRAQKATNINKVSEV

IQGKEESPAKFHERLCEAYCMYTPFDPDSPENQRMINMALVSQSTEDIRR

KLQKKAGFAGMNTSQLLEIANQVFVNRDAASRKETT*RMNVRPGETRLLA

AAIRGVPPKEARQKGGPGKETQPGCQSLQCNQCAYRKEIGYWKNKCPQLK

GKQGDSEQEAPDKEEGALLNLAEGLLD*
```

16. HERV-E having an amino acid sequence of the Env protein (SEQ ID No. 39):

```
MRKLIVGFIFLTFWTYTVRASTDLTQTGDCSQSIHQVTEVGQQIKTNFLF

YSYYECMGTLKETCLYNATQYKVCSPGNDRPDVCYNPSEPPATTVFEIRL

RTGLFLGDTSKIITRTVEKGIPKQITLRFDARAAINSNKLGTRCGSLNWE

RSYTVQNKYVCHESGVCENCAFWPCVIWATWKKNKKDPVHLQKGEANPSC

AAGHCNPLELIITNPLDPPWKKGERVTLGIDTGLNPQVAILVRGEVHKR

SPKPVFQTFYEELNLPAPELPKKTKSLFLQLAGNVAHSLNVTSCYVCRGT
```

-continued

```
TIGDRWPWEARELVPTDPAPDIIPVQKAQASNFWVLKTSIIGQYCIAREG

KEFIVPVGKLNCIGQKLYNSTTKTITWWGLNHTEKNPFSKFSKLKTAWAH

PESHQDWTAPTGLYRICGHTAYIQLPNKWAGSCVIGTIKLSFFLLPIKTG

ELLGFRVYTSREKRGIVIGNWKDNEWPPERIIQYYGPATWVQDGSWGYQT

PIYMLNQIIRLQTVLEIITNETGRALTVLARQETQMRNAIYQNRLALDYL

LAAEGGVCGKFNLTNCCLQIDDQGQVIENIVRDMTKLAHTPIQVWHKFDP

ESLFGKWFPAIGGFKTLIVGVLLVIRTCLLLPCVLPLLFQMIKGIVATLV

HQKTSAHVNYMNHYRSISQRDSKSEDESENSH
```

And having an amino acid sequence of the Gag protein (SEQ ID No. 40):

```
MLKNFKKGFNGDYGVTMTPGKLRILCEIDWPTLEVGWPSEGSLDRSLVSK

VWHKVTGKSGHSDQFPYIDTWLLQLVQDPPQWLRGQAAAVLVAKGQIAKE

GSRSTHWGKSTPEVLFDPTSEDPLQEMAPVIPVLPSPYQAERLPTFEPTV

LVPPQDKHIPRPPRVDKRGGEASGETPPLAACLRPKTGIQMPLREQRYTG

IEEDGHMVEKRVFVYQPFTSANLLNWKNNTLSYTEKPQALIDLLQTIIQT

HNSTRADCHQLLMFLFNTDERQRVLQAATKWVQEHAPADYQNPQECVRTQ

LPGTDPQWDPNEREDMQRLNRDREAVLEGLKRGAQKATNVNKVSEVIRGK

EESPAQFYQRLCEGYRMYTPFDPVSPENQRMVNMALVSQSAEDIRRKLQK

QDGFAGTNTSQLLEVANQVFVNRDAVSPKENRRENERQARRNAELLAAAV

GGVSSKRQGKGGPGKETQPGCQSLQCNQCAYCKEIGYWKNKCPQLKGKQG

DLEQEVPDKEEGALLNLAEELLD
```

The target cancer for HERV-K is prostate cancer, breast cancer, ovarian cancer, lymphomas, melanomas, leukemia and sarcomas. The target cancer for HERV-H is colorectal cancer. The target cancer for HERV-W is testicular cancer, ovarian cancer, breast cancer, lymphomas and leukemia, and the target cancer for HERV-E is lung cancer and liver cancer.

EXAMPLES

The materials and methods indicated below is common for the subsequent examples.

The prototype vaccines (DNA-MelARV and Ad5-MelARV) comprised of a DNA plasmid (768tet) or an adenovirus type 5 (Ad5) which encoded the gene MelARVgag_p2A_env under the strong human cytomegalovirus immediate-early promoter (CMV promoter). This gene simultaneously expressed the MelARV proteins Gag and Env linked via the self-cleavable peptide p2A. While Gag induced formation of virus-like particles (VLPs), the target protein Env was integrated into the forming VLPs.

Further, vaccines were designed to target the envelope (Env) protein of the human endogenous retroviruses type K (HERV-K or HML-2) expressed in tumor cells, and they were tested for induction of cellular and humoral immune responses and anti-cancer efficacy.

The designed vaccines comprise either a DNA plasmid (768tet), an adenovirus type 5 (Ad5), or an adenovirus type 19 (Ad19a), each of them encoding the group-specific antigen (Gag) and Env genes (HERV-KGag_p2A_Env) under the strong human cytomegalovirus immediate-early promoter (CMV promoter). These two proteins are expressed concurrently with the self-cleavable peptide p2A as linker, which remains associated to the Gag protein involved in virus-like particle (VLP) formation. The Env protein is incorporated to the forming VLPs, and it serves as a target to generate specific immune responses.

Figure 1:
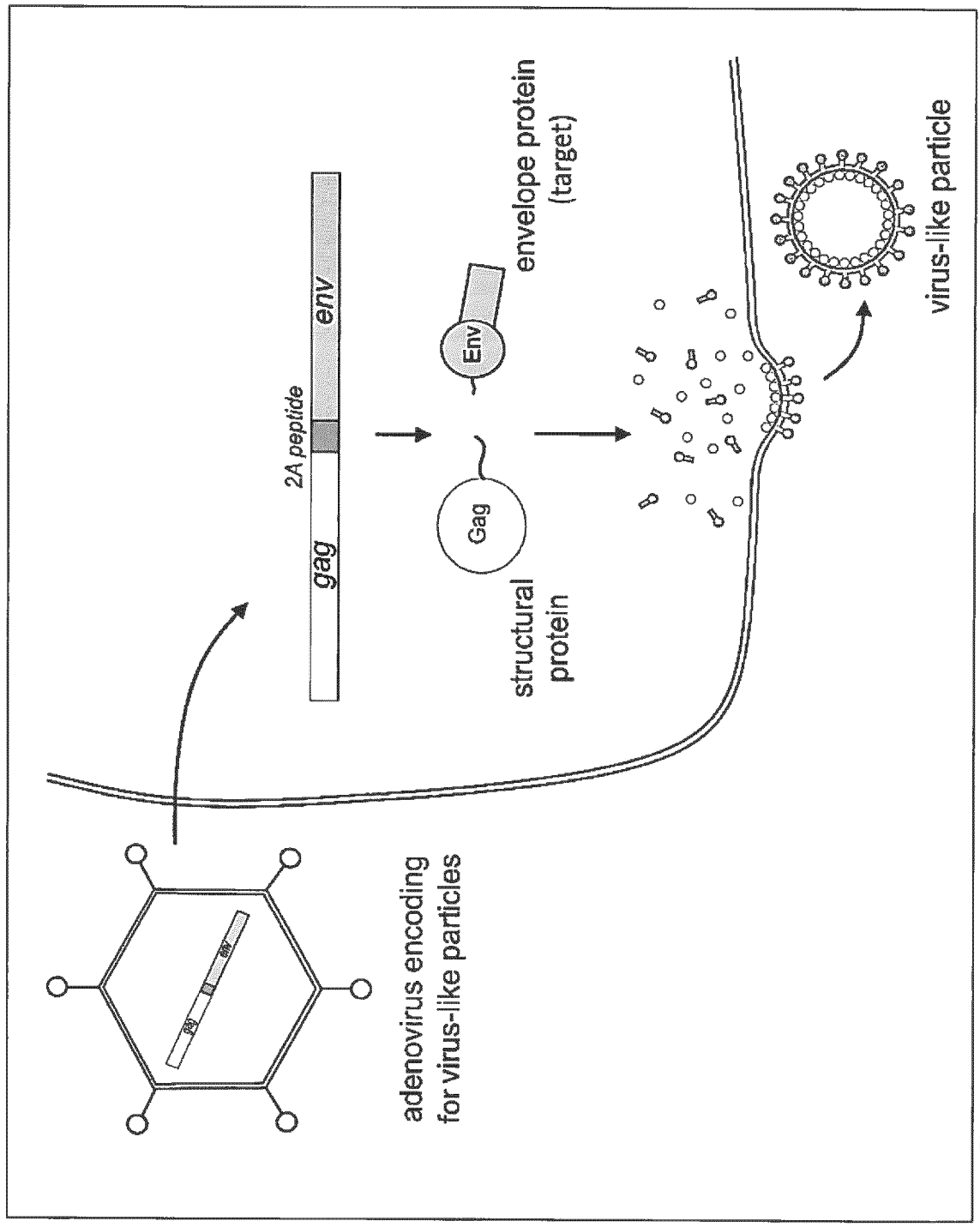
FIG. 1 discloses the mechanism of virus vector-encoded virus-like particles. The vaccine comprising a recombinant adenovirus (Ad5) encoding for viral Gag and Env proteins. Upon injection, Ad5 infects cells and induces expression of the encoded proteins. Gag and Env are coupled via a self-cleavable peptide (p2A) that assures equimolar expression of both proteins but also separation upon translation. The structural protein Gag alone is sufficient to induce budding of the cell membrane and formation of virus-like particles (VLP). During VLP formation, Env associates with Gag and is integrated into the released VLPs. Thus, vaccination with the Ad5 vector induces production of VLPs that display the target protein Env on their surface to the immune system.
Figure 2:
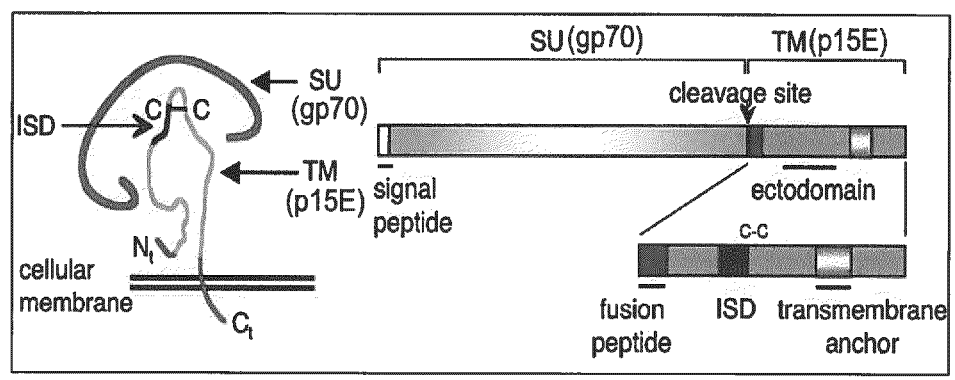
FIG. 2 shows the schematic structure of the MuLV/MelARV envelope protein. The envelope protein (Env) consists of two subunits. (left) The trans-membrane subunit p15E (TM) is anchored in the cell membrane and contains an immunosuppressive domain (ISD) and a fusion peptide. p15E is covalently coupled via disulfide bridges to the surface subunit gp70 (SU). p15E and especially the ISD are shielded by gp70 to prevent antibody binding. (right) The protein subunits are expressed as a precursor protein that is cleaved during processing and transported to the membrane. Figure modified from Mangeney et al 2007.
Figure 3:
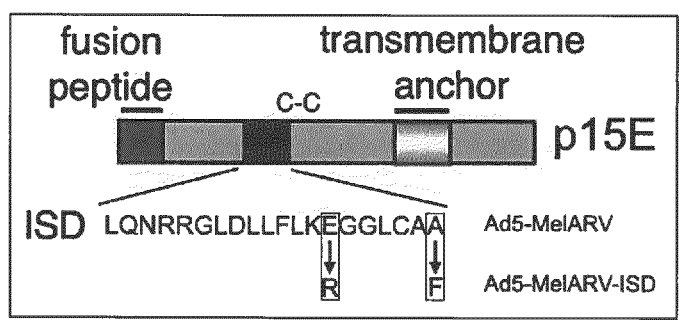
FIG. 3 shows the mutations in the ISD of vaccine-encoded MelARV Env (p15E). Two amino acids in the ISD of p15E were mutated to inactivate the immunosuppressive mechanism. Thus, the following amino acid changes were performed: $E_{14} \rightarrow R_{14}$ and $A_{20} \rightarrow F_{20}$. Figure discloses SEQ ID NO: 57.

To improve the vaccine regarding induction of immune responses an inactivating mutation of the ISD in the vaccine-encoded MelARV Env was prepared to prevent immunosuppressive effects by the vaccine itself. Two point mutations were induced in the sequence of the Env transmembrane subunit p15E. A glutamic acid at position 14 of the ISD was substituted with arginine and an alanine at position 20 was changed to phenylalanine (FIG. 3).

In the HERV-K vaccine, the immune response induced by the vaccine was enhanced by introducing a point mutation in the immunosuppressive domain (ISD) of the transmembrane (TM) subunit of HERV-K Env protein, namely p15E. This modification involved the replacement of glutamine at position 52 of the ISD with alanine (Schlecht-Louf G, et al., Proc Natl Acad Sci USA. 2010 Feb. 23; 107(8) :3782-7) (see 22). This change triggered the inactivation of the domain in order to prevent the vaccine itself from producing immunosuppressive effects.

Cell Culture

Various cell lines were used in the different experiments. All cell lines were maintained at 37° C. with 5% $CO_2$ in a humidified atmosphere.

HEK293: HEK293 originates from a human embryonal kidney culture and was generated by a transformation with sheared adenovirus type 5 (Ad5) DNA [ATCC. 293 [HEK-293]. [cited 2017 Jun. 8]; Available from: lgcstandards-atcc.org/Products/All/CRL-1573.aspx?geo_country=de.]. Advantages of this cell line include easy growth and efficient transfection. Another benefit is the expression of the Ad5 E1 gene [Kovesdi, I. and S. J. Hedley, *Adenoviral producer cells*. Viruses, 2010. 2 (8): p. 1681-703.]. Recombinant Ad5 vaccines are usually administered replication deficient which means that they are deleted in genes essential for viral replication, such as E1. In this case the lacking genes have to be provided externally during virus production. HEK293 cells provide the replication-required proteins and can therefore be used as producer cells during virus production [Kovesdi, I. and S. J. Hedley, *Adenoviral producer cells*. Viruses, 2010. 2 (8): p. 1681-703.]. In the current experiments, HEK293 cells were maintained in Dulbecco's Modified Eagle's Medium (DMEM) supplemented with 10% heat-inactivated fetal bovine serum (FBS), L-glutamine (2 mM), Na-Pyruvate (1 mM) and penicillin+streptavidin (Pen/Strep).

HEK293 T-REX Avtoxic (Avtoxic cells): Avtoxic cells are modified HEK293 cells, which are used to prevent expression of Ad5-encoded recombinant proteins during viral production. Inhibiting expression of these recombinant proteins is required, because some of the encoded target proteins are toxic to HEK293 cells and interfere with virus production [Cottingham, M. G., et al., *Preventing spontaneous genetic rearrangements in the transgene cassettes of adenovirus vectors*. Biotechnol Bioeng, 2012. 109 (3): p. 719-28.]. HEK293 cells were modified in two steps to include different protein-suppressive mechanisms. The first mechanism included suppression by the T-REX system [Fisher, T. *Inducible Protein Expression*—T-REx™ System. 2011 [cited 2017 Jun. 8]; Available from:
thermofisher.com/dk/en/home/references/protocols/proteins-expression-isolation-and-analysis/protein-expression-protocol/inducible-protein-expression-using-the-trex-system.html]. T-REX-293 cells were genetically modified to express the tetracycline repressor protein (Tet repressor), which binds to and suppresses the Tet operator. This leads to the expression of recombinant target proteins under control of the strong CMV promoter.

Since the T-REx system is not completely effective in preventing target protein expression, the T-REx-293 cell line was further modified by Sirion Biotech GmbH (Martinsried, Germany). The new cell line HEK293_T-REx_Avtoxic (Av-toxic cells) expresses a short hairpin RNA (shRNA), which targets a messenger RNA (mRNA) sequence called p2TS that is transcribed together with the target protein. The shRNA causes degradation of p2TS containing mRNA and thus further suppression of the recombinant protein. Avtoxic cells were maintained in DMEM supplemented with 10% heat-inactivated FBS, L-glutamine (2 mM), Na-Pyruvate (1 mM) and Pen/Strep.

HEK293(CCS)-shmir-pIX 221-puro (pIX-cells): pIX-cells are modified HEK293 cells used for production of Ad5-pIX viruses that display an antigen on the viral capsid protein pIX. The natural pIX protein is encoded by the adenoviral E1 gene expressed in HEK293 cells. To prevent integration of native pIX into the viral particle and to facilitate incorporation of recombinant pIX, HEK293 encoded pIX was suppressed by shRNA expression in pIX cells. Transcription of shRNA during virus production was induced by doxycycline. Additionally, cells were transduced with a pac gene encoding puromycin N-acetyl-transferase (PAC), which enables selection of shRNA-expressing cells with puromycin. Thus, cells were maintained in DMEM supplemented with 10% heat-inactivated FBS, L-glutamine (2 mM), Na-Pyruvate (1 mM), Pen/Strep and 0.5 µg/mL puromycin.

B16F10-GP: The B16 cell line is a murine melanoma cell line that originates from the C57BL/6J mouse strain [ATCC. B16-F10. [cited 2017 Jun. 8]; Available from:
  lgcstandards-atcc.org/Products/All/CRL-6475.aspx?geo_country=de]. B16F10 is a variant which is more proliferative and frequently used to analyze metastasis in C57BL/6 mice. It was obtained by 10 successive selection rounds for lung metastases after i.v. injections of B16 cells into mice [Fidler, I. J., *Selection of successive tumour lines for metastasis*. Nat New Biol, 1973. 242 (118): p. 148-9., Fidler, I. J. and G. L. Nicolson, Organ selectivity for implantation survival and growth of B16 melanoma variant tumor lines. J Natl Cancer Inst, 1976. 57 (5): p. 1199-202.]. The cell line used in the experiments, B16F10-GP, expresses additionally the immunodominant epitope of the glycoprotein (GP33-41) of lymphocytic choriomeningitis virus (LCMV) [Prévost-Blondel, A., et al., *Tumor-Infiltrating Lymphocytes Exhibiting High Ex Vivo Cytolytic Activity Fail to Prevent Murine Melanoma Tumor Growth In Vivo*. The Journal of Immunology, 1998. 161 (5): p. 2187-2194.]. Cells were maintained in DMEM supplemented with 10% heat-inactivated FBS, L-glutamine (2 mM), Na-Pyruvate (1 mM) and Pen/Strep.

CT26: CT26 is a mouse colon carcinoma cell line, derived from the Balb/C mouse strain and was obtained from Dr. Anders Elm Pedersen. This cell line was used to test primary tumor growth in mice [ATCC. CT26.WT. [cited 2017 Jun. 8]; Available from: lgcstandards-atcc.org/products/all/CRL-2638.aspx?geo_country=de #generalinformation]. Cells were maintained in Roswell Park Memorial Institute medium (RPMI) supplemented with 10% heat-inactivated FBS, L-glutamine (2 mM), Na-Pyruvate (1 mM) and Pen/Strep.

4T1-Luc: 4T1 is a murine breast cancer cell line originating from the Balb/C mouse strain. When injected into the mammary fat pad of mice, cells form primary tumors that metastasize to the lung, liver, lymph nodes and brain [ATCC. 4Tl. [cited 2017 Aug. 4]; Available from:
  lgcstandards-atcc.org/Products/All/CRL-2539.aspx?geo_country=de #characteristics]. The cell line was stably transfected with a luciferase reporter protein (Luc). Cells were maintained in RPMI supplemented with 10% heat-inactivated FBS, L-glutamine (2 mM), Na-Pyruvate (1 mM) and Pen/Strep.

Vero cells: Vero cells are a primate kidney cell line from an African green monkey (*Cercopithecus aethiops*) [ATCC. Vero. [cited 2017 Jun. 8]; Available from:
  lgcstandards-atcc.org/products/all/CCL-81.aspx?geo_country=de #characteristics]. This cell line is highly transducible by human Ad5 infection without supportive production of new virions and was therefore used to analyze protein expression and VLP release by the Ad5-vaccine. Cells were maintained in DMEM supplemented with 10% heat-inactivated FBS, L-glutamine (2 mM), Na-Pyruvate (1 mM) and Pen/Strep.

A549 cells are human lung epithelial cells appropriate for hosting virus transfection. Therefore, A549 cells were used for adenovirus transfection containing the sequence of interest for VLP production. The secretion of VLPs was analysed through Western blot (WB) technique, and their presence at the cell surface was detected using fluorescence-activated cell sorting (FACS), and visualized using electronic microscopy (EM). These cells were maintained in Kaighn's Modification of Ham's F-12 Medium (Ham's F-12K media) supplemented with 10% heat-inactivated FBS, Pen/Strep, and sodium pyruvate (1 mM).

Renca cells expressing Gag and Env proteins. Renca cells are mouse (*Mus musculus*) kidney epithelial cells. They are derived from a renal adenocarcinoma in balb/c mice. The tumor growth and progression resembles accurately the one observed in human renal cell carcinoma, especially mimicking the spontaneous metastasis to the liver and the lungs. The cells used in the following examples were kindly provided by Prof. Dr. Barbara Schnierle (Langen, Germany). In some of the following examples the cells were modified in order to express the human endogenous retrovirus type K (HERV-K) Env or Gag proteins. This allowed to induce tumors that express HERV-K proteins in mice, creating an appropriate murine model for testing our novel vaccination strategy directed to human cancers expressing ERV proteins. These cells were maintained in Roswell Park Memorial Institute Medium (RPMI-1640) supplemented with 10% heat-inactivated FBS, 20×106 IU/L Pen and 5 g/L Strep, 2.9 g/L L-glutamine (2 mM), and 3.7 g/L sodium pyruvate (1 mM) at pH 7.2.

Primary cultures of chicken embryonic fibroblasts (CEF) are extensively used for virus culture. Eleven day old chicken eggs from Jens Toft, Lohmann (Denmark) were used to prepare CEF cultures according to the protocol from (Staib et al. 2004). In this case, CEF cells were used for the production of Modified Vaccinia Virus Ankara (MVA) encoding for HERV-K Env and Gag foreign antigens. The reason for working with this specific type of cells is that MVA replication is limited to avian cells, meaning that MVA does not reproduce in the majority of mammalian cells, and making them not suitable for this purpose (Altenburg et al. 2014). CEF cells were cultured in CEF medium consisting of RPMI supplemented with 3.7 g/L sodium pyruvate, 10% heat-inactivated FBS, and 1% (v/v) antibiotic-antimycotic (Gibco™, 15240062).

Baby Hamster Kidney fibroblasts (BHK-21 cells) were originally derived from baby syrian golden hamster kidney cells (*Mesocricetus auratus*). The specific cell line used in the following examples kindly was supplied by Prof. Allan Randrup Thomsen (University of Copenhagen, Denmark). BHK-12 cells were used for MVA Env and Gag titration, since they are known for being one of the few cell lines that allow MVA replication. They were maintained in CEF medium consisting of RPMI supplemented with 3.7 g/L sodium pyruvate, 10% heat-inactivated FBS, and 1% (v/v) antibiotic-antimycotic (Gibco™, 15240062).

Plasmid Constructs

Figure 4:
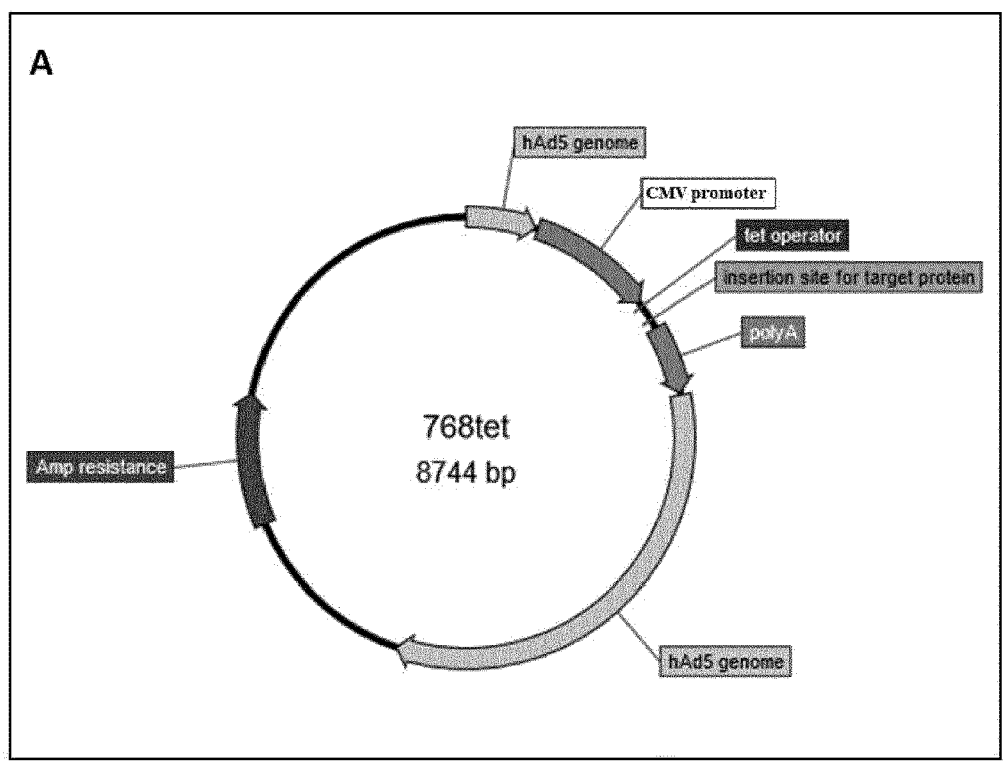
FIG. 4 shows the vector maps of 768tet and Capture-pBGH. The DNA vectors 768tet (A) and Capture-pBGH (B) with relevant genes. Additional genes present in the plasmids are not shown in the vector map. Target proteins were first cloned into the expression vector 768tet (A). The expression cassette, including the target protein, was subsequently cloned into the human Ad5 (hAd5) genome vector Capture-pBGH (B) by homologous recombination to produce recombinant viruses in producer cell lines.
Figure 4:
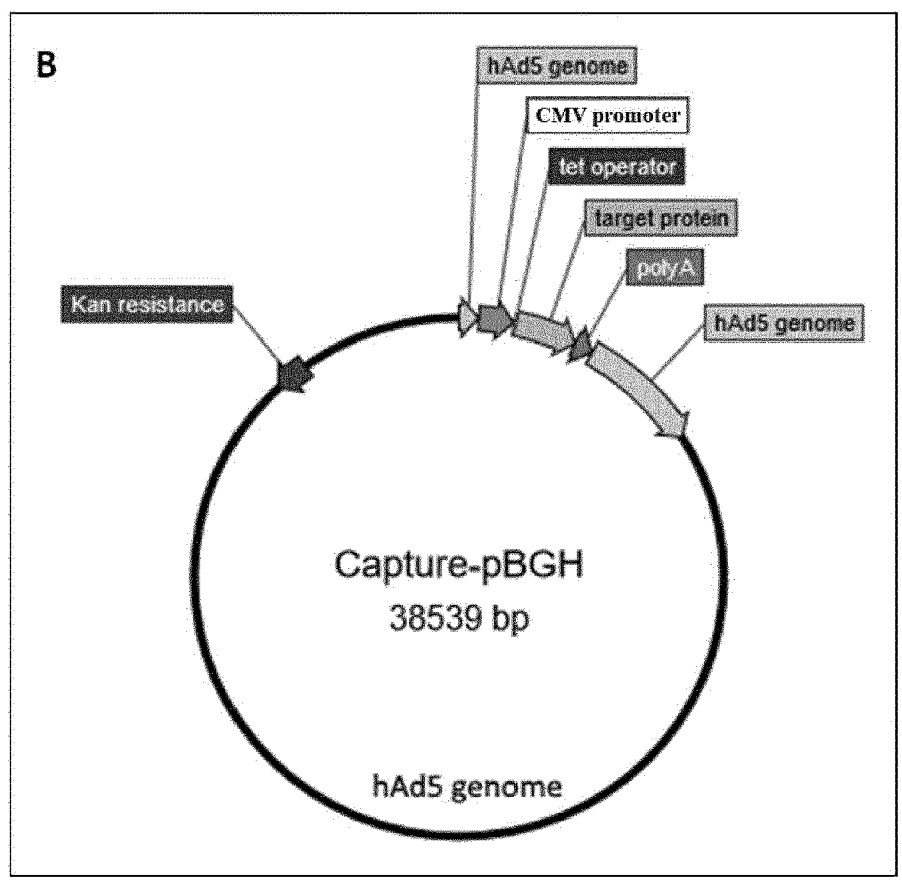
Figure 5:
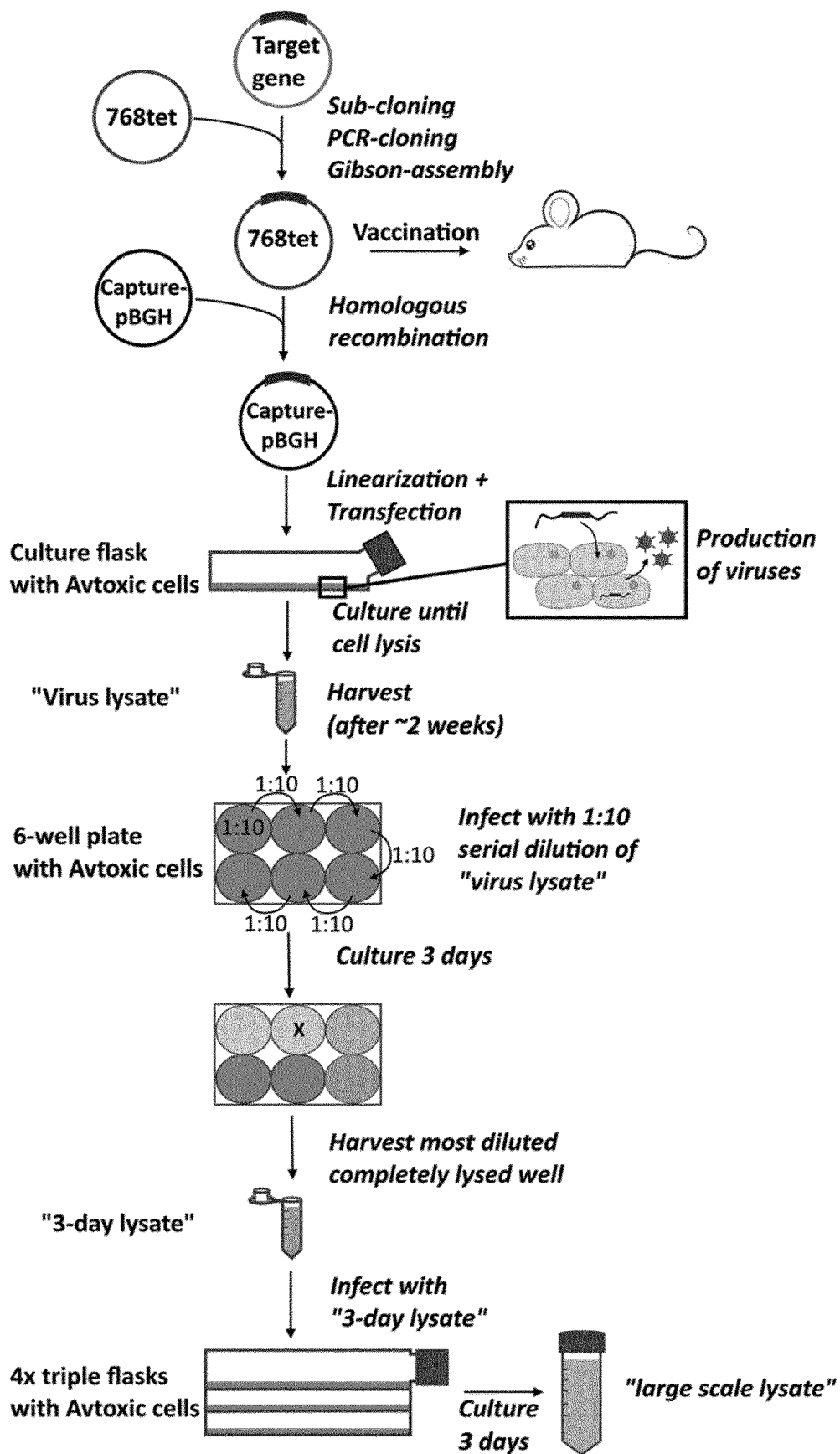
FIG. 5 discloses the steps for recombinant Ad5 production. The scheme shows the process of cloning a target protein into Capture-pBGH, followed by virus production. The production of recombinant Ad5 includes the consecutive steps of generating a "virus lysate", a "3-day lysate" and a "large-scale lysate" containing the recombinant virus.
Figure 6:
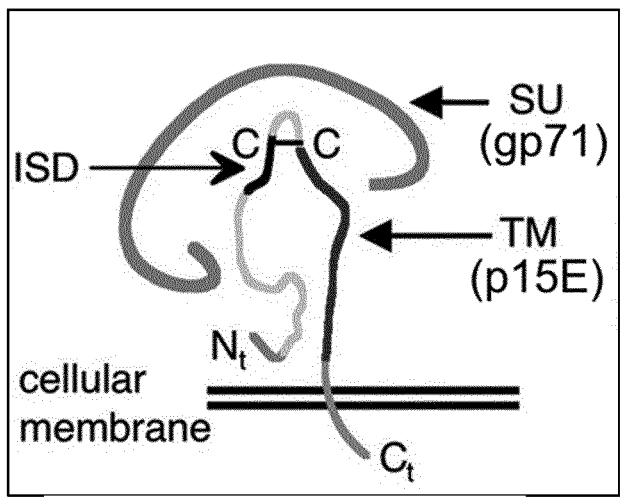
FIG. 6: The peptide used for ELISA analysis of p15E-specific antibody responses. The region of MelARV Env pointed to as TM (p15E) was synthesized as a peptide and was used for ELISA analysis of blood serum samples from vaccinated mice.

In order to produce recombinant adenoviruses, the target protein was cloned into the modified adenovirus vector Capture-pBGH. This vector contains the Ad5 genome with deletions in the E1 and E3 genes. Furthermore, it contains homologous regions to the vector 768tet that entails the CMV promoter and the 3' polyadenylation (polyA) tail, and expresses recombinant proteins under the Tet operator (FIG. 4) [Becker, T. C., et al., Use of recombinant adenovirus for metabolic engineering of mammalian cells. Methods Cell Biol, 1994. 43 Pt A: p. 161-89.]. Therefore, target proteins were first inserted into 768tet by sub-cloning, PCR-cloning or Gibson-assembly and were subsequently cloned into Capture-pBGH (FIG. 4) via homologous recombination (FIG. 5).

For pIX modifications of the adenovirus, target proteins were cloned into the common expression vector pcDNA3 that additionally encoded pIX and a linker sequence (containing a FLAG-tag) followed by restriction sites to insert the gene of interest (pcDNA3_pIX_Taglinker_xxx, with xxx=target antigen). The expression vector was transfected into producer cells to induce expression of recombinant pIX in these cells.

The different plasmid constructs used are listed in Table 1.

TABLE 1

List of plasmid constructs used for cloning, virus production and vaccination. DNA plasmids used during the project are listed including the abbreviations utilized in this work. Additionally, vector-encoded genes are explained ("Description") as well as the application of the DNA plasmids ("Purpose").

| Plasmid | Abbreviation | Description | Purpose |
| --- | --- | --- | --- |
| 768tet_MelARVgag_p2A_envSTOP | DNA-MelARV | Expression vector with MelARVgag and MelARVenv under CMV promoter and let operator | Vaccination cloning into Capture-pBGH |
| pBGH_MelARVgag_p2A_envSTOP | | Ad5 genome with MelARVgag and MelARVenv under CMV promoter | Ad5 production |
| 768tet_MelARVgag_p2A_envISDmutSTOP | DNA-MelARV-ISD | Expression vector with MelARVgag and ISD-mutated MelARVenv under CMV promoter and let operator | Vaccination cloning into Capture-pBGH |
| pBGH_MelARVgag_p2A_envSTOP | | Ad5 genome with MelARVgag and ISD-mutated MelARVenv under CMV promoter | Ad5 production |
| pcDNA3_pIX-Taglinker-p15E | DNA-pIX-p15E | Expression vector with p15E linked to pIX under CMV promoter | Ad5-pIX modification |
| pcDNA3_pIX-Taglinker-p15E-ISDmut | DNA-pIX-P15E-ISD | Expression vector with ISD-mutated p15E linked to pIX under CMV promoter | Ad5-pIX modification |
| pcDNA3_pIX-Taglinker-p15E-trunc-wC | DNA-pIX-p15E-trunc-wC | Expression vector with truncated p15E containing an additional cysteine linked to pIX under CMV promoter | Ad5-pIX modification |
| pcDNA3_pIX-Taglinker-p15E-trunc-w/oC | DNA-pIX-p15E-trunc-w/oC | Expression vector with truncated p15E without additional cysteine linked to pIX under CMV promoter | Ad5-pIX modification |
| pcDNA3_pIX-Taglinker-GFP | DNA-pIX-GFP | Expression vector with GFP linked to pIX under CMV promoter | control plasmid |
| 768tet_SIVgag_p2A_LucSP_MelARV_HA-TMCT | DNA-LucSP_MelARV_HA-TMCT | Expression vector with SIV gag and MelARVenv containing luciferase signal peptide and influenza hemagglutinin transmembrane domain + cytoplasmic tail | cloning into Capture-pBGH |
| pBGH_SIVgag_p2A_LucSP_MelARV_HA-TMCT | | Ad5 genome with SIV gag and MelARVenv containing luciferase signal peptide and influenza hemagglutinin transmembrane domain + cytoplasmic tail | Ad5 production |

TABLE 1-continued

List of plasmid constructs used for cloning, virus
production and vaccination. DNA plasmids used during the project
are listed including the abbreviations utilized in this work.
Additionally, vector-encoded genes are explained ("Description")
as well as the application of the DNA plasmids ("Purpose").

| Plasmid | Abbreviation | Description | Purpose |
|---|---|---|---|
| 768tet_SIVgag_p2A_LucSP_GCN4_p15E_HA-TMCT | DNA-LucSP_GCN4_p15E_HA-TMCT | Expression vector with SIV gag and MelARV p15E containing luciferase signal peptide, trimerization sequence and influenza hemagglutinin transmembrane domain + cytoplasmic tail | cloning into Capture-pBGH |
| pBGH_SIVgag_p2A_LucSP_GCN4_p15E_HA-TMCT | | Ad5 genome with SIV gag and MelARV p15E containing luciferase signal peptide, trimerization sequence and influenza hemagglutinin transmembrane domain + cytoplasmic tail | Ad5 production |
| pCI-neoGFP | DNA-GFP | Expression vector with GFP | control plasmid |
| p06A19a(II)-(TetO)-CMV-COHERV-K-P2TS | | Vector containing the WT HERV-K VLP insert under a tet-regulatable CMV promoter followed by a microRNA targeting signal expressed in ProVector cells and SV40 polyA sites. The expression cassette contains the hAd19a/64 5' region and at the C-terminus recombination signals for recombination into BAG plasmids containing the remainder of the E1 deleted hAd19a genome. | recombination in E-coli as described in EP2870236 |
| p06A19a(II)-(TetO)-CMV-ISDmut_coHERV-K-P2TS | | Vector containing the ISD mutated HERV-K VLP insert under a tet-regulatable CMV promoter followed by a microRNA targeting signal expressed in ProVector cells and SV40 polyA sites. The expression cassette contains the hAd19a/64 5' region and at the C-terminus recombination signals for recombination into BAG plasmids containing the remainder of the E1 deleted hAd19a genome. | recombination in E-coli as described in EP2870236 |

Cloning

Different cloning strategies were used to build new DNA constructs for production and testing of adenoviral vaccines.

Sub-Cloning

For sub-cloning, a target DNA sequence was transferred from one plasmid (donor vector) to another plasmid (target vector). Donor and target vector were cut via restriction digest at the ligation site. In order to prevent re-ligation, the target vector was treated with Calf intestinal alkaline phosphatase (CIP), which catalyzes dephosphorylation at the 5' and 3' ends of DNA. Digested DNA was separated on a 1% agarose gel containing GelGreen dye (#41004, Biotium). Desired DNA-bands were cut out and DNA content was extracted using the E.Z.N.A. Gel Extraction Kit (D2500; OMEGA bio-tek). Briefly, the gel was dissolved in one volume Binding buffer (XP2) and loaded on HiBind® DNA Mini Columns. After washing twice, the column was dried and DNA was double-eluted in Elution buffer.

After purification, vector and inserts were mixed in a stoichiometric ratio of 1:3. Ligation of the two DNA fragments was catalyzed using the Instant Sticky-end Ligase Master Mix (M0370; New England BioLabs). The ligated product was transformed into XL1-Blue Competent Cells (#200249, Agilent Technologies). For transformation, DNA was added to the bacterial suspension and incubated 10 min on ice. Subsequently, cells were permeabilized by heat shock at 42° C. for 45 sec. After 2 min incubation on ice, Super Optimal Broth media (SOC media) was added and bacteria were incubated shaking for 1 h at 37° C. The bacterial suspension was streaked on a Lysogeny broth media (LB media) agar plate containing the respective antibiotic and was incubated overnight at 37° C.

To screen for correct constructs, several bacterial colonies were amplified for mini-plasmid preparation (see "0 DNA-preparation" below). Isolated plasmid DNA was cut by restriction digest and analyzed by gel electrophoresis.

For the HERV-K constructs (and corresponding controls), the subcloning was performed in order to insert the DNA constructs containing the sequence of interest (DNA_ISD-mut_coHERV-K-P2TS and DNA_coHERV-K-P2TS) into an acceptor plasmid 768(TetO)-SP-alb-CIDR. To do this, the inserts and the acceptor were first amplified using PIR1 and XL1-Blue Cells, and Kan and Amp selection markers, respectively. All constructs were digested using XbaI (New England Biolabs, R0145) and SwaI (New England Biolabs, R0604) together with NEBuffer™ 3.1 (New England Biolabs, B7203) for 1 h and 30 min at 37° C., since the activity of XbaI enzyme when using NEBuffer 3.1 is only 75%. The DNA was separated by electrophoresis using 1% agarose gel plus GelGreen dye (100 V, 200 A, 1 h). The bands containing the insert as well as the ones containing 768(TetO) were cut and purified using E.Z.N.A.® Gel Extraction Kit (Omega bio-tek, D2500) following the manufacturer guidelines, and eluted in 20 µL of ultra-pure water (UPW).

For ligating the constructs, 40 ng of the acceptor vector and 120 ng of each insert were incubated during 15-30 min with 1:2 dilution of instant sticky end ligase master mix (2×) at 37° C. Transformation was performed using XL1-Blue cells and the DNA was obtained using mini-preparation (as described below). Then, a test cut was performed to corroborate if the sequence of interest was properly inserted into the acceptor vector. If so, new transformation and midi-preparation (as described below) were performed, to obtain a higher DNA concentration.

PCR-Cloning

In contrast to sub-cloning, PCR-cloning is characterized by the generation of inserts in a polymerase chain reaction (PCR). The target sequence is amplified via PCR from a donor vector using specific extension-primers to insert enzymatic restriction sites. Primers were ordered from TAG Copenhagen and mixed with template and PfuUltra II Hotstarter PCR Master Mix (#600850, Agilent Genomics). The PCR was initiated by incubating 2 min at 95° C. to activate the Taq polymerase and facilitate complete denaturation of the DNA template. The initial step was followed by 30 cycles of denaturation at 95° C., annealing at 60° C. and DNA extension at 72° C. The PCR was completed with a final step of 3 min at 72° C. to finalize DNA extension.

DNA was isolated from the reaction mix using the E.Z.N.A. Gel Extraction Kit (D2500; OMEGA bio-tek) protocol "Purification from enzymatic reaction". To remove residual genomic DNA, the purified PCR product was treated with DpnI (R0176, New England BioLabs), which is an enzyme that cuts methylated DNA. DNA was subjected to enzymatic digest at specific restriction sites and was purified using the E.Z.N.A. Gel Extraction Kit. Digest of the target vector and ligation were performed according to the previously described sub-cloning protocol.

In the context of the HERV-K constructs (and corresponding controls), in order to continue with the homologous recombination, the NotI site contained inside the HERV-K WT/ISDmut sequences had to be removed, so that NotI could be subsequently used to correctly linearize the plasmids, allowing for proper recombination. To do this, both sequences (768(TetO)-SP-alb-CSP-HERV-K WT/ISDmut) obtained from the sub-cloning procedure described above were cut with XbaI (New England Biolabs, R0145) and BspEI (New England Biolabs, R0540) together with NEBuffer™ 3.1 (New England Biolabs, B7203) for 1.5 h at 37° C., and separated by electrophoresis on a 1% agarose gel containing GelGreen dye. The DNA bands containing the NotI site to be removed were digested and eluted using the E.Z.N.A.® Gel Extraction Kit.

The forward primer used for the PCR reaction was annealing at the 3' end of the HERV-K Env sequence, specifically at the BspEI restriction site (5'-CCCGTG-ICCGGACCTGAG-3'; SEQ ID No.45), whereas the reverse primer was annealing at the 5' end of the HERV-K Env sequence, at the XbaI restriction site (5'-GTICTAGAC-TIGTCCTGAATTITCTGGITA-3'; (SEQ ID No.46). The reverse primer contained a modification at the NotI site in order to eliminate it. The primers were obtained from TAG Copenhagen A/S (Copenhagen, Denmark).

10 ng of template DNA (1 ng/µL), 10 µM of each primer and 1:2 dilution of PfuUltra II Hotstart PCR Master Mix (Agilent Technologies, 600850) were used to prepare the reaction mixture for each DNA construct. The PCR reaction consisted on an initial denaturation step (95° C., 5 min), followed by a loop of 35 cycles, which comprised a denaturation step (95° C., 30 s), an annealing step (58° C., 25 s), and a final elongation step (72° C., 45 s). Finally, a last elongation step was performed (72° C., 10 min) and the sample was stored at 4° C.

The PCR products, together with the acceptor plasmid, were separated by gel electrophoresis, and the desired bands were collected and processed as described in the section "sub-cloning" herein above 768(TetO)-HERV-K-Gag-p2A-Env WT and ISDmut constructs were therefore obtained, which now did not contain the restriction site for NotI enzyme in their sequence.

Gibson-Assembly

Gibson-assembly was used to combine several DNA fragments into one construct. Fragments were amplified by extension-PCR to add overhangs homologous to the target vector. PCR-products were treated and purified as described for PCR-cloning. The target vector was opened via restriction digest at the insertion site. To assemble the fragments, the opened target vector and purified inserts were mixed in a stoichiometric ratio of 1:3 and incubated 1 h at 50° C. with a Gibson Assembly Master Mix (E2611; New England BioLabs). Three key enzymes in the Master Mix facilitated assembly. The exonuclease removes DNA from the 5' end of the fragments and creates single-stranded 3' overhangs that anneal in homologous regions with other fragments. Nucleotides are inserted into the remaining gaps by a DNA polymerase. Finally, the DNA ligase joins nicks in the assembled DNA. Like in previously described cloning techniques, assembled DNA was transformed into bacteria followed by screening for correct constructs.

Homologous Recombination to Generate Recombinant Adenoviral Genomes

The insertion of a target gene into the adenoviral genome (Ad5) was performed by homologous recombination in *E. coli*. The insert (target gene) from 768tet with homologous regions to the target vector was cut out via restriction digest and purified by gel electrophoresis. The acceptor vector, Capture-pBGH (Ad5 genome), was likewise linearized by restriction digest. To prevent re-ligation, the cut vector was subjected to CIP treatment (see Sub-cloning). Subsequently, vector-DNA was purified by ethanol precipitation. Briefly, DNA was precipitated in 0.3M sodium acetate and 70% ethanol, frozen 20 min at −80° C. and centrifuged at 16.000 g for 15 min (4° C.). The pellet was washed in 70% ethanol and centrifuged for another 5 min. After drying at room temperature (RT), DNA was resuspended in water. To prevent further re-ligation, adenosine overhangs were generated using the Tempase hot start DNA polymerase (#230306; Ampliqon). Subsequently, DNA was purified via phenol chloroform extraction. To this end, phenol chloroform was added to the reaction mix followed by centrifugation at 16.000 g for 10 min. The upper, aqueous phase was transferred to a new reaction tube and DNA was extracted by ethanol precipitation as described above.

In order to combine the vector and insert by homologous recombination, both components were mixed in a stoichiometric ratio of 1:3 and were added to electroporation competent BJ5183 cells. The bacteria were transferred to an electroporation cuvette (#1652086; Bio-Rad) and were permeabilized by electroporation in a gene pulser machine (Bio-Rad) with 25 µFD, 2.5 kV and 200Ω. After electroporation, cells were transferred into SOC media and further treated as described in the heat-shock protocol (see "Subcloning").

The following plasmids were provided by Sirion biotech:
cDNA_HERV-K(Gag_p2A_Env)
cDNA_HERV-K(Gag_p2A_Env-(Q6A)ISD-mut).

The same constructs, but encoded by an Ad19a vector were also provided by Sirion.

The cDNA constructs were amplified and used as DNA vaccines as well as insert vectors for cloning strategies with the ultimate aim of obtaining Ad5 vectors encoding for the aforementioned sequences, which can be used as vaccines. Specifically, for the HERV-K constructs encoded in hAd5s (and corresponding controls), the gene of interest was cloned into the pBGH plasmid encoding the human Ad5 genome with deletions in E1 and E3 genes. The transgene was inserted in the place of E1 by homologous recombination with the 768tet plasmid encoding the gene of interest. This strategy was chosen because conventional cloning with restriction digest and ligation is very ineffective with the pBGH vector being a very big plasmid with more than 38 kbp.

The homologous recombination between 768tet and the pBGH capture plasmid was performed in *E. coli*. The capture vector contained green fluorescent protein (GFP) as an insert that would be replaced by the gene of interest.

Since the pBGH plasmid, encoding for the human Ad5 genome, is too large (<38 kbp) to undergo the common cloning strategy, which uses restriction enzyme digestion to insert the desired construct, homologous recombination was used to insert it in the place of E1.

First, the pBGH acceptor vector was linearized using SwaI enzyme (New England Biolabs, R0604) at 37° C. during 2 h. Meanwhile, the 768(TetO)-HERV-K-Gag-p2A-Env WT and ISDmut, were digested with NotI enzyme (New England Biolabs, R3189) during 1 h. The product of the reaction was separated by electrophoresis in 1% agarose gel containing GelGreen. The HERV-K sequence flanked by the homologous regions needed for the recombination was collected from the gel, and the DNA was isolated using the E.Z.N.A.® Gel Extraction Kit (Omega bio-tek, D2500) following the guidelines of the manufacturer and eluted in UPW.

After the pBGH was digested, both 3' and 5' ends were phosphorylated using Calf Intestinal Alkaline Phosphatase (30 min, 37° C.; M0290) to prevent re-ligation. Then, the vector underwent ethanol precipitation in 0.3 M sodium acetate and 70% (v/v) ethanol during 20 min at −80° C. Immediately after, the sample was centrifuged (15 min, 4° C., 16,000 g) and the pellet was washed with 70% (v/v) ethanol. The vector underwent another centrifugation (5 min, 4° C., 16,000 g) and the resulting pellet was left to dry at RT, and finally resuspended in UPW.

To prevent further re-ligation of the pBGH vector, it was treated with the Tempase Hot Start DNA polymerase (Ampliqon, A230306) during 30 min at 72° C., which added adenosine overhangs. The DNA was purified adding phenol/chloroform, centrifuging (10 min, 4° C., 16,000 g) and then the upper, aqueous phase, which contained the DNA, was transferred to a microcentrifuge tube. The DNA underwent ethanol precipitation as before in order to further purify it, and it was diluted into UPW.

All plasmids were stored in water, and not elution buffer, since salt content interferes with electroporation efficiency. The pBGH vector and the HERV-K WT/ISDmut inserts were combined in a 1:3 molar ratio, together with the electroporation competent BJ5183 cells (Agilent, 200154). Then, the mix was transferred into an electroporation cuvette (Bio-Rad, 1652086), which was used to permeabilize the cells with a gene pulser machine (Bio-Rad) at 25 µFD, 2.5 kV and 200Ω. Subsequently, SOC media was added to recover *E. coli* competent cells after transformation. Then they were incubated at a shaking incubator for 1 h at 37° C. Finally, the mixture was plated onto LB agar plates containing Kan and were incubated at 37° C. o/n.

To ascertain that the homologous recombination was performed properly, the DNA was isolated using mini-preparations as described herein below. Then, it was digested using restriction enzymes and separated in 1% agarose gel, containing GelGreen dye. The bands corresponding to the correct size for the pBGH and the inserts were cut and transformed into *E. coli*, and finally the DNA was again isolated through midi-preparation as described below.

DNA-Preparation

*Escherichia Coli* (*E. Coli*) Transformation

For transformation, chemically competent *E. coli* XL1-Blue Supercompetent Cells (Agilent, 200236) as well as One Shot™ PIR1 Chemically Competent Cells (ThermoFisher Scientific, C101010) were used. 20 µL of the latter together with 10 ng of plasmid-DNA were mixed together and kept on ice for 3 min. Afterwards, the mixture was heat shocked in a Waterbath TW80 (Julabo) for 45 s at 42° C., and placed again on ice for 3 min. Immediately after, 200 µL of Super Optimal Broth with Catabolite repression (SOC) medium (20 g Tryptone, 5 g Yeast extract, 0.58 g NaCl, 0.19 g KCl, 3.96 g glucose and 5.04 g $MgSO_4.7H_2O$) were added to the samples, which were placed into shaking incubators for 1 h at 37° C. The final step consisted on plating the samples onto LB agar plates containing the corresponding antibiotic (ampicillin (Amp): 100 µg/mL, kanamycin (Kan): 50 µg/mL), for which our plasmid has resistance, and into an incubator for *E. coli* agar plates (Binder) at 37° C. o/n.

Agarose Gel Electrophoresis

To check if the transformation was performed correctly, the DNA purified constructs were run on 1% (w/v) agarose gels containing ethidium bromide or GelGreen™ dye (Biotium, 41004) in order to be able to visualize the DNA under ultraviolet (UV) light. 1× loading buffer (6×) was added to the samples and they were loaded to the gel together with the size marker GeneRuler 1 kb Plus DNA Ladder (Thermo Fisher Scientific, SM1331). The buffer used was the tris-acetate-ethylenediaminetetraacetic acid (EDTA) (TAE) buffer (4.86 g/L Trizma® base, 0.37 g/L Na2EDTA.2H2O, and 0.11% (v/v) acetic acid at pH=8.3). The electrophoresis was performed during 1 h at 120 V using an electrophoresis power supply EPS 3501 XL (GE Healthcare).

Mini-Preparation

To screen for correct constructs after cloning, small-scale amplifications of DNA were performed. Bacterial colonies were transferred into 3 mL or 5 mL of LB media (containing the corresponding antibiotic Amp 100 µg/mL or Kan 50 µg/mL depending on the resistance gene in the plasmid of interest) and grown overnight at 37° C. Isolation of plasmid DNA was carried out using the E.Z.N.A.® Plasmid DNA Mini Kit I (D6943, Omega bio-tek). Briefly, the bacteria were pelleted by centrifugation and resuspended in RNase containing Solution I (Resuspension buffer). Solution II (Lysis buffer) was added to release DNA from the cells. To stop the reaction and precipitate genomic DNA with cell debris, solution III (Neutralization buffer) was added. The precipitate was pelleted by centrifugation and supernatant was transferred into HiBind® DNA Mini Columns. After DNA binding to the column membrane by centrifugation and addition of HB Buffer, the column was washed twice with DNA Wash Buffer and subsequently dried. Finally, plasmid DNA was eluted in Elution Buffer.

Midi-Preparation

In order to get higher and more purified DNA yields, midi-preparations were made from *E. coli*, grown overnight in 100 mL of LB media (again containing the appropriate antibiotic), using the NucleoBond® Xtra Midi kit (#740410, AH Diagnostics). The principle was similar to the mini-preparations, starting with resuspending and lysing the bacteria. After neutralization, the lysate was loaded on equilibrated NucleoBond® Xtra Columns and washed with Equilibration buffer. The inserted column filter, containing residual cell debris, was removed and columns were washed with Washing buffer. DNA was eluted in Elution buffer and subsequently precipitated in isopropanol. Precipitated DNA was pelleted by centrifugation and washed with 70% ethanol. After an additional centrifugation step, the supernatant was removed and the DNA pellet was dried at RT. DNA was reconstituted in 100 µL of 10 mM Tris-HCl buffer solution (pH 8.0) or with 100 µL of elution buffer from the E.Z.N.A.® Plasmid DNA Mini Kit and the concentration was determined at the NanoDrop™ 42000.

2.6 Virus Production

Different viruses were produced and tested in the experiments (Table 2). In addition to the usual recombinant adenoviruses, Ad5 vectors displaying recombinant pIX on their surface (Ad5-pIX) were tested and had to be produced in a distinct procedure.

TABLE 2

List of virus constructs used for immunization of mice:
The different recombinant adenoviruses used during the project are listed, including the abbreviations in this work and the genes encoded by virus.

| Virus | Abbreviation | Description |
|---|---|---|
| Ad5_MelARVgag_p2A_envSTOP | Ad5-MelARV | Ad5 encoding for MelARVgag and MelARVenv |
| Ad5_MelARVgag_p2A_envISDmutSTOP | Ad5-MelARV-ISD | Ad5 encoding for MelARVgag and ISD-mutated MelARVenv |
| Ad5_MelARVgag_p2A_envSTOP_pIX-p15E | Ad5-MelARV_pIX-p15E | Ad5 encoding for MelARVgag and MelARVenv displaying p15E on the viral pIX protein |
| Ad5_MelARVgag_p2A_envISDmutSTOP_pIX-p15E-ISD | Ad5-MelARV-ISD_pIX-P15E-ISD | Ad5 encoding for MelARVgag and ISD-mutated MelARVenv displaying ISD-mutated p15E on the viral pIX protein |
| Ad5_MelARVgag_p2A_envSTOP_pIX-p15E-trunc-wC | Ad5-MelARV_pIX-p15E-trunc-wC | Ad5 encoding for MelARVgag and MelARVenv displaying truncated p15E with additional cysteine on the viral pIX protein |
| Ad5_MelARVgag_p2A_envSTOP_pIX-p15E-trunc-w/oC | Ad5-MelARV_pIX-p15E-trunc-w/oC | Ad5 encoding for MelARVgag and MelARVenv displaying truncated p15E without additional cysteine on the viral pIX protein |
| Ad5_SIVgag_p2A_LucSP_MelARV_HA-TMCT | Ad5-LucSP_MelARV_HA-TMCT | Ad5 encoding for SIVgag and modified MelARVenv containing luciferase signal peptide and influenza hemagglutinin transmembrane domain + cytoplasmic tail |
| Ad5_SIVgag_p2A_LucSP_GCN4_p15E_HA-TMCT | Ad5-LucSP_GCN4_p15E_HA-TMCT | Ad5 encoding for SIVgag and modified MelARVenv containing luciferase signal peptide, trimerization sequenceand influenza |

TABLE 2-continued

List of virus constructs used for immunization of mice: The different recombinant adenoviruses used during the project are listed, including the abbreviations in this work and the genes encoded by virus.

| Virus | Abbreviation | Description |
|---|---|---|
| | | hemagglutinin transmembrane domain + cytoplasmic tail |
| Ad5_eGFP | Ad5-GFP | Ad5 encoding for GFP |

Sequence of MelARV Env Protein with Modified ISD

The Env protein has the following sequence (SEQ ID No: 41):

```
MESTTLSKPFKNQVNPWGPLIVLLILGGVNPVALGNSPHQVFNLSWEVTN
GDRETVWAITGNHPLWTWWPDLTPDLCMLALHGPSYWGLEYRAPFSPPPG
PPCCSGSSDSTSGCSRDCEEPLTSYTPRCNTAWNRLKLSKVTHAHNEGFY
VCPGPHRPRWARSCGGPESFYCASWGCETTGRASWKPSSSWDYITVSNNL
TSDQATPVCKGNKWCNSLTIRFTSFGKQATSWVTGHWWGLRLYVSGHDPG
LIFGIRLKITDSGPRVPIGPNPVLSDRRPPSRPRPTRSPPPSNSTPTETP
LTLPEPPPAGVENRLLNLVKGAYQALNLTSPDKTQECWLCLVSGPPYYEG
VAVLGTYSNHTSAPANCSVASQHKLTLSEVTGQGLCIGAVPKTHQVLCNT
TQKTSDGSYYLVAPTGTTWACSTGLTPCISTTILNLTTDYCVLVELWPRV
TYHSPSYVYHQFERRAKYKREPVSLTLALLLGGLTMGGIAAGVGTGTTAL
VATQQFQQLQAAMHDDLKEVESKITNLEKSLTSLSEVVLQNRRGLDLLFL
KRGGLCAFLKEECCFYADHTGLVRDSMAKLRERLSQRQKLFESQQGWFEG
LFNKSPWFTTLISTIMGPLIILLLILLFGPCILNRLVQFIKDRISVVQAL
VLTQQYHQLKTIGDCKSRE
```

The sequence has been modified by exchanging the original E to R at the grey background letter in the ISD sequence and A to F at the third amino acids outside the ISD, also marked by grey.

Recombinant Ad5 Production

Starting point of the Ad5 production is the adenoviral genome plasmid Capture-pBGH. The plasmid contains all genes required for the formation of infectious Ad5 particles but is deleted in the genes E1 and E3. E1 is required for viral replication and is instead provided by the producer cell line HEK293/Avtoxic (Kovesdi, I. and S. J. Hedley, *Adenoviral producer cells*. Viruses, 2010. 2(8): p. 1681-703). E3 is a non-essential gene for the virus production and is deleted in the genome to create space for recombinant target genes. In the process of capture cloning (see "0 Homologous recombination to generate recombinant adenoviral genomes") these target genes are inserted into the vector via homologous recombination. The process of cloning a target protein into Capture-pBGH and the following virus production is summarized in FIG. 5.

Avtoxic cells were transfected with the recombinant Capture-pBGH vector. To this end, cells were seeded into T75 culture flasks and grown to 50-70% confluency. Vector DNA was linearized by restriction digest with PI-SceI (#R0696S; New England BioLabs) in PI-SceI buffer for 1 h at 37° C. Subsequently, phenol chloroform purification was performed as described in "Capture cloning" and DNA was dissolved in OptiMEM (#11058-021; Invitrogen). A part of the DNA solution was loaded on a 1% agarose gel to confirm correct cutting of the plasmid. The residual DNA was mixed with polyethyleneimine (PEI) in a DNA:PEI ratio of 1:3. After incubating 15 min at RT the mixture was added dropwise to the media of Avtoxic cells. Transfected cells were incubated under normal cell culture conditions (see Becker, T C., et al., *Methods Cell Biol.* 1994; 43 Pt A:161-89.) while changing the media after 16 h and subsequently every 2-3 days. When cell lysis was visible as evident by detaching cells (after 2-3 weeks), the cell culture media containing the lysed cells (called "virus lysate") was harvested and stored at −80° C.

In the next step, cells were re-infected with the "virus lysate" to obtain a "3-day lysate". To this end, Avtoxic cells were grown in a 6-well plate until 70% confluency and were infected from well to well in a 1:10 serial dilution of the "virus lysate". Three days after infection, the supernatant of the most diluted, completely lysed well was harvested and frozen at −80° C. This viral sample was called a "3-day lysate"

To produce the virus in a large scale ("large scale lysate"), Avtoxic cells were seeded into four Nunc™ Cell Culture Treated TripleFlasks™ (500 $cm^2$) (#132913; Thermo Fisher). When cells reached 70% confluence, flasks were infected with 150 µL of the "3-day lysate". After complete lysing of the cells (approximately three days), the supernatant was harvested and frozen at −80° C.

Recombinant Ad5 Purification

In the first step of virus purification 0.5% of Igepal CA-630 (#56741; Sigma-Aldrich) was added to the harvested large scale lysates. During 10 min of incubation at RT, the detergent caused destruction of remaining cells and release of viral content into the media. To remove cell residues, the lysate was centrifuged at 12186 g for 20 min at 4° C. The supernatant was recovered and half of the volume was added as a 20% polyethylene glycol (PEG)+2.5 M NaCl solution, followed by gentle shaking overnight at 4° C. During this step, virus in the supernatant was precipitated, which allowed concentration of the virus in the next step. The precipitated virus was pelleted by centrifugation at 12186 g for 20 min. The virus pellet was resuspended in 5 mL cold phosphate buffered saline (PBS) and transferred to a 15 mL falcon tubes. The sample was centrifuged at 784 g for 5 min to remove remaining cell residues. The supernatant was transferred to a fresh 15 mL falcon tube and the previous centrifugation step was repeated several times until only a minor pellet of cell remnant was present in the tube, which could not be removed completely. An almost saturated CsCl solution was added to the virus-containing supernatant to reach a final density of 1.34 g/mL. The resulting solution was transferred into an ultracentrifuge tube (#342413; Beckman Coulter) which was subsequently sealed and centrifuged overnight in a Beckman Coulter Ti 70.1 rotor at 257,300 g. The clearly visible virus band was extracted with a needle and syringe and was loaded on an equilibrated PD-10 desalting column (#17-0851-01; GE Healthcare). Flow through fractions were collected in 70% glycerol with a final glycerol concentration of 10%. Fractions with the highest virus concentration (highest turbidity) were pooled, aliquoted and stored at −80° C. Virus aliquots were not thawed and frozen more than two times.

Production and Purification of Recombinant Ad5 Vectors Displaying Antigens on pIX The production of Ad5-pIX viruses was performed using a different strategy than normal recombinant Ad5 viruses. The producer cell line was the earlier described HEK293 (CCS)-shmir-pIX_221-puro cell line (pIX cells). pIX cells were seeded into 175 cm² flasks (four flasks per virus) and grown to 70% confluency. To produce recombinant pIX proteins, cells were transfected with a pcDNA3_pIX plasmid in which pIX was coupled to a recombinant protein by genetic fusion. Doxycycline was added to the culture medium (0.5 µg/mL) prior to transfection, which induced transcription of pIX-specific shRNA that inhibited translation of native pIX. Cell culture medium was changed 18 h after transfection and doxycycline was added again. Subsequently, cells were infected with 5 MOI (multiplicity of infection) of the respective base adenovirus (adenovirus encoding for recombinant protein of interest). Replication of the virus was allowed for 48 h under normal culture conditions until cytopathic effect of the virus was visible. Cells were harvested and pelleted by centrifugation at 750 g for 10 min. The pellet was resuspended in PBS with 0.5% sodium deoxycholate and incubated 30 min at RT to degrade cells and release viruses. In order to digest genomic DNA from the producer cell line, 0.2 M $MgCl_2$ and 0.05 mg/mL DNAse I (A3778, AppliChem) were added and incubated for 1 h at 37° C. Cell debris was removed by centrifugation at 3000 g for 15 min and CsCl was added to the virus-containing supernatant to a final concentration of 1.34 g/mL. Viruses were ultracentrifuged in the CsCl gradient as described before for Ad5 purification. The extracted virus band was transferred to a dialysis membrane (Spectra/Por® Dialysis Membrane, 300 kDa, #131450, Biotech CE Tubing) and was dialyzed overnight in PBS at 4° C. Finally, the virus was aliquoted in 10% glycerol and stored at −80° C.

Virus Titration

For reproducibility of experiments, purified viruses were titrated to obtain the number of infectious units per mL (IFU/mL). Flat bottomed Δ treated surface 96-well plates were coated with poly lysine for 15 min and washed three times with PBS. HEK293 cells were seeded into the wells with a concentration of $5\times10^4$ cells in 100 µL culture medium. The virus was diluted in a 10-fold serial dilution in culture medium, starting with a dilution of 1:50. 50 µL of dilution factors $5\times10^4$ to $5\times10^7$ were added in doublets to the cell suspensions in the 96-well plate. The infected cells were incubated for 48 h under normal cell culture conditions. After removing the media, wells were dried at RT and cells were fixed in cold methanol for 10 min at −20° C. Subsequently, wells were washed three times with PBS containing 1% bovine serum albumin (BSA). To detect virus-infected cells, anti-Ad5 hexon antibodies (1E11; #sc-51746; Santa Cruz Biotechnologies) were added with a dilution of 1:1000 in PBS+BSA and incubated for 1 h at 37° C. After washing three times with PBS+BSA, secondary antibodies against mouse immunoglobulins coupled to horseradish peroxidase (HRP) (#P0447; Dako), diluted 1:500 in PBS+BSA, were incubated in the wells for 1 h at 37° C. Residual antibodies were washed off and virus plaques were visualized with 3,3'-Diaminobenzidine (DAB) substrate at RT for 10 min.

To determine the titer of the virus, plaques at a suitable dilution were counted under the microscope at 20× magnification. Several vision fields were counted in each well until approximately 100 plaques were detected. The final number of IFU per mL was calculated using the following formula:

$$\overline{P} * VF * DF * W = \overline{P} * 52.7 \text{ vision fields/well} * DF * 20 \text{ wells/mL}$$

$$= P/\text{mL} = IFU/\text{mL}$$

$\overline{P}$=average number of plaques per vision field (total number of counted plaques/counted vision fields); VF=number of vision fields per well at 20× magnification (52.7 vision fields/well); DF=dilution factor of the virus in the counted well (e.g. 500,000×); W=number of infected wells per mL virus dilution (1000 µL/mL/50 µL/well=20 wells/mL); P=number of plaques.

As an additional quality control, the measured concentration of infectious units per mL (IFU/mL) was compared to the virus particle (VP) count. The VP/mL was determined using the NanoDrop™ 2000 by measuring the absorbance at 260 nm. An absorbance of 1 unit corresponds to a concentration of $10^{12}$ VP/mL. The ratio of IFU/mL to VP/mL indicated the viability of the virus with an ideal/typical ratio of 1:30-1:100.

Genomic DNA Purification from Recombinant Ad5

Isolation of DNA from recombinant adenoviruses was performed in order to assure correct insertion of recombinant genes into the adenoviral genome. DNA was extracted with the GenElute™ Mammalian Genomic DNA Miniprep Kit (G1N70; Sigma-Aldrich) using a modified protocol. To this end, 100 µL purified virus sample was mixed with 100 µL Resuspension Solution. Proteinase K and Lysis Solution C were added, followed by 10 min incubation at 70° C. After adding 96% ethanol, the solution was loaded on a prepared GenElute Miniprep Binding Column. The subsequent steps followed the original protocol with two washing steps and subsequent drying of the column. Viral DNA was eluted in Elution Solution. For quality assurance of the virus, DNA was send for sequencing (GENEWIZ UK Ltd.) to exclude mutations in the region of homologous recombination. Additionally, viral DNA was cut with restriction enzymes to confirm correct band sizes by gel electrophoresis.

Production and Purification of VLPs

Production and purification of virus-like particles (VLPs) were primarily performed to test functionality of VLP-encoding vaccines. VLP production was tested in Vero cells, which were seeded with a density of $1\times10^7$ cells into a 175 cm² culture flasks and were incubated for 2 h to allow attaching. Subsequently, cells were infected with 50 MOI of Ad5 ($5\times10^8$ IFU/flask) for 5 h. After removing the culture medium, cells were washed twice with PBS and incubated for 48 h in serum-free medium. The supernatant (SN) was centrifuged at 282 g for 10 min and filtered through a 0.45 µM membrane to remove cell contaminants. VLPs were purified by pelleting through a 20% sucrose cushion at 82.700 g in a Beckman Coulter Ti 70 rotor using open 32 mL thickwall tubes (#355631; Beckman Coulter). SN was removed and the pellet was resuspended in 100 µL PBS (160× the original concentration).

The Adv-vaccine encoding for HERV-K-Gag-p2A-Env wild type (WT)/ISDmut was translated into functional proteins able to generate VLPs, a cell lysate was produced from infected cells, and VLPs were purified from the cell culture supernatant (SN):

Vero, A549 and HEK293 cell lines were used to produce and purify VLPs. $10 \times 10^6$ Vero, $10 \times 10^6$ A549 or $10 \times 10^5$ HEK293 cells were seeded at day one at T175 (175 cm$^2$) flasks, or T25 (25 cm$^2$) flasks, in case of the HEK cells, containing the corresponding media. After 2 h, the cells were infected with different viral vectors encoding for our sequences of interest (see Table 2b) using a multiplicity of infection (MOI) of 50 or 20 (HEK293) that indicates the number of virions/cell for a given infection. After 5 h, the cells were washed twice with Phosphate Buffered Saline (PBS) containing 8 g/L NaCl, 0.2 g/L KCl, 1.15 g/L Na$_2$HPO$_4$.2H$_2$O, 0.2 g/L KH$_2$PO$_4$ at pH 7.4. Then, the media was changed for the corresponding cell media, but without FBS. The cells were incubated within optimal maintenance conditions during 48 h, or 16 h when using HEK293 cells.

Thereafter, in order to obtain VLPs from the cell cultures, two different procedures were followed. On the one hand, the SN was kept for purifying and analysing the cell-secreted VLPs. On the other hand, the cells were lysed in order to analyse VLPs contained into the cells.

For the first procedure, cells were centrifuged at 12000 rpm for 10 min at 4° C., and the supernatant was filtered through a 0.45 µM membrane (Sartorius, 16555) to remove cell impurities. 13.5 mL of the SN were added dropwise to 3 mL of 20% (w/v) sucrose dissolved in PBS, in open 32 mL thickwall ultracentrifuge tubes (Beckman Coulter, 355631). The tubes were weighted for an equal volume and were placed into a Ti 70 rotor (Beckman Coulter, 337922), which was introduced into the ultracentrifuge set to 82.700 g, 4° C. for 2.5 h. When finished, the SN was cautiously removed, and the remaining pellet was resuspended in 100 µL PBS and stored at −20° C.

The second procedure consisted of a first step of cold PBS wash. Then, 10 mL of cold PBS were added to the flasks and the cells were mechanically scraped off. 4 mL were transferred into a 15 mL conical tube, and centrifuged at 12000 rpm for 5 min at 4° C.

The SN was discarded and 1300 µL of the mix containing NP40 Cell Lysis Buffer (Invitrogen, FNN0021) with 7 µL/mL Protease Inhibitor Cocktail (Sigma-Aldrich, P8340) were added to each tube. Then, tubes were left on ice for 30 min while vortexing every 10 min using a Shaker Vortex 3 (IKA). Finally, the tubes were centrifuged at 13.000 rpm for 10 min at 4° C. to remove the cell debris, and SN were transferred into new tubes and stored at −20° C.

TABLE 2b

List of adenoviruses encoding different constructs used for analysing and comparing VLP production and expression.

| Code | Vector and sequence |
| --- | --- |
| LA512 | Ad5-(TetO)-CMV-Ii-fur-HB3var03-IT4var20 |
| LA551 | Ad5-(TetO)-CMV-SIVgag_p2A_LucSP_Syncytin1_HA-TMCT |
| LA546 | Ad5-(TetO)-CMV-SIVgag_p2A_HERV-K108env_P2TS |
| Ad19_HERV-K | Ad19a(II)-(TetO)-CMV-coHERV-K-P2TS |
| Ad19_HERV-K_ISD | Ad19a(II)-(TetO)-CMV-ISDmut_coHERV-K-P2TS |
| Ad19_MelARV | Ad19a(II)-(TetO)-CMV-MelARV-P2TS |
| Ad19_MelARV_ISD | Ad19a(II)-(TetO)-CMV-ISDmut_MelARV-P2TS |

MVA Production and Titration

The procedure for MVA production, purification and titration was performed using the guidelines described by Staib et al. 2004. The initial MVA expressing the HERV-K Gag or Env protein seed lysate used to perform this experiment was provided by Prof. Dr. Barbara Schnierle (Langen, Germany). Before generating the MVA in a big scale using 175 cm² flasks, the amount of virus was augmented in a small scale using also 175 cm² flasks, in both cases seeded with CEF cells.

In this case, the MVA titration was performed in BHK-21 cells. A primary polyclonal rabbit anti-vaccinia virus (Bio-Rad, 9503-2057), diluted 1:1000, and a secondary HRP-conjugated polyclonal goat anti-rabbit Ig antibody (Dako, P0448), diluted 1:500, were used to detect the infected cells. In order to determine the titer (IFU/mL), the number of stained foci was counted on a diluted sample with approximately 20-100 viral foci/well, in order to maximize precision.

Animal Experiments

Female C57BL/6, Balb/C and CD1 mice at age of 6-8 weeks were obtained from Taconic (C57BL/6) or Envigo (Balb/C and CD1). The mice were allowed to acclimatize for one week prior to the initiation of an experiment. All experiments were performed according to national guidelines and experimental protocols approved by the national animal experiments inspectorate (Dyreforsøgstilsynet in Danish).

Isolating Blood Serum Samples To obtain serum samples, approximately 10% of the total blood volume was taken from mice by puncturing the facial vein with a Goldenrod lancet.

Alternatively, for final bleed of the mice (full bleed), animals were anaesthetized with 1 mg/mL Xylazine and 10 mg/mL Ketamine in PBS at a dose of 100 μL per 10 g mouse, injected intraperitoneally (i.p.). The maximum volume of blood was taken by puncturing the facial vein and mice were subsequently euthanized by cervical dislocation.

In the HERV-K experiments, for full bleed cardiac puncture, mice underwent full isoflurane anesthesia. Straight after, mice were placed upward with a facial mask which continuously supplied isoflurane, and the cardiac puncture was performed using a G27 needle connected to a 1 mL syringe. Approximately, 800-1000 μL were collected, and the mice were subsequently euthanized by cervical dislocation.

Alternatively, mice underwent full anesthesia with isoflurane. They were then tested for involuntary reflexes and, only after making sure they did not present any, the maximum blood volume was collected from the eye, specifically through the orbital sinus. Then, mice were euthanized immediately by gentle cervical dislocation.

Blood samples were stored overnight at 4° C. to allow coagulation and blood cells were removed from the serum by two centrifugations at 800 g for 10 min. The serum was then stored at −20° C.

Injections: i.v., s.c., i.m., i.p.

Different injection procedures were performed. For intravenous (i.v.) injection, mice were warmed up in a heating chamber to increase superficial venous blood flow. A maximum of 200 μL were injected into the tail vein. In the HERV-K related experiments, a volume of 100 μL containing $10^6$ RLZ Gag and Env cells (from B. Schnierle) was injected i.v. to the mice, in order to induce lung metastasis.

Subcutaneous (s.c.) injection into the footpad (f.p.) was performed under isoflurane anesthesia by injecting 30 μL under the skin of the foot pad. For the HERV-K experiments, This type of injection was used to inject $10^6$ RLZ Gag and Env cells (from B. Schnierle) (in 100 μL), in order to grow subcutaneous tumors in mice and establish a murine tumor model expressing HERV-K Env.

For intramuscular (i.m.) injection, a maximum volume of 60 μL was injected into the thigh muscle.

In the context of the HERV-K experiments, this type of injection was used mainly for immunizing (priming) and boosting the mice with the vaccines of interest (see Table 2c below). 50 μL per mouse were used for adenoviral or MVA vaccination/boost, respectively. The injection was performed at the thigh muscle under isoflurane anaesthesia which confers both analgesia and muscle relaxation.

TABLE 2c

| Virus-based vaccines used for i.m. mice immunization. | | |
| --- | --- | --- |
| Virus | IFU/mouse | Type of vaccination |
| Ad19a(II)-(TetO)-Hiso-MfPV3-P2TS (IP1321_A2953_V_7b) from Sirion | $1 \times 10^8$ | Prime |
| Ad5-(TetO)-CMV-SIVgag_p2A_HERV-K108env_P2TS | $1 \times 10^8$ | Prime |
| Ad19a(II)-(TetO)-CMV-coHERV-K-P2TS from Sirion | $1 \times 10^8$ | Prime |
| Ad19a(II)-(TetO)-CMV-ISDmut_coHERV-K-P2TS from Sirion | $1 \times 10^8$ | Prime/Boost |
| MVA-expressing the HERV-K Env protein | $1 \times 10^8$ | Prime/Boost |
| DNA-(TetO)-CMV-ISDmut_coHERV-K-P2TS | 1 μg/μL | Prime/Boost |

Intraperitoneal (i.p.) injection was performed by administering up to 500 μL into the abdominal cavity.

Vaccinations

5 Different vaccination trials were performed in mice:

Vaccination timeline I. Balb/C mice were vaccinated in a prime-boost regimen of two DNA vaccinations followed by one Ad5 vaccination, or by either DNA or Ad5 alone. As a control, mice were injected with PBS. Four weeks after Ad5 vaccination, blood samples were collected and spleens were isolated from some mice. Subsequently, mice were challenged s.c. with CT26 tumor cells in the right flank and tumor growth was measured.

Vaccination timeline II. Balb/C mice were challenged s.c. with CT26 tumor cells. Mice were vaccinated with Ad5-MelARV either on day 2 post challenge (d.2 p.c.) or d.5 p.c. (previously primed with DNA). Additionally one group was vaccinated on d.2 p.c. and subsequently received four injections of anti-PD1 antibodies as soon as tumors were palpable (d.8 p.c.). As control groups mice were injected with PBS or anti-PD1 only.

Vaccination timeline III. C57BL/6 mice were vaccinated in a prime-boost regimen with two DNA-MelARV injections followed by an Ad5 vaccination. Blood samples were taken 3 weeks after the last vaccination and mice were challenged i.v. with 2×105 B16F10-GP cells. The number of metastases in the lungs was determined two weeks after challenge.

Vaccination timeline IV. CD1 mice were vaccinated first with DNA plasmids encoding for MelARVgag_p2A_env (DNA-MelARV) or the ISD mutated version MelARVgag_p2A_env_ISD (DNA-MelARV-ISD). The DNA prime was followed by adenoviral vaccination with either Ad5-MelARV or Ad5-MelARV-ISD. Blood samples were taken four weeks after vaccination and were analyzed for serum antibodies.

Vaccination timeline V: C57BL/6 mice were vaccinated twice with adenoviruses, either Ad5-MelARV_pIX-p15E or Ad5-MelARV. Ad5-GFP was used as a control. Subsequently, blood samples were taken and mice were challenged i.v. with 2×105 B16F10-GP cells. Lungs were isolated two weeks after challenged and were analyzed for metastases.

For DNA-vaccination, 50 µg DNA in 50 µL TRIS/PBS (142 mM) were injected i.m. Adenoviruses were injected with $2\times10^8$ IFU in 30 µL PBS into the foot pad. In experiments including pIX-modified viruses (vaccine timeline IV and V), $10^{10}$ virus particles in 60 µL PBS were injected i.m. Due to lower concentrations of pIX-viruses, injection of a small volume into the foot pad was not possible.

Another experiment included the administration of anti-PD1 antibodies (RMP1-14; #BE0146; BioXCell) in tumor challenged mice (see "0 Tumor challenge"). Anti-PD1 was administered with 200 µg antibody in 200 µL PBS, injected i.p. The treatment was started at day 8 after tumor challenge when subcutaneously growing tumors were palpable. Mice were injected four times every fourth day (day 8, 12, 16 and 20 after tumor challenge) (Kim, K., et al., *Eradication of metastatic mouse cancers resistant to immune checkpoint blockade by suppression of myeloid-derived cells*. Proc Natl Acad Sci USA, 2014. 111(32): p. 11774-9 and Shindo, Y., et al., *Combination immunotherapy with 4-1BB activation and PD-1 blockade enhances antitumor efficacy in a mouse model of subcutaneous tumor*. Anticancer Res, 2015. 35(1): p. 129-36.

In the HERV-K experiments, the Adv and/or MVA boost was performed approximately 4 or 8 weeks after the priming with the Adv or DNA vaccine (day 0). Blood samples were taken both prior and after (day 14) prime vaccination. Mice were also bled at day 14 and 28 after the MVA/Adv/DNA boost. The blood samples were used for analysing the humoral responses (production of antibodies against HERV-K Env) of the vaccinated mice. Moreover, mice were euthanized 10 days after MVA boost to test their cellular immune responses (generation of CD8+T HERV-K Env specific T cells).

For testing the therapeutic effects of the novel vaccination strategy, only one dose of the vaccine was given 10 days after the tumor challenge.

Tumor Challenge

To assess metastasis of B16F10-GP cells in vivo, cultured cells were washed three times with PBS and detached by incubating in Versene for 15 min at 37° C. Cells were subsequently centrifuged at 282 g, washed with PBS and diluted to a concentration of $2\times10^6$ cells/mL in PBS. $2\times10^5$ cells in 100 µL PBS were injected i.v. into the tail vein of mice, which resulted in tumor metastases in the lungs. Challenged mice were euthanized after 14 days. Lungs were isolated and fixed overnight in a solution of 2% paraformaldehyde (PFA) in PBS followed by storage in PBS at 4° C. Metastases were counted as black nodules on the surface of the lungs under a dissection microscope. Samples were blinded and metastases were counted by at least two individuals.

In order to analyze primary growth of CT26 tumors, CT26 cells were prepared as described for B16F10-GP cells and were diluted to a concentration of $5\times10^6$ cells/mL in PBS. S.c. injection in the right thigh of $5\times10^5$ cells in 100 µL PBS resulted in the formation of a tumor at the injection site. Tumor size was measured three times a week in length and width. The tumor volume was determined as: length*width$^2$*0,5236 (Janik, P., et al., *The Effect of Estrone-Progesterone Treatment on Cell Proliferation Kinetics of Hormone-dependent GR Mouse Mammary Tumors*. Cancer Research, 1975. 35(12): p. 3698-3704). Mice were euthanized when tumors exceeded 16 mm on any side, necrotic wounds emerged or mobility of the mice was markedly reduced. During tumor measurements, the different vaccinated groups were blinded to prevent biased assessment.

Additionally to CT26 challenge, Balb/C mice were injected with $2.5\times10^4$ 4T1-Luc cells in 100 µL PBS into the thoracic mammary fat pad. To visualize tumor formation after 6 weeks, mice were injected i.p. with Luciferin (1.5 mg per 10 g mouse) and were imaged 12 min after injection using an IVIS Spectrum in vivo imaging system. IVIS imaging was performed by Andreea-Cornelia Udrea and Melanie Schwerdtfeger.

To analyse tumor growth and metastasis of RLZ Gag and Env cells in vivo, cells were cultured until 60-80% confluence. Once the desired confluence was achieved, RLZ cells were washed with PBS three times, before adding Versene for 15 min at 37° C. in order to detach the cells. Afterwards, the cells were spun down at 282 g, washed using PBS, and finally diluted to 107 cells/mL into PBS. Every mouse was injected with 106 cells/100 µL, i.v. for lung metastasis and s.c. for subcutaneous tumors. To assess lung metastasis, mice were weighted at days 0, 7 and 14, and afterwards every 2 days. If mice lost about 15-20% weight within a few days, they were euthanized. The end point for termination was set at day 40 after tumor challenge. Mice with s.c. tumors were checked at the same time points as the i.v.-challenged mice, and euthanized when they tumors were exceed 16 mm diameter.

Both s.c. tumors and lungs were isolated and embathed into 4% paraformaldehyde (PFA) and phosphate buffer 0.01 mol/L at pH=7.2 (Rigshospitalet, Copenhagen, Denmark) and stored at 4° C. Samples were processed and tissues analysed for HERV-K Env specific staining using high titer serum from vaccinated mice.

Western Blotting

For detection of pIX-proteins, cell lysates (~10 µg) or purified viruses ($10^{10}$ virus particles) were mixed with 6× SDS-loading buffer containing DDT and were heated 5 min at 95° C. To show expression of MelARV proteins, cell lysates (5 µg), cell supernatant (15 µg) and purified VLPs (~2 µg) were likewise mixed with DDT-containing loading buffer, but without heating the samples. The mixture was loaded on a NuPAGE™ 4-12% Bis-Tris Protein Gel (#NP0322, Thermo Fisher) and run for 1 h at 150V in MOPS buffer. The protein content in the gel was blotted in a wet transfer system to a nitrocellulose membrane for 1 h at 30V.

After transfer, the membrane was blocked for 1 h with 5% skimmed milk in tris-buffered saline+Tween 20 (TBS-T). Subsequently, the membrane was washed three times with TBS-T for 10 min on a shaker and was incubated with diluted primary antibody (Table 3) (in TBS-T+3% skimmed milk) overnight at 4° C. After additional three washing steps, HRP-conjugated secondary antibody in TBS-T was added and the membrane was incubated for 1 h at RT. Unbound secondary antibody was washed off and the target protein was visualized using LumiGLO Reserve Chemiluminescent Substrate (54-61-00 or 54-71-02) in an ImageQuant LAS 4000.

TABLE 3

List of primary and secondary antibodies used for western blotting and ELISA. The table lists the different primary antibodies used for western blotting and their origin. Further shown are the used dilutions and which secondary antibody was chosen for detection. Some antibodies were also used for ELISA analysis at the later described dilutions.

| Primary antibody | Product number/Origin | Dilution | Secondary anitbody |
|---|---|---|---|
| Anti-p2A | #ABS31; Millipore | 1:1000 | anti-rabbit Ig-HRP (#P0448, Dako) |
| MM2-9B6 | 20× cell culture supernatant from hybridomas (provided by Tsuyoshi Takami, University of Arizona Health Sciences Center) | 1:200 | anti-mouse Ig-HRP (#P0447, Dako) |
| 4F5 | concentrated cell culture supernatant from hybridomas (provided by George Cianciolo, Duke University Medical Center) | 1:200 | anti-mouse Ig-HRP (#P0447, Dako) |
| 19F8 | concentrated cell culture supernatant from hybridomas (provided by George Cianciolo, Duke University Medical Center) | 1:200 | anti-mouse Ig-HRP (#P0447, Dako) |
| anti-pIX | antibody produced in rabbit (provided by David T. Curiel, Washington University in St.Louis) | 1:1000 | anti-rabbit Ig-HRP (#P0448, Dako) |

In the HERV-K related experiments VLP expression at protein level was analysed through WB technique. To guarantee an equal loading of the samples, the protein concentration of both VLPs (SN) and cell lysates was measured using the Pierce™ bicinchoninic acid (BCA) Protein Assay Kit (Thermo Fisher Scientific, 23225) according to the manufacturer guidelines. 6× Sodium dodecyl sulfate (SDS) loading buffer containing dithiothreitol (DTT) was added into the different samples, which were placed into a block heater SBH130DC (Stuart) at 95° C. for 5 min. Subsequently, 5 µg of protein, as well as 7 µL of RunBlue™ Prestained Marker (Expedeon, NXA05160) were loaded into NuPAGE™ 4-12% Bis-Tris Protein Gels (Thermo Fisher Scientific, NP0322) together with NuPAGE™ MOPS SDS Running Buffer (Thermo Fisher Scientific, NP0001). The samples were separated by SDS polyacrylamide gel electrophoresis (SDS-PAGE) for 45 min at 180 V.

Thereafter, the samples were transferred to a 0.45 µm nitrocellulose blotting membrane (Bio-Rad, 1620115) at 30 V for 45 min. For this step, transfer buffer (3.75 g/L Trizma® base, 18.1 g/L glycin at pH 8.5) with 20% ethanol was used.

To prevent non-specific binding, the membrane was blocked for 1 h at room temperature (RT) using 5% (w/v) skimmed milk powder in Tris-buffered saline with Tween (TBS-T) (6.06 g/L Trizma® base, 8.76 g/L NaCl, 0.25% (v/v) Tween-20 at pH 7.6). Afterwards, the membrane was washed with TBS-T for 10 min, and incubated with the corresponding primary antibodies (see Table 3a) in 3% (w/v) skimmed milk powder in TBS-T on a shaker CERTOMAT® MO II (Sartorius) at 4° C. overnight (o/n).

TABLE 3a

List of specific primary antibodies used for the detection of VLP proteins.

| Antibody | Dilution | Source |
|---|---|---|
| Polyclonal rabbit anti-2A peptide (Gag) | 1:1000 | Millipore, ABS31 |
| Monoclonal (IgG) mouse anti-human Endogenous Retrovirus type K (HERV K) envelope protein (p15E, TM) | 1:8000 | Austral Biologicals, HERM-1811-5 |
| Monoclonal (IgG) mouse anti-human Endogenous Retrovirus type K (HERV K) envelope protein (gp70, SU) | 1:2000 | Austral Biologicals, HERM-1821-5 |

Subsequently, the membrane was washed three times with TBS-T for 10 min. Then, it was incubated with the corresponding secondary antibody (see Table 3b) diluted in TBS-T for 1 h at RT.

TABLE 3b

List of HRP-conjugated secondary antibodies used for WB.

| Antibody | Dilution | Source |
|---|---|---|
| Polyclonal goat anti-rabbit Ig antibody, HRP-conjugated | 1:2000 | Dako, P0448 |
| Polyclonal rabbit anti-mouse Ig antibody, HRP-conjugated | 1:2000 | Dako, P0260 |

The membrane was then washed 3 times (10 min each time) with TBS-T. Peroxidase Chemiluminescent Substrate (KPL, 54-61-00) was used for detection of the proteins in an ImageQuant LAS 4000 camera (GE Healthcare Life Sciences).

Enzyme-Linked Immunosorbent Assay (ELISA)

For detection of MelARV-specific antibodies in vaccinated mice, peptides of the MelARV Env subunit p15E conjugated to BSA were purchased from Schafer-N (Copenhagen, Denmark).

TABLE 4

Specification of the peptide used for ELISA. The table describes the peptide used for coating the ELISA plate in order to analyze antibody-responses in mice. Further specified are the protein of origin (target protein), the location of the peptide in the target protein (region) and the sequence.

| Peptide Name | Target-Protein | Region | Sequence |
|---|---|---|---|
| MelARVp15E (94-136) | MelARV p15E | Between ISD and trans-membrane domain (94-136) | CFYADHTGLVRDSMAKLRER LSQRQKLFESQQGWFEGLFNKSP (SEQ ID No: 42) (conjugated to BSA) |

MaxiSorp flat bottom plates (Thermo Fisher) were coated overnight at 4° C. with 100 µL peptide solution (2 µg/mL in PBS) per well and were subsequently washed twice with washing buffer (PBS+2.07% NaCl+0.1% Tween-20). Wells were blocked with dilution buffer (PBS+2.07% NaCl+ 0.05% BSA+0.05% Tween-20) for 2 h at 37° C., washed once with washing buffer and incubated with diluted mouse serum (1:50 in dilution buffer) for 3 h at 37° C. After washing twice, peptide-bound serum antibodies were incubated with a HRP-coupled goat anti-mouse immunoglobulins antibody (Dako, P0447) for 2 h at 37° C. in a 1:2000 dilution. After additional two washing steps, 100 µL TMB PLUS2 (Kem-En-Tec Diagnostics, 4395A) were added and incubated for 8 min at RT. The reaction was stopped with 100 µL 0.2M $H_2SO_4$ and quantified by measuring optical density at 450 nm.

Detection of Ad5-specific antibodies in mouse serum was performed by coating ELISA plates with heat inactivated Ad5 (30 min, 56° C.) at $5 \times 10^9$ virus particles/mL. The assay was conducted as described above but with shorter incubation times for blocking and antibody-binding of 1 h at RT. The primary antibody was mouse serum diluted in a 1:2 serial dilution starting with 1:200.

Detection of MelARV proteins in cell lysate, supernatant and purified VLPs of infected Vero cells was accomplished by coating ELISA plates with the respective samples. Cell lysates were diluted 1:2 in PBS (100 µL), supernatant was applied undiluted (100 µL) and purified VLPs were diluted 1:25 in PBS (50 µL). Detection was achieved using anti-p2A (1:500), MM2-9B6 (1:100), 4F5 (1:100) and 19F8 (1:100) as primary antibodies and using the same procedure as before with secondary antibodies stated in Table 3.

Flow Cytometry

In the HERV-K related experiments, FACS was used to detect both extracellular and intracellular markers of activated immune cells from vaccinated mice, as well as the presence of the HERV-K Env protein on the surface of infected A549 cells. The machine used for the cell sorting was the flow cytometer BD LSR II (BD Biosciences).

The following buffers were used for FACS:

TABLE 3c

Description of the ingredients contained in the different buffers used for FACS.

| Buffer | Ingredients |
|---|---|
| Fluorescence-activated cell sorting (FACS) buffer | PBS<br>10 g/L Bovine Serum Albumin (BSA)<br>1 g/L $NaN_3$ |

TABLE 3c-continued

Description of the ingredients contained in the different buffers used for FACS.

| Buffer | Ingredients |
|---|---|
| FACS washing buffer | PBS<br>1 g/L $NaN_3$ |
| Hank's Balanced Salt Solution (Hank's BSS) | Hank's BSS (Corning, 55-022-PB)<br>185 mg/L $CaCl_2*2H_2O$<br>232 mg/L $MgSO_4*7H_2O$<br>10 mg/L Phenolred |
| PBS | 8 g/L NaCl<br>0.2 g/L KCl<br>1.15 g/L $Na_2HPO_4*2H_2O$<br>0.2 g/L $KH_2PO_4$<br>pH 7.4 |

Extracellular Staining with Serum Antibodies

In the non-HERV-K experiments, flow cytometry was performed in order to detect binding of serum antibodies to cancer cells. B16F10-GP cells or CT26 cells were resuspended (as described in "0 Tumor challenge") and seeded with $4 \times 10^5$ cells per well in a round bottom 96-well plate. The plate was centrifuged at 784 g for 3 min (4° C.) to fix cells at the bottom of the well. Media was removed by flicking the plate upside down and cells were resuspended in 50 µL fluorescence-activated cell sorting (FACS) medium (PBS+1% BSA+0.1% $NaN_3$) containing mouse serum at a dilution of 1:50. After 20 min incubation at 4° C., the plates were centrifuged at 784 g for 3 min (4° C.) and medium was removed. Cells were washed twice with 200 µL wash medium (PBS+0.1% $NaN_3$) and resuspended in 50 µL FACS medium containing fluorescent-labeled secondary antibody against mouse Immunoglobulin G (IgG) (goat anti-mouse IgG APC; #405308, Biolegend) diluted 1:100. Cells were incubated 20 min at 4° C., washed twice with wash medium and fixed for 15 minutes at 4° C. in 200 µL PFA solution (1% in PBS). Cells were resuspended twice in FACS medium and analyzed for fluorescence in a BD LSR II Flow Cytometer.

Detection of MelARV Env on the surface of infected Vero cells was performed after the same protocol using monoclonal antibodies against different epitopes (Table 5). Secondary antibodies were anti-mouse IgG_APC (1:100) or goat anti-mouse IgM Heavy Chain_RPE (1:100; A10689, Invitrogen).

Further, this technique was performed to characterize the new vaccine strategy based on an Ad19-vector encoding for HERV-K wt and HERV-K ISD mut transgenes (Sirion), as well as to compare the use of different adenoviral vectors (Ad19 vs. Ad5). Surface staining was used to detect the presence of HERV-K Env protein on the surface of infected A549 cells by flow cytometry.

3×10⁶ A549 cells were seeded into 75 cm² flasks in 15 mL of Ham's F-12K medium, and were incubated for 2 h at 37° C. Each flask was infected with 50 MOI of the following viruses (1.5×108 IFU/flask):

Ad5-(TetO)-CMV-SIVgag_p2A_HERV-K108env_P2TS
Ad19a(II)-(TetO)-CMV-ISDmut_MelARV-P2TS
Ad19a(II)-(TetO)-CMV-coHERV-K-P2TS from Sirion
Ad19a(II)-(TetO)-CMV-ISDmut_coHERV-K-P2TS from Sirion They were then incubated 5 h at 37° C., after which the medium was changed for Ham's F-12K FBS free medium. Then, the cells were incubated for 48 h at 37° C.

Cells were kept on ice inside the LAF bench. The media was aspirated, and the cells were washed carefully with cold PBS and scraped off in cold PBS before separating the cells by centrifugation (3 min, 4° C., 784 g). The cells were resuspended in PBS and distributed into a round-bottom 96-well plate (Thermo Fisher Scientific, 163320). The plate was centrifuged (3 min, 4° C., 784 g), and the SN was removed by flicking the plate. The cells were resuspended in 50 µL of FACS buffer containing 2 µg/mL of the mouse monoclonal (IgG) primary antibody, which is directed against the p15E (TM) domain of the HERV-K Env protein (Austral Biologicals, HERM-1811-5), for 20 min at 4° C. Afterwards, the cells were washed with FACS washing buffer (using a first volume of 150 µL and afterwards 200 µL) and centrifuged (3 min, 4° C., 784 g) 3 times. The plates were incubated with 100 µL FACS buffer, into which was previously added at 1:100 dilution of the goat anti-mouse IgG APC secondary antibody (BioLegend, 405308). They underwent an incubation of 20 min at 4° C. protected from light. The cells were centrifuged (3 min, 4° C., 784 g) and washed 3 times with 200 µL of FACS washing buffer. Subsequently, they were incubated in 200 µL 1% (w/v) paraformaldehyde (PFA; Rigshospitalet, Copenhagen, Denmark) during 15 min at 4° C. protected from light. Following that, they were centrifuged (3 min, 4° C., 784 g) and resuspended in 100 µL of FACS buffer and centrifuged again (3 min, 4° C., 784 g). They were finally resuspended in 200 µL and preserved o/n at 4° C. in the dark. The following day, the fluorescence of the cells was analyzed using the flow cytometer BD LSR II and he data was processed and analyzed using FlowJo 10 (FlowJo LLC).

Intracellular Staining (ICS) of Stimulated Splenocytes

Mice were euthanized 3-4 weeks after vaccination and spleens were isolated. The extracted spleens were transferred into HANKS B.S.S. and were mashed through a sterile net to obtain a single cell suspension. After centrifugation and resuspension in complete RPMI, the concentration of splenocytes was determined and cells were diluted to the required concentration.

Splenocytes were added into a round bottom 96-well plate with 2.5×10⁶ cells/well. The cells were centrifuged at 784 g for 3 min and resuspended in complete RPMI (+50 µM 2-mercaptoethanol) containing 3 µM monensin (pathway inhibitor) and 1 µg/mL peptide (AH1), while negative controls did not receive the peptide. Subsequently, cells were incubated for 5 h at 37° C. After washing the cells in FACS medium (PBS+1% BSA+0.1% NaN₃+3 µM monensin), cells were incubated for 20 min at 4° C. with fluorescent-labeled surface antibodies (anti-CD4, anti-CD8, anti-CD44, anti-B220) diluted 1:100 in FACS medium. Cells were washed twice with PBS+3 µM monensin and fixed in 1% PFA for 15 min at 4° C. After washing in FACS medium, cells were permeabilized with 0.5% saponin in PBS for 10 min at RT. Intracellular antibodies (anti-IFNγ, anti-TNFα) were added with a dilution of 1:100 in PBS+0.5% saponin and incubated for 20 min at 4° C. Cells were washed twice and finally resuspended in PBS+1% BSA+0.1% NaN₃. Fluorescence of the cells was analyzed in a BD LSR II Flow Cytometer. Analysis of the flow cytometry data is shown in Suppl. FIG. 5.

TABLE 5

List of primary antibodies used for flow cytometry. The table lists the primary antibodies used for flow cytometry, their origin,the working dilution and the respective flucrescent-conjugated secondary antibody. Some primary antibodies were directly conjugated to a fluorescent and did not have to be labeled with a secondary antibody.

| Primary antibody | Product number/Origin | Dilution | Secondary antibody |
|---|---|---|---|
| mouse serum | isolated from vaccinated mice | 1:50 | goat anti-mouse IgG_APC |
| 19F8 (anti-MelARV Env; p15E) | concentrated cell culture supernatant from hybridomas (provided by George Cianciolo, Duke University Medical Center) | 1:50 | goat anti-mouse IgG_APC |
| 4F5 (anti-MelARV Env; p15E) | concentrated cell culture supernatant from hybridomas (provided by George Cianciolo, Duke University Medical Center) | 1:50 | goat anti-mouse IgG_APC |
| MM2-9B6 (anti-MelARV Env; gp70) | 20× cell culture supernatant from hybridomas (provided by Tsuyoshi Takami, University of Arizona Health Sciences Center) | 1:50 | goat anti-mouse IgG_APC |
| MM2-3C6 (anti-MelARV Env; gp70) | 20× cell culture supernatant from hybridomas (provided by Tsuyoshi Takami, University of Arizona Health Sciences Center) | 1:50 | goat anti-mouse IgM_PE |
| MM2-9A3 (anti-MelARV Env; gp70) | cell culture supernatant from hybridomas (provided by Tsuyoshi Takami, University of Arizona Health Sciences Center) | undiluted | goat anti-mouse IgG_APC |

TABLE 5-continued

List of primary antibodies used for flow cytometry. The table lists the primary antibodies used for flow cytometry, their origin, the working dilution and the respective flucrescent-conjugated secondary antibody. Some primary antibodies were directly conjugated to a fluorescent and did not have to be labeled with a secondary antibody.

| Primary antibody | Product number/Origin | Dilution | Secondary antibody |
| --- | --- | --- | --- |
| PerCP/Cy5.5-CD8 | #100734, Biolegend | 1:100 | |
| FITC-CD4 | #317407, Biolegend | 1:100 | |
| PacificBlue-B220 | #RM2628, Invitrogen | 1:100 | |
| APC/Cy7-CD44 | #103028, Biolegend | 1:100 | |
| APC-IFN | #505810, Biolegend | 1:100 | |
| PE/Cy7-TNF& | #506324, Biolegend | 1:100 | |
| PE/Cy7-CD8 | #100721, Biolegend | 1:100 | |
| PacificBlue-CD8 | #100728, Biolegend | 1:100 | |
| APC-CD8 | #100711, Biolegend | 1:100 | |
| APC/Cy7-CD8 | #100713, Biolegend | 1:100 | |

In the HERV-K related experiments splenocyte ICS was performed to assess specific cellular responses derived from vaccinated mice. To be able to perform this experiment, different strong binding (SB) HERV-K peptides constituted of 8-10 amino acids of both C57BL/6 and BALB/c mice strains were previously tested for their capacity of stimulating CD8+ T cells of HERV-K vaccinated mice. Only one BALB/c 10-mer peptide (TYHMVSGMSL; SEQ ID No.47) at position 192 of the HERV-K Env sequence gave a response. Therefore, this peptide named P-HKE was used to stimulate the splenocytes of BALB/c mice immunized with an Ad5 and Ad19 vectors encoding for HERV-K Env together with the improved Ad19 vaccine that contains a mutation at Env ISD.

TABLE 5a

Antibodies used for extracellular and intracellular staining of splenocytes obtained from vaccinated mice, to test their derived cellular responses.

| Antibody | Source |
| --- | --- |
| Monoclonal rat anti-mouse TNFα, PE/Cy7-conjugated | BioLegend, 506324 |
| Monoclonal rat anti-mouse interferon γ (IFNγ), APC-conjugated | BioLegend, 505810 |
| Monoclonal rat anti-mouse B220, Pacific Blue ™-conjugated | Invitrogen, RM2628 |
| Monoclonal rat anti-mouse/human CD44, APC/Cy7-conjugated | BioLegend, 103028 |
| Monoclonal rat anti-mouse CD8a, PerCP/Cy5.5-conjugated | BioLegend, 100734 |
| Monoclonal rat anti-mouse CD4, FITC-conjugated | BioLegend, 100406 |
| Monoclonal rat anti-mouse CD8a, APC/Cy7-conjugated | BioLegend, 100713 |
| Monoclonal rat anti-mouse CD8a, APC-conjugated | BioLegend, 100711 |
| Monoclonal rat anti-mouse CD8a, Pacific Blue ™-conjugated | BioLegend, 10072 |
| Monoclonal rat anti-mouse CD8a, PE/Cy7-conjugated | BioLegend, 100721 |

Ad5 and Ad19 HERV-K/ISDmut vaccinated (primed) mice were used for this experiment with the objective of comparing the efficacy of the different vaccines containing different vectors and insert improvement strategy. Mice were euthanized 10 days after the booster immunization with MVA vector, and their spleens were collected in 5 mL Hank's BSS media. The spleens were mashed through a sterile net Corning® 70 μm cell strainers (Sigma-Aldrich, CLS431751) with the purpose of obtaining a suspension of single cells. Subsequently, the number of cells was counted in order to seed the desired amount of cells/well, as well as to provide the total number of cells/spleen to later calculate the absolute number of IFNγ+ CD8+ and CD4+ T-cells per spleen.

Approximately $3 \times 10^6$ cells/well were seeded into round bottom 96-well plates, which were centrifuged (3 min, 4° C., 784 g) and resuspended in RPMI media. The 10mer peptide of HERV-K Env mentioned before TYHMVSGMSL (SEQ ID NO:47) named P-HKE was dissolved in dimethyl sulfoxide (DMSO) to a concentration of 400 ng/μL. Then it was dissolved again in PBS to a concentration of 100 ng/μL, and finally RPMI was added to the former dilution to obtain a concentration of 6.67 ng/μL. Before adding the P-HKE peptide, in order to prevent cytokines from exiting the cells, 50 μL of the protein transport inhibitor, monensin (3 μM), were added to the wells. In addition, 30 μL/well of the aforementioned P-HKE peptide were added to the stimulated wells to induce T cell cytokines production. The rest of the wells did not received any peptide, but only DMSO at the same concentration as the stimulated samples, and were used as negative controls. The cells were incubated at 37° C. for 5 h.

After the incubation time the cells were centrifuged (3 min, 4° C., 784 g) and washed with 100 μL of FACS buffer containing monensin (3 μM) twice. The surface antibodies (PerCP/Cy5.5-CD8, FITC-CD4, Pacific Blue™-B220, APC/Cy7-CD44) were diluted 1:100 into FACS buffer containing monensin (3 μM). The splenocytes were resuspended with 50 μL of the prior solution and 50 μL FACS/monensin (3 μM) containing 1:100 diluted antibodies:PerCP/Cy5.5-CD8, FITC-CD4, Pacific Blue™-CD8, APC/Cy7-CD8, APC-CD8, PE/Cy7-CD8, used for making the compensation. The plates were incubated for 20 min at 4° C., at dark. The wells were washed twice with 100 μL of PBS with 3 μM monensin. Then, 100 μL of PBS/monensin (3 μM) were added together with 100 μL PFA (2%) in order to fix the cells during 4° C. in the dark. The cells were washed again twice using FACS/monensin (3 μM) and resuspended for 10 min at 20° C. (in the dark) with 150 μL of 0.5% Saponin in PBS. Once the cells are permeabilized, the intracellular antibodies (APC-IFNγ, PE/Cy7-TNFα) are diluted 1:100 in 0.5%

Saponin/PBS, and 50 µL were added to the wells, and the plates were incubated for 10 min at 4° C. in the dark. The cells were washed with PBS containing 1% BSA and 0.1% NaN$_3$ and finally resuspended in 200 µL of the same buffer. Plates were kept o/n at 4° C.

In addition, intracellular staining of A549 transfected cells was performed to corroborate the presence of HERV-K Env protein inside the cells. In this instance, the production (and not the secretion to the cell membrane) was assessed. The latter protocol was followed adding a 10 min incubation step with 150 µL of 0.5% (w/v) Saponin (Sigma Aldrich, 47036) diluted in PBS at 4° C., in the dark. This extra step is needed so as to permeabilize the cell membrane. The antibodies were also diluted into 0.5% Saponin.

Gating Strategy

FlowJo 10 (FlowJo LLC) was used to analyse data from both extracellular and IC FACS staining (see FIG. 27). Initially, cells were plotted in a forward scatter (FSC)-H and FSC-A and gated. This gate was used to isolate the lymphocyte population in a side scatter (SSC)-A and FSC-A plot. The latter population was gated for CD8+ CD4– cells and afterwards for CD8+ B220– cells, to obtain a CD8+ T cell population, removing both CD4+ T-cells and B cells (B220 marker) (Coffman & Weissman 1981) from the analysis. Then, the cells were gated for CD8+ CD44+ T cells, to obtain only the activated CD8+ T cells. These were further gated for IFNγ+ CD44+ cells, which are both markers expressed consequent to T cell activation. Moreover, IFNγ is known to be a higher sensitive marker for activated CD8+ T cells, when compared with TNFα cytokine (Badovinac & Harty 2000), (Kristensen et al. 2004). In addition, CD8+ CD44+ T cells were gated for IFNγ+ TNFα+ cells, since it is known that CD4+ T cells that produce multiple cytokines have a higher level of activity, activation, and turn into memory cells (Kannanganat et al. 2007).

To estimate the absolute number of IFNγ+ CD44+ B220– CD8+ T-cells the % of IFNγ+ CD44+ B220– CD8+ T cells of the lymphocytes was multiplied by the number of lymphocytes per spleen.

Additionally, the % of double positive (IFNγ+ TNFα+) cells of IFNγ+ CD8+ was calculated dividing the IFNγ+ TNFα+ cells by the sum of IFNγ+ TNFα+ and IFNγ+ TNFα– cells.

Enzyme-Linked ImmunoSpot (ELISPOT)

ELISPOT assays were performed to detect antigen-specific T cells. The peptide used in this experiment was AH1 (SPSYVYHQF (SEQ ID NO: 56)), which is a known H2-Ld-restricted T-cell epitope in Balb/C mice that is located in the MelARV Env subunit gp70, (Huang, A. Y., et al., *The immunodominant major histocompatibility complex class I-restricted antigen of a murine colon tumor derives from an endogenous retroviral gene product*. Proc Natl Acad Sci U S A, 1996. 93 (18): p. 9730-5).

Splenocytes of vaccinated mice were prepared as described for the ICS.

The assay was performed using the Mouse IFN-γ T cell ELISPOT kit (CT317-PRS, U-CyTech). Briefly, the membrane of a polyvinylidene difluoride (PVDF) 96-well plate (MSIP 54510, Millipore) was activated with 70% ethanol and subsequently coated overnight with an anti-murine IFN-γ antibody. After removing coating antibody and blocking the membrane, splenocytes were seeded with 2×10^5 cells/well in complete RPMI culture medium containing 1 µg/mL AH1. As controls splenocytes were either left unstimulated or were stimulated with the potent T-cell activator Concanavalin A (ConA) (2 µg/mL). After 48 h incubation under normal cell culture conditions, cells were removed, wells were washed and subsequently incubated with biotinylated detection antibody targeting IFN-γ. Streptavidin-HRP conjugate was added and IFN-γ spots were visualized using AEC substrate solution. Spots were counted using a CTL ImmunoSpot analyzer.

Positive Control (Control Serum LEV76)

The positive control serum LEV76 was used as a standard for flow cytometry and ELISA analysis of mouse serum samples. The LEV76 serum originates from an earlier pilot study in which C57BL/6 mice were vaccinated against MelARV Env and showed protection from B16F10-GP lung metastases. Thus, the antibody response in this serum corresponded to a level that is potentially able to protect from tumor challenge and therefore served as a reference value for a successful antibody response. In addition, using the LEV76 control serum as a standard enabled comparison between different experiments.

Statistical Analyses

All statistical analyses were performed using GraphPad Prism software (v5.03). Groups were compared using two-tailed, unpaired Mann-Whitney tests. Significances are indicated by asterisks: (P≤0.05);  (P≤0.01); * (P≤0.001). When comparing different groups of vaccinated mice, results are shown as a mean of each group with standard error of mean (SEM).

The Kaplan-Meier estimator was used to compare mice survival curves. This test measures the fraction of surviving subjects over a period of time after a given treatment. The significant results were shown with asterisks (*), with * (P≤0.05);  (P≤0.01); * (P≤0.001).

To assess correlations between the responses, Spearman correlation was used followed by adjustment of p-values by the Holm-Sidak method.

Example 1

Mutation in the Vaccine-Encoded Immuno-Suppressive Domain (ISD)

As a first strategy of improvement two point mutations were introduced in the sequence of MelARV Env to inactive the immuno-suppressive domain (ISD) (FIG. 3). These specific mutations were tested and analyzed before by Schlecht-Louf et al. for the murine leukemia virus (Schlecht-Louf, G., et al., *Retroviral infection in vivo requires an immune escape virulence factor encrypted in the envelope protein of oncoretroviruses*. Proc Natl Acad Sci USA, 2010. 107(8): p. 3782-7). The virus encoding for this modified version of MelARV Env is called Ad5-MelARV-ISD.

Effect of Ad5-MelARV-ISD on Antibody Responses in CD1 Mice

Outbred CD1 mice were primed with DNA-MelARV or DNA-MelARV-ISD and were subsequently boosted with either AD5-MelARV or Ad5-MelARV-ISD according to Vaccination timeline IV. Four weeks after adenovirus vaccination, blood samples were collected and analyzed by ELISA.

Figure 7A:
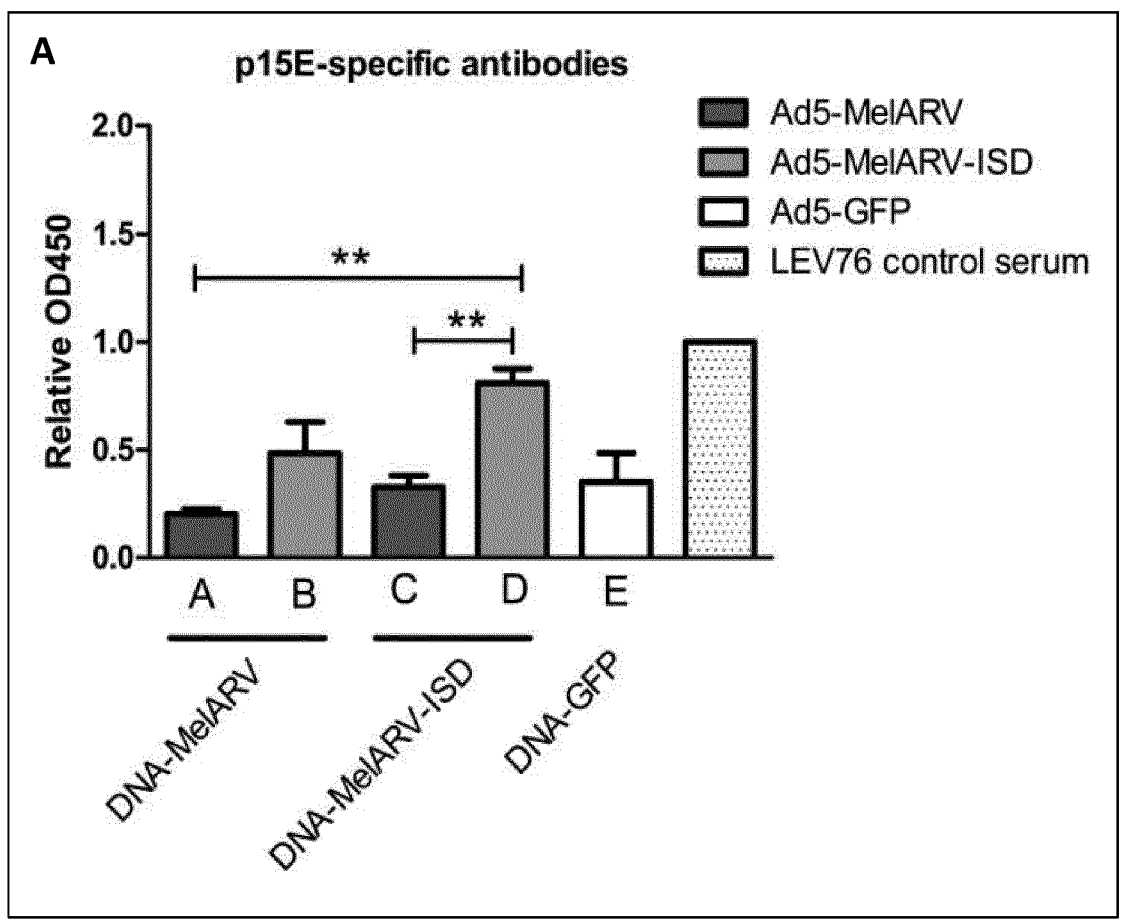
FIG. 7: Antibody responses induced by Ad5-MelARV-ISD in CD1 mice. (A) p15E-specific antibodies in the serum of vaccinated CD1 mice (Vaccination timeline IV). Mice were vaccinated first with DNA encoding for MelARV, MelARV-ISD or GFP (described under the graph) followed by different Ad5 boost (leg ELISA plates with Ad5 particles. Serum from each mouse was tested in a 1:2 serial dilution to obtain the antibody-titer. Cutoff value for a positive result was 4 times the background OD450. The bars show the mean titer of each group with SEM. Groups contained n=5 mice. Asterisks indicate significant difference between the groups, with * (P≤0.05);  (P≤0.01); * (P≤0.001).

As shown in FIG. 7A, p15E-specific antibodies were increased in Ad5-MelARV-ISD vaccinated mice. Especially the combination of DNA-MelARV-ISD and Ad5-MelARV-ISD (bar D) yielded high antibody responses that were comparable to the LEV76 control serum.

Figure 7B:
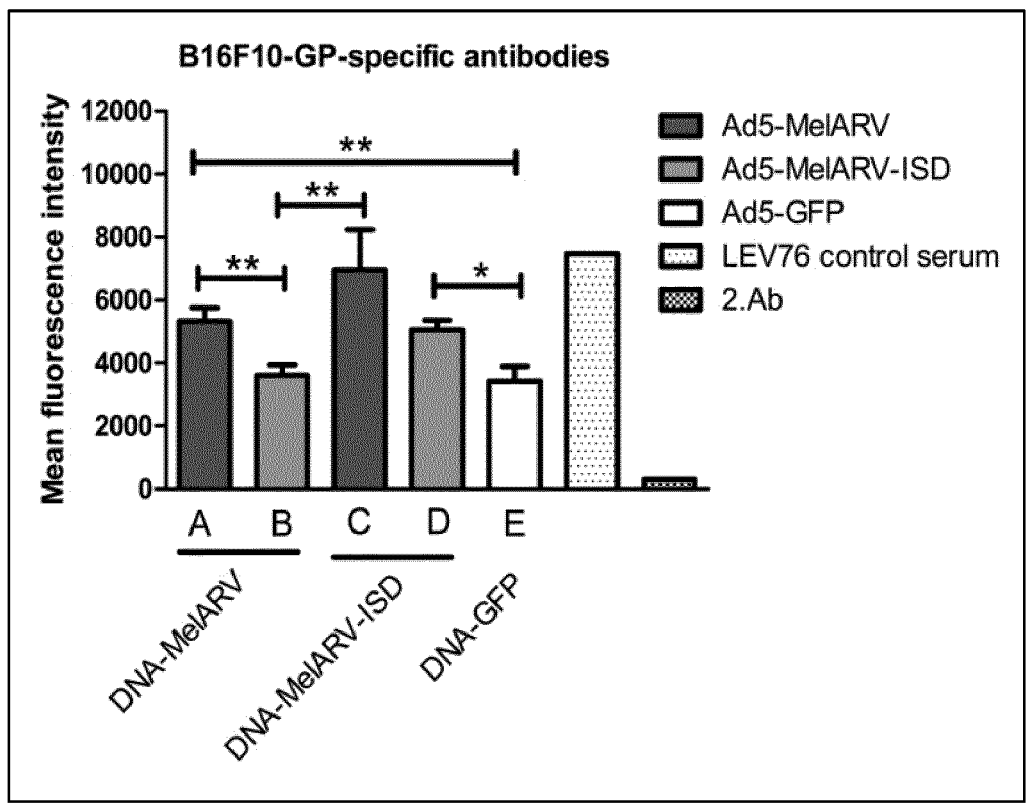

In addition, vaccination with Ad5-MelARV (bars A and C) and Ad5-MelARV-ISD (bars B and D) increased the level of tumor-cell specific antibodies (FIG. 7B) compared to the GFP control (bar E). However, Ad5-MelARV-ISD induced significantly lower levels of tumor-binding antibodies than Ad5-MelARV (bars A vs B; also bars C vs D but not significantly).

Both p15E- and B16F10-GP-binding antibody levels suggested that priming with DNA-MelARV-ISD generally increased antibody responses compared to the DNA-MelARV primed mice, although these results were not significant.

Example 2

Effect of Ad5-MelARV-ISD on Antibody Responses and Metastases in C57BL/6 Mice

Figure 8A:
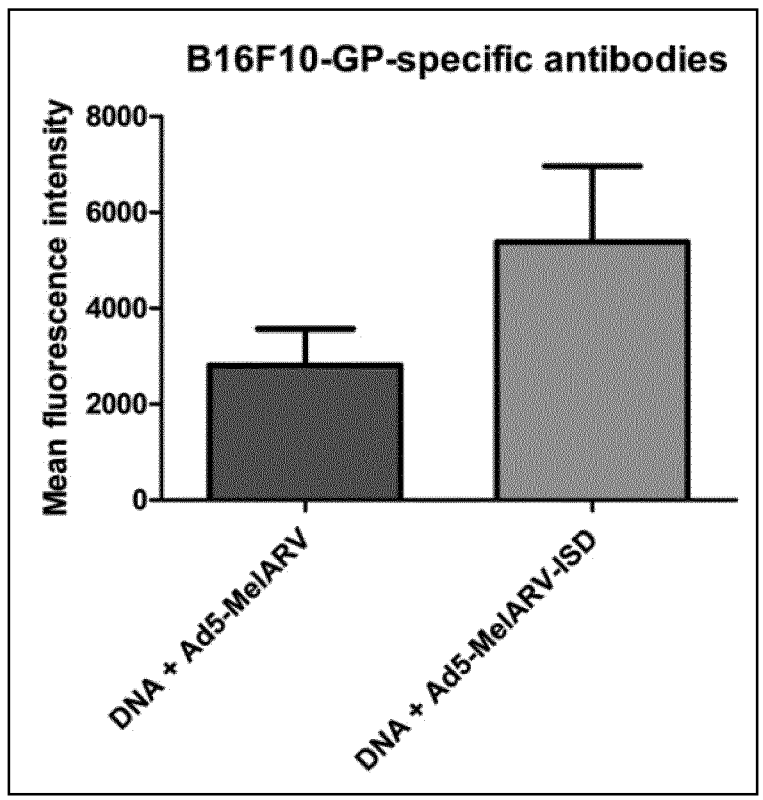
Figure 8B:
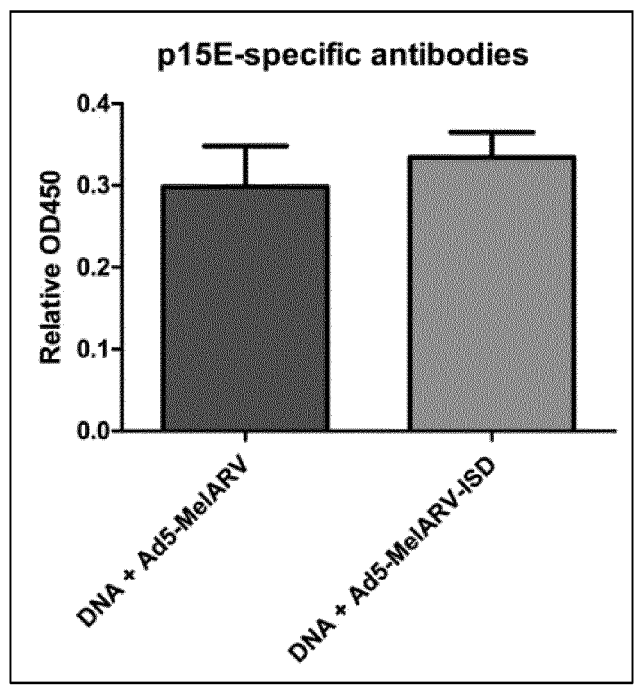
Figure 8C:
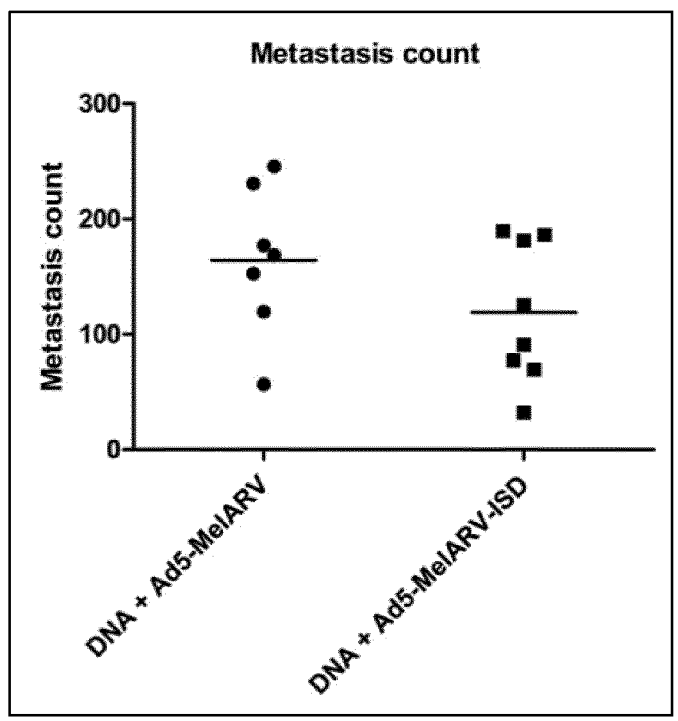

C57BL/6 mice were vaccinated and challenged according to Vaccination timeline III. Mice received either DNA-MelARV or DNA-MelARV-ISD followed by the respective adenovirus. Analysis of antibody responses revealed that MelARV-ISD slightly increased the level of B16F10-GP cell-specific antibodies (FIG. 8A). The increase, however, was not significant and barely above background of the PBS vaccinated mice. As shown in FIG. 8B no effect on antibodies specific for p15E was observed. Corresponding to the tumor cell-binding antibodies, metastases were slightly reduced in MelARV-ISD vaccinated mice but without a significant difference (FIG. 8C)

Example 3

Effect of Ad5-MelARV-ISD on T Cell Responses in Balb/C Mice

Figure 9:
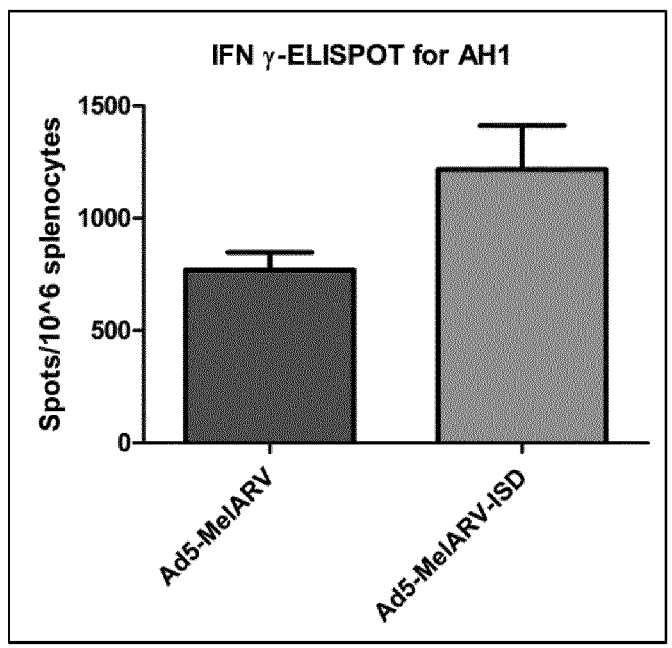
Figure 10A:
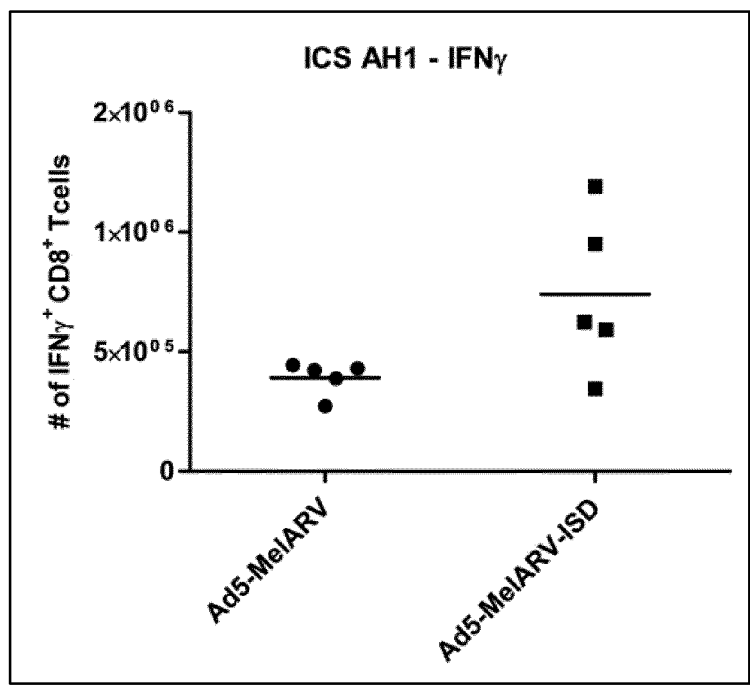
Figure 10B:
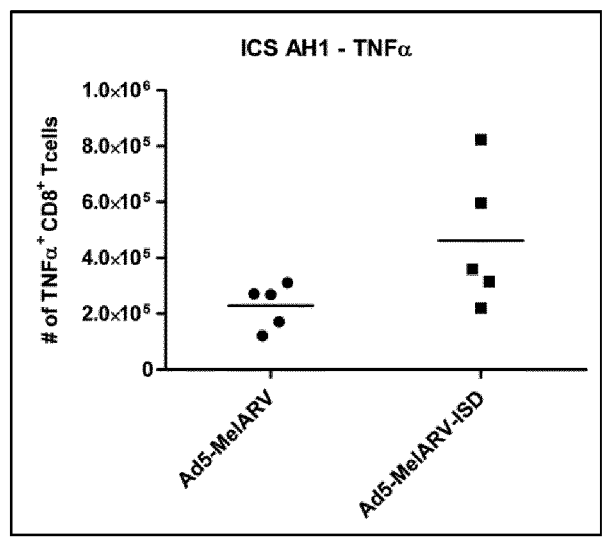
Figure 10C:
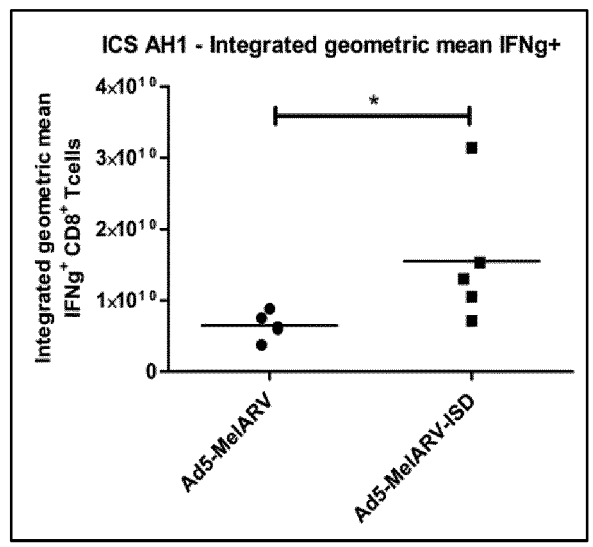
Figure 10D:
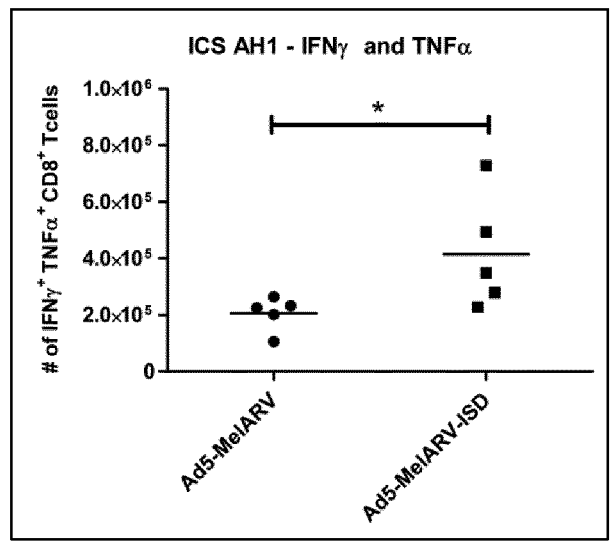
Figure 11:
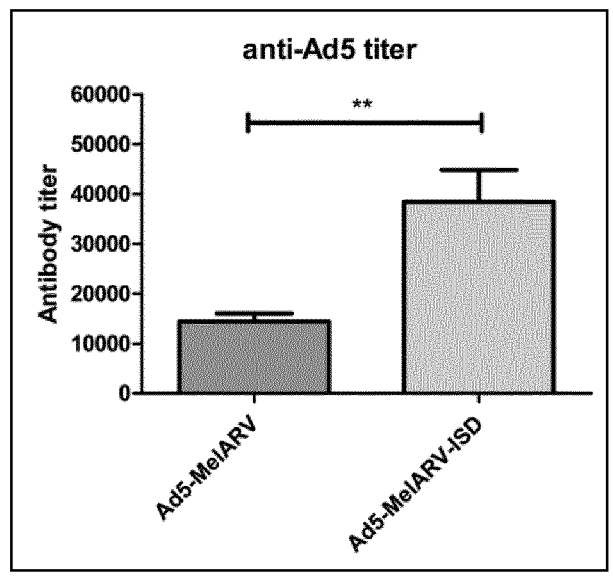

In addition to antibody responses, the effect of Ad5-MelARV-ISD on priming and activation of T cells was analyzed. Both ELISPOT (FIG. 9) and ICS (FIG. 10) showed increased levels of AH1-specific T cells in Ad5-MelARV-ISD vaccinated mice compared to Ad5-MelARV. As observed by ICS, double positive IFNγ$^+$ TNFα$^+$ CD8$^+$ T cells were significantly increased in Ad5-MelARV-ISD vaccinated mice compared to the native form. Also the integrated geometric mean (IGM) of IFNγ$^+$ cells shows a significant difference to the native Ad5-MelARV. The IGM combines the number of positive cells with the mean fluorescence intensity and thus also consider the quality of activated immune cells. The IGM of TNFα was still not significant (data not shown).

Example 4

Effect of Ad5-MelARV/Ad5-MelARV-ISD on Immunosuppression

In order to analyze the mechanisms behind the increased immune responses of Ad5-MelARV-ISD, immunosuppression by the vaccine was analyzed. The same mice sera as in FIG. 7 of Ad5-MelARV or Ad5-MelARV-ISD vaccinated mice were analyzed for immune responses against the viral vector Ad5 by ELISA. The ISD-inactivated MelARV Env vaccine (Ad5-MelARV-ISD) showed a significantly increased titer of Ad5-binding antibodies compared to the native version of MelARV Env (Ad5-MelARV with functional ISD).

Example 5

Displaying Antigens on the Capsid Protein pIX of the Adenoviral Vector

With the attempt to increase protective antibody responses, p15E was coupled to the adenoviral capsid protein pIX on the previously tested adenoviral vaccines. The different constructs that were tested are shown in FIG. 12. Either the native p15E (excluding the transmembrane subunit and cytoplasmic tail) was added to pIX (1) or alternatively an ISD-mutated version (2). Additionally, variants of p15E truncated to the ISD were tested, either displaying an additional cysteine (3) or not (4). The core of the viral vector was matched to the displayed p15E: Ad5-MelARV for pIX-p15E, pIX-p15E-trunc-wC and pIX-p15E-trunc-w/oC, and Ad5-MelARV-ISD for pIX-p15E-ISD.

Characterization of Ad5 Vectors Displaying p15E on the Capsid Protein pIX

New pIX plasmid-constructs (pcDNA3-pIX-Taglinker-xxx, with xxx=p15E antigen) were tested for the correct expression of recombinant pIX by transfecting HEK293 cells. Lysates of transfected cells were analyzed by western blotting using an anti-pIX antibody FIG. 13A. All four constructs showed expression of recombinant pIX with the expected lower bands for truncated p15E versions (Line 3 and 4). GFP, coupled to pIX, was used as a positive control with a higher band around 50 kDa. To validate integration of the recombinant pIX into the viral vector, purified viruses were analyzed by western blotting using an anti-pIX antibody FIG. 13B. Next to the native pIX band (around 10 kDa) all constructs showed expression of recombinant pIX. The negative control of an unmodified Ad5 (Ø) exhibited only the native pIX band. Band intensities were quantified using the ImageJ software (version 1.51n) and percentages of recombinant pIX are shown in Table 8.

TABLE 8

Integration efficiency of recombinant pIX into the Ad5 vector. Recombinant Ad5 viruses displaying a protein on the viral pIX where analyzed for integration efficiency of the recombinant pIX into the viral vector. Viruses were analyzed by western blotting (FIG. 13) and band intensities were quantified. The table shows the percent recombinant pIX of the total pIX in the viral particle.

| Virus | % recombinant pIX of total pIX |
|---|---|
| Ø | 0% |
| Ad5-MelARV_pIX-p15E | 32% |
| Ad5-MelARV-ISD_pIX-p15E-ISD | 29% |
| Ad5-MelARV_pIX-p15E-trunc-wC | 35% |
| Ad5-MelARV_pIX-p15E-trunc-w/oC | 35% |

Example 6

Analysis of Antibody Responses Induced by pIX-Modified Viruses in CD1 Mice

Figure 14A:
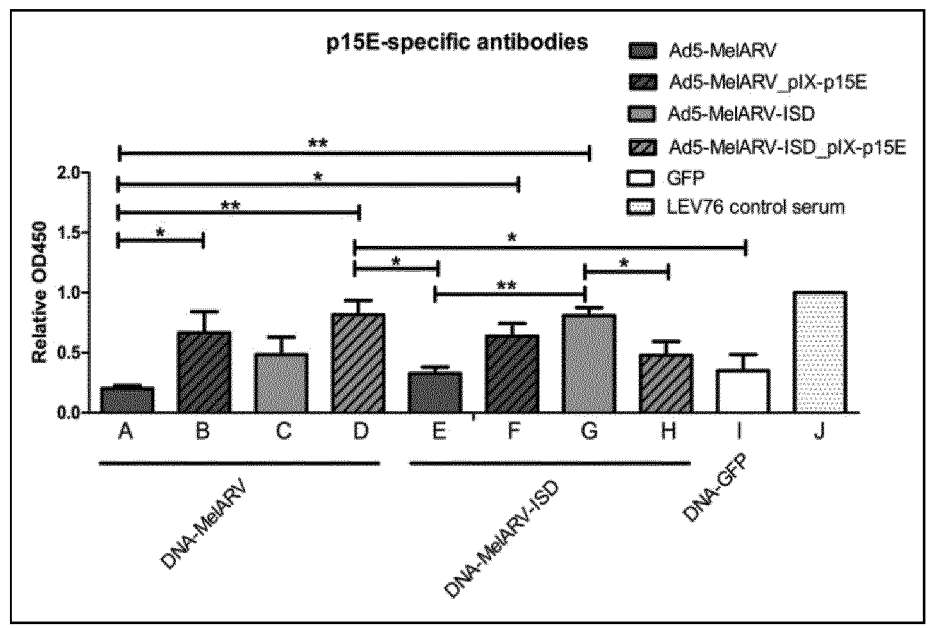
FIG. 14: Antibody responses in Ad5-pIX vaccinated CD1 mice. (A) pIX modified Ad5 vaccines (striped bars) were tested in CD1 mice (Vaccination timeline IV) and were compared to their unmodified counterparts (plain bars). Adenoviruses (Ad5-MelARV or Ad5-MelARV-ISD displaying native or recombinant pIX) were tested on the foundation of DNA prime-vaccinations, either with DNA-MelARV or DNA-MelARV-ISD. GFP-vaccinated mice served as a negative control. Binding of antibodies to a peptide of the MelARV Env transmembrane subunit p15E were assessed at 450 nm and were normalized to the absorbance of the standard LEV76 control serum. (B) The same serum samples as in (A) were analyzed for binding to B16F10-GP cancer cells. Binding-antibodies were detected with an APC-coupled secondary antibody against mouse IgG using flow cytometry and were quantified by mean fluorescence intensity. LEV76 control serum and secondary antibody only (2.Ab only) served as positive and negative controls, respectively. Bars show the mean of each group (n=5) with SEM. Asterisks indicate significant difference between the groups, with * (P≤0.05);  (P≤0.01); * (P≤0.001).
Figure 14B:
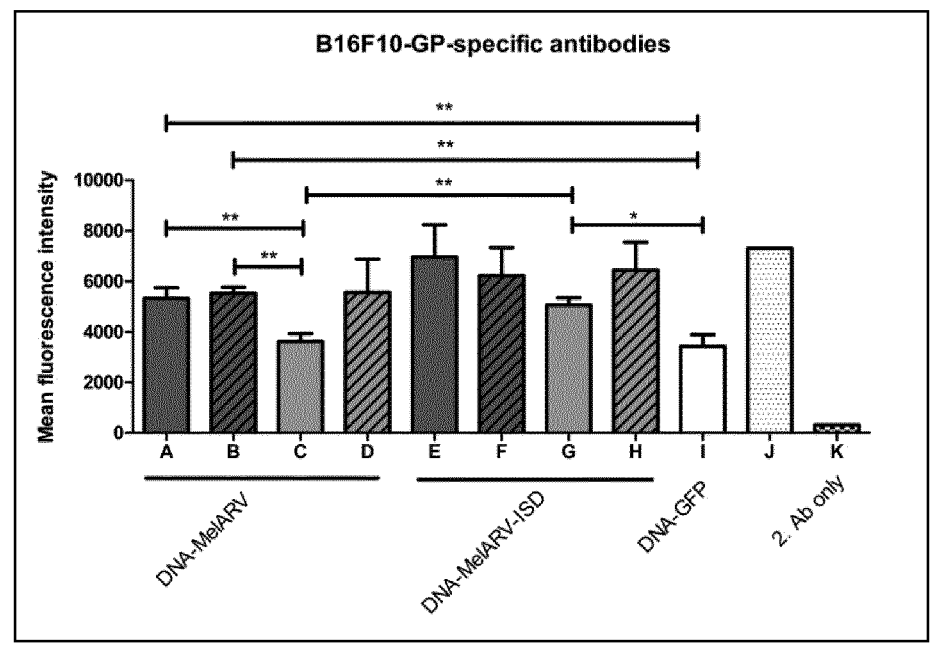
Figure 15:
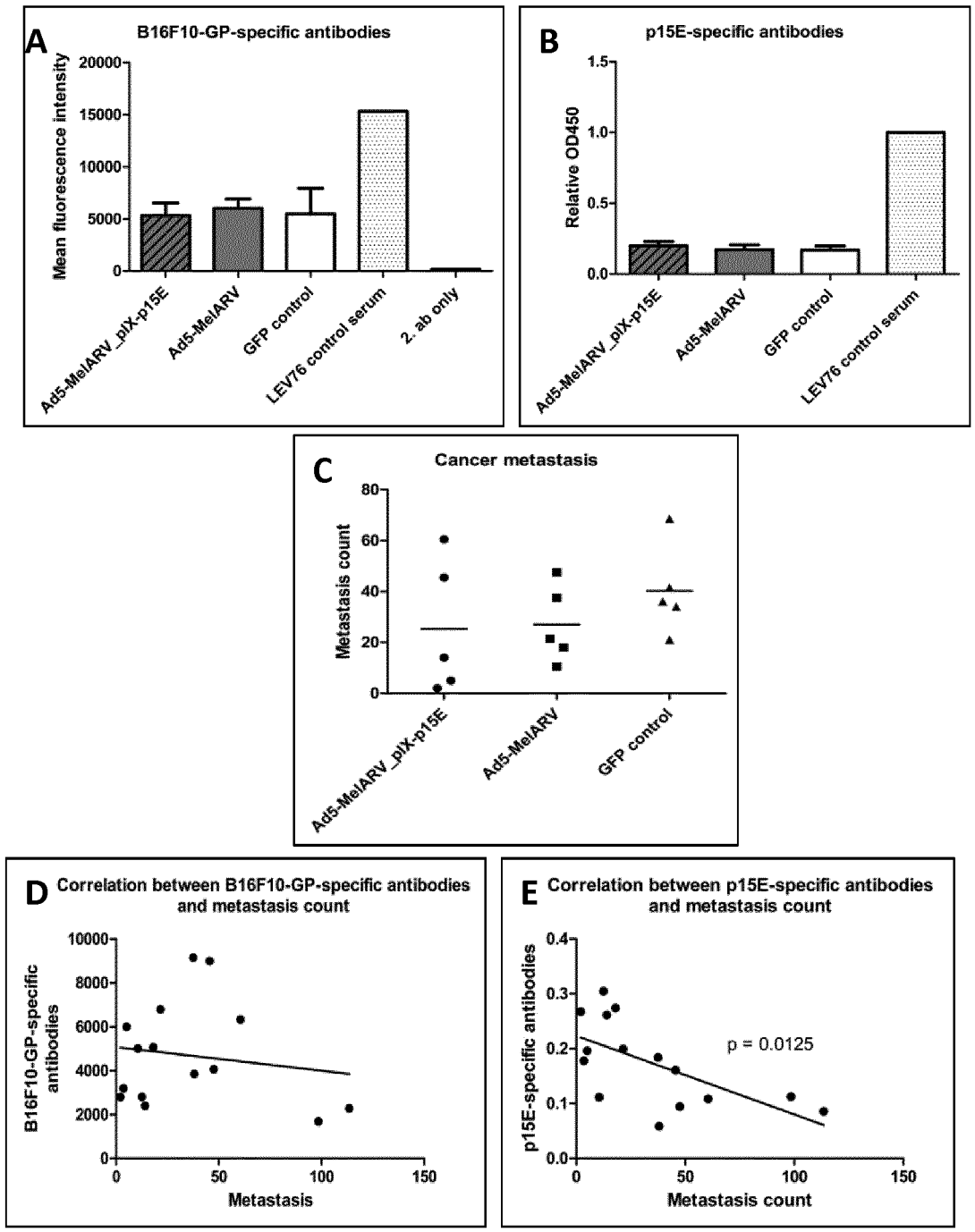
FIG. 15: Antibody responses and metastatic count in Ad5-MelARV pIX-p15E vaccinated C57BL/6 mice. Mice were vaccinated with Ad5-MelARV_pIX-p15E or the native version of this virus (Ad5-MelARV) according to Vaccination timeline V. GFP vaccinated mice served as a negative control. (A) Antibody responses against B16F10-GP tumor cells in serum of vaccinated mice were analyzed by flow cytometry. LEV76 control serum was included as a positive control. Tumor cells incubated with only the secondary antibody (2.Ab only) served as a negative control. (B) p15E-specific antibody responses were analyzed by ELISA. The measured absorbance at 450 nm was normalized to the LEV76 control serum. Each group in (A) and (B) contained n=5 mice. The shown values are the mean of each group with SEM. (C) Number of tumor metastases in vaccinated mice upon challenge with B16F10-GP cells. The horizontal line indicates the mean of each group. (D) Correlation between B16F10-GP-specific antibodies and the metastatic count. (E) Correlation of p15E-specific antibodies and the metastatic count. The negative control (GFP control) was not included in the calculation of correlation.
Figure 17:
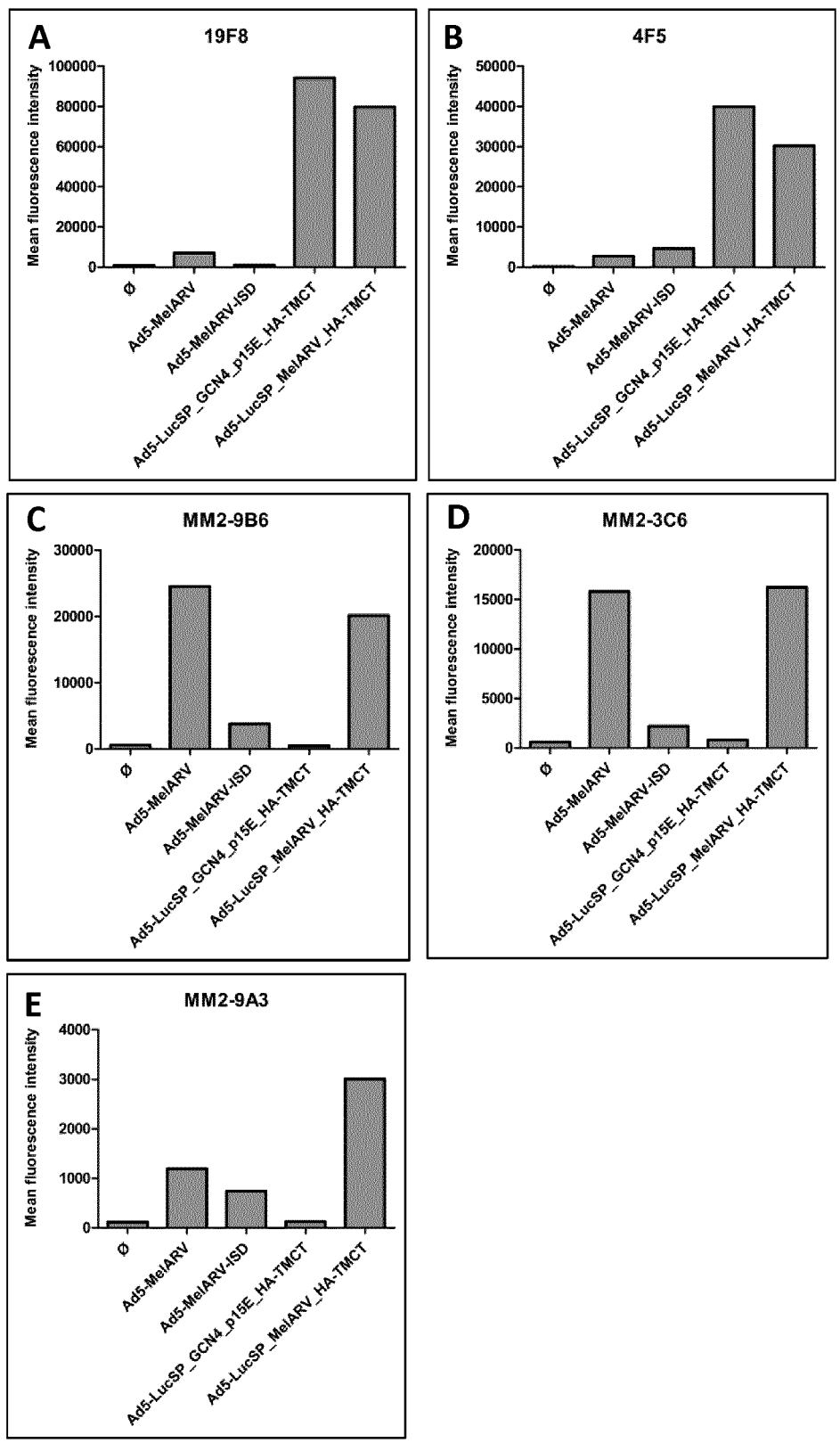
FIG. 17: Expression of MelARV Env on cells upon infection with recombinant Ad5 encoding chimeric MelARV Env proteins. Vaccine viruses with modified MelARV Env sequences (Ad5-LucSP_MelARV_Ha-TMCT and Ad5-LucSP_GCN4_p15E_Ha-TMCT) were tested for expression of the target protein on infected Vero cells. To compare results, Ad5-MelARV and Ad5-MelARV-ISD were included as well. Vero cells were infected with the modified viruses and target protein expression on cells was analyzed with diverse antibodies against MelARV Env: (A) 19F8 (anti-p15E, targeting ISD), (B) 4F5 (anti-p15E), (C) MM2-9B6 (anti-gp70), (D) MM2-3C6 (anti-gp70), (E) MM2-9A3 (anti-gp70). Binding of antibodies to infected cells was detected with respective fluorescent-coupled secondary antibodies by flow cytometry. Bars (with n=1) represent the mean fluorescence intensity elicited by the fluorescent-conjugated antibodies.
Figure 18E:
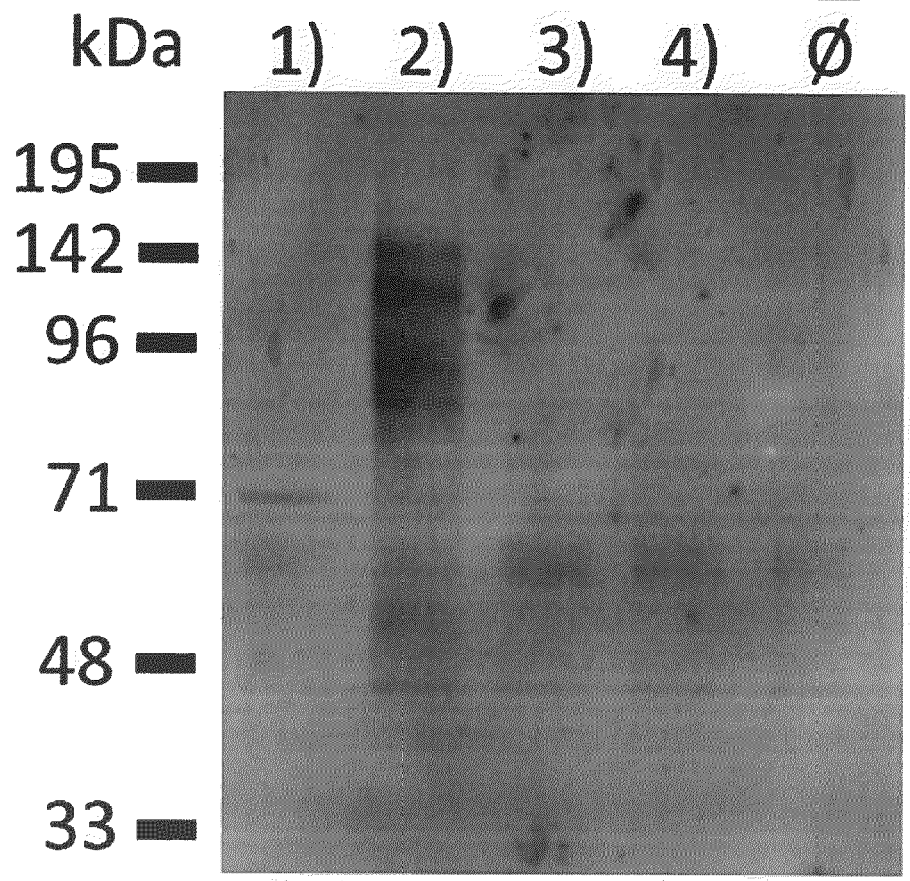
FIG. 18: Analysis of target protein expression and VLP release in cells infected with Ad5 encoding chimeric MelARV Env (western blotting): Vero cells were infected with the modified viruses. Cell lysates and released VLPs were analyzed for target protein expression by western blotting with diverse antibodies: (A) anti-p2A (MelARV Gag), (B) 4F5 (anti-p15E), (C) MM2-9B6 (anti-gp70). Additionally supernatant of infected cells was analyzed by western blotting for secretion of p15E (4F5) (D) and gp70 (MM2-9B6) (E). Line 1) Ad5-MelARV, Line 2) Ad5-MelARV-ISD, Line 3) Ad5-LucSP_GCN4_p15E_Ha-TMCT, Line 4) Ad5-LucSP_MelARV_Ha-TMCT, Line Ø negative control virus. The expected band sizes are listed in Table 6.
Figure 19:
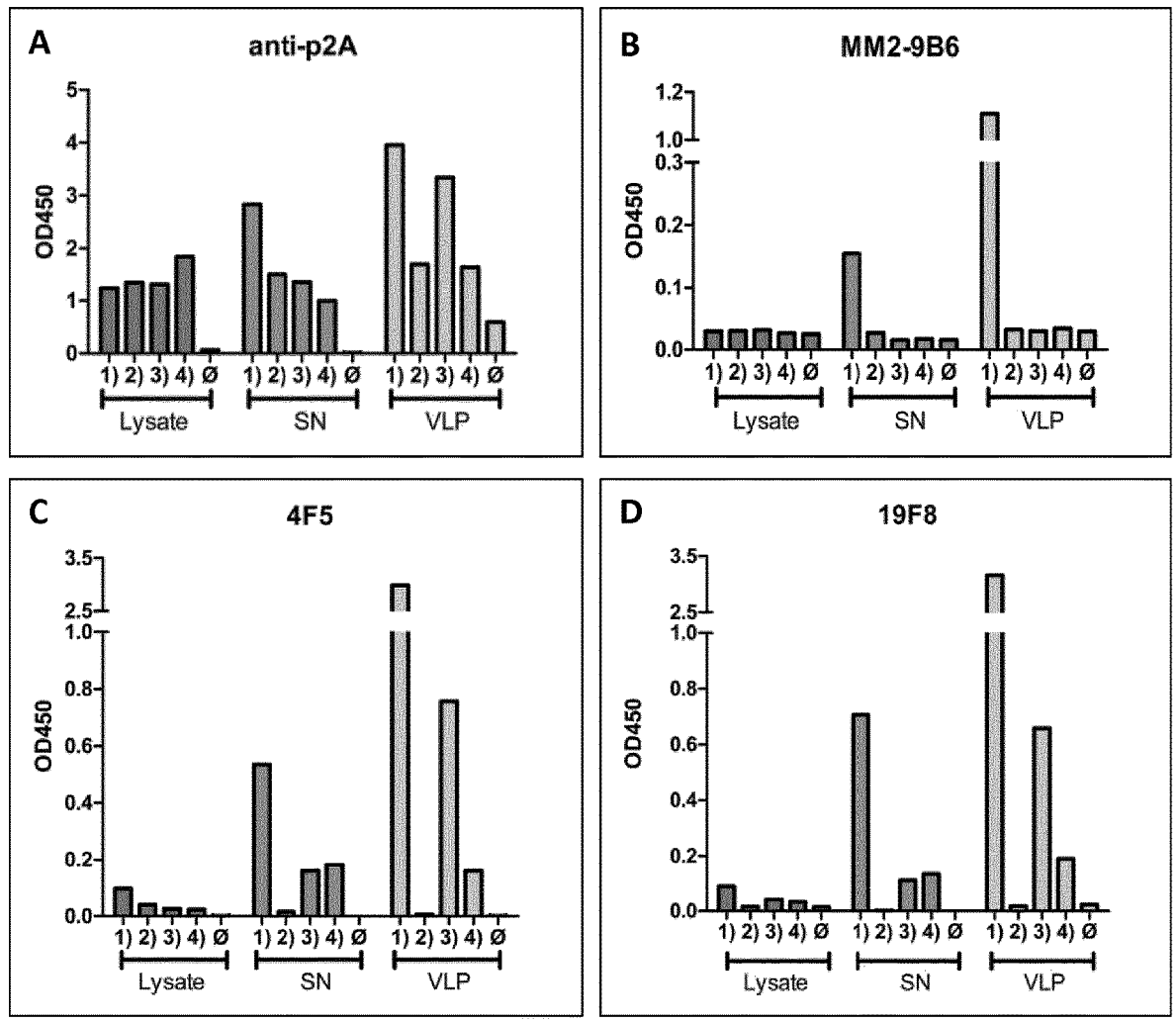
FIG. 19: Analysis of target protein expression and VLP release in cells infected with Ad5 encoding chimeric MelARV Env (ELISA): Vero cells were infected with the prototype and modified viruses: Line 1) Ad5-MelARV, Line 2) Ad5-MelARV-ISD, Line 3) Ad5-LucSP_GCN4_p15E_Ha-TMCT, Line 4) Ad5-LucSP_MelARV_Ha-TMCT, Line Ø negative control virus. ELISA plates were coated with cell lysate, supernatant (SN) or purified VLPs from infected Vero cells. The presence of MelARV Env proteins and Gag proteins was detected by binding of primary antibodies (anti-p2A, MM2-9B6, 4F5 and 19F8). (A) anti-p2A antibodies showed expression of Gag. (B) MM2-9B6 binding visualized expression of the MelARV Env surface subunit gp70. (C) (D) 4F5 and 19F8 (ISD-binding) bound to the transmembrane subunit p15E.

CD1 mice were vaccinated according to vaccination timeline IV with a DNA prime (DNA-MelARV or DNA-MelARV-ISD) followed by adenovirus boost (normal virus vs. pIX-modifications). Blood serum was analyzed by ELISA for p15E-specific antibodies FIG. 14A. Since the p15E peptide sequence used for ELISA was not included in the truncated versions of pIX modification, only Ad5-MelARV_pIX-p15E and Ad5-MelARV-ISD_pIX-p15E-ISD could be evaluated in this setting. In most cases display of p15E on pIX increased the level of p15E-specific antibodies (A vs. B; C vs. D; E vs. F). However, in these comparisons the only significant difference was observed for DNA-MelARV+Ad5-MelARV (A vs. B). In the case of DNA-MelARV-ISD+Ad5-MelARV-ISD (G vs. H) the display of pIX-p15E-ISD had a worsening effect and significantly decreased antibody-responses compared to the unmodified vaccine. Additionally, binding of serum antibodies to B16F10-GP cells was analyzed (FIG. 14B). Display of the native p15E on pIX did not influence antibody responses against tumor cells. Ad5-MelARV-ISD_pIX-p15E-ISD, on the other hand, was able to restore the lack of B16F10-GP-specific antibodies, reduced due to the ISD-mutated MelARV Env (compare to FIG. 7).

Example 7

Effect of Ad5-MelARV_pIX-p15E on Antibody Responses and Metastases in C57BL/6 Mice The pIX-modified virus Ad5-MelARV_pIX-p15E was tested in a pilot study for antibody responses and protection from metastasis in C57BL/6 mice. Mice were vaccinated twice and challenged according to Vaccination timeline V. As shown in FIGS. 15A and 15B neither of the vaccines significantly increased antibody responses to B16F10-GP cells (15A) or p15E (FIG. 15B). Also, the number of metastases was not significantly decreased by vaccination (FIG. 15C). However, while no correlation was detected between tumor cell-specific antibodies and metastatic count (FIG. 15D), a significant negative correlation was observed between the level of p15E-specific antibodies and the number of metastases (FIG. 15E).

Example 8

In the attempt to improve MelARV Env presentation on VLPs regarding quantity but also quality (in a more natural conformation), functional domains were inserted in the native sequence. These modifications were applied to the full length MelARV Env but also p15E alone (FIG. 16). The modifications included a signal peptide from Gaussia luciferase (LucSP), a transmembrane domain and cytoplasmic tail from Influenza A virus Hemagglutinin H3N2 (HA-TMCT) and a trimerization sequence (GCN4) (FIG. 16). The chimeric Env or p15E proteins were co-encoded with the Gag protein of SIV.

Characterization of Vaccines Encoding Chimeric MelARV Env or p15E

The modified vaccines were not tested in mice yet but expression from adenoviruses was tested by flow cytometry in infected Vero cells (FIG. 17). The experiment did not only show expression of the proteins but also characterized some of the anti-MelARV Env antibodies regarding their target epitope. Both 19F8 (FIG. 17A) and 4F5 (FIG. 17B) showed highly increased binding to the modified versions of MelARV Env and p15E compared to the native vaccines (Ad5-MelARV and Ad5-MelARV-ISD). Since binding to Ad5-LucSP_GCN4_p15E_Ha-TMCT could be observed as well, this experiment indicates that both antibodies bind the transmembrane subunit p15E. Furthermore, no binding of 19F8 to Ad5-MelARV-ISD infected cells was observed, while a clear signal was detected for 4F5, confirming the ISD as the target epitope of 19F8. Neither of the MM2 antibodies showed binding to the p15E construct, demonstrating that all three antibodies are directed against the surface subunit gp70. MM2-9B6 (FIG. 17C) and MM2-3C6 (FIG. 17D) showed similar profiles with equally strong binding of the antibody to Ad5-MelARV and Ad5-LucSP-_MelARV_Ha-TMCT infected cells. Ad5-MelARV-ISD infected cells on the other hand showed much less antibody binding. The profile of MM2-9A3 (FIG. 17E) is similar except that Ad5-MelARV infected cells bound less antibody than Ad5-LucSP_MelARV_Ha-TMCT infected cells.

The new constructs were also tested for their ability to produce and display the target protein upon infection. Lysates of infected Vero cells and purified VLPs were analyzed by western blot (FIG. 18). Binding of anti-p2A antibody (FIG. 18A) showed bands that indicated MelARV Gag (Line 1 and 2) and SIV Gag (Line 3 and 4) expression in both the lysate and the VLPs. As shown in FIG. 18B, p15E (bound by 4F5) was only detected in the lysates of Ad5-MelARV infected cells (Line 1) with a low band around 20 kDa corresponding to p15E and a higher band of 70 kD, showing full length Env (gp70+p15E). The full length Env was also detectable for Ad5-MelARV-ISD (Line 2), whereas no single p15E band was visible. Only in Ad5-MelARV induced VLPs, p15E and the full length Env were detectable. Other weak bands were present for the different constructs, but it is not clear to which protein they correspond to.

A similar result as for 4F5 has been shown in FIG. 18C in which gp70 was visualized by MM2-9B6. Only Ad5-MelARV induced VLPs (Line 1) displayed MM2-9B6-detected gp70.

In addition to cell lysates, supernatants of infected cells were analyzed to investigate whether proteins are secreted (FIG. 18D,E). p15E (bound by 4F5) in the supernatant (FIG. 18D) was only detectable for Ad5-MelARV (Line 1) and might be due to VLPs in the supernatant. MM2-9B6 (Figure E), on the other hand, revealed that Ad5-MelARV-ISD infected cells (Line 2) released great amounts of gp70 which were detected as conjugates of different sizes (FIG. 18E). In contrast, Ad5-MelARV induced the release of a minor amount of gp70 (Line 1).

Neither of the new modified MelARV Env proteins (Line 3 and 4) showed expression of the protein in lysate, supernatant or purified VLPs despite the detectable expression on the cell surface under non-denaturing conditions.

Due to the absence of bands for the new constructs in western blot analyses, the assumption was that the synthesized protein was not able to bind to the nitrocellulose membrane. Therefore, an ELISA analysis was performed using an ELISA plate, coated with cell lysate, supernatant or VLPs (FIG. 19). As expected, Gag protein, detected by anti-p2A, was present in all samples (FIG. 19A). In contrast MelARV Env gp70 (bound by MM2-9B6) was only detected in VLPs of AD5-MelARV infected cells (Line 1) but not in cells infected with the modified MelARV viruses (FIG. 19B). A similar result was observed for p15E expression (bound by 4F5 and 19F8) (FIG. 19C,D). Ad5-MelARV (Line 1) induced high expression of the transmembrane subunit, which was successfully integrated into VLPs. For Ad5-MelARV-ISD (Line 2), on the other hand, almost no protein was detected in either of the samples. The modified vaccines (Line 3 and 4) induced the expression and VLP integration of p15E to some degree but at a much lower level than the native MelARV Env vaccine (FIG. 19C,D).

Example 9

Comparison

The following constructs were used to immunize balb/c mice: HIV B gag P2A ConB gp140 G/CD (WT), HIV B gag P2A ConB gp140 G/CD ISD#4 (Y75G), HIV B gag P2A ConB gp140 G/CD ISD#19 (L70Q), HIV B gag P2A ConB gp140 G/CD G19Rdb (G83K, S88F). Antibody responses were analyzed 4 weeks (d.28—FIG. 20A) and 7 weeks (d. 49—FIG. 20B) post immunization against HIV ConB gp140

WT protein. A separate group of mice immunized with both IiGP-P2A-IFNalpha4 and HIV B gag P2A ConB gp140 G/CD (WT) (420B) serve as a control group for type I interferon induced responses.

Figure 20:
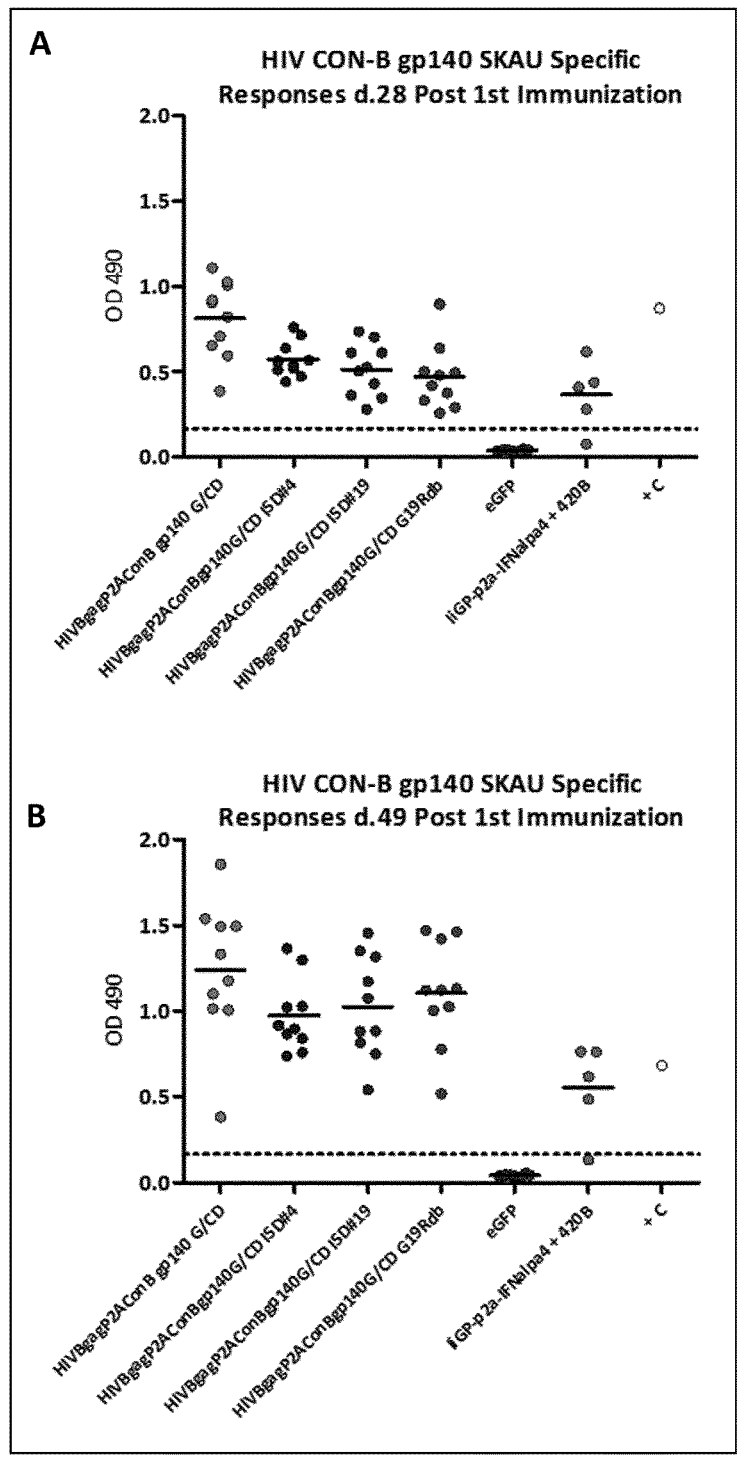
FIG. 20: Shows a comparison with HIV ISD-antibodies.
Figure 20:
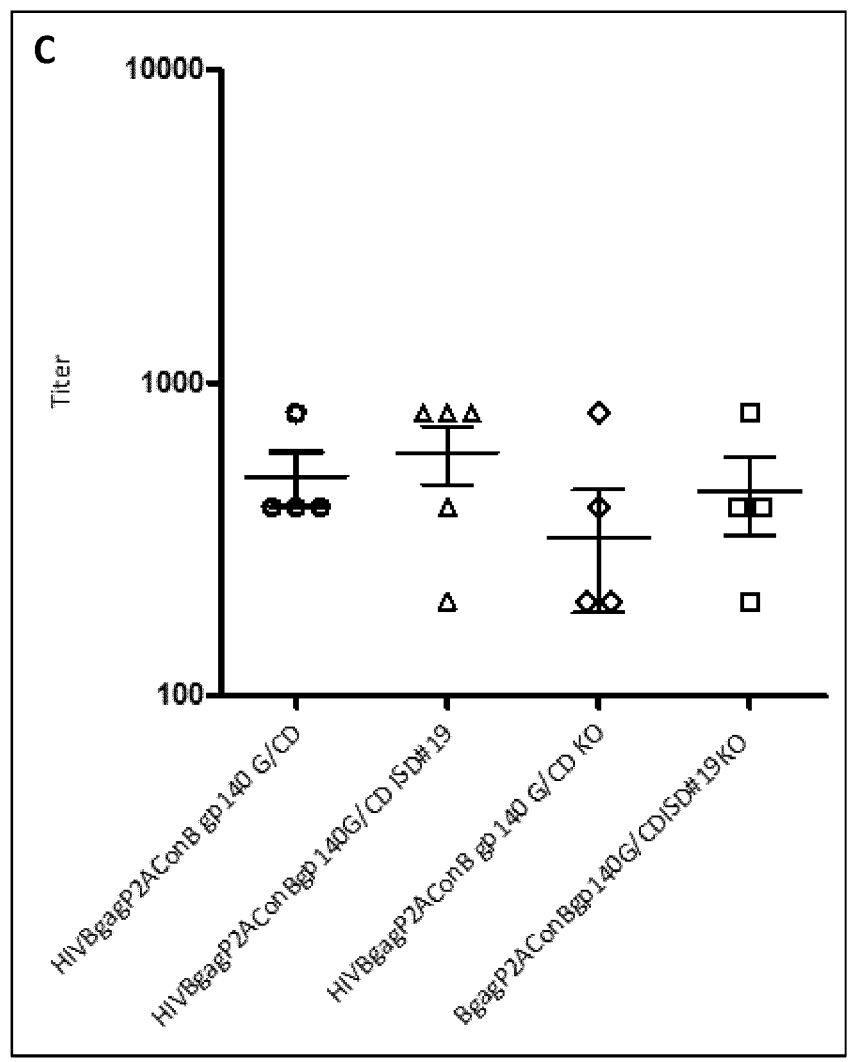
Figure 21:
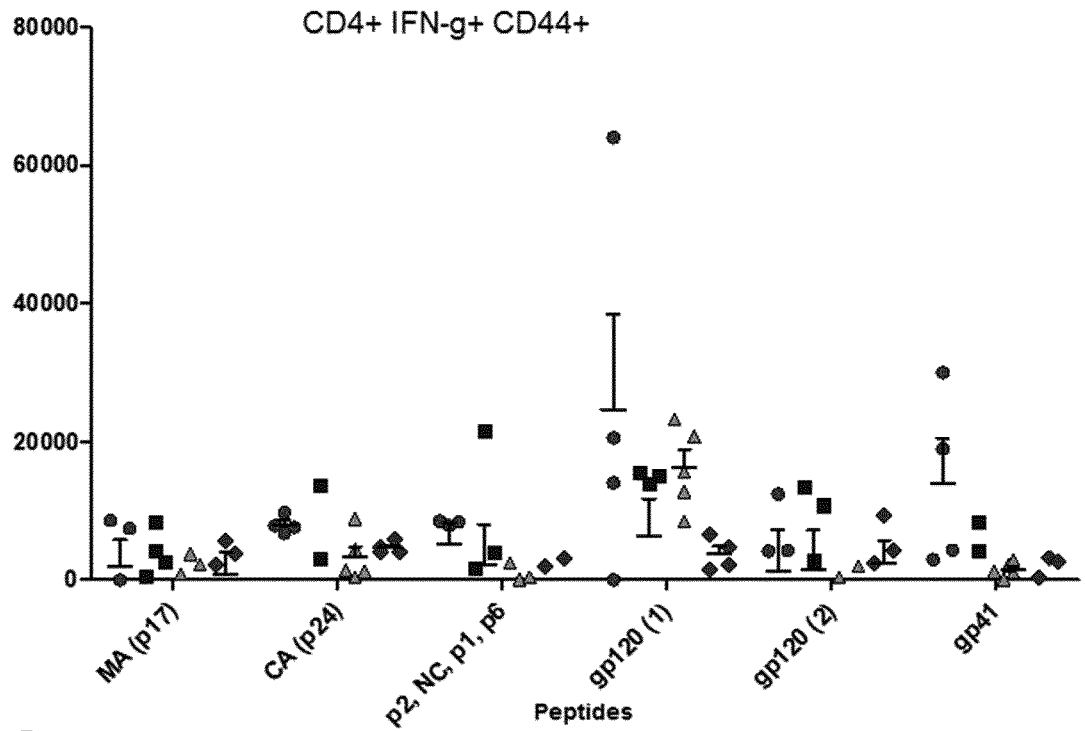
FIG. 21: Shows a comparison for HIV ISD-T cells, in which
- ● HIVBgagP2AConBgp140G/CDVSVCT
- ■ HIVBgagP2AConBgp140G/CDISD#4VSVCT
- ▲ HIVBgagP2AConBgp140G/CDISD#19VSVCT
- ♦ HIVBgagP2AConBgp140G/CDG19R(db mut)VSVCT
Figure 21:
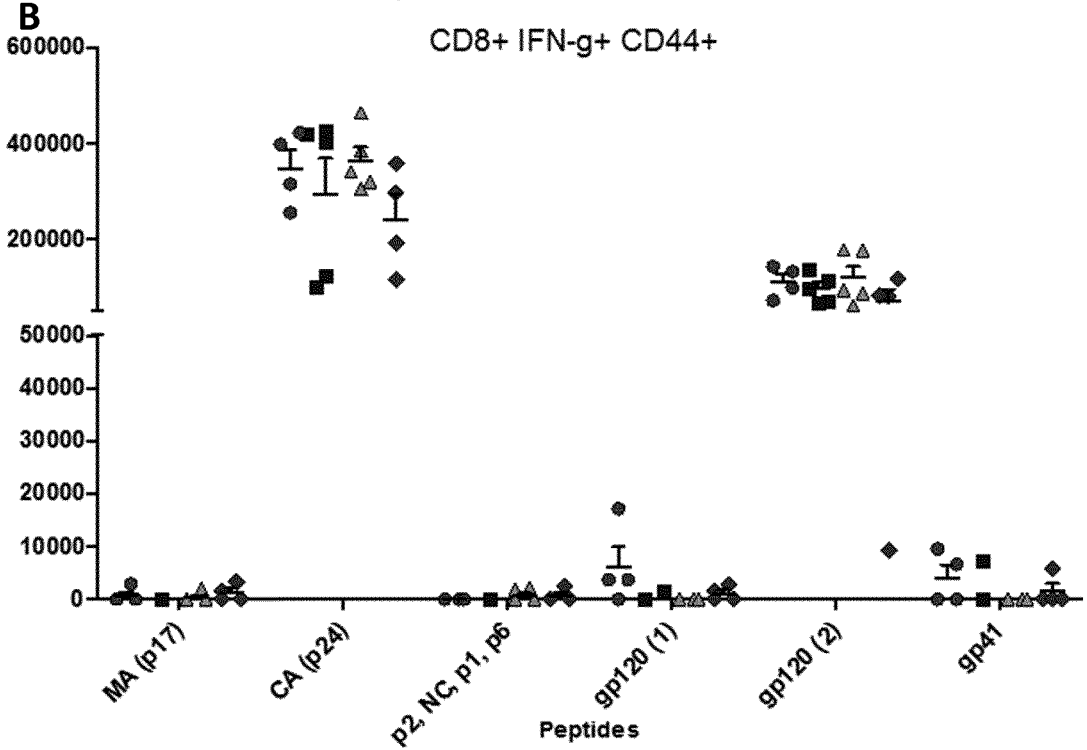
Figure 21:
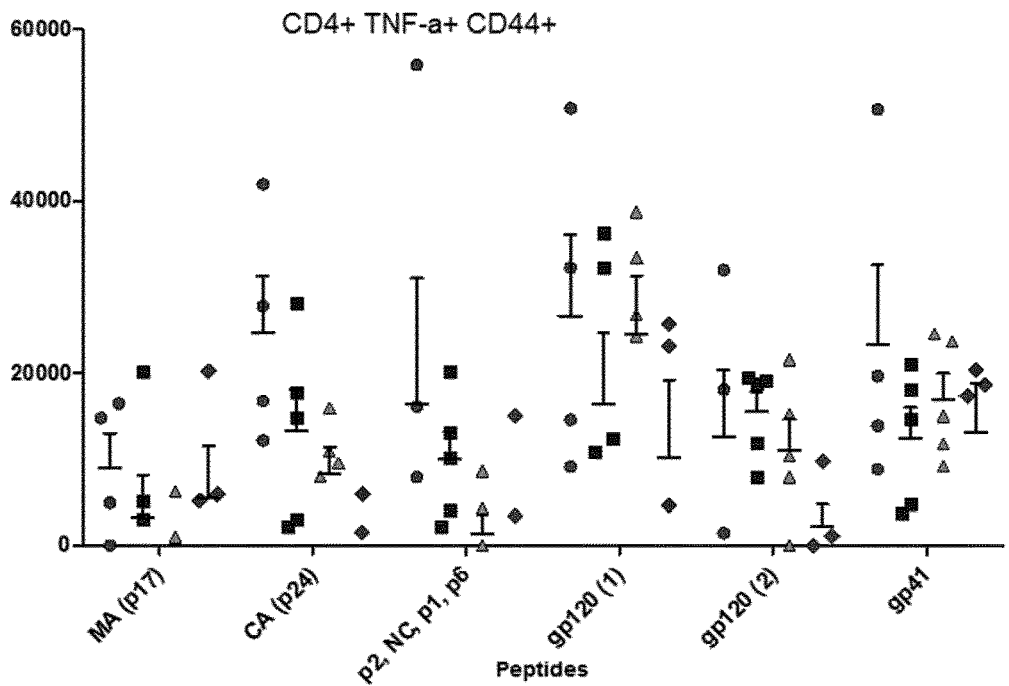
Figure 21:
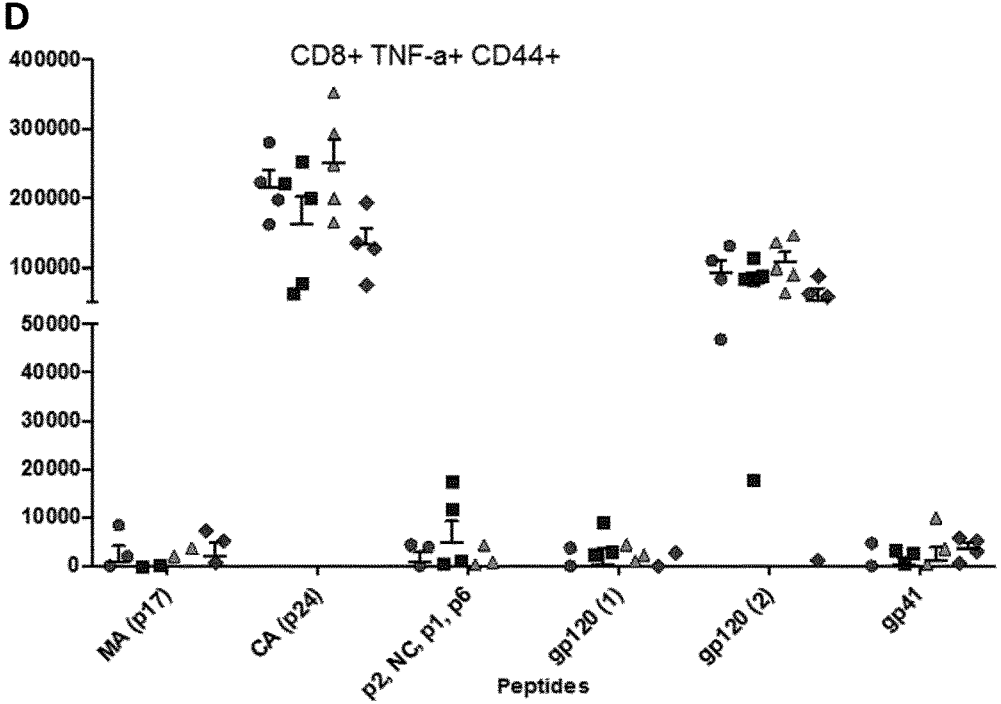

The following constructs were used to immunize c57/bl6 or c57/bl6 IFN-g KO mice: Adenovirus encoding HIV B clade gag p2A followed by the gp140 sequence of the B Glade consensus sequence (HIV B gag P2A ConB gp140 G/CD) (WT) and HIV B gag P2A ConB gp140 G/CD ISD#19 (L70Q). Antibody responses were determined 4 weeks post immunization (d. 26—FIG. 20C) against HIV ConB gp140 CF protein.

Example 10

The following constructs were used to immunize balb/c mice: HIV B gag P2A ConB gp140 G/CD (WT), HIV B gag P2A ConB gp140 G/CD ISD#4 (Y75G), HIV B gag P2A ConB gp140 G/CD ISD#19 (L70Q), HIV B gag P2A ConB gp140 G/CD G19Rdb (G83K, S88F). Four months post immunization (d.114) mice were analyzed for their T cell responses against pools of peptides covering the Gag gene (MA (p17, matrix) (peptides 1-31), CA (p24, capsid) (peptides 32-89), a single pool covering p2, NC (nucleo capsid), p1, and p6 (peptides 90-124), gp120 (1) (peptides 1-62), gp120 (2) (peptides 63-124), gp41 (peptides 125-211).

Example 11

BALB/c mice are vaccinated with either MVA expressing gag, env, gag+env, gag+envISDmut as VE-VLP or adenovirus expressing gag-env or gag+envISDmut VE-VLP and combinations hereof and peptide responses are measured towards predicted MHC binding 9 amino acids long peptides with ELISPOT or intracellular cytokine staining.

Gag-env or gag+envISDmut VEVLP, in particular in adenovirus vectors, are strongly expected to outperform previously described MVA vectors in induction of T cell responses.

Example 12

BALB/c mice are vaccinated with either MVA expressing gag, env, gag+env, gag+envISDmut as VE-VLP or adenovirus expressing gag-env or gag+envISDmut VEVLP and combinations hereof and peptide responses are measured towards peptides derived from the sequence of the extracellular portion of the transmembrane domain p15E of HERV-Kcon.

Gag-env or gag+envISDmut VEVLP vectors, are expected to outperform previously described MVA vectors in induction of T cell responses.

Example 13

Animals are challenged subcutaneously with RENCA renal carcinoma cells expressing HERVcon-gag and HERVcon-env, respectively. Animals are subsequently vaccinated with either MVA expressing gag, env, gag+env, gag+envISDmut as VE-VLP or adenovirus expressing gag-env or gag+envISDmut VEVLP and combinations hereof and growth of tumor is monitored.

Tumor control is expected to be improved using VE-VLP vaccines and the gag-env VEVLP vaccines uniquely capable of controlling tumor growth in both cell lines Example 14

Animals are challenged intravenously with RENCA renal carcinoma cells expressing HERVcon-gag and HERVcon-env respectively. Animals are subsequently vaccinated with either MVA expressing gag, env, gag+env, gag+envISDmut as VE-VLP or adenovirus expressing gag-env or gag+envISDmut VEVLP and combinations hereof and growth of tumor are monitored by vivisection and counting of metastasis 30 days post tumor challenge.

Tumor control is expected to be improved using VE-VLP vaccines and the gag-env VEVLP vaccines uniquely capable of controlling tumor growth of both cell lines Example 15

Figure 22:
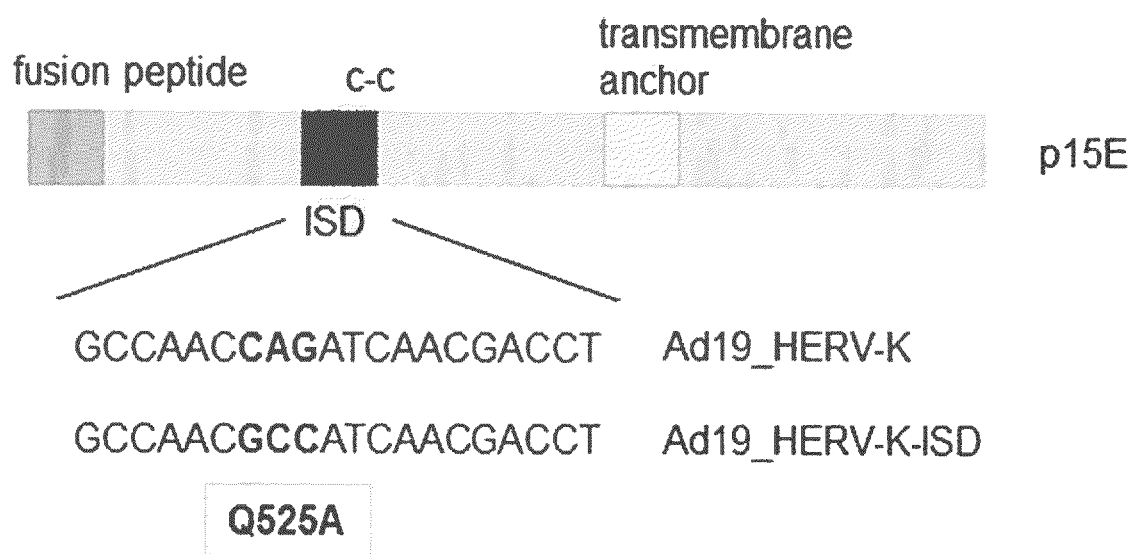
FIG. 22: Strategy followed to improve the vaccine design: point mutation at the ISD domain (p15E) of the HERV-K Env protein encoded in the vaccine. Glutamine (Q) (see "Ad19_HERV-K"; coding sequence shown in SEQ ID No.43) was mutated to alanine (A) ("HERV—K-ISD; coding sequence shown in SEQ ID No. 44) in order to inactivate the ISD domain that mediates the immunosuppressive effect. Figure modified from (Mangeney et al. 2007). Figure discloses SEQ ID NOS 43-44, respectively, in order of appearance.

With regard to translational work on the immunotherapy strategy described in the preceding examples, a human relevant version of the vaccine was designed using an adenovirus vector (Ad5/Ad19a) encoding for the consensus Human Endogenous Retrovirus Type K (HERV-K) envelope (Env) and group-specific antigen (Gag) proteins (Dewannieux, M., et al., Genome Res. 2006 December; 16(12): 1548-56), intended to lead to VLPs formation in transduced cells (Muster T, et. al., Cancer Res. 2003 Dec. 15; 63(24): 8735-41). To improve the vaccination strategy, the ISD contained in the p15E subunit of HERV-K Env protein (Morozov, V A., et al. PLoS One 2013 Aug. 7; 8(8), was inactivated by a single point mutation (see FIG. 22), the selection of which was based on Morozov, V A., et al., Retrovirology 2012 Aug. 13; 9:67, and conservation between HERV-K and HIV (van der Kuyl A C., Retrovirology 2012 Jan. 16; 9:6) (Dewannieux, M., et al., J Virol. 2005 December; 79(24):15573-7).

HERV-K Gag-p2A-EnvISDmut had the amino acid sequence (SEQ ID No. 48):

MGQTKSKIKSKYASYLSFIKILLKRGGVKVSTKNLIKLFQIIEQFCPWFP

EQGTLDLKDWKRIGKELKQAGRKGNIIPLTVWNDWAIIKAALEPFQTEED

SVSVSDAPGSCIIDCNENTRKKSQKETEGLHCEYVAEPVMAQSTQNVDYN

QLQEVIYPETLKLEGKGPELVGPSESKPRGTSPLPAGQVPVTLQPQKQVK

ENKTQPPVAYQYWPPAELQYRPPPESQYGYPGMPPAPQGRAPYPQPPTRR

LNPTAPPSRQGSELHEIIDKSRKEGDTEAWQFPVTLEPMPPGEGAQEGEP

PTVEARYKSFSIKMLKDMKEGVKQYGPNSPYMRTLLDSIAHGHRLIPYDW

EILAKSSLSPSQFLQFKTWWIDGVQEQVRRNRAANPPVNIDADQLLGIGQ

NWSTISQQALMQNEAIEQVRAICLRAWEKIQDPGSTCPSFNTVRQGSKEP

YPDFVARLQDVAQKSIADEKARKVIVELMAYENANPECQSAIKPLKGKVP

AGSDVISEYVKACDGIGGAMHKAMLMAQAITGVVLGGQVRTFGGKCYNCG

QIGHLKKNCPVLNKQNITIQATTTGREPPDLCPRCKKGKHWASQCRSKFD

KNGQPLSGNEQRGQPQAPQQTGAFPIQPFVPQGFQGQQPPLSQVFQGISQ

LPQYNNCPPPQAAVQQGSGATNFSLLKQAGDVEENPGPMNPSEMQRKAPP

RRRRHRNRAPLTHKMNKMVTSEEQMKLPSTKKAEPPTWAQLKKLTQLATK

YLENTKVTQTPESMLLAALMIVSMVVSLPMPAGAAAANYTYWAYVPFPPL

IRAVTWMDNPIEVYVNDSVWVPGPIDDRCPAKPEEEGMMINISIGYRYPP

ICLGRAPGCLMPAVQNWLVEVPTVSPISRFTYHMVSGMSLRPRVNYLQDF

SYQRSLKFRPKGKPCPKEIPKESKNTEVLVWEECVANSAVILQNNEFGTI

IDWAPRGQFYHNCSGQTQSCPSAQVSPAVDSDLTESLDKHKHKKLQSFYP

-continued

```
WEWGEKGISTPRPKIVSPVSGPEHPELWRLTVASHHIRIWSGNQTLETRD

RKPFYTVDLNSSLTVPLQSCVKPPYMLVVGNIVIKPDSQTITCENCRLLT

CIDSTFNWQHRILLVRAREGVWIPVSMDRPWEASPSVHILTEVLKGVLNR

SKRFIFTLIAVIMGLIAVTATAAVAGVALHSSVQSVNFVNDWQKNSTRLW

NSQSSIDQKLANAINDLRQTVIWMGDRLMSLEHRFQLQCDWNTSDFCITP

QIYNESEHHWDMVRRHLQGREDNLTLDISKLKEQIFEASKAHLNLVPGTE

AIAGVADGLANLNPVTWVKTIGSTTIINLILILVCLFCLLLVCRCTQQLR

RDSDHRERAMMTMAVLSKRKGGNVGKSKRDQIVTVSV*
```

These vaccines were tested for immunogenicity in BALB/c, C57BL/6 and CD1 mice and challenged with murine renal carcinoma (Renca or RLZ) cells expressing the HERV-K Env target protein in BALB/c mice, in order to study their efficiency as measured by mice survival curves. The immune responses were evaluated for their capacity of inducing cellular and humoral responses, tested for the presence of INFγ+ CD8+ T cells (by FACS analysis), as well as specific antibodies (detected by ELISA) against HERV-K Env target-protein in mice immunized with DNA/Adv-HERV-K WT/ISD vaccines and boosted with MVA Env.

The Ad19-HERV-K WT vaccine and its improved version containing an ISD mutation were tested and compared for their capacity of inducing expression of the VLPs formed by Gag_p2A_Env HERV-K Adv-encoded proteins. Pre-existing immunity in humans that lead to neutralizing antibodies (NAbs) that block the immune response can be a drawback of using Ad5 vectors. Moreover, Ad19 vectors are known for being more successful at transducing different kind of cells (Kiener R, et. al., Sci Rep. 2018 Jan. 24; 8(1):1474). Therefore, the usage of different adenoviral vectors (Ad19 vs Ad5) was also analysed and compared.

Figure 23:
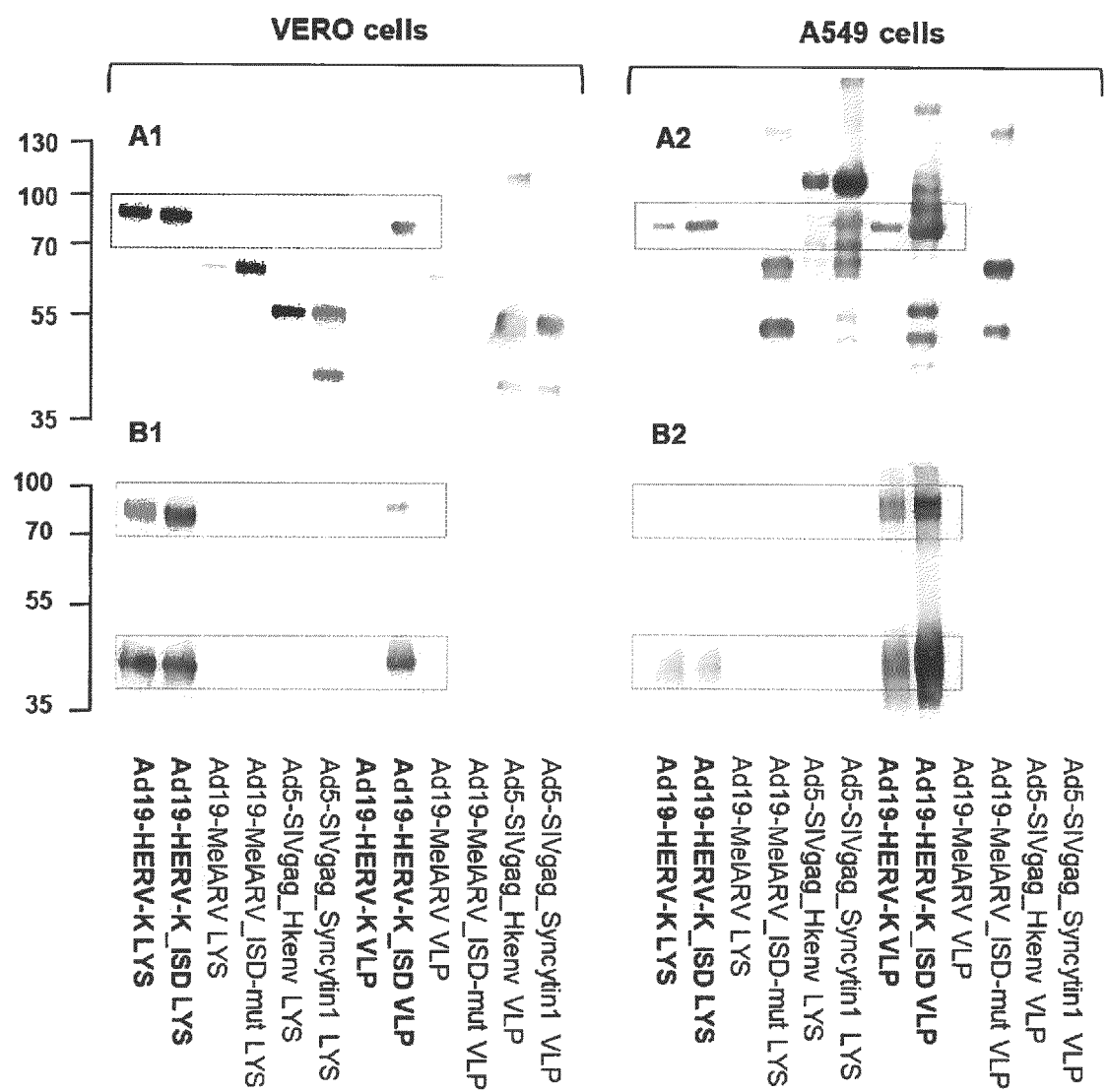
FIG. 23: Detection of HERV-K Env and Gag proteins (VLPs) from SN and cell lysate of virus transfected cells. Presence of functional Gag (A) and Env (B) proteins in the SN and cell lysate of Ad19_HERV-K WT/ISDmut transfected A549 and VERO cells is highlighted by square boxes. The molecular masses of approximately 90, 80 and 40 kDa were equivalent to HERV-K Gag, HERV-K Env full-length unprocessed precursor (with and without signal peptide), and HERV-K p15E (TM, Env) reported values of 80, 90, 80, and 42 kDa respectively as shown in the following Table (Opstelten D J, et. al., *J Virol*. 1998 August; 72(8):6537-45)

For the purpose of analysing the functionality of the novel strategy, the vaccines were analysed for induction of HERV-K Gag and Env target proteins. Therefore, VLP production and secretion was tested in VERO and A549 cell lines transfected with different virus-based vaccines containing different sequences of interest (see FIG. 23). Supernatants (SN) and cell lysates from the aforementioned transfected cell lines were tested for the presence of HERV-K Gag and Env proteins by Western Blot (WB). HERM-1811-5 and HERM-1821-5, monoclonal antibodies against p15E (TM) and gp70 (SU), were specifically used to detect HERV-K Env domains, whereas a polyclonal rabbit anti-p2A antibody was used to detect Gag protein linked to p2A. HRP-conjugated secondary antibodies were employed for detection.

WB results indicated the presence of HERV-K Gag_p2A protein, as well as HERV-K Env protein in both SN and cell lysates of Ad19_HERV-K WT/ISDmut transfected VERO and A549 cells. The higher expression of both Gag and Env proteins derived from Ad19_HERV-K ISDmut transfected cells (showed in rows 2 and 8 of FIG. 23), suggests an enhanced functionality and greater potential of the modified prototype vaccine, when compared to the Ad19_HERV-K_WT and Ad5_HERV-K_Env vaccines. Moreover, the absence of Gag and Env proteins in the SN of Ad19_HERV-K-transfected VERO cells could be explained due to the low concentration of protein obtained after VLP purification of the corresponding sample.

To further validate the expression of the HERV-K Env target protein, A549 cells were transfected with VLP-encoded adenovirus vaccines (see FIG. 24). 48 h post-infection, the cells were incubated with primary anti-HERV-K Env antibodies (HERM-1811) and subsequently labeled with a goat anti-mouse IgG APC secondary antibody with and without prior fixation and permeabilization. The intracellular and extracellular fluorescence of the bound antibodies and therefore the expression of HERV-K Env inside and outside the infected cells was analysed by FACS. The results suggested a better transfection efficiency when using an Ad19 vector compared to an Ad5, since although both encoded for the same target protein, a higher signal was detected when using Ad19. When comparing Ad19_HERVK WT and ISDmut vaccines, a greater cell surface signal and similar intracellular signal was detected from the Ad19_HERV-K_ISDmut-transfected cells, which indicates an improved cell surface sorting of the mutated sequence.

To visually confirm the generation of the structural protein Gag and the following release of Env HERV-K, A549 cells were infected with 50 MOI of Ad19_HERV-K_ISDmut and fixed at 24 h and 48 h post-infection. Budding and secreted VLPs were then detected by electron microscopy (see FIG. 29) indicating that the vaccines were fully capable of expressing HERV-K Gag and Env target protein, which were incorporated into the secreted VLPs.

Example 16

To test the T cell response induced by the Ad19_HERV-K WT/ISDmut vaccines, T lymphocytes response against P-HKE (10mer peptide of HERV-K Env with sequence TYHMVSGMSL (SEQ ID NO: 47)) in BALB/c mice was analysed. Since P-HKE is an MHC class I restricted epitope, the activation of CD8+T cells and, thus, the secretion of interferon gamma (IFNγ) and tumor necrosis factor alpha (TNFα) cytokines after peptide stimulation in BALB/c mice was measured by intracellular staining (ICS) of cytokines using FACS.

BALB/c mice were primed with various vaccines consisting of different vectors (Ad5/Ad19/MVA) encoding for HERV-K proteins. Following that, half of them received an MVA Env boost to test if the cellular response elicited by the first immunization regimen could be increased. Mice were euthanized 10 days after the MVA boost, and their splenocytes were analyzed by FACS upon P-HKE stimulation (see FIG. 25). The groups receiving Ad19_HERV-K_WT/ISDmut vaccines showed a higher number of specific CD8+ T cells secreting INFγ, in both boosted (MVA-Env) and non-boosted (Ø) regimens. Moreover, the cellular responses elicited by all adv-vaccines seem to increase after an MVA boost regimen. This boost seem to accentuate the differences between the employed vaccines, especially when studying the ratio of IFNγ/TNFα CD8+ T cells, with a significant superior percentage in the group of mice that received the improved adv-vaccine (Ad19 HERV-K ISDmut). This suggested that the Ad19 vector encoding for the sequence of interest was the most suitable for inducing relevant CD8+ T cell responses in prime-boost regimens, when compared to Ad5 and MVA vectors. Additionally, the results suggested that the MVA vector could be used in boost regimens to increase the cytotoxic T cell response against the HERV-K Env target protein. These outcomes together indicated a particularly efficient vaccination design that raised IFNγ+ CD8+ T cell specific responses against HERV-K Env expressing tumor cells, would consist of an immunization with an Ad19 vector, preferably encoding for HERV- K_Gag_p2A_Env-ISDmut proteins, and on a boost regimen with an MVA vector encoding for HERV-K_Env protein.

Example 17

To test and compare the efficacy of the vaccines, mice were challenged and subsequently vaccinated, and their survival, which correlated with tumor progression, was rated (see FIG. 26). For this experiment, BALB/c mice were intravenously challenged with RENCA cells expressing HERV-K Env. 10 days after the tumor challenge, mice were vaccinated with MVA Env, Ad19_HERV-K WT/ISDmut, and an irrelevant vaccine as a control. The experiment was based upon (Kraus et al., 2013 PLoS One. August 30; 8(8):e72756)with the intention to score metastatic tumor burden at 40 days post injection, but the animals were longitudinally weighed and if any physical, behavioral or physiological changes were observed in the animals, or a weight loss greater than 10%, mice were euthanized. Once the mice were killed, the lungs were harvested and stored in 4% PFA to be further analyzed for presence of metastasis. Notably, all animals sacrificed due to weight loss had substantial gross tumor burden. Unexpectedly, significant mortality was recorded during the execution of the experiment and a survival curve was established and compared between the different groups. This indicated a faster progression of the RENCA-HERV-K tumors compared to what has previously been reported. Under this rather stringent tumor challenge model, mice receiving the Ad19_HERV-K_ISDmut vaccine showed significant increase in their life expectancy when compared to the control. Three different statistical tests (Log-rank, Wilcoxon, and Tarone-Ware) showed significant p-values (0.037, 0.046 and 0.040). This suggested that the Ad19_HERV-K_ISDmut vaccine delayed lung tumor progression and metastasis in BALB/c mice in agreement with the aforementioned results showing increased antibody and CD8+ T cell responses. None of the other vaccines extended the survival time.

Example 18

To further corroborate the findings also in a human system, tissue samples were obtained from a human mammary tumor. They were sliced at 4 μm and stained with 1:1000 diluted primary antibodies obtained from non-immunized mice (pre-bleed serum), Ad5_HERV-K_Env primed mice boosted with Ad19_HERV-K_ISD (8 w later) and MVA_Env (2 m later) vaccination regimens. As shown in FIG. 28 HERV-K antibodies from vaccinated mice are able to stain cancer tissue expressing the HERV-K target protein.

The various aspects and implementations have been described in conjunction with various embodiments herein. However, other variations to the disclosed embodiments can be understood and effected by those skilled in the art in practicing the claimed subject-matter, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems.

The reference signs used in the claims shall not be construed as limiting the scope.

Sequences are disclosed in the main body of the description and in a separate sequence listing according to WIPO standard ST.25. A SEQ ID specified with a specific number should be the same in the main body of the description and in the separate sequence listing. By way of example SEQ ID no.: 1 should define the same sequence in both, the main body of the description and in the separate sequence listing. Should there be a discrepancy between a sequence definition in the main body of the description and the separate sequence listing (if e.g. SEQ ID no.: 1 in the main body of the description erroneously corresponds to SEQ ID no.: 2 in the separate sequence listing) then a reference to a specific sequence in the application, in particular of specific embodiments, is to be understood as a reference to the sequence in the main body of the application and not to the separate sequence listing. In other words a discrepancy between a sequence definition/designation in the main body of the description and the separate sequence listing is to be resolved by correcting the separate sequence listing to the sequences and their designation disclosed in the main body of the application which includes the description, examples, figures and claims.

Patent Items

1. A vaccine for use in the prophylaxis and/or treatment of a disease, comprising an adenoviral vector capable of encoding a virus-like particle (VLP), said VLP displaying an inactive immune-suppressive domain (ISD).

2. The vaccine according to item 1, which is for the prophylaxis and/or treatment of cancer.

3. The vaccine according to items 1 or 2, wherein the ISD has the peptide sequence LANQINDLRQTVIW (SEQ ID NO. 1), LASQINDLRQTVIW (SEQ ID NO. 2), LQNRRGLDLLTAEKGGL (SEQ ID NO. 3), LQNRRALDLLTAERGGT (SEQ ID NO. 4), LQNRRGLDMLTAAQGGI (SEQ ID NO. 5), or YQNRLALDYLLAAEGGV (SEQ ID NO. 6) having at least one of the amino acids deleted or exchanged with a different amino acid.

4. The vaccine according to item 3, wherein the amino acid different from the original is selected among naturally occurring amino acids.

5. The vaccine according to any of the preceding items, wherein at least one of the amino acids in a region of 10 amino acids upstream or downstream of the ISD is exchanged with a different amino acid.

6. The vaccine according to any of the preceding items, wherein the VLP further is displaying an endogenous retrovirus (ERV) envelope protein or an immunogenic part thereof.

7. The vaccine according to any of the preceding items, wherein the ERV envelope protein is a human endogenous retrovirus (HERV) protein or an immunogenic part thereof.

8. The vaccine according to any of the preceding items, wherein said HERV is selected among the group consisting of HERV-K, HERV-H, HERV-W, HERV-FRD, and HERV-E.

9. The vaccine according to any of the items 1 to 8, wherein the HERV-K is selected among the group consisting of HERV-K108 (=ERVK-6), ERVK-19, HERV-K115 (=ERVK-8), ERVK-9, HERV-K113, ERVK-21, ERVK-25, HERV-K102 (=ERVK-7), HERV-K101 (=ERVK-24), and HERV-K110 (=ERVK-18); HERV-H is selected among the group consisting of HERV-H19 (=HERV-H_2q24.3), and HERV-H_2q24.1; HERV-W is selected as ERVW-1 (=Syncytin-1); and HERV-FRD is selected as ERVFRD-1 (=Syncytin-2).

10. The vaccine according to any of the preceding items, wherein the adenoviral vector is derived from mammalian adenovirus types, human adenovirus types, chimpanzee adenovirus types, or gorilla adenovirus types.

11. The vaccine according to any of the preceding items, wherein the human adenovirus vector is derived from D group vectors, human adenovirus serotype Ad5, human adenovirus serotype Ad19a, human adenovirus serotype Ad26, or Chimpanzee adenovirus serotypes.

12. The vaccine according to any of the preceding items, wherein the adenoviral vector is adenovirus, serotype 5 (Ad5).

13. The vaccine according to any of the preceding items, wherein the protein product of the adenovirus vector includes a gag protein, a 2A peptide, and an envelope protein (Env).

14. The vaccine according to any of the preceding items, wherein the gag protein is exogenous retroviral gag protein or endogenous retroviral gag protein.

15. The vaccine according to any of the precedings items, wherein the Env protein comprises a Surface Unit (gp70), a cleavage site, and a transmembrane unit (p15E).

16. The vaccine according to any of the preceding items, wherein transmembrane unit (p15E) comprises a fusion peptide, an immunosuppressive domain (ISD), a transmembrane anchor, and/or a cytoplasmatic tail.

17. The vaccine according to any of the preceding items, wherein p15E or an immunogenic part thereof is coupled to the adenoviral capsid protein pIX.

18. The vaccine according to any of the preceding items, wherein the signal peptide coded for by the adenoviral vector is exchanged with a signal peptide from Gaussia luciferase (LucSP).

19. The vaccine according to any of the preceding items, wherein the transmembrane anchor and the cytoplasmatic tail coded for by the adenoviral vector are exchanged with the transmembrane domain and cytoplasmic tail from Influenza A virus Hemagglutinin.

20. The vaccine according to any of the preceding items, wherein the transmembrane anchor and the cytoplasmatic tail coded for by the adenoviral vector are exchanged with the transmembrane domain and cytoplasmic tail from Influenza A virus Hemagglutinin H3N2 (HA-TMCT).

21. The vaccine according to any of the preceding items, wherein a trimerization sequence is provided adjacent to the signal peptide.

22. The vaccine according to any of the preceding items, wherein the trimerization sequence is GCN4.

23. The vaccine according to any of the preceding items wherein the VLP comprises a gag protein.

24. The vaccine according to any of the precedings items, wherein the gag protein is exogenous retroviral gag protein or endogenous retroviral gag protein.

25. The vaccine according to any of the preceding items, wherein the VLP is produced in a cell of the body of a patient having been infected by the adenoviral vector.

26. The vaccine according to any of the preceding items, wherein the VLP is produced in an isolated mammal cell.

27. A nucleic acid construct encoding a target protein capable of forming of a virus-like particle (VLP), wherein the target protein comprises an immune-suppressive domain (ISD), said ISD being inactive.

28. The nucleic acid construct according to item 27, wherein the ISD has the peptide sequence LANQINDLRQTVIW (SEQ ID NO. 1), LASQINDLRQTVIW (SEQ ID NO. 2), LQNRRGLDLLTAEKGGL (SEQ ID NO. 3), LQNRRALDLLTAERGGT (SEQ ID NO. 4), LQNRRGLDMLTAAQGGI (SEQ ID NO. 5), or YQNRLALDYLLAAEGGV (SEQ ID NO. 6) having at least one of the amino acids deleted or exchanged with a different amino acid.

29. The nucleic acid construct according to item 27 or 28, wherein the amino acid different from the original is selected among naturally occurring amino acids.

30. The nucleic acid construct according to items 27 to 29, wherein at least one of the amino acids in a region of 10 amino acids upstream or downstream of the ISD is exchanged with a different amino acid.

31. The nucleic acid construct according to items 27 to 30, the VLP further is displaying an endogenous retrovirus (ERV) envelope protein or an immunogenic part thereof.

32. The nucleic acid construct according to items 27 to 31, wherein the ERV envelope protein is a human endogenous retrovirus (HERV) protein or an immunogenic part thereof.

33. The nucleic acid construct according to items 27 to 32, wherein said HERV is selected among the group consisting of HERV-K, HERV-H, HERV-W, HERV-FRD, and HERV-E.

34. The nucleic acid construct according to items 27 to 33, wherein the HERV-K is selected among the group consisting of HERV-K108 (=ERVK-6), ERVK-19, HERV-K115 (=ERVK-8), ERVK-9, HERV-K113, ERVK-21, ERVK-25, HERV-K102 (=ERVK-7), HERV-K101 (=ERVK-24), and HERV-K110 (=ERVK-18); HERV-H is selected among the group consisting of HERV-H19 (=HERV-H_2q24.3), and HERV-H_2q24.1; HERV-W is selected as ERVW-1 (=Syncytin-1); and HERV-FRD is selected as ERVFRD-1 (=Syncytin-2).

35. The nucleic acid construct according to items 27 to 34, wherein the adenoviral vector is derived from mammalian adenovirus types, human adenovirus types, chimpanzee adenovirus types, or gorilla adenovirus types.

36. The nucleic acid construct according to items 27 to 35, wherein the human adenovirus vector is derived from D group vectors, human adenovirus serotype Ad5, human adenovirus serotype Ad19a, human adenovirus serotype Ad26, or Chimpanzee adenovirus serotypes.

37. The nucleic acid construct according to items 27 to 36 wherein the adenoviral vector is adenovirus, serotype 5 (Ad5).

38. The nucleic acid construct according to items 27 to 37, wherein the protein product of the adenovirus vector includes a gag protein, a 2A peptide, and an envelope protein (Env).

39. The nucleic acid construct according to items 27 to 38, wherein the gag protein is exogenous retroviral gag protein or endogenous retroviral gag protein.

40. The nucleic acid construct according to items 27 to 39, wherein the Env protein comprises a Surface Unit (gp70), a cleavage site, and a transmembrane unit (p15E).

41. The nucleic acid construct according to items 27 to 40, wherein the transmembrane unit (p15E) comprises a fusion peptide, an immunosuppressive domain (ISD), a transmembrane anchor, and/or a cytoplasmatic tail.

42. The nucleic acid construct according to items 27 to 41, wherein p15E or an immunogenic part thereof is coupled to the adenoviral capsid protein pIX.

43. The nucleic acid construct according to items 27 to 42, wherein the signal peptide coded for by the adenoviral vector is exchanged with a signal peptide from Gaussia luciferase (LucSP).

44. The nucleic acid construct according to items 27 to 43, wherein the transmembrane anchor and the cytoplasmatic tail coded for by the adenoviral vector are exchanged with the transmembrane domain and cytoplasmic tail from Influenza A virus Hemagglutinin.

45. The nucleic acid construct according to items 27 to 44, wherein transmembrane anchor and the cytoplasmatic tail coded for by the adenoviral vector are exchanged with the transmembrane domain and cytoplasmic tail from Influenza A virus Hemagglutinin H3N2 (HA-TMCT).

46. The nucleic acid construct according to items 27 to 45, wherein a trimerization sequence is provided adjacent to the signal peptide.

47. The nucleic acid construct according to items 27 to 46, the trimerization sequence is GCN4.

48. A protein comprising the expression product of the nucleic acid construct according to any of the items 27 to 47.

49. A virus-like particle (VLP) comprising a nucleic acid construct according to any of the item 27 to 47.

50. A vaccine according to any of the items 1 to 27 for use in the prophylaxis and/or treatment of cancer.

51. A vaccine according to any of the items 1 to 27 for use in the prophylaxis and/or treatment of cancer, comprising the step of priming the patient with the nucleic acid construct according to any of the items 27 to 47 at least 5 days before boosting with the vaccine according to any of the items 1 to 26.

52. A vaccine according to any of the items 1 to 26 for use in the prophylaxis and/or treatment of cancer, comprising the step of post treating the patient 5 days or more after the exposure of the patient for the vaccine according to any of the items 1 to 26 with a virus encoded VLP different from the VLP derived from an adenoviral vector.

53. The vaccine according to item 52, wherein the virus encoded VLP different from the VLP derived from an adenoviral vector is a VLP derived from Modified Vaccina Ankara (MVA).

54. A vaccine for use in prophylaxis and/or treatment a disease, comprising a viral vector capable of encoding a virus-like particle (VLP), said VLP displaying an inactive immune-suppressive domain (ISD).

55. The vaccine according to item 54, wherein the viral vector is derived from Modified Vaccina Ankara (MVA), adeno-associated virus (AAV), or lentivirus.

56. A method for prophylaxis and/or treatment of cancer comprising the administration of the vaccine according to any of the items 1 to 26.

57. A method for prophylaxis and/or treatment of cancer, comprising the step of priming the patient with the nucleic acid according to any of the items 27 to 47 at least 5 days before boosting with the vaccine according to any of the items 1 to 26.

58. A method for prophylaxis and/or treatment of cancer, comprising the step of post-treating the patient 5 days or more after the exposure of the patient for the vaccine according to any of the items 1 to 20 with a virus encoded VLP different from the VLP derived from an adenoviral vector.

59. The method according to item 58, wherein the virus encoded VLP different from the VLP derived from an adenoviral vector is a VLP derived from Modified Vaccina Ankara (MVA). Also the following patent items are disclosed:

60. A nucleic acid molecule for use in the prophylaxis and/or treatment of a disease, said nucleic acid molecule encoding an endogenous retrovirus (ERV) envelope protein or an immunogenic part thereof, wherein the ISD of said protein contains mutations that render the ISD inactive.

61. A vector comprising the nucleic acid molecule according to item 60 for use according to item 60, the vector preferably being an adenoviral vector, more preferably an adenoviral vector derived from mammalian adenovirus types, human adenovirus types, chimpanzee adenovirus serotypes, or gorilla adenovirus serotypes, wherein the human adenovirus vector is derived from D group vectors, human adenovirus serotype Ad5, human adenovirus serotype Ad19a, human adenovirus serotype Ad26, or Chimpanzee adenovirus serotype, and wherein the adenoviral vector is adenovirus, serotype 5 (Ad5) or adenovirus, serotype 19 (Ad19).

62. The vector according to item 61 for use according to item 61, wherein said vector encodes a virus-like particle (VLP), said VLP displaying an endogenous retrovirus (ERV) envelope protein or an immunogenic part thereof with an inactive immune-suppressive domain (ISD).

63. A protein comprising the expression product of the vector of item 62 for use in the prophylaxis and/or treatment of a disease.

64. A vaccine comprising the nucleic acid molecule or the vector according to any of the preceding items 60-62 or the protein according to item 63 for use in the prophylaxis and/or treatment of a disease.

65. The nucleic acid molecule, the vector, the protein or the vaccine according to any of the preceding items 60-64 for use according to the preceding item, wherein the disease is cancer, more preferably an ERV-expressing cancer, yet more preferably a cancer selected from prostate cancer, breast cancer, ovarian cancer, lymphomas, melanomas, leukemia, sarcomas, colorectal cancer, testicular cancer, lung cancer, and liver cancer.

66. The nucleic acid molecule, vector or vaccine according to any of the preceding items 60-65 for use according to the preceding items 60-65, wherein the ISD has the peptide sequence LANQINDLRQTVIW (SEQ ID No.1), LASQINDLRQTVIW (SEQ ID No.2), LQNRRGLDLL-TAEKGGL (SEQ ID No.3), LQNRRALDLLTAERGGT (SEQ ID No.4), LQNRRGLDMLTAAQGGI (SEQ ID No.5), YQNRLALDYLLAAEGGV (SEQ ID No.6) or NSQSSIDQKLANQINDLRQT (SEQ ID No.49) having at least one of the amino acids exchanged with a different amino acid.

67. The nucleic acid molecule, the vector or the vaccine according to any of the preceding items 60-66 for use according to the preceding item, wherein at least one of the amino acids in a region of 10 amino acids upstream or downstream of the ISD is exchanged with a different amino acid.

68. The nucleic acid molecule, the vector or the vaccine according to any of the preceding items 60-67 for use according to the preceding item, wherein the ERV protein is a human endogenous retrovirus (HERV) protein or an immunogenic part thereof, wherein said HERV is selected among the group consisting of HERV-K, HERV-H, HERV-W, HERV-FRD, and HERV-E, and wherein the HERV-K is selected among the group consisting of HERV-K108 (=ERVK-6), ERVK-19, HERV-K115 (=ERVK-8), ERVK-9, HERV-K113, ERVK-21, ERVK-25, HERV-K102 (=ERVK-7), HERV-K101 (=ERVK-24), and HERV-K110 (=ERVK-18); HERV-H is selected among the group consisting of HERV-H19 (=HERV-H_2q24.3), and HERV-H_2q24.1; HERV-W is selected as ERVW-1 (=Syncytin-1); and HERV-FRD is selected as ERVFRD-1 (=Syncytin-2).

69. The vector according to any of items 62 to 67 or the vaccine according to any of the preceding items 60-68 for use according to the preceding items 60-68, wherein the protein product of the adenovirus vector includes a gag protein, a 2A peptide, and an envelope protein (Env), the Env protein comprises a Surface Unit (gp70), a cleavage site, and a transmembrane unit (p15E), wherein the transmembrane unit (p15E) comprises a fusion peptide, an immunosuppressive domain (ISD), a transmembrane anchor, and a cytoplasmatic tail, and wherein p15E or an immunogenic part thereof is coupled to the adenoviral capsid protein pIX and/or wherein the signal peptide coded for by the adenoviral vector is exchanged with a signal peptide from Gaussia luciferase (LucSP) and/or wherein the transmembrane anchor and the cytoplasmatic tail coded for by the adenoviral vector are exchanged with the transmembrane domain and cytoplasmic tail from Influenza A virus Hemagglutinin H3N2 (HA-TMCT).

70. A vaccine according to any of the preceding items 60-69 for use in the prophylaxis and/or treatment of cancer, comprising the step of priming the patient with the adenoviral vector at least 5 days before boosting with the vaccine according to any of the preceding items 60-69.

71. A vaccine according to any of the preceding items 60-70 for use in the prophylaxis and/or treatment of cancer, comprising the step of post treating the patient 5 days or more after the exposure of the patient for the vaccine with a virus encoded VLP different from the VLP derived from an adenoviral vector, wherein the virus encoded VLP different from the VLP derived from an adenoviral vector is a VLP derived from Modified Vaccina Ankara (MVA).

72. A nucleic acid molecule encoding a Gag protein and an ERV envelope protein (Env) or an immunogenic part thereof wherein the native genomic structure connecting Gag and the Env has been replaced by an operative linker, wherein the linker preferably is p2A.

73. A VLP encoded by the nucleic acid molecule of item 72.

74. The nucleic acid molecule according to item 72 or the VLP according to item 73 for use in the prophylaxis and/or treatment of a disease.

75. The nucleic acid molecule according to item 60, the VLP according to item 73 or the nucleic acid molecule or VLP according to item 74 for use according to item 74, wherein the ERV is HERV-K, preferably HERV-K 113.

The invention claimed is:

1. A nucleic acid molecule encoding human endogenous retrovirus K (HERV-K) envelope protein or an immunogenic part thereof, wherein the immune-suppressive domain (ISD) of said protein contains at least one mutation that renders the ISD inactive, and wherein the at least one mutation in the inactivated ISD replaces Q525 with an alanine, wherein the numbering of said mutation is based on a HERV-K isolate comprising the sequence of any one of SEQ ID NO.: 9, 10, 11, 13, 17 and 21.

2. The nucleic acid molecule of claim 1, wherein the HERV-K is selected from the group consisting of HERV-K108 (ERVK-6), ERVK-19, HERV-K115 (ERVK-8), ERVK-9, HERV-K113, ERVK-21, ERVK-25, HERV-K102 (ERVK-7), HERV-K101 (ERVK-24), and HERV-K110 (ERVK-18).

3. The nucleic acid molecule of claim 1, wherein the nucleic acid molecule is comprised in an adenoviral vector.

4. The nucleic acid molecule of claim 1, wherein the nucleic acid encodes a VLP.

5. A nucleic acid vector comprising the nucleic acid molecule of claim 1, wherein the vector encodes a virus-like particle (VLP), wherein said VLP displaying an endogenous retrovirus (ERV) envelope protein or an immunogenic part thereof with an inactive immune-suppressive domain (ISD).

6. A vaccine comprising: the nucleic acid molecule of claim 1 or a vector comprising the nucleic acid molecule of claim 1.

7. A method of treating or preventing a disease, comprising administering a vector comprising the nucleic acid molecule of claim 1 to a patient in need thereof, wherein the disease is an HERV-K-envelope protein expressing adenocarcinoma, renal cancer, or lung tumor or metastasis.

8. The method of claim 7, comprising the step of priming the patient with an adenovirus vector at least 5 days before boosting with a vaccine comprising the nucleic acid molecule, and wherein the adenovirus vector comprises the nucleic acid molecule.

9. The method of claim 7, further comprising post treating the patient with a virus encoded VLP different from the VLP derived from an adenoviral vector, wherein the virus encoded VLP different from the VLP derived from an adenoviral vector is a VLP derived from Modified Vaccina Ankara (MVA);

wherein the post treating step with the virus is performed 5 days or more after the exposure of the patient with a vaccine comprising the nucleic acid molecule.

10. The nucleic acid molecule of claim 1, wherein the inactivated ISD comprises the peptide sequence NSQSSIDQKLANAINDLRQT (SEQ ID NO:50).

11. The nucleic acid molecule of claim 10, wherein the ERV protein is a human endogenous retrovirus (HERV) protein.

12. The nucleic acid molecule of claim 10, wherein the nucleic acid molecule is comprised in an adenoviral vector.

13. The nucleic acid molecule of claim 10, wherein the nucleic acid encodes a VLP.

14. A nucleic acid vector comprising the nucleic acid molecule of claim 1, wherein the vector encodes a virus-like particle (VLP), wherein said VLP displaying an endogenous retrovirus (ERV) envelope protein or an immunogenic part thereof with an inactive immune-suppressive domain (ISD), wherein the inactivated ISD comprises the peptide sequence NSQSSIDQKLANAINDLRQT (SEQ ID NO:50).

15. The method of claim 8, wherein the boosting is administered 4 to 8 weeks after the priming.

* * * * *